(12) United States Patent
Praefke et al.

(10) Patent No.: US 11,858,927 B2
(45) Date of Patent: Jan. 2, 2024

(54) PROTEIN KINASE MKK4 INHIBITORS FOR PROMOTING LIVER REGENERATION OR REDUCING OR PREVENTING HEPATOCYTE DEATH

(71) Applicant: HEPAREGENIX GMBH, Tuebingen (DE)

(72) Inventors: Bent Praefke, Tübingen (DE); Philip Klövekorn, Pliezhausen (DE); Roland Selig, Ulm (DE); Wolfgang Albrecht, Ulm (DE); Stefan Laufer, Tübingen (DE)

(73) Assignee: HepaRegeniX GmbH, Tuebingen (DE)

( * ) Notice: Subject to any disclaimer, the term of this patent is extended or adjusted under 35 U.S.C. 154(b) by 81 days.

(21) Appl. No.: 16/965,912

(22) PCT Filed: Jan. 30, 2019

(86) PCT No.: PCT/EP2019/052213
§ 371 (c)(1),
(2) Date: Jul. 29, 2020

(87) PCT Pub. No.: WO2019/149738
PCT Pub. Date: Aug. 8, 2019

(65) Prior Publication Data
US 2021/0078995 A1    Mar. 18, 2021

(30) Foreign Application Priority Data

Jan. 31, 2018 (EP) .................................. 18154454
Jul. 16, 2018 (EP) .................................. 18183692

(51) Int. Cl.
C07D 471/04 (2006.01)

(52) U.S. Cl.
CPC .................................. C07D 471/04 (2013.01)

(58) Field of Classification Search
CPC .................................................. C07D 471/04
See application file for complete search history.

(56) References Cited

U.S. PATENT DOCUMENTS

| | | |
|---|---|---|
| 6,514,981 B1 | 2/2003 | Tang et al. |
| 11,040,027 B2 | 6/2021 | Albrecht et al. |
| 2020/0399241 A1 | 12/2020 | Scheidt et al. |
| 2021/0078995 A1 | 3/2021 | Praefke et al. |
| 2021/0261545 A1 | 8/2021 | Juchum et al. |
| 2022/0281864 A1 | 9/2022 | Albrecht et al. |
| 2022/0340561 A1 | 10/2022 | Pfaffenrot et al. |
| 2023/0088395 A1 | 3/2023 | Selig et al. |

FOREIGN PATENT DOCUMENTS

| | | |
|---|---|---|
| CA | 3075477 A1 | 2/2019 |
| CN | 112778311 A | 5/2021 |
| CN | 113072497 A | 7/2021 |
| EP | 2161271 A1 | 3/2010 |
| FR | 2876377 A1 | 4/2006 |
| JP | 2006282745 A | 10/2006 |
| RU | 2678455 C1 | 1/2019 |
| WO | 2003035621 A1 | 5/2003 |
| WO | 2003037898 A1 | 5/2003 |
| WO | 2004058764 A1 | 7/2004 |
| WO | 2007002325 A1 | 1/2007 |
| WO | 2007002433 A1 | 1/2007 |
| WO | 2007013896 A2 | 2/2007 |
| WO | 2008063888 A2 | 5/2008 |
| WO | 2008064255 A2 | 5/2008 |
| WO | 2008064265 A2 | 5/2008 |
| WO | 2008079903 A1 | 7/2008 |
| WO | 2008079906 A1 | 7/2008 |
| WO | 2010104945 A1 | 9/2010 |
| WO | 2010111527 A1 | 9/2010 |
| WO | 2010129567 A1 | 11/2010 |
| WO | 2010129570 A1 | 11/2010 |
| WO | 2011047432 A1 | 4/2011 |
| WO | 2011079133 A2 | 6/2011 |
| WO | 2012109075 A1 | 8/2012 |

(Continued)

OTHER PUBLICATIONS

Chemical Abstracts Registry No. 1246614-26-5, entered in the Registry file on STN CAS Online Oct. 20, 2010. (Year: 2010).*
A machine generated English translation of Leonov et al., RU 2678455 C1, Jan. 29, 2019. (Year: 2019).*
Grueninger, F, et al., "Novel screening cascade identifies MKK4 as key kinase regulating Tau phosphorylation at Ser422", Mol Cell Biochem 357, 199-207 (2011).
Ogura, M, et al., "Prenylated quinolinecarboxylic acid derivative prevents neuronal cell death through inhibition of MKK4", Biochemical Pharmacology 1-37, doi: https://doi.org/10.1016/j.bcp.2018.10.008 (2018).

(Continued)

Primary Examiner — Laura L Stockton
(74) Attorney, Agent, or Firm — Viksnins Harris Padys Malen LLP

(57) ABSTRACT

The invention relates to pyrazolo-pyridine compounds which inhibit mitogen-activated protein kinase kinase 4 (MKK4) and in particular, selectively inhibit MKK4 over protein kinases JNK1 and MKK7. The compounds are useful for promoting liver regeneration or reducing or preventing hepatocyte death. They are further useful for treating osteoarthritis or rheumatoid arthritis, or CNS-related diseases.

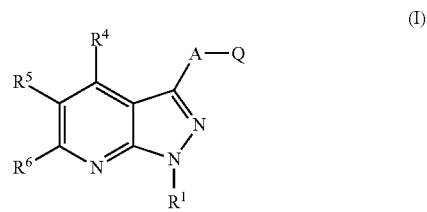

(I)

19 Claims, No Drawings

(56) References Cited

FOREIGN PATENT DOCUMENTS

| WO | 2012129562 A2 | 9/2012 |
|---|---|---|
| WO | 2012135631 A1 | 10/2012 |
| WO | 2012136859 A1 | 10/2012 |
| WO | 2013032951 A1 | 3/2013 |
| WO | 2014035846 A2 | 3/2014 |
| WO | 2014047648 A1 | 3/2014 |
| WO | 2014194127 A1 | 12/2014 |
| WO | 2017066193 A1 | 4/2017 |
| WO | 2018134254 A1 | 7/2018 |
| WO | 2019031990 A1 | 2/2019 |
| WO | 2019243315 A1 | 12/2019 |
| WO | 2020016243 A1 | 1/2020 |
| WO | 2020051207 A2 | 3/2020 |
| WO | 2020123675 A1 | 6/2020 |
| WO | 2021018820 A1 | 2/2021 |
| WO | 2021144287 A1 | 7/2021 |

OTHER PUBLICATIONS

Patent Cooperation Treaty, International Searching Authority, Search Report for PCT/EP2019/052213, 5 pages, dated Mar. 21, 2019.
Vin, H, et al., "BRAF inhibitors suppress apoptosis through off-target inhibition of JNK signaling", eLife 2, e00969, DOI: 10.755/4/eLife.00969, 1-25 (2013).
Vin, H, et al., "BRAF inhibitors suppress apoptosis through off-target inhibition of JNK signaling", eLife 2, e00969, DOI: 10.7554/eLife.00969, 1-25, Supporting Information—Figures and Supplements (2013).
Wuestefeld, T, et al., "A Direct in Vivo RNAi Screen Identifies MKK4 as a Key Regulator of Liver Regeneration", Cell 153, 389-401 (2013).
Deibler, K, et al., "A Chemical Probe Strategy for Interrogating Inhibitor Selectivity Across the MEK Kinase Family", ACS Chem Biol 12, 1245-1256, Supporting Information, 82 pages (2017).
Deibler, K, et al., "Synthesis and Biological Evaluation of 3-Arylindazoles as Selective MEK4 Inhibitors", ChemMedChem 14, 615-620 (2019).
Erion, M, et al., "Liver-Targeted Drug Delivery Using HepDirect1 Prodrugs", Journal of Pharmacology and Experimental Therapeutics 312(2), 554-560 (2005).
Hu, G, et al., "MicroRNA-145 attenuates TNF-α-driven cartilage matrix degradation in osteoarthritis via direct suppression of MKK4", Cell Death and Disease 8, e3140, 13 pages (2017).
Kim, D, et al., "Novel Small Molecule Raf Kinase Inhibitors for Targeted Cancer Therapeutics", Arch Pharm Res 35(4), 605-612 (2012).
Krishna, S, et al., "A Fluorescence-Based Thermal Shift Assay Identifies Inhibitors of Mitogen Activated Protein Kinase Kinase 4", PLoS One 8(12), e81504, 11 pages (2013).
Willenbring, H., et al., "A Therapy for Liver Failure Found in the JNK Yard", Cell 153, 283-284 (2013).
Schneider, C, et al., "Synthesis of 6-Substituted Pyrido[2,3-b]indoles by Electrophilic Substitution", Synlett 14, 2237-2241 (2007).
Wadsworth, A, et al., "A review of the synthesis of a-carbolines", European Journal of Medicinal Chemistry 97, 816-829 (2015).
Merriam-Webster, "Prevent", https:/www.merriam-webster.com/dictionary/prevent, 2022.
Asaoka, Y, "Diverse physiological functions of JNK signaling networks during early embryogenesis", Comparative Physiology and Biochemistry 30 (2), 59-67 (2013). [English Abstract].
PUBCHEM, "Vemurafenib", CID No. 42611257, 54 pages (Create date: Jun. 22, 2009).
Ibrahim, P., "Case History: Vemurafenib, a Potent, Selective, and First-in-Class Inhibitor of Mutant BRAF for the Treatment of Metastatic Melanoma", Annual Reports in Medicinal Chemistry 48(26), 435-449 (2013).
Wermuth, C., et al., "Molecular Variation Based on Isosteric Replacements", The Practice of Medicinal Chemistry 13, 203-237 (1996).

* cited by examiner

PROTEIN KINASE MKK4 INHIBITORS FOR PROMOTING LIVER REGENERATION OR REDUCING OR PREVENTING HEPATOCYTE DEATH

CROSS-REFERENCE TO RELATED APPLICATION(S)

This application is a 35 U.S.C § 371 application of International Application No. PCT/EP2019/052213, filed on Jan. 30, 2019, which claims priority to European Application No. 18154454.5, filed on Jan. 31, 2018 and European Application No. 18183692.5 filed Jul. 16, 2018.

The present invention relates to pyrazolo-pyridine protein kinase inhibitors which inhibit mitogen-activated protein kinase kinase 4 (MKK4) and in particular, selectively inhibit MKK4 over protein kinases JNK1 and MKK7.

BACKGROUND OF THE INVENTION

Liver diseases may be caused by infection, injury, exposure to toxic compounds, like alcohol or drugs, autoimmune processes, genetic defects, and other factors. Liver has a remarkable regenerative capacity which, however, may be impaired in disease state and may therefore be insufficient to compensate for the loss of hepatocytes and organ function. WO 2007/002433 describes compounds which are protein kinase inhibitors useful to treat diseases and conditions associated with aberrant activity of protein kinases. These compounds are inhibitors of Raf protein kinase, in particular B-Raf and c-Raf and mutations thereof and are therefore useful for cancer treatment. Further, they are said to inhibit a large variety of other protein kinases, among them c-Jun N-terminal kinases (JNK) and in particular JNK1. WO 2007/002325 has a similar disclosure and WO 2012/109075 and WO 2014/194127 disclose modified compounds having Raf protein kinase inhibiting activity. H. Vin et al. refer to two compounds of WO 2007/002433 as B-Raf inhibitors that suppress apoptosis through off-target inhibition of JNK signaling. WO 2010/111527 describes pyrazolo[3,4-b]pyridine compounds which are protein kinase inhibitors useful to treat a Raf protein kinase mediated disease or condition, like cancer. Further, they are said to inhibit a large variety of other protein kinases, among them c-Jun N-terminal kinases (JNK) and in particular JNK1. WO 2012/136859 discloses some compounds which are described as inhibitors of mitogen-activated protein kinase 4 (MKK4) and as being useful in the treatment of liver failure, for the protection of hepatocytes against apoptosis and for the regeneration of hepatocytes. Wuestefeld et al. (Cell 153:389-401, 2013) describe a functional genetic approach for the identification of gene targets that can be exploited to increase the regenerative capacity of hepatocytes. In particular, Wuestefeld et al. identify protein kinase MKK4 as a key regulator of liver regeneration and report that MKK4 suppression increased hepatocyte regeneration via compensatory upregulation of MKK7 and a JNK1-dependent activation of ATF2 and ELK1. On the basis of the findings of the prior art it has been concluded that MKK4 and JNK1 inhibitors could be useful to treat JNK1-mediated diseases. However, despite the recognition that inhibition of JNK1 could be beneficial for treatment of liver diseases, no clinical studies have been performed. WO 2018/134254 discloses pyrrolo-pyridine compounds that are protein kinase inhibitors for promoting liver regeneration or reducing or preventing hepatocyte death.

SUMMARY OF THE INVENTION

The problem underlying the invention was to provide compounds that are useful MKK4 inhibitors, in particular MKK4 inhibitors which selectively inhibit MKK4 over MKK7 and JNK1. A further problem was to provide compounds that are MKK4 inhibitors which selectively inhibit MKK4 over MKK7 and JNK1, which are useful for treating liver diseases and especially for promoting liver regeneration or reducing or preventing hepatocyte death.

This problem was solved by providing the compounds of formula (I).

Thus, the invention relates to the following embodiments:

1. A compound having formula (I)

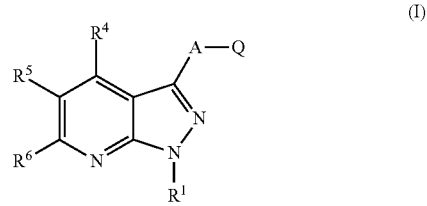

and the pharmaceutically acceptable salts, prodrugs, biologically active metabolites, solvates and stereoisomers thereof, wherein the variables in formula (I) have the meanings as follows:

$R^1$ is H, alkyl or heterocycloalkyl having 4 to 5 ring carbon atoms and 1 or 2 heteroatoms independently selected from O, NH or N-alkyl;

A is a bond or a linking group selected from
—CO—,
—S—,
—SO—,
—SO$_2$—,
—O—,
—C(=N—NHR$^{10}$)—,
—CH<,
—NR$^{10}$—,
alkylene which is optionally substituted with OH or alkoxy,
alkylene-NR$^{10}$-alkylene,
alkylene-NR$^{10}$SO$_2$-alkylene,
alkylene-NR$^{10}$CONR$^{10}$-alkylene,
alkylene-NR$^{10}$CSNR$^{10}$-alkylene,
—CONR$^{10}$,
—NR$^{10}$CO—,
—NR$^{10}$—SO$_2$—,
—O$_2$S—NR$^{10}$—,
—CO-alkylene,
alkylene-CO—,
alkylene-NR$^{10}$CO—,
—OCNR$^{10}$-alkylene,
alkylene-NR$^{10}$,
NR$^{10}$-alkylene,
alkylene-NR$^{10}$SO$_2$—,
—SO$_2$NR$^{10}$-alkylene,

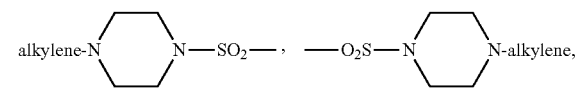

alkylene-CONR$^{10}$-alkylene,
alkylene-NR$^{10}$CO-alkylene,
alkylene-NR$^{10}$CONR$^{10}$—,
—NR$^{10}$CONR$^{10}$-alkylene,
alkylene-NR$^{10}$CSNR$^{10}$—,
—NR$^{10}$CSNR$^{10}$-alkylene,
alkylene-NR$^{10}$-alkylene-NR$^{10}$—,
—NR$^{10}$-alkylene-NR$^{10}$-alkylene-,
—CO-alkylene-O—, and
—O-alkylene-CO—;

Q is an aromatic or heteroaromatic 5- or 6-membered monocyclic or aromatic or heteroaromatic 9- or 10-membered bicyclic group wherein the heteroaromatic groups have 1, 2 or 3 heteroatoms independently selected from O, N and S, wherein Q is substituted with —NR$^{10}$SO$_2$R$^{12}$ or —N=S(=O)R$^{10}$NR$^{10}$R$^{10}$;

and is optionally substituted with 1, 2 or 3 groups independently selected from alkyl which is optionally substituted with 1 or 2 substituents independently selected from phenyl, halogen substituted phenyl, halogen, OH, CN, —NR$^{10}$R$^{10}$, cycloalkyl and a heteroaromatic 5- or 6-membered monocyclic group having 1, 2 or 3 heteroatoms independently selected from O, N and S;
halogen;
hydroxy;
alkoxy;
haloalkoxy;
phenyl, which is optionally substituted with 1 or 2 groups independently selected from alkyl, hydroxyalkyl, alkoxy, halogen, alkylthio and NR$^{10}$R$^{10}$;
—NR$^{10}$R$^{10}$;
—NR$^{10}$SO$_2$R$^{12}$;
—NR$^{10}$SO$_2$R$^{13}$;
—NR$^{10}$SO$_2$NHR$^{10}$;
—NR$^{10}$CONR$^{10}$R$^{17}$;
—NR$^{10}$COR$^{18}$;
—NR$^{10}$COOR$^{10}$;
—CO—NR$^{10}$R$^{19}$;
alkylene-NR$^{10}$SO$_2$R$^{20}$;
—SO$_2$R$^{21}$; and
alkylene-NR$^{10}$COR$^{23}$;

R$^4$ is
H,
halogen,
CN,
NO$_2$,
alkyl,
phenyl which is optionally substituted with 1, 2 or 3 groups independently selected from alkyl, alkoxy, haloalkyl, hydroxyalkyl, alkylsulfonyl, CN, and NO$_2$, or a heteroaromatic or non-aromatic heterocyclic 5- or 6-membered monocyclic or heteroaromatic 9- or 10-membered bicyclic group having 1, 2 or 3 heteroatoms independently selected from O, N and S which group is optionally substituted with 1 or 2 groups independently selected from alkyl, alkoxy, halogen, cycloalkyl, and NR$^{10}$R$^{10}$;

R$^5$ is
halogen,
alkyl, which is optionally substituted with 1 or 2 groups independently selected from
alkoxy, NR$^{10}$R$^{10}$, —COOR$^{10}$, and oxadiazolyl,
alkoxy,
alkenyl,
alkinyl,
phenyl or naphthyl which phenyl or naphthyl is optionally substituted with 1, 2 or 3 groups independently selected from alkyl, halogen, haloalkyl, hydroxy, hydroxyalkyl, alkylthio, alkylsulfinyl, alkylsulfonyl, alkylSO(=NR$^{10}$)—, alkylsulfonyl-NR$^{10}$—, NR$^{10}$R$^{10}$, R$^{10}$R$^{10}$NSO$_2$—, R$^{10}$R$^{11}$NSO$_2$—, alkyl-C(=O)—NR$^{10}$SO$_2$—, R$^{10}$R$^{11}$N(C=O)—, alkoxy, benzyloxy, haloalkoxy, —OCH$_2$— (methylenedioxy attached in neighboring positions to the phenyl ring), —OCH$_2$CH$_2$— (ethylenedioxy attached in neighboring positions to the phenyl ring), NO$_2$, —COOR$^{10}$, —COOR$^{10}$, R$^{10}$R$^{10}$N(C=O)—, CN, alkylcarbonyl-NR$^{10}$—, tetrazolyl, alkenyl, —CONR$^{10}$—O-alkylene-OH, —CONR$^{10}$—O-alkylene-O-alkyl, and carboxyl-substituted alkenyl, phenylalkenyl wherein the phenyl group is optionally substituted with 1, 2 or 3 groups independently selected from OH, alkoxy and —CONR$^{10}$R$^{19}$, or
a heteroaromatic or non-aromatic heterocyclic 5- or 6-membered monocyclic or heteroaromatic 9- or 10-membered bicyclic group having 1, 2 or 3 heteroatoms independently selected from O, N and S which group is optionally substituted with 1 or 2 groups independently selected from alkyl, haloalkyl, alkoxy, —NR$^{10}$R$^{10}$, halogen, —NR$^{10}$-cycloalkyl, tetrazolyl, —O-alkylene-NR$^{10}$R$^{10}$, —NR$^{10}$-alkylene-O-alkyl, —CN, —CONR$^{10}$R$^{10}$, alkylSO(=NR$^{10}$)—, —CONR$^{10}$—O-alkylene-OH, —CONR$^{10}$—O-alkylene-O-alkyl, —COOR$^{10}$, morpholinyl, piperazinyl, oxadiazolyl and phenylcarbonyl;

R$^6$ is H, alkoxy, NR$^{10}$R$^{10}$, or —NR$^{10}$-phenyl wherein the phenyl group is optionally substituted with NR$^{10}$R$^{10}$, alkoxy, morpholinyl, halogen or —SO$_2$ morpholinyl;

R$^{10}$ at each occurrence independently is H, alkyl, phenyl which is optionally substituted with hydroxyl or alkoxy or is phenylalkyl wherein the phenyl group is optionally substituted with halogen;

R$^{11}$ is alkyl which is substituted with 1, 2 or 3 hydroxy groups;

R$^{12}$ is H, alkyl, phenylalkyl, phenyl-NR$^{10}$—, —NR$^{10}$R$^{10}$, heteroalkyl having 1, 2 or 3 heteroatoms independently selected from O, N and S, or is phenyl which is optionally substituted with 1, 2 or 3 groups independently selected from alkyl, alkoxy, alkoxycarbonyl, haloalkoxy, halogen, haloalkyl, CN, NO$_2$, alkylcarbonylamino, oxazolyl, —OCH$_2$— (methylenedioxy attached in neighboring positions to the phenyl ring), and —OCH$_2$CH$_2$— (ethylenedioxy attached in neighboring positions to the phenyl ring), R$^{13}$ is a heteroaromatic or non-aromatic heterocyclic 5- or 6-membered group having 1, 2 or 3 heteroatoms independently selected from O, N and S which group is optionally substituted with 1 or 2 groups independently selected from alkyl, pyridyl, alkoxycarbonyl, oxazolyl and oxazolyl which is substituted with alkyl or alkoxycarbonyl;

R$^{14}$ is alkyl which is substituted with 1 or 2 groups independently selected from —NR$^{10}$R$^{10}$, hydroxy or alkoxy;

R$^{17}$ is H,
alkyl,
haloalkyl,
alkoxyalkyl,
cycloalkyl, a heteroaromatic 5- or 6-membered group having 1, 2 or 3 heteroatoms independently selected from O, N and S which group is optionally substituted with alkyl or alkoxy,
morpholinoalkyl,
cycloalkylalkyl,
N-benzylpyrrolidinyl,
phenyl which is optionally substituted with alkyl, alkoxy, haloalkyl, —NR$^{10}$R$^{10}$ or halogen, or
phenylalkyl wherein the phenyl group is optionally substituted with alkyl, haloalkyl or halogen, or
R$^{17}$ and R$^{10}$ together form a cycloalkyl ring which is optionally substituted with acetylamino,
R$^{18}$ is alkyl, haloalkyl, phenyl, phenyl-alkylene-N⟨  ⟩N-alkylene morpholinyl or pyrrolidinyl which is optionally substituted with —NR$^{10}$R$^{10}$;
R$^{19}$ is H, alkyl, phenylalkyl, phenyl, phenyl which is substituted with alkoxy, or is alkylene-SO$_2$-alkyl or

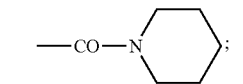

R$^{20}$ is phenyl which is optionally substituted with alkyl, phenyl or phenyl which is substituted with alkyl or hydroxyalkyl;
R$^{21}$ is NR$^{10}$R$^{10}$, alkyl or phenyl which is optionally substituted with halogen;
R$^{23}$ is phenyl or phenyl substituted with alkyl which is optionally substituted with piperazinyl or alkyl substituted piperazinyl;

2. The compound and the pharmaceutically acceptable salts, prodrugs, solvates and optical isomers thereof, of embodiment 1, wherein
R$^1$ is H, alkyl or heterocycloalkyl having 4 to 5 ring carbon atoms and 1 or 2 heteroatoms independently selected from O, NH or N-alkyl;
A is a bond or a linking group selected from
—CO—,
—CO—CO—,
—S—,
—SO—,
—SO$_2$—,
—O—,
—NR$^{10}$—,
alkylene which is optionally substituted with 1 or 2 groups independently selected from OH and alkoxy,
—CONR$^{10}$—,
—NR$^{10}$CO—,
—NR$^{10}$—SO$_2$—, and
—O$_2$S—NR$^{10}$—;
Q is an aromatic or heteroaromatic 5- or 6-membered monocyclic or 9- or 10-membered bicyclic group wherein Q is substituted with —NR$^{10}$SO$_2$R$^{12}$ or —N=S(=O)R$^{10}$NR$^{10}$R$^{10}$ and is optionally substituted with 1, 2 or 3 groups independently selected from alkyl which is optionally substituted with 1 or 2 substituents independently selected from phenyl, halogen substituted phenyl, and halogen; and halogen;
R$^4$ is H, halogen, or alkyl;
R$^5$ is
halogen,
alkyl, which is optionally substituted with 1 or 2 groups independently selected from
alkoxy, NR$^{10}$R$^{10}$, —COOR$^{10}$, and oxadiazolyl,
alkenyl,
alkinyl,
phenyl or naphthyl which phenyl or naphthyl is optionally substituted with 1, 2 or 3 groups independently selected from
alkyl,
halogen,
haloalkyl,
hydroxy,
hydroxyalkyl,
alkylthio,
alkylsulfinyl,
alkylsulfonyl,
alkylSO(=NR$^{10}$)—,
alkylsulfonyl-NR$^{10}$—,
—NR$^{10}$R$^{10}$,
R$^{10}$R$^{10}$NSO$_2$—,
R$^{10}$R$^{11}$NSO$_2$—,
alkyl-C(=O)—NR$^{10}$SO$_2$—,
R$^{10}$R$^{10}$N(C=O)—,
alkoxy,
benzyloxy,
haloalkoxy,
—OCH$_2$— (methylenedioxy attached in neighboring positions to the phenyl ring),
—OCH$_2$CH$_2$— (ethylenedioxy attached in neighboring positions to the phenyl ring),
NO$_2$,
—COOR$^{10}$,
—COOR$^{14}$,
R$^{10}$R$^{10}$N(C=O)—,
CN,
alkylcarbonyl-NR$^{10}$—,
tetrazolyl,
alkenyl,
—CONR$^{10}$—O-alkylene-OH,
—CONR$^{10}$—O-alkylene-O-alkyl, and
carboxyl-substituted alkenyl,
phenylalkenyl wherein the phenyl group is optionally substituted with 1, 2 or 3 groups independently selected from OH, alkoxy and —CONR$^{10}$R$^{19}$, or
a heteroaromatic or non-aromatic heterocyclic 5- or 6-membered monocyclic or heteroaromatic 9- or 10-membered bicyclic group having 1, 2 or 3 heteroatoms independently selected from O, N and S which group is optionally substituted with 1 or 2 groups independently selected from
alkyl,
haloalkyl,
alkoxy,
—NR$^{10}$R$^{10}$,
halogen,
—NR$^{10}$-cycloalkyl,
tetrazolyl,
—O-alkylene-NR$^{10}$R$^{10}$,
—NR$^{10}$-alkylene-O-alkyl,
—CN,
—CONR$^{10}$R$^{10}$, —COOR$^{10}$,
alkylSO(=NR$^{10}$)—,
—CONR$^{10}$—O-alkylene-OH,
—CONR$^{10}$—O-alkylene-O-alkyl,
morpholinyl,
piperazinyl,
oxadiazolyl and
phenylcarbonyl;

R$^6$ is H, or alkyl;

R$^{10}$ at each occurrence independently is H, alkyl, phenyl which is optionally substituted with hydroxyl or alkoxy or is phenylalkyl wherein the phenyl group is optionally substituted with halogen;

R$^{11}$ is alkyl which is substituted with 1, 2 or 3 hydroxy groups;

R$^{12}$ is H, alkyl, phenylalkyl, or —NR$^{10}$R$^{10}$;

R$^{14}$ is alkyl which is substituted with 1 or 2 groups independently selected from —NR$^{10}$R$^{10}$, hydroxy or alkoxy;

R$^{19}$ is H, alkyl, phenylalkyl, phenyl, phenyl which is substituted with alkoxy, or is alkylene-SO$_2$-alkyl or

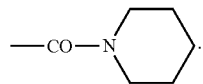

3. The compound and the pharmaceutically acceptable salts, prodrugs, solvates and optical isomers thereof, of embodiment 1 or 2, wherein R$^1$ is H or heterocycloalkyl having 4 to 5 ring carbon atoms and 1 oxygen heteroatom.

4. The compound and the pharmaceutically acceptable salts, prodrugs, solvates and optical isomers thereof, of embodiment 1 or 2, wherein R$^1$ is H.

5. The compound and the pharmaceutically acceptable salts, prodrugs, solvates and optical isomers thereof, of embodiment 1 or 2, wherein R$^1$ is heterocycloalkyl having 4 to 5 ring carbon atoms and 1 oxygen heteroatom.

6. The compound and the pharmaceutically acceptable salts, prodrugs, solvates and optical isomers thereof, of any one of the preceding embodiments, wherein A is a linking group selected from
—CO—,
—S—,
—SO—,
—SO$_2$—,
alkylene which is optionally substituted with 1 or 2 groups independently selected
from OH and alkoxy,
—CONR$^{10}$—, and
—NR$^{10}$CO—.

7. The compound and the pharmaceutically acceptable salts, prodrugs, solvates and optical isomers thereof, of any one of the preceding embodiments, wherein Q is phenyl or naphthyl, and is substituted and optionally substituted as defined in claim 2.

8. The compound and the pharmaceutically acceptable salts, prodrugs, solvates and optical isomers thereof, of embodiment 7, wherein Q is phenyl and is substituted and optionally substituted as defined in claim 2.

9. The compound and the pharmaceutically acceptable salts, prodrugs, solvates and optical isomers thereof, of embodiments 7 or 8, wherein Q is phenyl substituted with —NR$^{10}$SO$_2$R$^{12}$ and further substituted with 1, 2 or 3 groups independently selected from halogen and alkyl which is optionally substituted with 1 or 2 substituents independently selected from phenyl and halogen substituted phenyl.

10. The compound and the pharmaceutically acceptable salts, prodrugs, solvates and optical isomers thereof, of embodiment 9, wherein Q is phenyl substituted with —NR$^{10}$SO$_2$R$^{12}$ and further substituted with 1, 2 or 3 halogen atoms.

11. The compound and the pharmaceutically acceptable salts, prodrugs, solvates and optical isomers thereof, of embodiment 10, wherein the phenyl is substituted with —NR$^{10}$SO$_2$R$^{12}$ and further substituted with 2 or 3 halogen atoms.

12. The compound and the pharmaceutically acceptable salts, prodrugs, solvates and optical isomers thereof, of any one of embodiments 9, 10 or 11, wherein the halogen atom or halogen atoms are F or Cl, in particular F.

13. The compound and the pharmaceutically acceptable salts, prodrugs, solvates and optical isomers thereof, of any one of the preceding embodiments, wherein R$^4$ and R$^6$ are H or alkyl.

14. The compound and the pharmaceutically acceptable salts, prodrugs, solvates and optical isomers thereof, of any one of embodiments 1 to 13, wherein propane-1-sulfonic acid [3-(5-bromo-1H-pyrazolo[3,4-b]pyridine-3-carbonyl)-2,4-difluorophenyl]amide is excluded.

15. The compound and the pharmaceutically acceptable salts, prodrugs, solvates and optical isomers thereof, of any one of embodiments 2 to 13, wherein R$^5$ is
alkyl, which is optionally substituted with 1 or 2 groups independently selected from
alkoxy, NR$^{10}$R$^{10}$, —COOR$^{10}$, and oxadiazolyl,
alkenyl,
alkinyl,
phenyl or naphthyl which phenyl or naphthyl is optionally substituted with 1, 2 or 3 groups independently selected from
alkyl,
halogen,
haloalkyl,
hydroxy,
hydroxyalkyl,
alkylthio,
alkylsulfinyl,
alkylsulfonyl,
alkylSO(=NR$^{10}$)—,
alkylsulfonyl-NR$^{10}$—,
—NR$^{10}$R$^{10}$,
R$^{10}$R$^{10}$NSO$_2$—,
R$^{10}$R$^{11}$NSO$_2$—,
alkyl-C(=O)—NR$^{10}$SO$_2$—,
R$^{10}$R$^{11}$N(C=O)—,
alkoxy,
benzyloxy,
haloalkoxy,
—OCH$_2$— (methylenedioxy attached in neighboring positions to the phenyl ring),
—OCH$_2$CH$_2$— (ethylenedioxy attached in neighboring positions to the phenyl ring),
NO$_2$,
—COOR$^{10}$,
—COOR$^{14}$,
R$^{10}$R$^{10}$N(C=O)—,
CN,
alkylcarbonyl-NR$^{10}$—,
tetrazolyl,
alkenyl,
—CONR$^{10}$—O-alkylene-OH, —CONR$^{10}$—O-alkylene-O-alkyl, and
carboxyl-substituted alkenyl,
phenylalkenyl wherein the phenyl group is optionally substituted with 1, 2 or 3 groups independently selected from OH, alkoxy and —CONR$^{10}$R$^{19}$, or
a heteroaromatic or non-aromatic heterocyclic 5- or 6-membered monocyclic or heteroaromatic 9- or 10-membered bicyclic group having 1, 2 or 3 heteroatoms independently selected from O, N and S which group is optionally substituted with 1 or 2 groups independently selected from
alkyl,
haloalkyl,
alkoxy,
—NR$^{10}$R$^{10}$,
halogen,
—NR$^{10}$-cycloalkyl,
tetrazolyl,
—O-alkylene-NR$^{10}$R$^{10}$,
—NR$^{10}$-alkylene-O-alkyl,
—CN,
—CONR$^{10}$R$^{10}$,
—COOR$^{10}$,
morpholinyl,
piperazinyl,
oxadiazolyl,
alkylSO(=NR$^{10}$)—,
—CONR$^{10}$—O-alkylene-OH,
alkylSO(=NR$^{10}$)—,
—CONR$^{10}$—O-alkylene-O-alkyl, and
phenylcarbonyl.

16. The compound and the pharmaceutically acceptable salts, prodrugs, solvates and optical isomers thereof, of any one of the preceding embodiments, wherein R$^5$ is
phenyl or naphthyl which phenyl or naphthyl is optionally substituted with 1, 2 or 3 groups independently selected from
alkyl,
halogen,
haloalkyl,
hydroxy,
hydroxyalkyl,
alkylthio,
alkylsulfinyl,
alkylsulfonyl,
alkylSO(=NR$^{10}$)—,
alkylsulfonyl-NR$^{10}$—,
—NR$^{10}$R$^{10}$,
R$^{10}$R$^{10}$NSO$_2$—,
R$^{10}$R$^{11}$NSO$_2$—,
alkyl-C(=O)—NR$^{10}$SO$_2$—,
R$^{10}$R$^{11}$N(C=O)—,
alkoxy,
benzyloxy,
haloalkoxy,
—OCH$_2$— (methylenedioxy attached in neighboring positions to the phenyl ring),
—OCH$_2$CH$_2$— (ethylenedioxy attached in neighboring positions to the phenyl ring),
NO$_2$,
—COOR$^{10}$,
—COOR$^{14}$,
R$^{10}$R$^{10}$N(C=O)—,
CN,
alkylcarbonyl-NR$^{10}$—,
tetrazolyl,
alkenyl,
—CONR$^{10}$—O-alkylene-OH,
—CONR$^{10}$—O-alkylene-O-alkyl, and
carboxyl-substituted alkenyl, or
a heteroaromatic or non-aromatic heterocyclic 5- or 6-membered monocyclic or heteroaromatic 9- or 10-membered bicyclic group having 1, 2 or 3 heteroatoms independently selected from O, N and S which group is optionally substituted with 1 or 2 groups independently selected from
alkyl,
haloalkyl,
alkoxy,
—NR$^{10}$R$^{10}$,
halogen,
—NR$^{10}$-cycloalkyl,
tetrazolyl,
—O-alkylene-NR$^{10}$R$^{10}$,
—NR$^{10}$-alkylene-O-alkyl,
—CN,
—CONR$^{10}$R$^{10}$,
—COOR$^{10}$,
morpholinyl,
piperazinyl,
oxadiazolyl,
alkylSO(=NR$^{10}$)—,
alkylSO(=NR$^{10}$)—,
—CONR$^{10}$—O-alkylene-OH,
—CONR$^{10}$—O-alkylene-O-alkyl, and
phenylcarbonyl.

17. The compound and the pharmaceutically acceptable salts, prodrugs, solvates and optical isomers thereof, of embodiment 16, wherein R$^5$ is phenyl or naphthyl which phenyl or naphthyl is substituted with 1, 2 or 3 groups independently selected from alkyl, hydroxy, halogen, haloalkyl, alkylsulfonyl, alkylSO(=NR$^{10}$)—, alkylsulfonyl-NR$^{10}$—, —NR$^{10}$R$^{10}$, R$^{10}$R$^{10}$NSO$_2$—, R$^{10}$R$^{11}$NSO$_2$—, alkyl-C(=O)—NR$^{10}$SO$_2$—, R$^{10}$R$^{11}$N(C=O)—, alkoxy, —OCH$_2$O— (methylenedioxy attached in neighboring positions to the phenyl ring), —OCH$_2$CH$_2$O— (ethylenedioxy attached in neighboring positions to the phenyl ring), —NO$_2$, —COOR$^{10}$, —COOR$^{14}$, R$^{10}$R$^{10}$N(C=O)—, tetrazolyl, —CONR$^{10}$—O-alkylene-OH, and —CONR$^{10}$—O-alkylene-O-alkyl.

18. The compound and the pharmaceutically acceptable salts, prodrugs, solvates and optical isomers thereof, of any one of embodiments 2 to 16, wherein R$^5$ is a heteroaromatic 5- or 6-membered monocyclic or heteroaromatic 9- or 10-membered bicyclic group having 1, 2 or 3 heteroatoms independently selected from O, N and S which group is optionally substituted with 1 or 2 groups independently selected from alkyl, haloalkyl, alkoxy, —NR$^{10}$R$^{10}$, halogen, —NR$^{10}$-cycloalkyl, tetrazolyl, —O-alkylene-NR$^{10}$R$^{10}$, —NR$^{10}$-alkylene-O-alkyl, —CN, —CONR$^{10}$R$^{10}$, —COOR$^{10}$, alkylSO(=NR$^{10}$)—, —CONR$^{10}$—O-alkylene-OH, and —CONR$^{10}$—O-alkylene-O-alkyl.

19. The compound and the pharmaceutically acceptable salts, prodrugs, solvates and optical isomers thereof, of embodiment 18, wherein R$^5$ is a heteroaromatic 5- or 6-membered monocyclic group having 1, 2 or 3 heteroatoms independently selected from O, N and S which group is optionally substituted with 1 or 2 groups independently selected from alkyl, haloalkyl, alkoxy, —NR$^{10}$R$^{10}$, halogen, —NR$^{10}$-cycloalkyl, tetrazolyl, —O-alkylene-NR$^{10}$R$^{10}$, —NR$^{10}$-alkylene-O-alkyl, —CN, —CONR$^{10}$R$^{10}$, —COOR$^{10}$, alkylSO(=NR$^{10}$)—, —CONR$^{10}$—O-alkylene-OH, and —CONR$^{10}$—O-alkylene-O-alkyl.

20. The compound and the pharmaceutically acceptable salts, prodrugs, solvates and optical isomers thereof, of embodiment 19, wherein $R^5$ is a heteroaromatic 5- or 6-membered monocyclic group having 1, 2 or 3 heteroatoms independently selected from O, N and S which group is unsubstituted or substituted with 1 or 2 groups independently selected from alkyl, haloalkyl, alkoxy, —$NR^{10}R^{10}$, halogen, —$NR^{10}$-cycloalkyl, tetrazolyl, —O-alkylene-$NR^{10}R^{10}$, —$NR^{10}$-alkylene-O-alkyl, —CN, —$CONR^{10}R^{10}$, and —$COOR^{10}$.

21. The compound and the pharmaceutically acceptable salts, prodrugs, solvates and optical isomers thereof, of embodiment 20, wherein the heteroaromatic group is unsubstituted or substituted with 1 or 2 groups independently selected from alkyl, haloalkyl, or —$COOR^{10}$.

22. The compound and the pharmaceutically acceptable salts, prodrugs, solvates and optical isomers thereof, of embodiment 20, wherein the heteroaromatic group is pyridyl, pyridyl substituted with —$COOR^{10}$, pyrimidinyl or pyrimidinyl substituted with a group selected from $CF_3$, haloalkyl, alkoxy, —$NR^{10}R^{10}$, halogen, —$NR^{10}$-cycloalkyl, tetrazolyl, —O-alkylene-$NR^{10}R^{10}$, —$NR^{10}$-alkylene-O-alkyl, —CN, and —$CONR^{10}R^{10}$.

23. The compound and the pharmaceutically acceptable salts, prodrugs, solvates and optical isomers thereof, of embodiment 22, wherein the heteroaromatic group is pyrimidinyl or pyrimidinyl substituted in 2-position.

24. The compound and the pharmaceutically acceptable salts, prodrugs, solvates and optical isomers thereof, of embodiment 22, wherein the the heteroaromatic group is pyridyl or pyridyl substituted with —$COOR^{10}$.

25. The compound and the pharmaceutically acceptable salts, prodrugs, solvates and optical isomers thereof, of any one of the preceding embodiments, wherein $R^{10}$ is H or alkyl.

26. The compound and the pharmaceutically acceptable salts, prodrugs, solvates and optical isomers thereof, of any one of the preceding embodiments, wherein $R^{12}$ is alkyl or phenylalkyl.

27. The compound and the pharmaceutically acceptable salts, prodrugs, solvates and optical isomers thereof, of embodiment 26, wherein $R^{12}$ is $C_1$-$C_3$-alkyl or benzyl.

28. The compound and the pharmaceutically acceptable salts, prodrugs, solvates and optical isomers thereof, of any one of embodiments 2 to 24 having formula (Ia)

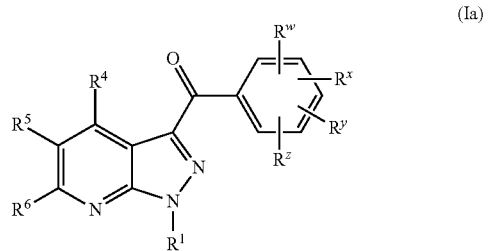

(Ia)

wherein
$R^w$ is —$NR^{10}SO_2R^{12}$ or —N=S(=O)$R^{10}NR^{10}R^{10}$;
$R^x$ is H, halogen or alkyl;
$R^y$ is H, halogen or alkyl;
$R^z$ is H, halogen or alkyl;
wherein one or two of $R^x$, $R^y$ or $R^z$ are halogen, and the other(s) of $R^x$, $R^y$ and $R^z$ is H, halogen or alkyl;
$R^1$, $R^4$, $R^5$, $R^6$, $R^{10}$ and $R^{12}$ are as defined any one of embodiments 2 to 27.

29. The compound and the pharmaceutically acceptable salts, prodrugs, solvates and optical isomers thereof, of embodiment 28, wherein
$R^1$ is H or alkyl;
$R^4$ is H or alkyl;
$R^6$ is H or alkyl;
$R^{10}$ is H, alkyl, or phenylalkyl;
$R^{12}$ is H, alkyl, or phenylalkyl;
$R^w$ is-$NR^{10}SO_2R^{12}$ or —N=S(=O)$R^{10}NR^{10}R^{10}$;
$R^x$ is H, halogen or alkyl;
$R^y$ is H, halogen or alkyl;
$R^z$ is H, halogen or alkyl;
wherein one or two of $R^x$, $R^y$ or $R^z$ are halogen, and the other(s) of $R^x$, $R^y$ or $R^z$ is H, halogen or alkyl;
$R^5$ is
phenyl substituted with 1, 2 or 3 groups independently selected from
alkyl,
hydroxy,
halogen,
haloalkyl,
alkylsulfonyl,
alkylSO(=$NR^{10}$)—,
alkylsulfonyl-$NR^{10}$—,
—$NR^{10}R^{10}$,
$R^{10}R^{10}NSO_2$—,
$R^{10}R^{11}NSO_2$—,
alkyl-C(=O)—$NR^{10}SO_2$—,
$R^{10}R^{11}N(C=O)$—,
alkoxy,
—$OCH_2$— (methylenedioxy attached in neighboring positions to the phenyl ring),
—$OCH_2CH_2$— (ethylenedioxy attached in neighboring positions to the phenyl ring),
—$NO_2$,
—$COOR^{10}$,
—$COOR^{14}$,
$R^{10}R^{10}N(C=O)$—,
tetrazolyl,
—$CONR^{10}$—O-alkylene-OH, and
—$CONR^{10}$—O-alkylene-O-alkyl, or
a heteroaromatic 5- or 6-membered monocyclic group having 1, 2 or 3 heteroatoms
independently selected from O, N and S which group is unsubstituted or substituted with 1 or 2 groups independently selected from
alkyl,
haloalkyl,
alkoxy,
—$NR^{10}R^{10}$,
halogen,
—$NR^{10}$-cycloalkyl,
tetrazolyl,
—O-alkylene-$NR^{10}R^{10}$,
—$NR^{10}$-alkylene-O-alkyl,
—CN,
—$CONR^{10}R^{10}$,
—$COOR^{10}$,
alkylSO(=$NR^{10}$)—,
—$CONR^{10}$—O-alkylene-OH, and
—$CONR^{10}$—O-alkylene-O-alkyl;
$R^{11}$ is alkyl which is substituted with 1, 2 or 3 hydroxy groups; and
$R^{14}$ is alkyl which is substituted with 1 or 2 groups independently selected from —$NR^{10}R^{10}$, hydroxy or alkoxy.

30. The compound and the pharmaceutically acceptable salts, prodrugs, solvates and optical isomers thereof, of embodiment 29, wherein $R^5$ is phenyl substituted with 1, 2 or 3 groups independently selected from alkyl, hydroxy, halogen, haloalkyl, alkylsulfonyl, alkylSO(=NR$^{10}$)—, alkylsulfonyl-NR$^{10}$—, —NR$^{10}$R$^{10}$, R$^{10}$R$^{10}$NSO$_2$—, R$^{10}$R$^{11}$NSO$_2$—, alkyl-C(=O)—NR$^{10}$SO$_2$—, R$^{10}$R$^{11}$N(C=O)—, alkoxy, —OCH$_2$O— (methylenedioxy attached in neighboring positions to the phenyl ring), —OCH$_2$CH$_2$O— (ethylenedioxy attached in neighboring positions to the phenyl ring), —NO$_2$, —COOR$^{10}$, —COOR$^{14}$, R$^{10}$R$^{10}$N(C=O)—, tetrazolyl, —CONR$^{10}$—O-alkylene-OH, and —CONR$^{10}$—O-alkylene-O-alkyl, or a heteroaromatic 5- or 6-membered monocyclic group having 1, 2 or 3 heteroatoms independently selected from O, N and S which group is unsubstituted or substituted with 1 or 2 groups independently selected from alkyl, haloalkyl, and —COOR$^{10}$.

31. The compound and the pharmaceutically acceptable salts, prodrugs, solvates and optical isomers thereof, of any one of embodiments 28 to 30 having formula (Iaa)

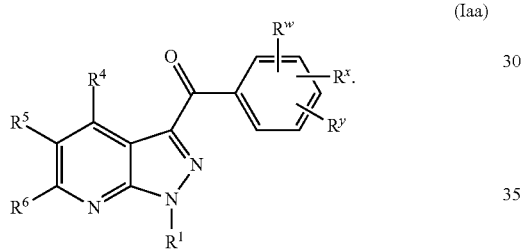

(Iaa)

32. The compound and the pharmaceutically acceptable salts, prodrugs, solvates and optical isomers thereof, of any one of embodiments 2 to 27 having formula (Ib)

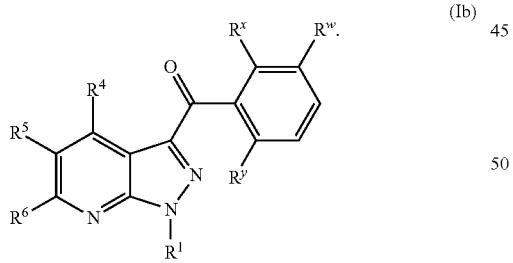

(Ib)

wherein $R^w$ is —NR$^{10}$SO$_2$R$^{12}$ or —N=S(=O)R$^{10}$NR$^{10}$R$^{10}$;
$R^x$ is halogen;
$R^y$ is halogen; and
$R^1$, $R^4$, $R^5$, $R^6$, $R^{10}$ and $R^{12}$ are as defined any one of embodiments 2 to 30.

33. The compound and the pharmaceutically acceptable salts, prodrugs, solvates and optical isomers thereof, of embodiment 32, wherein $R^w$ is —NR$^{10}$SO$_2$R$^{12}$;
$R^x$ is halogen;
$R^y$ is halogen;

$R^5$ is phenyl substituted with 1, 2 or 3 groups independently selected from
alkyl,
hydroxy,
halogen,
haloalkyl,
alkylsulfonyl,
alkylSO(=NR$^{10}$)—,
alkylsulfonyl-NR$^{10}$—,
—NR$^{10}$R$^{10}$,
R$^{10}$R$^{10}$NSO$_2$—,
R$^{10}$R$^{11}$NSO$_2$—,
alkyl-C(=O)—NR$^{10}$SO$_2$—,
R$^{10}$R$^{11}$N(C=O)—,
alkoxy,
—OCH$_2$— (methylenedioxy attached in neighboring positions to the phenyl ring),
—OCH$_2$CH$_2$— (ethylenedioxy attached in neighboring positions to the phenyl ring),
—NO$_2$,
—COOR$^{10}$,
—COOR$^{14}$,
R$^{10}$R$^{10}$N(C=O)—,
tetrazolyl,
alkylSO(=NR$^{10}$)—,
—CONR$^{10}$—O-alkylene-OH, and
—CONR$^{10}$—O-alkylene-O-alkyl, or a heteroaromatic 5- or 6-membered monocyclic group having 1, 2 or 3 heteroatoms independently selected from O, N and S which group is unsubstituted or substituted with 1 or 2 groups independently selected from
alkyl,
haloalkyl,
—COOR$^{10}$,
alkylSO(=NR$^{10}$)—,
—CONR$^{10}$—O-alkylene-OH, and
—CONR$^{10}$—O-alkylene-O-alkyl;

$R^{11}$ is alkyl which is substituted with 1, 2 or 3 hydroxy groups; and
$R^{14}$ is alkyl which is substituted with 1 or 2 groups independently selected from —NR$^{10}$R$^{10}$, hydroxy or alkoxy.

34. The compound and the pharmaceutically acceptable salts, prodrugs, solvates and optical isomers thereof, of embodiment 33, wherein $R^5$ is phenyl substituted with 1, 2 or 3 groups independently selected from alkyl, hydroxy, halogen, haloalkyl, alkylsulfonyl, alkylsulfonyl-NR$^{10}$—, —NR$^{10}$R$^{10}$, R$^{10}$R$^{10}$NSO$_2$—, R$^{10}$R$^{11}$NSO$_2$—, alkyl-C(=O)—NR$^{10}$SO$_2$—, R$^{10}$R$^{11}$N(C=O)—, alkoxy, —NO$_2$, —COOR$^{10}$, R$^{10}$R$^{10}$N(C=O)—, and tetrazolyl.

35. The compound and the pharmaceutically acceptable salts, prodrugs, solvates and optical isomers thereof, of embodiment 33, wherein $R^5$ is a heteroaromatic 5- or 6-membered monocyclic group having 1, 2 or 3 heteroatoms independently selected from O, N and S which group is unsubstituted or substituted with 1 or 2 groups independently selected from alkyl, haloalkyl, —COOR$^{10}$.

36. The compound and the pharmaceutically acceptable salts, prodrugs, solvates and optical isomers thereof, of any one of embodiments 2 to 31 having formula (Ic)

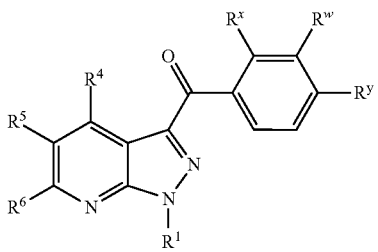

(Ic)

wherein
$R^w$ is $-NR^{10}SO_2R^{12}$ or $-N=S(=O)R^{10}NR^{10}R^{10}$;
$R^x$ is halogen;
$R^y$ is halogen; and
$R^1$, $R^4$, $R^5$, $R^6$, $R^{10}$ and $R^{12}$ are as defined any one of embodiments 2 to 30.

37. The compound and the pharmaceutically acceptable salts, prodrugs, solvates and optical isomers thereof, of embodiment 36, wherein
$R^w$ is $-NR^{10}SO_2R^{12}$;
$R^x$ is halogen;
$R^y$ is halogen;
$R^5$ is
halogen,
phenyl substituted with 1, 2 or 3 groups independently selected from
alkyl,
hydroxy,
halogen,
haloalkyl,
alkylsulfonyl,
alkylSO(=$NR^{10}$)—,
alkylsulfonyl-$NR^{10}$—,
—$NR^{10}R^{10}$,
$R^{10}R^{10}NSO_2$—,
$R^{10}R^{11}NSO_2$—,
alkyl-C(=O)—$NR^{10}SO_2$—,
$R^{10}R^{11}N(C=O)$—,
alkoxy,
—OCH$_2$— (methylenedioxy attached in neighboring positions to the phenyl ring),
—OCH$_2$CH$_2$— (ethylenedioxy attached in neighboring positions to the phenyl ring),
—NO$_2$,
—COOR$^{10}$,
—COOR$^{14}$,
$R^{10}R^{10}N(C=O)$—,
alkylSO(=$NR^{10}$)—,
—CONR$^{10}$—O-alkylene-OH,
—CONR$^{10}$—O-alkylene-O-alkyl, and
tetrazolyl, or
a heteroaromatic 5- or 6-membered monocyclic group having 1, 2 or 3 heteroatoms independently selected from O, N and S which group is unsubstituted or substituted with 1 or 2 groups independently selected from
alkyl,
haloalkyl,
alkoxy,
—$NR^{10}R^{10}$,
halogen,
—$NR^{10}$-cycloalkyl,
tetrazolyl,
—O-alkylene-$NR^{10}R^{10}$,
—$NR^{10}$-alkylene-O-alkyl,
—CN,
—CONR$^{10}R^{10}$,
—COOR$^{10}$,
alkylSO(=$NR^{10}$)—,
—CONR$^{10}$—O-alkylene-OH, and
—CONR$^{10}$—O-alkylene-O-alkyl;
$R^{11}$ is alkyl which is substituted with 1, 2 or 3 hydroxy groups; and
$R^{14}$ is alkyl which is substituted with 1 or 2 groups independently selected from —$NR^{10}R^{10}$, hydroxy or alkoxy.

38. The compound and the pharmaceutically acceptable salts, prodrugs, solvates and optical isomers thereof, of embodiment 37, wherein $R^5$ is
phenyl substituted with 1, 2 or 3 groups independently selected from
alkyl,
hydroxy,
halogen,
haloalkyl,
alkylsulfonyl,
alkylSO(=$NR^{10}$)—,
alkylsulfonyl-$NR^{10}$—,
—$NR^{10}R^{10}$,
$R^{10}R^{10}NSO_2$—,
$R^{10}R^{11}NSO_2$—,
alkyl-C(=O)—$NR^{10}SO_2$—,
$R^{10}R^{11}N(C=O)$—,
alkoxy,
—OCH$_2$— (methylenedioxy attached in neighboring positions to the phenyl ring),
—OCH$_2$CH$_2$— (ethylenedioxy attached in neighboring positions to the phenyl ring),
—NO$_2$,
—COOR$^{10}$,
—COOR$^{14}$,
$R^{10}R^{10}N(C=O)$—,
tetrazolyl,
alkylSO(=$NR^{10}$)—,
—CONR$^{10}$—O-alkylene-OH, and
—CONR$^{10}$—O-alkylene-O-alkyl, or
a heteroaromatic 5- or 6-membered monocyclic group having 1, 2 or 3 heteroatoms independently selected from O, N and S which group is unsubstituted or substituted with 1 or 2 groups independently selected from
alkyl,
haloalkyl,
alkoxy,
—$NR^{10}R^{10}$,
halogen,
—$NR^{10}$-cycloalkyl,
tetrazolyl,
—O-alkylene-$NR^{10}R^{10}$,
—$NR^{10}$-alkylene-O-alkyl,
—CN,
—CONR$^{10}R^{10}$,
—COOR$^{10}$,
alkylSO(=$NR^{10}$)—,
—CONR$^{10}$—O-alkylene-OH, and
—CONR$^{10}$—O-alkylene-O-alkyl.

39. The compound and the pharmaceutically acceptable salts, prodrugs, solvates and optical isomers thereof, of embodiment 37, wherein
$R^5$ is phenyl substituted with 1, 2 or 3 groups independently selected from alkyl, hydroxy, halogen, alkylSO 40. The compound and the pharmaceutically acceptable salts, prodrugs, solvates and optical isomers thereof, of embodiment 37, wherein $R^5$ is pyridyl, pyridyl substituted with —COOR$^{10}$, pyrimidinyl or pyrimidinyl substituted with CF$_3$.

41. The compound and the pharmaceutically acceptable salts, prodrugs, solvates and optical isomers thereof, of any one of embodiments 2 to 31 having formula (Id)

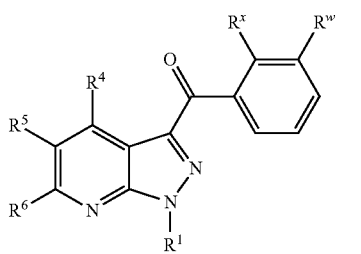

wherein
$R^w$ is —NR$^{10}$SO$_2$R$^{12}$ or —N=S(=O)R$^{10}$NR$^{10}$R$^{10}$;
$R^x$ is halogen; and
$R^1$, $R^4$, $R^5$, $R^6$, $R^{10}$ and $R^{12}$ are as defined any one of embodiments 2 to 30.

42. The compound and the pharmaceutically acceptable salts, prodrugs, solvates and optical isomers thereof, of embodiment 41, wherein
$R^w$ is —NR$^{10}$SO$_2$R$^{12}$;
$R^x$ is halogen;
$R^5$ is
halogen,
phenyl substituted with 1, 2 or 3 groups independently selected from alkyl, hydroxy, halogen, haloalkyl, alkylsulfonyl, alkylSO(=NR$^{10}$)—, alkylsulfonyl-NR$^{10}$—, —NR$^{10}$R$^{10}$, R$^{10}$R$^{10}$NSO$_2$—, R$^{10}$R$^{11}$NSO$_2$—, alkyl-C(=O)—NR$^{10}$SO$_2$—, R$^{10}$R$^{11}$N(C=O)—, alkoxy, —OCH$_2$O— (methylenedioxy attached in neighboring positions to the phenyl ring), —OCH$_2$CH$_2$O— (ethylenedioxy attached in neighboring positions to the phenyl ring), —NO$_2$, —COOR$^{10}$, —COOR$^{14}$, R$^{10}$R$^{10}$N(C=O)—, and tetrazolyl, or
a heteroaromatic 5- or 6-membered monocyclic group having 1, 2 or 3 heteroatoms independently selected from O, N and S which group is unsubstituted or substituted with 1 or 2 groups independently selected from alkyl, haloalkyl, alkoxy, —NR$^{10}$R$^{10}$, halogen, —NR$^{10}$-cycloalkyl, tetrazolyl, —O-alkylene-NR$^{10}$R$^{10}$, —NR$^{10}$-alkylene-O-alkyl, —CN, —CONR$^{10}$R$^{10}$, and —COOR$^{10}$;
$R^{11}$ is alkyl which is substituted with 1, 2 or 3 hydroxy groups; and
$R^{14}$ is alkyl which is substituted with 1 or 2 groups independently selected from —NR$^{10}$R$^{10}$, hydroxy or alkoxy.

43. The compound and the pharmaceutically acceptable salts, prodrugs, solvates and optical isomers thereof, of embodiment 42, wherein $R^5$ is
phenyl substituted with 1, 2 or 3 groups independently selected from alkyl, hydroxy, halogen, haloalkyl, alkylsulfonyl, alkylSO(=NR$^{10}$)—, alkylsulfonyl-NR$^{10}$—, —NR$^{10}$R$^{10}$, R$^{10}$R$^{10}$NSO$_2$—, R$^{10}$R$^{11}$NSO$_2$—, alkyl-C(=O)—NR$^{10}$SO$_2$—, R$^{10}$R$^{11}$N(C=O)—, alkoxy, —OCH$_2$O— (methylenedioxy attached in neighboring positions to the phenyl ring), —OCH$_2$CH$_2$O— (ethylenedioxy attached in neighboring positions to the phenyl ring), —NO$_2$, —COOR$^{10}$, and —COOR$^{14}$, or a heteroaromatic 5- or 6-membered monocyclic group having 1, 2 or 3 heteroatoms independently selected from O, N and S which group is unsubstituted or substituted with 1 or 2 groups independently selected from alkyl, haloalkyl, alkoxy, halogen, —NR$^{10}$-cycloalkyl, and —COOR$^{10}$.

44. The compound and the pharmaceutically acceptable salts, prodrugs, solvates and optical isomers thereof, of embodiment 42, wherein $R^5$ is phenyl substituted with 1, 2 or 3 groups independently selected from alkyl, halogen, alkoxy, —OCH$_2$— (methylenedioxy attached in neighboring positions to the phenyl ring), —OCH$_2$CH$_2$— (ethylenedioxy attached in neighboring positions to the phenyl ring).

45. The compound and the pharmaceutically acceptable salts, prodrugs, solvates and optical isomers thereof, of embodiment 42, wherein $R^5$ is pyridyl, pyridyl substituted with —COOR$^{10}$, pyrimidinyl or pyrimidinyl substituted with CF$_3$.

46. The compound and the pharmaceutically acceptable salts, prodrugs, solvates and optical isomers thereof, of any one of embodiments 2 to 31 having formula (Ie)

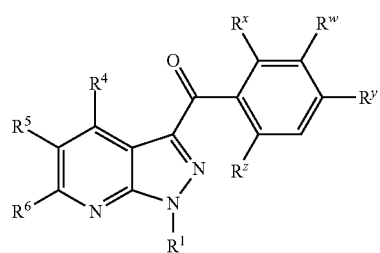

wherein
$R^w$ is -NR$^{10}$SO$_2$R$^{12}$ or —N=S(=O)R$^{10}$NR$^{10}$R$^{10}$;
$R^x$ is halogen;
$R^y$ is halogen;
$R^z$ is halogen; and
$R^1$, $R^4$, $R^5$, $R^6$, $R^{10}$ and $R^{12}$ are as defined any one of embodiments 2 to 30.

47. The compound and the pharmaceutically acceptable salts, prodrugs, solvates and optical isomers thereof, of embodiment 46, wherein
$R^w$ is —NR$^{10}$SO$_2$R$^{12}$;
$R^x$ is halogen;
$R^y$ is halogen;
$R^5$ is
halogen,
phenyl substituted with 1, 2 or 3 groups independently selected from alkyl, hydroxy, halogen, haloalkyl, alkylsulfonyl, alkylSO(=NR$^{10}$)—, alkylsulfonyl-NR$^{10}$—, —NR$^{10}$R$^{10}$, R$^{10}$R$^{10}$NSO$_2$—, R$^{10}$R$^{11}$NSO$_2$—, alkyl-C(=O)—NR$^{10}$SO$_2$—, R$^{10}$R$^{11}$N(C=O)—, alkoxy, —OCH$_2$O— (methylenedioxy attached in neighboring positions to the phenyl ring), —OCH$_2$CH$_2$O— (ethylenedioxy attached in neighboring positions to the phenyl ring), —NO$_2$, —COOR$^{10}$, —COOR$^{14}$, R$^{10}$R$^{10}$N(C=O)—, tetrazolyl, alkylSO(=NR$^{10}$)—, —CONR$^{10}$—O-alkylene-OH, and —CONR$^{10}$—O-alkylene-O-alkyl or a heteroaromatic 5- or 6-membered monocyclic group having 1, 2 or 3 heteroatoms independently selected from O, N and S which group is unsubstituted or substituted with 1 or 2 groups independently selected from alkyl, haloalkyl, alkoxy, —NR$^{10}$R$^{10}$, halogen, —NR$^{10}$-cycloalkyl, tetrazolyl, —O-alkylene-NR$^{10}$R$^{10}$, —NR$^{10}$-alkylene-O-alkyl, —CN, —CONR$^{10}$R$^{10}$, —COOR$^{10}$, alkylSO(=NR$^{10}$)—, —CONR$^{10}$—O-alkylene-OH, and —CONR$^{10}$—O-alkylene-O-alkyl;

R$^{11}$ is alkyl which is substituted with 1, 2 or 3 hydroxy groups; and

R$^{14}$ is alkyl which is substituted with 1 or 2 groups independently selected from —NR$^{10}$R$^{10}$, hydroxy or alkoxy.

48. The compound and the pharmaceutically acceptable salts, prodrugs, solvates and optical isomers thereof, of embodiment 47, wherein R$^5$ is phenyl substituted with 1, 2 or 3 groups independently selected from alkyl, hydroxy, halogen, haloalkyl, alkylsulfonyl, alkylSO(=NR$^{10}$)—, alkylsulfonyl-NR$^{10}$—, —NR$^{10}$R$^{10}$, R$^{10}$R$^{10}$NSO$_2$—, R$^{10}$R$^{11}$NSO$_2$—, alkyl-C(=O)—NR$^{10}$SO$_2$—, R$^{10}$R$^{11}$N(C=O)—, alkoxy, —OCH$_2$O— (methylenedioxy attached in neighboring positions to the phenyl ring), —OCH$_2$CH$_2$O— (ethylenedioxy attached in neighboring positions to the phenyl ring), —NO$_2$, —COOR$^{10}$, —COOR$^{14}$, R$^{10}$R$^{10}$N(C=O)—, tetrazolyl, alkylSO(=NR$^{10}$)—, —CONR$^{10}$—O-alkylene-OH, and —CONR$^{10}$—O-alkylene-O-alkyl or a heteroaromatic 5- or 6-membered monocyclic group having 1, 2 or 3 heteroatoms independently selected from O, N and S which group is unsubstituted or substituted with 1 or 2 groups independently selected from alkyl, haloalkyl, alkoxy, —NR$^{10}$R$^{10}$, halogen, —NR$^{10}$-cycloalkyl, tetrazolyl, —O-alkylene-NR$^{10}$R$^{10}$, —NR$^{10}$-alkylene-O-alkyl, —CN, —CONR$^{10}$R$^{10}$, —COOR$^{10}$, alkylSO(=NR$^{10}$)—, —CONR$^{10}$—O-alkylene-OH, and —CONR$^{10}$—O-alkylene-O-alkyl.

49. The compound and the pharmaceutically acceptable salts, prodrugs, solvates and optical isomers thereof, of embodiment 43, wherein R$^5$ is phenyl substituted with 1, 2 or 3 groups independently selected from alkyl, hydroxy, halogen, alkylSO(=NR$^{10}$)—, R$^{10}$R$^{10}$NSO$_2$—, —COOR$^{10}$, —COOR$^{14}$, R$^{10}$R$^{10}$N(C=O)—, and tetrazolyl.

50. The compound and the pharmaceutically acceptable salts, prodrugs, solvates and optical isomers thereof, of embodiment 47 or 48, wherein R$^5$ is pyridyl, pyridyl substituted with —COOR$^{10}$, pyrimidinyl or pyrimidinyl substituted with CF$_3$.

51. The compound and the pharmaceutically acceptable salts, prodrugs, solvates and optical isomers thereof, of any one of embodiments 28 to 25 to 41, wherein R$^x$, R$^y$ or R$^z$ are F or Cl, in particular F.

52. The compound and the pharmaceutically acceptable salts, prodrugs, solvates and optical isomers thereof, having formula (Ic)

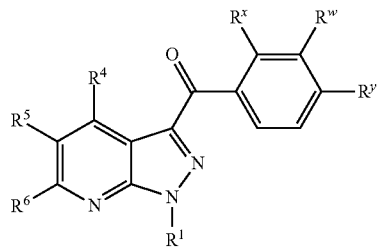

(Ic)

R$^1$ is H or alkyl;
R$^4$ is H or alkyl;
R$^5$ is
halogen,
phenyl substituted with 1, 2 or 3 groups independently selected from
alkyl,
hydroxy,
halogen,
haloalkyl,
alkylsulfonyl,
alkylSO(=NR$^{10}$)—,
alkylsulfonyl-NR$^{10}$—,
—NR$^{10}$R$^{10}$,
R$^{10}$R$^{10}$NSO$_2$—,
R$^{10}$R$^{11}$NSO$_2$—,
alkyl-C(=O)—NR$^{10}$SO$_2$—,
R$^{10}$R$^{11}$N(C=O)—,
alkoxy,
—OCH$_2$— (methylenedioxy attached in neighboring positions to the phenyl ring),
—OCH$_2$CH$_2$— (ethylenedioxy attached in neighboring positions to the phenyl ring),
—NO$_2$,
—COOR$^{10}$,
—COOR$^{14}$,
R$^{10}$R$^{10}$N(C=O)—,
tetrazolyl,
alkylSO(=NR$^{10}$)—,
—CONR$^{10}$—O-alkylene-OH, and
—CONR$^{10}$—O-alkylene-O-alkyl or
a heteroaromatic 5- or 6-membered monocyclic group having 1, 2 or 3 heteroatoms independently selected from O, N and S which group is unsubstituted or substituted with 1 or 2 groups independently selected from
alkyl,
haloalkyl,
alkoxy,
—NR$^{10}$R$^{10}$,
halogen,
—NR$^{10}$-cycloalkyl,
tetrazolyl,
—O-alkylene-NR$^{10}$R$^{10}$,
—NR$^{10}$-alkylene-O-alkyl,
—CN,
—CONR$^{10}$R$^{10}$,
—COOR$^{10}$,
alkylSO(=NR$^{10}$)—,
—CONR$^{10}$—O-alkylene-OH, and
—CONR$^{10}$—O-alkylene-O-alkyl;
R$^6$ is H or alkyl;
R$^{10}$ is H, alkyl, or phenylalkyl;

$R^{11}$ is alkyl which is substituted with 1, 2 or 3 hydroxy groups;

$R^{12}$ is H, alkyl, or phenylalkyl;

$R^{14}$ is alkyl which is substituted with 1 or 2 groups independently selected from —$NR^{10}R^{10}$, hydroxy or alkoxy.

$R^w$ is -$NR^{10}SO_2R^{12}$ or —N=S(=O)$R^{10}NR^{10}R^{10}$;

$R^x$ is halogen; and $R^y$ is halogen.

53. The compound and the pharmaceutically acceptable salts, prodrugs, solvates and optical isomers thereof, of embodiment 52, wherein $R^1$, $R^4$ and $R^6$ are H.

54. The compound and the pharmaceutically acceptable salts, prodrugs, solvates and optical isomers thereof, of embodiment 52 or 53, wherein $R^w$ is —$NR^{10}SO_2R^{12}$.

55. The compound and the pharmaceutically acceptable salts, prodrugs, solvates and optical isomers thereof, of any one of embodiments 52 to 54, wherein $R^{12}$ is $C_1$-$C_4$-alkyl, in particular $C_1$-$C_3$-alkyl or benzyl.

56. The compound and the pharmaceutically acceptable salts, prodrugs, solvates and optical isomers thereof, of any one of embodiments 52 to 55, wherein $R^5$ is phenyl substituted with 1, 2 or 3 groups independently selected from alkyl, hydroxy, halogen, haloalkyl, alkylsulfonyl, alkylSO(=$NR^{10}$)—, alkylsulfonyl-$NR^{10}$—, —$NR^{10}R^{10}$, $R^{10}R^{10}NSO_2$—, $R^{10}R^{11}NSO_2$—, alkyl-C(=O)—$NR^{10}SO_2$—, $R^{10}R^{11}N(C=O)$—, alkoxy, —$OCH_2O$— (methylenedioxy attached in neighboring positions to the phenyl ring), —$OCH_2CH_2O$— (ethylenedioxy attached in neighboring positions to the phenyl ring), —$NO_2$, —$COOR^{10}$, —$COOR^{14}$, $R^{10}R^{10}N(C=O)$—, tetrazolyl, alkylSO(=$NR^{10}$)—, —$CONR^{10}$—O-alkylene-OH, and —$CONR^{10}$—O-alkylene-O-alkyl or a heteroaromatic 5- or 6-membered monocyclic group having 1, 2 or 3 heteroatoms independently selected from O, N and S which group is unsubstituted or substituted with 1 or 2 groups independently selected from alkyl, haloalkyl, alkoxy, —$NR^{10}R^{10}$, halogen, —$NR^{10}$-cycloalkyl, tetrazolyl, —O-alkylene-$NR^{10}R^{10}$, —$NR^{10}$-alkylene-O-alkyl, —CN, —$CONR^{10}R^{10}$, —$COOR^{10}$, alkylSO(=$NR^{10}$)—, —$CONR^{10}$—O-alkylene-OH, and —$CONR^{10}$—O-alkylene-O-alkyl.

57. The compound and the pharmaceutically acceptable salts, prodrugs, solvates and optical isomers thereof, of embodiment 56, wherein $R^5$ is phenyl substituted with 1, 2 or 3 groups independently selected from alkyl, hydroxy, halogen, haloalkyl, alkylsulfonyl, alkylSO(=$NR^{10}$)—, alkylsulfonyl-$NR^{10}$—, —$NR^{10}R^{10}$, $R^{10}R^{10}NSO_2$—, $R^{10}R^{11}NSO_2$—, alkyl-C(=O)—$NR^{10}SO_2$—, $R^{10}R^{11}N(C=O)$—, alkoxy, —$OCH_2O$— (methylenedioxy attached in neighboring positions to the phenyl ring), —$OCH_2CH_2O$— (ethylenedioxy attached in neighboring positions to the phenyl ring), —$NO_2$, —$COOR^{10}$, —$COOR^{14}$, $R^{10}R^{10}N(C=O)$—, tetrazolyl, alkylSO(=$NR^{10}$)—, —$CONR^{10}$—O-alkylene-OH, and —$CONR^{10}$—O-alkylene-O-alkyl or a heteroaromatic 6-membered monocyclic group having 1, 2 or 3 heteroatoms independently selected from O, N and S which group is unsubstituted or substituted with 1 or 2 groups independently selected from alkyl, haloalkyl, alkoxy, —$NR^{10}R^{10}$, halogen, —$NR^{10}$-cycloalkyl, tetrazolyl, —O-alkylene-$NR^{10}R^{10}$, —$NR^{10}$-alkylene-O-alkyl, —CN, —$CONR^{10}R^{10}$, —$COOR^{10}$, alkylSO(=$NR^{10}$)—, —$CONR^{10}$—O-alkylene-OH, and —$CONR^{10}$—O-alkylene-O-alkyl.

58. The compound and the pharmaceutically acceptable salts, prodrugs, solvates and optical isomers thereof, of any one of embodiments 52 to 57, wherein $R^5$ is phenyl substituted with 1, 2 or 3 groups independently selected from alkyl, hydroxy, halogen, alkylSO(=$NR^{10}$)—, $R^{10}R^{10}NSO_2$—, —$COOR^{10}$, —$COOR^{14}$, $R^{10}R^{10}N(C=O)$—, and tetrazolyl.

59. The compound and the pharmaceutically acceptable salts, prodrugs, solvates and optical isomers thereof, of any one of embodiments 52 to 58, wherein $R^5$ is pyridyl, pyridyl substituted with —$COOR^{10}$, pyrimidinyl or pyrimidinyl substituted with haloalkyl, alkoxy, —$NR^{10}R^{10}$, halogen, —$NR^{10}$-cycloalkyl, tetrazolyl, —O-alkylene-$NR^{10}R^{10}$, —$NR^{10}$-alkylene-O-alkyl, —CN, —$CONR^{10}R^{10}$, and —$COOR^{10}$.

60. The compound and the pharmaceutically acceptable salts, prodrugs, solvates and optical isomers thereof, of embodiment 59, wherein $R^5$ is pyridyl, pyridyl substituted with —$COOR^{10}$, pyrimidinyl or pyrimidinyl substituted with haloalkyl, in particular $CF_3$.

61. The compound and the pharmaceutically acceptable salts, prodrugs, solvates and optical isomers thereof, of embodiment 59 or 60, wherein $R^5$ is pyrimidinyl substituted in 2-position (i.e. at the carbon atom between the two nitrogen atoms).

62. The compound and the pharmaceutically acceptable salts, prodrugs, solvates and optical isomers thereof, of any one of embodiments 52 to 61, wherein $R^x$ and $R^y$ are F or Cl, in particular F.

DETAILED DESCRIPTION OF THE INVENTION

In an embodiment, $R^5$ is not halogen. In a further embodiment, $R^1$, $R^4$, and $R^6$, independently of each other, are H or alkyl, and in particular are H.

In a still further embodiment, $R^{10}$ is H, alkyl or phenylalkyl wherein the phenyl group is optionally substituted with halogen, and in particular $R^{10}$ is H or alkyl.

In a still further embodiment, A is —CO—.

In a still further embodiment, Q is phenyl which is substituted as defined above.

In a still further embodiment, the invention relates to a compound of the formula I and the pharmaceutically acceptable salts, prodrugs, esters, solvates and optical isomers thereof, wherein $R^1$, $R^4$ to $R^6$, $R^{10}$, A and Q are as defined above in any combination.

In a still further embodiment, the invention relates to a compound of formula (Ia), (Ib), (Ic) and (Id) and the pharmaceutically acceptable salts, prodrugs, esters, solvates and optical isomers thereof, wherein the variables are as defined in the embodiments above.

In a further embodiment, at least one or at least two of $R^x$, $R^y$ or $R^z$ are halogen, and the other of $R^x$, $R^y$ or $R^z$ is H, halogen or alkyl, in particular alkyl or halogen. Halogen is preferably F or Cl.

In a further embodiment, $R^1$, $R^4$ and $R^6$ are H.

In a further embodiment, $R^{12}$ is methyl, ethyl or propyl.

In an embodiment, the invention relates to MKK4 inhibitors of formula (I) and (Ia) to (Id) and the pharmaceutically acceptable salts, prodrugs, solvates and optical isomers thereof, and in particular to MKK4 inhibitors which selectively inhibit protein kinase MKK4 over protein kinases JNK1 and MKK7.

Further, the invention also relates to the compounds of the invention for use in inhibiting protein kinase MKK4 and in particular for use in selectively inhibiting protein kinase MKK4 over protein kinases JNK1 and MKK7.

Further, the invention also relates to said compounds for use in promoting liver regeneration or reducing or preventing hepatocyte death and, at the same time, increasing hepatocyte proliferation.

The invention also includes the pharmaceutically acceptable salts of the compounds mentioned above. The pharmaceutically acceptable salts are especially acid or base addition salts with pharmaceutically acceptable acids or bases. Examples of suitable pharmaceutically acceptable organic and inorganic acids are hydrochloric acid, hydrobromic acid, phosphoric acid, sulfuric acid, sulfamic acid, $C_1$-$C_4$-alkylsulfonic acids, such as methanesulfonic acid, cycloaliphatic sulfonic acids, such as S-(+)-10-camphor sulfonic acid, aromatic sulfonic acids, such as benzenesulfonic acid and toluenesulfonic acid, di- and tricarboxylic acids and hydroxycarboxylic acids having 2 to 10 carbon atoms, such as oxalic acid, malonic acid, maleic acid, fumaric acid, lactic acid, tartaric acid, citric acid, glycolic acid, adipic acid and benzoic acid. Other utilizable acids are described, e.g., in Fortschritte der Arzneimittelforschung [Advances in drug research], Volume 10, pages 224 ff., Birkhäuser Verlag, Basel and Stuttgart, 1966. Examples of suitable pharmaceutically acceptable organic and inorganic bases are alkali metal hydroxides, such as sodium hydroxide or potassium hydroxide, alkaline earth metal hydroxides such as calcium or magnesium hydroxide, ammonium hydroxide, organic nitrogen bases such as dimethylamine, trimethylamine, ethanolamine, diethanolamine, triethanolamine, choline, 2-amino-2-hydroxymethyl-propane-1,3-diol, meglumine, procaine etc. L-arginine, L-lysine, ethylenediamine, or hydroxyethylpyrrolidine.

The invention also includes any tautomeric, crystal and polymorphic form of the compounds and salts of the present invention and mixtures thereof.

The invention also includes solvates such as hydrates.

The compounds of the invention may contain one or more chiral centers, and exist in different optically active forms such enantiomers and diastereomers.

As used herein, the term "pro-drug" refers to an agent which is converted into the parent drug in vivo by some physiological chemical process. An example, without limitation, of a pro-drug would be a compound of the present invention in the form of an ester.

Pro-drugs have many useful properties. For example, a pro-drug may be more water soluble than the ultimate drug, thereby facilitating intravenous administration of the drug. A pro-drug may also have a higher level of oral bioavailability than the ultimate drug. After administration, the prodrug is enzymatically or chemically cleaved to deliver the ultimate drug in the blood or tissue. Exemplary pro-drugs include, but are not limited to, compounds with carboxylic acid substituents wherein the free hydrogen is replaced by ($C_1$-$C_4$)alkyl, ($C_1$-$C_{12}$)alkanoyloxy-methyl, ($C_4$-$C_9$)1-(alkanoyloxy)ethyl, 1-methyl-1-(alkanoyloxy)-ethyl having from 5 to 10 carbon atoms, alkoxycarbonyloxymethyl having from 3 to 6 carbon atoms, 1-(alkoxycarbonyl-oxy)ethyl having from 4 to 7 carbon atoms, 1-methyl-1-(alkoxycarbonyloxy)-ethyl having from 5 to 8 carbon atoms, N-(alkoxycarbonyl) aminomethyl having from 3 to 9 carbon atoms, 1-(N-(alkoxycarbonyl)amino)ethyl having from 4 to 10 carbon atoms, 3-phthalidyl, 4-crotono-lactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di ($C_1$-$C_2$)-alkylcarbamoyl-($C_1$-$C_2$)alkyl and piperidino-, pyrrolidino- or morpholino($C_2$-$C_3$)alkyl. Other exemplary pro-drugs release an alcohol of Formula (I) wherein the free hydrogen of the hydroxyl substituent (e.g., R group contains hydroxyl) is replaced by ($C_1$-$C_6$)alkanoyloxy-methyl, 1-(($C_1$-$C_6$)alkanoyloxy)-ethyl, 1-methyl-1-(($C_1$-$C_6$)alkanoyloxy)ethyl, ($C_1$-$C_{12}$)alkoxy-carbonyloxy-methyl, N—($C_1$-$C_6$)-alkoxy-carbonylaminomethyl, succinoyl, ($C_1$-$C_6$)alkanoyl, α-amino($C_1$-$C_4$)alkanoyl, arylactyl and α-aminoacyl, or α-aminoacyl-α-aminoacyl wherein said α-aminoacyl moieties are independently any of the naturally occurring L-amino acids found in proteins, P(O)(OH)$_2$, —P(O)(O($C_1$-$C_6$)alkyl)$_2$ or glycosyl (the radical resulting from detachment of the hydroxyl of the hemiacetal of a carbohydrate).

The expression MKK4 inhibitor means that the kinase activity of MKK4 is inhibited with an IC$_{50}$ of <10 μmol/l, preferably <1 μmol/l, and in particular <0.5 μmol/l. The expression "selectively inhibit protein kinase MKK4 over protein kinases JNK1 and MKK7" as used herein means that the ratio of MKK7 inhibiting activity to MKK4 inhibiting activity or the ratio of JNK1 inhibiting activity to MKK4 inhibiting activity, expressed as either percent of control or Kd, is ≥10, as measured with KINOMEscan™.

The expression "promoting liver regeneration or reducing or preventing hepatocyte death" as used herein means an increase in the relative number of proliferating hepatocytes by at least 30%, preferably at least 50%, as compared to the number of proliferating cells at the beginning of therapy. In particular, the expression means an increase by 100% when compared to the number of proliferating cells at the beginning of therapy. In this context, the experimental determination and quantification will be performed using standard methods, e.g. the quantification of the protein Ki67, which is strictly associated with cell proliferation. For quantification of proliferating hepatocytes in a tissue slide, several immunohistochemical standard methods are available, which use a primary anti-Ki67 antibody followed by visualization of anti-Ki67-binding by using, for example, a horseradish peroxidase conjugated secondary antibody. The amount of peroxidase activity, which is visualized by enzymatic conversion of chromogenic substrates, correlates with the amount of Ki67 protein and the number of proliferating cells.

In the experiments described below, hepatocyte proliferation was quantified by Ki67-staining using the primary polyclonal rabbit anti-Ki67 antibody from Abcam (article no. ab15580, Abcam, Cambridge, USA) and the fluorophore tetramethylrhodamine containing secondary goat polyclonal antibody from Invitrogen (article no. 16101, Invitrogen/ThermoFisher). Based on data obtained from several preclinical mouse models it was found that shRNA (small hairpin RNA) mediated suppression of MKK4 in a chronic CCl$_4$ (carbon tetrachloride) mediated liver damage mouse model increased hepatocyte proliferation from 13% to 27% (compared to a control shRNA) and was associated with decreased liver damage (transaminases) and decreased liver fibrosis. According to the definition in the previous chapter, the relative increase of proliferating cells was 108%. In a model of alcohol induced steatohepatitis (ASH), shRNA mediated silencing of MKK4 resulted in a hepatocyte proliferation rate of 4% as compared to 2% when a control shRNA was used (relative increase: 100%). The duplication of hepatocyte proliferation was associated with decreased steatosis (fat deposition) and decreased liver damage as measured by transaminases. Along the same lines, shRNA mediated MKK4 silencing increased hepatocyte proliferation from 16% (control shRNA) to 33% (relative increase: 106%) in a model of partial hepatectomy (48 hrs after surgical removal of two thirds of the liver). Again, increased hepatocyte proliferation was associated with improved liver regeneration and a faster restoration of liver mass. In conclusion, these studies validate MKK4 as a therapeutic target for treatment of acute and chronic liver diseases. Furthermore, WO 2018/134254 discloses new compounds, which inhibit MKK4 selectively over MKK7 and JNK1. In experimental in vitro and in vivo models of liver regeneration, these compounds were effective in the prevention of acute liver failure induced by administration of a Jo2 antibody and induced the proliferation of isolated primary mouse hepatocytes.

The new compounds disclosed in the present application are potent MKK4 inhibitors with selectivity against MKK7 and JNK1 and therefore, in analogy to the compounds disclosed in WO 2018/134254 can be used for treatment of liver disease and for promoting liver regeneration or reducing or preventing hepatocyte death.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine or chlorine and preferably fluorine.

Alkyl is a straight-chain or branched alkyl group which is preferably a $C_1$-$C_6$-alkyl group, i.e. an alkyl group having from 1 to 6 carbon atoms, and more preferably a $C_1$-$C_4$-alkyl group and in particular a $C_1$-$C_3$-alkyl group. Examples of an alkyl group are methyl, ethyl, n-propyl, iso-propyl, n-butyl, 2-butyl, iso-butyl, tert-butyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

The definition of alkyl is likewise applicable to any group which includes an alkyl group.

Haloalkyl is a halogenated alkyl group as defined above, wherein at least one, e.g. 1, 2, 3, 4 or all of the hydrogen atoms are replaced by 1, 2, 3, 4 or a corresponding number of identical or different halogen atoms, such as trifluoromethyl, chloromethyl, bromomethyl, difluoromethyl, fluoromethyl, difluoroethyl, etc. Particular examples include the fluorinated $C_1$-$C_4$alkyl groups as defined, such as trifluoromethyl, difluoromethyl, fluoromethyl, or difluoroethyl.

Cycloalkyl is a cycloaliphatic radical which is preferably $C_3$-$C_5$-cycloalkyl, i.e. a cycloalkyl group having from 3 to 8 carbon atoms. In particular, 3 to 6 carbon atoms form the cyclic structure, such as cyclopropyl, cyclobutyl, cyclopentyl and cyclohexyl. The cyclic structure may be unsubstituted or may carry 1, 2, 3 or 4 $C_1$-$C_4$ alkyl radicals, preferably one or more methyl radicals.

Carbonyl is >C=O.

Aminocarbonyl is $NH_2C(O)$—.

Alkenyl is a singly unsaturated hydrocarbon radical which is preferably a $C_2$-$C_6$-alkenyl group, i.e. an alkenyl group having 2, 3, 4, 5 or 6 carbon atoms, e.g. vinyl, allyl (2-propen-1-yl), 1-propen-1-yl, 2-propen-2-yl, methallyl (2-methylprop-2-en-1-yl) and the like. $C_3$-$C_5$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl, 2-hexen-1-yl.

Alkinyl is a singly unsaturated hydrocarbon radical which is preferably a $C_2$-$C_6$-alkinyl group, i.e. an alkinyl group having 2, 3, 4, 5 or 6 carbon atoms, e.g. ethynyl, 2-propyn-1-yl, 1-propyn-1-yl, 2-propyn-2-yl and the like. $C_3$-$C_5$-Alkinyl is, in particular, 2-propyn-1-yl, 2-butyn-1-yl, 3-butyn-1-yl, 2-pentyn-1-yl, 3-pentyn-1-yl, 4-pentyn-1-yl.

Alkylene is straight-chain or branched alkylene group which is preferably a $C_1$-$C_5$-alkylene group, i.e. an alkylene group having from 1 to 5 carbon atoms. Alkylene groups having 2 to 4 and in particular 2 to 3 carbon atoms are especially preferred. Examples include methylene, ethylene and 1-methylethylene. A further example is propylene. Another further example is butylene. The definition of alkylene is likewise applicable to any group which includes an alkylene group.

Heteroalkylene is a straight-chain or branched alkyl group having 1, 2 or 3 heteroatoms which are selected from oxygen, nitrogen and sulfur. Examples for heteroalkylene are alkyloxyalkyl, alkylaminoalkyl, dialkylaminoalkyl or alkylthioalkyl. Any alkyl or alkylene group is as defined above. Alkyloxyalkyl is preferred.

Alkenylene is straight-chain or branched alkenylene group which is preferably a $C_2$-$C_4$-alkenylene group, i.e. an alkenylene group having from 2 to 4 carbon atoms. Examples include vinyl and propenyl.

Alkinylene is straight-chain or branched alkinylene group which is preferably a $C_2$-$C_4$-alkinylene group, i.e. an alkinylene group having from 2 to 4 carbon atoms. Examples include propynylene.

Aryl (or aromatic group) is a 6- to 12-membered, in particular 6- to 10-membered, aromatic cyclic radical which can be a monocyclic aromatic ring, for example, phenyl etc., or a fused polycyclic aromatic ring comprising a first monocyclic aromatic ring and one or more carbocycles which are saturated, partially unsaturated or aromatic, for example, naphthyl, indenyl, tetrahydronaphthyl, indanyl.

A heteroaromatic (or heteroaryl) group is a 5- or 6-membered monocyclic or 9- or 10-membered bicyclic aromatic group having 1, 2 or 3 heteroatoms selected from O, N or S.

The heteroaryl or heteroaromatic group may be bound to the neighboring group via a carbon atom (C-bound) or via a nitrogen heteroatom (N-bound). The heterocyclic radicals may be bound via a carbon atom (C-bound) or a nitrogen atom (N-bound). Preferred heteroaromatic radicals comprise 1 nitrogen atom as ring member atom and optionally 1 or 2 further heteroatoms as ring members, which are selected, independently of each other from O, S and N. Examples are:

C-bound, 5-membered, heteroaromatic rings:

2-furyl, 3-furyl, 5-furyl, 2-thienyl, 3-thienyl, 5-thienyl, pyrrol-2-yl, pyrrol-3-yl, pyrrol-5-yl, pyrazol-3-yl, pyrazol-4-yl, pyrazol-5-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, imidazol-5-yl, oxazol-2-yl, oxazol-4-yl, oxazol-5-yl, thiazol-2-yl, thiazol-4-yl, thiazol-5-yl, 1,2,3-oxadiazol-imidazol-4-yl,4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

C-bound, 6-membered, heteroaromatic rings:

pyridin-2-yl, pyridin-3-yl (3-pyridyl), pyridin-4-yl (4-pyridyl), pyridin-5-yl, pyridazin-3-yl, pyridazin-4-yl, pyridazin-6-yl, pyrimidin-2-yl, pyrimidin-4-yl, pyrimidin-5- yl, pyrazin-2-yl, pyrazin-5-yl, 1,3,5-triazin-2-yl, 1,2,4-triazin-3-yl, 1,2,4-triazin-5-yl, 1,2,4-triazin-6-yl, 1,2,4,5-tetrazin-3-yl;

N-bound, 5-membered, heteroaromatic rings:
pyrrol-1-yl, pyrazol-1-yl, imidazol-1-yl, 1,2,3-triazol-1-yl, 1,2,4-triazol-1-yl.

Bicyclic heteroaromatic groups include one of the described 5- or 6-membered heteroaromatic rings and a further anellated, saturated or unsaturated or aromatic carbocycle, such as a benzene, cyclohexane, cyclohexene or cyclohexadiene ring. Examples are quinolinyl, isoquinolinyl, indolyl, indolizinyl, isoindolyl, 4-, 5-, 6- or 7-azaindole, indazolyl, benzofuryl, benzthienyl, benzo[b]thiazolyl, benzoxazolyl, benzthiazolyl, benzimidazolyl, imidazo[b]thiazolyl, thieno[b]pyridyl, imidazo[a]pyridyl, pyrazo[a]pyridyl and pyrrol[d]pyrimidyl. Examples of 5- or 6-membered heteroaromatic compounds comprising an anellated cycloalkenyl ring include dihydroindolyl, dihydroindolizinyl, dihydroisoindolyl, dihydroquinolinyl, dihydroisoquinolinyl, dihydrobenzofuryl, chromenyl, chromanyl, dihydropyrrol[a]imidazolyl and tetrahydrobenzothiazolyl.

A non-aromatic 5- or 6-membered group (heterocyclic group) may be saturated or partially unsaturated and includes 1, 2 or 3 heteroatoms selected from O, N and S. The heterocyclic radicals may be bound via a carbon atom (C-bound) or a nitrogen atom (N-bound). Preferred heterocyclic groups comprise 1 nitrogen atom as ring member atom and optionally 1 or 2 further heteroatoms as ring members, which are selected, independently of each other from O, S and N. Examples are:

C-bound, 5-membered, saturated rings, such as
tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydro-pyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

C-bound, 6-membered, saturated rings, such as
tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

N-bound, 5-membered, saturated rings, such as
tetrahydropyrrol-1-yl (pyrrolidin-1-yl), tetrahydropyrazol-1-yl, tetrahydroisoxazol-2-yl, tetrahydroisothiazol-2-yl, tetrahydroimidazol-1-yl, tetrahydrooxazol-3-yl, tetrahydrothiazol-3-yl;

N-bound, 6-membered, saturated rings, such as
piperidin-1-yl, hexahydropyrimidin-1-yl, hexahydropyrazin-1-yl (piperazin-1-yl), hexahydro-pyridazin-1-yl, tetrahydro-1,3-oxazin-3-yl, tetrahydro-1,3-thiazin-3-yl, tetrahydro-1,4-thiazin-4-yl, tetrahydro-1,4-oxazin-4-yl (morpholin-1-yl), tetrahydro-1,2-oxazin-2-yl;

C-bound, 5-membered, partially unsaturated rings, such as
2,3-dihydrofuran-2-yl, 2,3-dihydrofuran-3-yl, 2,5-dihydrofuran-2-yl, 2,5-di-hydrofuran-3-yl, 4,5-dihydrofuran-2-yl, 4,5-dihydrofuran-3-yl, 2,3-dihydro-thien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydro-oxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl;

C-bound, 6-membered, partially unsaturated rings, such as
2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydrothiopyran-6-yl, 2H-3,4-dihydrothiopyran-5-yl, 2H-3,4-dihydrothiopyran-4-yl, 2H-3,4-dihydrothiopyran-3-yl, 2H-3,4-dihydrothiopyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6-yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5- tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl-, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydro-pyridin-3-yl, 1,2-dihydropyridin-4-yl, 1,2-dihydropyridin-5-yl, 1,2-dihydro-pyridin-6-yl, 3,4-dihydropyridin-2-yl, 3,4-dihydropyridin-3-yl, 3,4-dihydro-pyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydro-pyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetra-hydropyridazin-5-yl, 1,2,5,6-tetrahydropyridazin-6-yl, 1,2,3,6-tetrahydro-pyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5-6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydro-pyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-thiazin-4-yl, 6H-1,3-thiazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

N-bound, 5-membered, partially unsaturated rings, such as 2,3-dihydro-1H-pyrrol-1-yl, 2,5-dihydro-1H-pyrrol-1-yl, 4,5-dihydro-1H-pyrazol-1-yl, 2,5-dihydro-1H-pyrazol-1-yl, 2,3-dihydro-1H-pyrazol-1-yl, 2,5-dihydroisoxazol-2-yl, 2,3-dihydroisoxazol-2-yl, 2,5-dihydroisothiazol-2-yl, 2,3-dihydroisoxazol-2-yl, 4,5-dihydro-1H-imidazol-1-yl, 2,5-dihydro-1H-imidazol-1-yl, 2,3-dihydro-1H-imidazol-1-yl, 2,3-dihydrooxazol-3-yl, 2,3-dihydrothiazol-3-yl;

N-bound, 6-membered, partially unsaturated rings, such as 1,2,3,4-tetrahydropyridin-1-yl, 1,2,5,6-tetrahydropyridin-1-yl, 1,4-dihydro-pyridin-1-yl, 1,2-dihydropyridin-1-yl, 2H-5,6-dihydro-1,2-oxazin-2-yl, 2H-5,6-dihydro-1,2-thiazin-2-yl, 2H-3,6-dihydro-1,2-oxazin-2-yl, 2H-3,6-dihydro-1,2-thiazin-2-yl, 2H-3,4-dihydro-1,2-oxazin-2-yl, 2H-3,4-dihydro-1,2-thiazin-2-yl, 2,3,4,5-tetrahydropyridazin-2-yl, 1,2,5,6-tetrahydropyridazin-1-yl, 1,2,5,6-tetrahydropyridazin-2-yl, 1,2,3,6-tetrahydropyridazin-1-yl, 3,4,5,6-tetrahydropyrimidin-3-yl, 1,2,3,4-tetrahydropyrazin-1-yl, 1,2,3,4-tetrahydropyrimidin-1-yl, 1,2,3,4-tetrahydropyrimidin-3-yl, 2,3-dihydro-1,4-thiazin-4-yl, 2H-1,2-oxazin-2-yl, 2H-1,2-thiazin-2-yl, 4H-1,4-oxazin-4-yl, 4H-1,4-thiazin-4-yl, 1,4-dihydropyridazin-1-yl, 1,4-dihydropyrazin-1-yl, 1,2-dihydropyrazin-1-yl, 1,4-dihydropyrimidin-1-yl or 3,4-dihydropyrimidin-3-yl.

Any group containing heteroatoms may contain 1, 2 or 3 heteroatoms which may be the same or different.

The compounds of the invention can be prepared as disclosed in WO 2010/111527 which is incorporated herein in its entirety by reference or according to analogous procedures. The acid or base addition salts are prepared in a customary manner by mixing the free base with a corresponding acid or by mixing the free acid with the desired base. Optionally, the reaction is carried out in solution in an organic solvent, for example a lower alcohol, such as MeOH, ethanol or propanol, an ether, such as methyl tert-butyl ether or diisopropyl ether, a ketone, such as acetone or methyl ethyl ketone, or an ester, such as EtOAc.

The compounds of the invention are useful for promoting liver regeneration or reducing or preventing hepatocyte death and, at the same time, increasing hepatocyte proliferation. The compounds are therefore useful in treating, modulating, improving or preventing diseases which involve acute or chronic damages to the liver that may be caused by infection, injury, exposure to toxic compounds, an abnormal build-up of normal substances in the blood, an autoimmune process, a genetic defect or unknown causes.

Such liver diseases comprise all diseases where increased liver regeneration and reduction or prevention of hepatocyte death may be helpful to achieve a potential therapeutic effect, i.e. partial or complete restoration of liver functions. Such diseases comprise acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;

metabolic liver diseases such as metabolic syndrome, fatty liver like non-alcoholic fatty liver (NAFL), non-alcoholic steatohepatitis (NASH), alcoholic steatohepatitis (ASH), Morbus Wilson, Hemochromatosis, alpha1-antitrypsin deficiency, glycogen storage diseases;

all types of liver cirrhosis, such as primary biliary cirrhosis, ethyl toxic liver cirrhosis, cryptogenic cirrhosis;

acute (fulminant) or chronic liver failure such as toxic liver failure like acetaminophen (paracetamol) induced liver failure, alpha-amanitin induced liver failure, drug induced hepatotoxicity, liver failure caused, for example, by antibiotics, nonsteroidal anti-inflammatory drugs and anticonvulsants, acute liver failure induced by herbal supplements (kava, ephedra, skullcap, pennyroyal etc), liver disease and failure due to vascular diseases such as Budd-Chiari syndrome, acute liver failure of unknown origin, chronic liver disease due to right heart failure;

galactosemia, cystic fibrosis, porphyria, hepatic ischemia perfusion injury, small for size syndrome after liver transplantation, primary sclerosing cholangitis or hepatic encephalopathy.

For promoting liver regeneration or reducing or preventing hepatocyte death the compounds of the invention are administered to a patient in need thereof in a therapeutically effective amount. Various diagnostic methods are available to detect the presence of a liver disease.

Blood levels of alanine aminotransferase (ALT) and aspartate aminotransferase (AST), above clinically accepted normal ranges, are known to be indicative of on-going liver damage. Blood bilirubin levels or other liver enzymes may be used as detection or diagnostic criteria. Routine monitoring of liver disease patients for blood levels of ALT and AST is used to measure progress of the liver disease while on medical treatment. Reduction of elevated ALT and AST levels to within the accepted normal range is taken as clinical evidence reflecting a reduction in the severity of the patients' liver damage. Commercial assays such as FibroTest/FibroSURE, HepaScore®, FibroMeter or Cirrhometer evaluate the combined results of five and more biochemical parameters for the detection of liver steatosis, fibrosis and cirrhosis. Furthermore, non-invasive, innovative physical imaging techniques such as magnetic resonance imaging, sonography and, in particular, elastography techniques are available to detect and monitor the status and progression of liver diseases.

It has further been found that shRNA mediated MKK4 suppression attenuate TNF-α-driven cartilage matrix degradation in osteoarthritis (Cell Death and Disease (2017) 8, e3140). Therefore, inhibition of the activity of MKK4 using the compounds of the invention are further useful for treating osteoarthritis and rheumatoid arthritis.

Furthermore, MKK4 inhibitors may also be useful for treatment of neurodegenerative diseases such as Alzheimer's disease and Parkinson's disease. Grueninger et al. found that in human neuroblastoma cells, MKK4 plays a key role in the phosphorylation of Tau protein at serine 422 which promotes Tau aggregation (Mol Cell Biochem (2011) 357: 199-207). Inhibitors of Tau phosphorylation which prevents the aggregation of Tau are being considered useful for prevention or treatment of Alzheimer's disease.

Recently, a MKK4 inhibitor has been described with potent neuroprotective effects in vitro and in vivo. In hippocampal cultures, the incubation with an MKK4-inhibitor prevented glutamate-induced cell death and caspase-3 activation, and also inhibited N-Methyl-4-phenylpyridinium iodide- and amyloid (31-42-induced cell death in SH-SY5Y cells. The same compound also alleviated 1-methyl-4-phenyl-1,2,3,6-tetrahydropyridine-induced degeneration of nigrostriatal dopaminergic neurons in mice (Biochemical Pharmacology (2018), doi: doi.org/10.1016/j.bcp.2018.10.008).

The compounds of the invention are customarily administered in the form of pharmaceutical compositions which comprise at least one compound according to the invention, optionally together with an inert carrier (e.g. a pharmaceutically acceptable excipient) and, where appropriate, other drugs. These compositions can, for example, be administered orally, rectally, transdermally, subcutaneously, intraperitoneally, intravenously, intramuscularly or intranasally.

Examples of suitable pharmaceutical compositions are solid medicinal forms, such as powders, granules, tablets, in particular film tablets, lozenges, sachets, cachets, sugar-coated tablets, capsules, such as hard gelatin capsules and soft gelatin capsules, or suppositories, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations. In addition, it is also possible to use liposomes or microspheres.

When producing the compositions, the compounds according to the invention are optionally mixed or diluted with one or more carriers (excipients). Carriers (excipients) can be solid, semisolid or liquid materials which serve as vehicles, carriers or medium for the active compound.

Suitable carriers (excipients) are listed in the specialist medicinal monographs. In addition, the formulations can comprise pharmaceutically acceptable auxiliary substances, such as wetting agents; emulsifying and suspending agents; preservatives; antioxidants; antiirritants; chelating agents; coating auxiliaries; emulsion stabilizers; film formers; gel formers; odor masking agents; taste corrigents; resins; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Cantor-Verlag, 1996.

The compounds of the invention may also be suitable for combination with other therapeutic agents. The invention therefore further relates to a combination comprising a compound of the invention with one or more further therapeutic agents, in particular for use in promoting liver regeneration or reducing or preventing hepatocyte death. The combination therapies of the invention may be administered adjunctively. By adjunctive administration is meant the coterminous or overlapping administration of each of the components in the form of separate pharmaceutical compositions or devices. This regime of therapeutic administration of two or more therapeutic agents is referred to generally by those skilled in the art and herein as adjunctive therapeutic administration; it is also known as add-on therapeutic administration. Any and all treatment regimes in which a patient receives separate but coterminous or overlapping therapeutic administration of the compounds of the invention and at least one further therapeutic agent are within the scope of the current invention. In one embodiment of adjunctive therapeutic administration as described herein, a patient is typically stabilized on a therapeutic administration of one or more of the components for a period of time and then receives administration of another component.

The combination therapies of the invention may also be administered simultaneously. By simultaneous administration is meant a treatment regime wherein the individual components are administered together, either in the form of a single pharmaceutical composition or device comprising or containing both components, or as separate compositions or devices, each comprising one of the components, administered simultaneously. Such combinations of the separate individual components for simultaneous combination may be provided in the form of a kit-of-parts.

Suitable agents for use in combination with the compounds of the inventions include for example:

ACC inhibitors such as TOFA (5-(tetradecyloxy)-2-furoic acid), PF-05221304,
GS 0976, and ACC inhibitors as disclosed in WO 2016/112305,
angiotensin II receptor antagonists,
angiotensin converting enzyme (ACE) inhibitors, such as enalapril,
caspase inhibitors, such as emricasan,
cathepsin B inhibitors, such as a mixed cathepsin B/hepatitis C virus NS3 protease inhibitor. like VBY-376,
CCR2 chemokine antagonists, such as a mixed CCR2/CCR5 chemokine antagonist like cenicriviroc,
CCR5 chemokine antagonists,
chloride channel stimulators, such as cobiprostone,
cholesterol solubilizers,
diacylglycerol 0-acyltransferase 1 (DGAT1) inhibitors, such as LCQ908,
diacylglycerol O-Acyltransferase 2 (DGAT2) Inhibitor, such as PF-06865571,
ketohexokinase (KHK) Inhibitor, such as PF-06835919,
dipeptidyl peptidase IV (DPPIV) inhibitors, such as linagliptin,
farnesoid X receptor (FXR) agonists, such as INT-747 (obeticholic acid), LJN452 (tropifexor) and analogues disclosed in Tully et al (J. Med. Chem., 2017 60 (24), 9960-9973), or GS-9674 (PX-102),
FXR/TGR5 dual agonists, such as INT-767,
galectin-3 inhibitors, such as GR-MD-02,
glucagon-like peptide 1 (GLP1) agonists, such as liraglutide or exenatide,
glutathione precursors,
hepatitis C virus NS3 protease inhibitors, such as a mixed cathepsin B/hepatitis C virus NS3 protease inhibitor like VBY-376,
HMG CoA reductase inhibitors, such as a statin like atorvastatin,
11ß-hydroxysteroid dehydrogenase (11ß-HSD1) inhibitors, such as R05093151,
IL-1ß antagonists,
IL-6 antagonists, such as a mixed IL-6/IL-1ß/TNFα ligand inhibitor like BLX-1002,
IL-10 agonists, such as peg-ilodecakin,
IL-17 antagonists, such as KD-025,
ileal sodium bile acid cotransporter inhibitors, such as SHP-626,
leptin analogs, such as metreleptin,
5-lipoxygenase inhibitors, such as a mixed 5-lipoxygenase/PDE3/PDE4/PLC inhibitor like tipelukast,
LPL gene stimulators, such as alipogene tiparvovec,
lysyl oxidase homolog 2 (LOXL2) inhibitors, such as an anti-LOXL2 antibody like GS-6624, PDE3 inhibitors, such as a mixed 5-ipoxygenase/PDE3/PDE4/PLC inhibitor like tipelukast, PDE4 inhibitors, such as ASP-9831 or a mixed 5-ipoxygenase/PDE3/PDE4/PLC inhibitor like tipelukast,
phospholipase C (PLC) inhibitors, such as a mixed 5-ipoxygenase/PDE3/PDE4/PLC inhibitor like tipelukast,
PPARα agonists, such as a mixed PPARα/δ agonist like GFT505,
PPARγ agonists, such as pioglitazone,
PPARδ agonists,
Rho associated protein kinase 2 (ROCK2) inhibitors, such as KD-025,
sodium glucose transporter-2 (SGLT2) inhibitors, such as remogliflozin etabonate,
stearoyl CoA desaturase-1 inhibitors, such as aramchol or CVT-12805,
thyroid hormone receptor ß agonists, such as MGL-3196,
tumor necrosis factor α (TNFα) ligand inhibitors,
transglutaminase inhibitors and transglutaminase inhibitor precursors, such as mercaptamine,
PTPIb inhibitors, such as A119505, A220435, A321842, CPT633, ISIS-404173, JTT-551, MX-7014, MX-7091, MX-7102, NNC-521246, OTX-001, OTX-002, orTTP814 and ASK1 inhibitors such as GS4977.

In some embodiments, the one or more further therapeutic agents are selected from acetylsalicylic acid, alipogene tiparvovec, aramchol, atorvastatin, BLX-1002, cenicriviroc, cobiprostone, colesevelam, emncasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, GS-9674, remogliflozin etabonate, SHP-626, solithromycin, tipelukast, TRX-318, ursodeoxycholic acid, and VBY-376.

In some embodiments, one of the one or more further therapeutic agents is selected from acetylsalicylic acid, alipogene tiparvovec, aramchol, atorvastatin, BLX-1 002, and cenicriviroc.

In an embodiment the invention relates to a method of inhibiting protein kinase MKK4,
selectively inhibiting protein kinase MKK4 over protein kinases JNK1 and MKK7, promoting liver regeneration or preventing hepatocyte death,
treating acute, acute-on-chronic or chronic liver disease,
treating acute and chronic or acute on chronic liver diseases such as acute and chronic viral hepatitis like hepatitis B, C, E, hepatitis caused by Epstein-Barr virus, cytomegalovirus, herpes simplex virus and other viruses, all types of autoimmune hepatitis, primary sclerosing hepatitis, alcoholic hepatitis;
treating metabolic liver diseases such as metabolic syndrome, fatty liver like non-alcoholic fatty liver (NAFL), non-alcoholic steatohepatitis (NASH), alcoholic steatohepatitis (ASH), Morbus Wilson, hemochromatosis, alpha1-antitrypsin deficiency, glycogen storage diseases;
treating all types of liver cirrhosis, such as primary biliary cirrhosis, ethyl toxic liver cirrhosis, cryptogenic cirrhosis;
treating acute (fulminant) or chronic liver failure such as toxic liver failure like acetaminophen (paracetamol)

induced liver failure, alpha-amanitin induced liver failure, drug induced hepatotoxicity and liver failure caused, for example, by antibiotics, nonsteroidal anti-inflammatory drugs, anticonvulsants, acute liver failure induced by herbal supplements (kava, ephedra, skullcap, pennyroyal etc.), liver disease and failure due to vascular diseases such as Budd-Chiari syndrome, acute liver failure of unknown origin, chronic liver disease due to right heart failure;

treating galactosemia, cystic fibrosis, porphyria, hepatic ischemia perfusion injury, small for size syndrome after liver transplantation, primary sclerosing cholangitis or hepatic encephalopathy, treating osteoarthritis, rheumatoid arthritis, or CNS-related diseases such as Alzheimer disease and Parkinson disease, which comprises administering an effective amount of a compound or a composition as defined above to a subject in need thereof.

In an embodiment, the compounds of the invention are administered in a dosage of 0.2 to 15 mg/kg or 0.5 to 12 mg/kg of the subject being treated. The compounds can be administered once or several times a day. The compounds are administered over 4 to 12 weeks.

The following examples illustrate the invention without limiting it.

EXAMPLES

Abbreviations

Boc$_2$O di-tert.-butyloxycarbonate
CPME cyclopentylmethyl ether
DCM dichloromethane
4-DMAP 4-dimethylaminopyridine
DME dimethyl ether
DMF dimethylformamide
DMSO dimethylsulfoxide
EtOAc ethyl acetate
HPLC high performance liquid chromatography
LDA lithium diisopropylamide
MeCN acetonitrile
MeOH methanol
NaHCO$_3$ sodium bicarbonate
NH$_4$Cl ammonium chloride
Na$_2$SO$_4$ sodium sulfate
Pd$_2$(dba)$_3$ tris(dibenzylideneacetone)dipalladium(0)
PE petrolether
RT room temperature
Sol. Solution
THF tetrahydrofurane
TLC thin layer chromatography
Xantphos 4,5-bis(diphenylphosphino)-9,9-dimethylxanthene Example 1: Synthesis of N-(3-(5-bromo-1H-pyrazolo[3,4-b]pyridine-3-carbonyl)-2,4-difluorophenyl)propane-1-sulfonamide (VI)

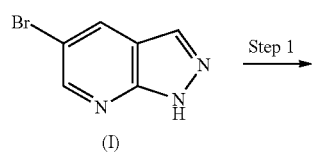

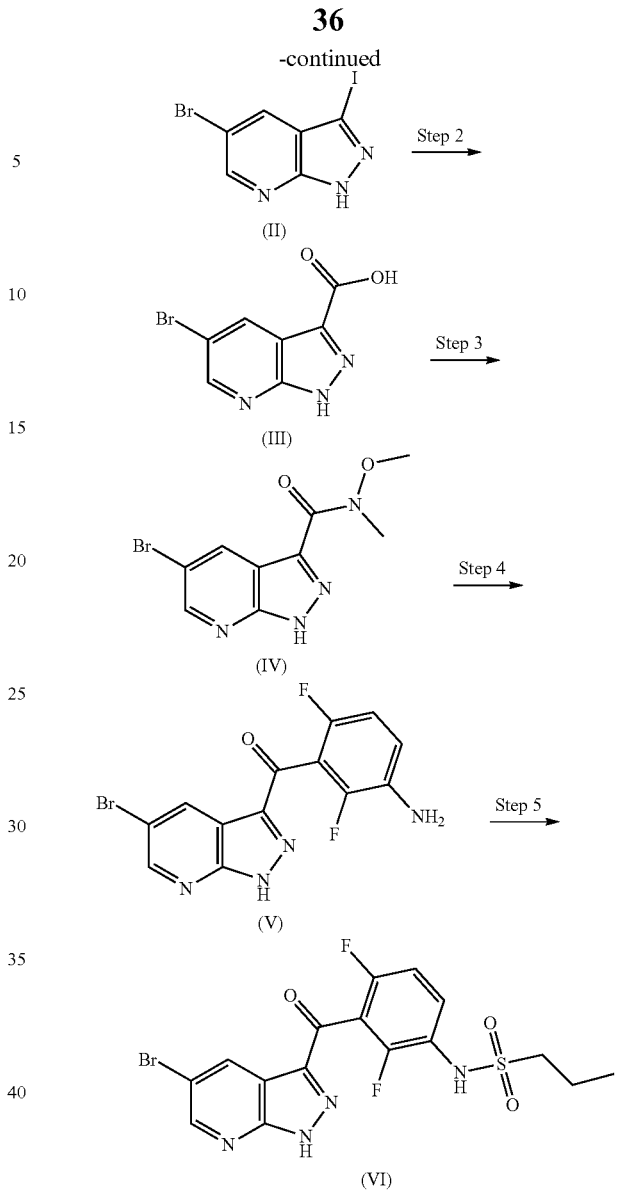

Step 1: Synthesis of 5-Bromo-3-iodo-1H-pyrazolo[3,4-b]pyridine (II)

To a stirred mixture of 5-bromo-1H-pyrazolo[3,4-b]pyridine ((I), 6.81 g, 34.4 mmol) and KOH (6.75 g, 120.4 mmol) in DMF (45 mL) was added iodine (9.60 g, 37.8 mmol) in one portion at RT. After a short induction period the exothermic reaction began. After 1 h, an additional 1 g portion of iodine was added and the mixture stirred at 45° C. for 1 h. The mixture was poured into 300 mL of a dilute solution of Na$_2$SO$_3$ and the mixture was acidified with 2N HCl. The solids were collected by suction filtration, washed with water and dried in an oven at 110° C. Yield: 10.92 g, HPLC purity: 95%, $^1$H NMR (200 MHz, DMSO) δ 14.29 (s, 1H), 8.62 (s, 1H), 8.17 (s, 1H); $^{13}$C NMR (50 MHz, DMSO) δ 150.53, 150.17, 131.86, 120.58, 112.43, 91.95; [M–H]$^-$= 322.0/324.0.

Step 2: Synthesis of 5-Bromo-1H-pyrazolo[3,4-b]pyridine-3-carboxylic acid (III)

5-Bromo-3-iodo-1H-pyrazolo[3,4-b]pyridine ((II), 10.44 g, 32.2 mmol) was combined with DMF, MeOH and triethylamine (75 mL each). The vessel was evacuated and flushed with argon (4×). XantPhos (1.12 g, 1.93 mmol) and Pd(OAc)$_2$ (217 mg, 0.97 mmol) were added and carbon monoxide (generated from formic acid and sulfuric acid) was bubbled through the solution while heating to 60° C. The mixture was stirred under an atmosphere of carbon monoxide (balloon) for 8 h. Every 1.5 h carbon monoxide was bubbled through the solution for 5 minutes. The mixture was concentrated under reduced pressure and the residue was triturated with 2N HCl. The solids were heated at 95° C. in about 100 mL 1N NaOH overnight. After cooling to RT, the mixture was acidified with conc. HCl and the precipitate collected by suction filtration and washed with water. The solids were dried in an oven at 110° C. to constant mass. The solids were sonicated in 100 mL of toluene for 5 minutes and stirred for 30 minutes. The product was filtered, washed with an additional 20 mL of toluene and dried at 110° C. Yield: 7.92 g HPLC purity: >99%, $^1$H NMR (200 MHz, DMSO) δ 8.64 (d, J=7.9 Hz, 2H), 5.69 (bs, 1H); $^{13}$C NMR (50 MHz, DMSO) δ 163.27, 150.97, 149.67, 136.69, 132.65, 115.73, 113.6; [M−H]$^-$=239.9/241.9.

Step 3: Synthesis of 5-bromo-N-methoxy-N-methyl-1H-pyrazolo[3,4-b]pyridine-3-carboxamide (IV)

5-Bromo-1H-pyrazolo[3,4-b]pyridine-3-carboxylic acid ((III), 7.91 g, 32.7 mmol) and 1,1'-carbonyldiimidazole (5.83 g, 35.9 mmol) were stirred in 200 mL of DMF at 60° C. for 45 minutes. To the resulting suspension was added N,O-dimethylhydroxylamine hydrochloride (3.51 g, 35.9 mmol) and the mixture was stirred for 4 h at 65° C. Most of the solvent was removed under vacuum and to the residue half sat. NaHCO$_3$-solution was added. The solids were collected by suction filtration, washed with water and dried at 110° C. Yield: 7.94 g, HPLC purity: 96%, $^1$H NMR (200 MHz, DMSO) δ 14.46 (s, 1H), 8.62 (d, J=20.4 Hz, 2H), 3.76 (s, 3H), 3.44 (s, 3H), [M−H]$^-$=283.0/285.0.

Step 4: Synthesis of (3-amino-2,6-difluorophenyl)(5-bromo-1H-pyrazolo[3,4-b]pyridin-3-yl)methanone (V)

2,4-Difluoroaniline (6.25 g, 48.4 mmol) was dissolved in 50 mL dry THF and cooled to −78° C. under an atmosphere of argon. 2.5 M n-butyllithium in hexane (19.4 mL, 48.4 mmol) was added dropwise. After 15 minutes 1,2-bis(chlorodimethylsilyl)ethane (10.9 g, 49.5 mmol) in 15 mL dry THF was added dropwise and the mixture was stirred for 30 minutes. 2.5 M n-butyllithium in hexane (19.4 mL, 48.4 mmol) was added dropwise and the mixture was allowed to reach RT within 1 h. After cooling to −78° C. 2.5 M n-butyllithium in hexane (19.4 mL, 48.4 mmol) was added dropwise and stirred for 1 h at −78° C. (This is considered solution A).

5-bromo-N-methoxy-N-methyl-1H-pyrazolo[3,4-b]pyridine-3-carboxamide ((IV), 6.00 g, 21.1 mmol) was suspended in 50 mL dry THF and cooled to 0° C. under an atmosphere of argon. NaH (60% in mineral oil, 0.88 g, 22.1 mmol) was added portionwise and the solution was stirred at RT for 1 h. (This is considered solution B).

Solution B was added dropwise to solution A at −78° C. After complete addition, the mixture was warmed to RT within 30 minutes. 12 mL conc. HCl were added carefully and the mixture was stirred for 30 minutes. Solid NaHCO$_3$ was added to neutralize the solution, the solids were filtered off and washed with THF. The filtrate was evaporated and the residue triturated with MeOH and water and dried at 110° C. Yield: 4.03 g; HPLC purity: 97%, $^1$H NMR (200 MHz, DMSO) δ 14.91 (s, 1H), 8.77 (dd, J=5.4, 2.1 Hz, 2H), 7.18-6.59 (m, 2H), 5.25 (s, 2H); $^{13}$C NMR (50 MHz, DMSO) δ 183.95, 151.04, 150.79, 150.27 (dd, J=161.0, 6.8 Hz), 145.50 (dd, J=167.3, 6.8 Hz), 141.34, 133.35 (dd, J=12.8, 2.6 Hz), 132.28, 117.45 (dd, J=8.4, 6.5 Hz), 116.24 (dd, J=22.7, 19.1 Hz), 115.55, 114.81, 111.26 (dd, J=21.7, 3.5 Hz); [M−H]$^-$=351.1/353.1.

Step 5: Synthesis of N-(3-(5-bromo-1H-pyrazolo[3,4-b]pyridine-3-carbonyl)-2,4-difluorophenyl)propane-1-sulfonamide (VI)

(3-Amino-2,6-difluorophenyl)(5-bromo-1H-pyrazolo[3,4-b]pyridin-3-yl)methanone ((V), 2.00 g, 5.66 mmol) and 4-DMAP (35 mg, 0.28 mmol) were heated in 9 mL pyridine to 65° C. and 1-propanesulfonyl chloride (1.21 g, 0.96 mL, 8.50 mmol) was added. After 2 h, another 0.19 mL 1-propanesulfonyl chloride were added. The warm solution was added to about 80 mL 2N HCl, the solid collected and washed with water. The solid was taken up in EtOAc, washed with 2N HCl and brine and dried over Na$_2$SO$_4$. The solvent was evaporated and the product purified by flash chromatography (SiO$_2$, DCM/EtOAc gradient, from 0% to 20% EtOAc) and triturated with n-hexane. Yield: 1.68 g, HPLC purity: 97%, $^1$H NMR (200 MHz, DMSO) δ 9.86 (s, 1H), 8.79 (dd, J=5.3, 2.0 Hz, 3H), 7.64 (td, J=9.0, 6.0 Hz, 1H), 7.30 (t, J=8.9 Hz, 1H), 3.17-2.96 (m, 3H), 1.87-1.62 (m, 2H), 0.96 (t, J=7.4 Hz, 4H); $^{13}$C NMR (50 MHz, DMSO) δ 182.75, 157.39 (dd, J=177.1, 7.4 Hz), 152.42 (dd, J=180.3, 7.3 Hz), 151.56, 151.34, 141.39, 132.59, 130.78-130.05 (m), 122.20 (dd, J=13.5, 3.6 Hz), 117.19 (dd, J=23.0, 20.9 Hz), 116.14, 115.18, 112.59 (dd, J=22.2, 3.8 Hz), 54.14, 17.22 12.97; [M−H]$^-$=457.1/459.1.

Example 2: Synthesis of N-(2,4-difluoro-3-(5-phenyl-1H-pyrazolo[3,4-b]pyridine-3-carbonyl)phenyl)propane-1-sulfonamide

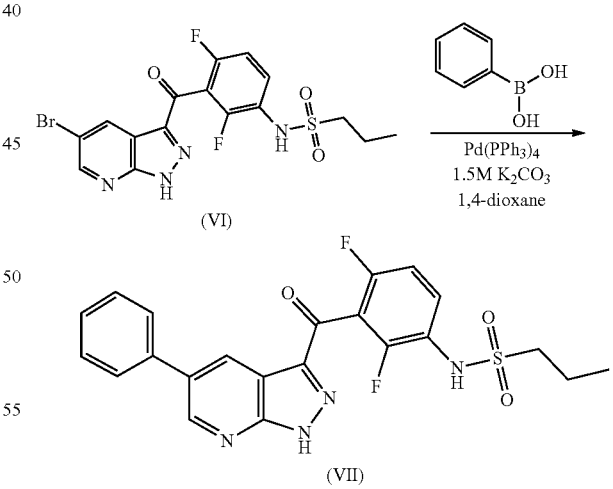

A microwave vessel was charged with a magnetic stir bar, N-(3-(5-bromo-1H-pyrazolo[3,4-b]pyridine-3-carbonyl)-2,4-difluorophenyl)propane-1-sulfonamide ((VI), 50 mg, 0.11 mmol), phenylboronic acid (15 mg, 0.12 mmol), Pd(PPh$_3$)$_4$ (6 mg, 5 mol %) and purged with argon. Degassed 1,4-dioxane (0.3 mL) and degassed aqueous 1.5 M K$_2$CO$_3$ (0.25 mL, 0.38 mmol) were added and the mixture was heated to 120° C. under microwave irradiation for 30 minutes. After cooling, the mixture was diluted with EtOAc and neutralized with sat. NH$_4$Cl solution. The solvents were removed and the product isolated by flash chromatography and dried at 100° C. in a vacuum oven. Yield: 27 mg, HPLC purity: 97, $^1$H NMR (200 MHz, DMSO) δ 7.84 (d, J=7.2 Hz, 2H), 7.71-7.40 (m, 4H), 7.31 (t, J=8.7 Hz, 1H), 3.18-3.04 (m, 2H), 1.87-1.63 (m, 2H), 0.97 (t, J=7.4 Hz, 3H). [M−H]$^-$= 455.1.

General procedure for Suzuki coupling: A microwave vessel is charged with a magnetic stir bar, N-(3-(5-bromo-1H-pyrazolo[3,4-b]pyridine-3-carbonyl)-2,4-difluorophenyl)propane-1-sulfonamide, the appropriate boronic acid or boronic acid pinacole ester (1.1 eq.) and Pd(PPh$_3$)$_4$ [(tBu)$_3$P Pd G4 and/or XPhos Pd G4 (G4: 4$^{th}$ generation; commercially available) for nitrophenylboronic acids, 4-hydroxyphenylboronic acid and 4-dimethylaminophenyl-boronic acid pinacol ester] (0.05 eq.) and purged with argon. Degassed 1,4-dioxane (0.4 M) and degassed aqueous 1.5 M K$_2$CO$_3$ (3.5 eq.) are added and the mixture is heated to 120° C. under microwave irradiation until complete conversion (usually 30 minutes). After cooling, the mixture is diluted with EtOAc and neutralized with sat. NH$_4$Cl solution. The solvents are removed and the product isolated by flash chromatography and dried at 100° C. in a vacuum oven.

In analogy, the compounds given in the following table 1 were prepared.

TABLE 1

| Ex. | Boronic acid/Pinacol ester | Structure | MW | IUPAC | 1H-NMR/MS |
|---|---|---|---|---|---|
| 3 | 4-chlorophenylboronic acid | 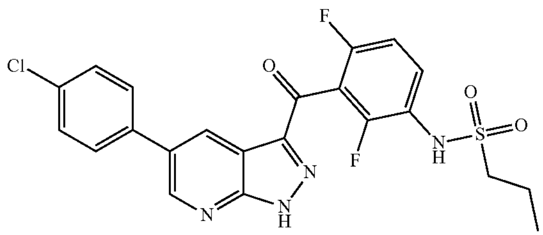 [SMILES: CCCS(=O)(=O)Nc1ccc(F)c(C(=O)c2n[nH]c3ncc(-c4ccc(Cl)cc4)cc23)c1F] | 490.91 | N-(3-(5-(4-chlorophenyl)-1H-pyrazolo[3,4-b]pyridine-3-carbonyl)-2,4-difluorophenyl)-propane-1-sulfonamide | 1H NMR (200 MHz, DMSO) δ 9.04 (s, 1H), 8.78 (s, 1H), 7.89 (d, J = 8.5 Hz, 2H), 7.71-7.54 (m, 3H), 7.31 (t, J = 8.7 Hz, 1H), 3.19-3.05 (m, 2H), 1.75 (dd, J = 14.8, 7.6 Hz, 2H), 0.97 (t, J = 7.2 Hz, 3H); [M − H]⁻ = 489.2 |
| 4 | 4-fluoro-2-methylphenylboronic acid | 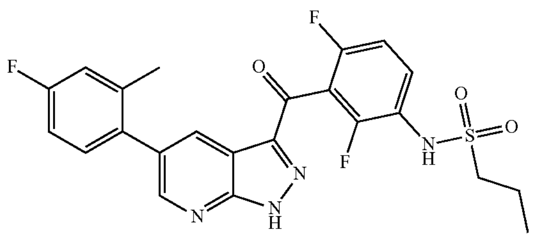 [SMILES: CCCS(=O)(=O)Nc1ccc(F)c(C(=O)c2n[nH]c3ncc(-c4ccc(F)cc4C)cc23)c1F] | 488.49 | N-(2,4-difluoro-3-(5-(4-fluoro-2-methylphenyl)-1H-pyrazolo[3,4-b]pyridine-3-carbonyl)-phenyl)-propane-1-sulfonamide | 1H NMR (200 MHz, DMSO) δ 14.95 (s, 1H), 9.85 (s, 1H), 8.70 (d, J = 1.8 Hz, 1H), 8.48 (d, J = 1.8 Hz, 1H), 7.64 (td, J = 9.1, 6.0 Hz, 1H), 7.48-7.10 (m, 4H), 3.21-3.03 (m, 2H), 2.28 (s, 3H), 1.85-1.65 (m, 2H), 0.97 (t, J = 7.3 Hz, 3H); [M − H]⁻ = 486.9 |
| 5 | 2-chloro-4-methoxyphenylboronic acid | 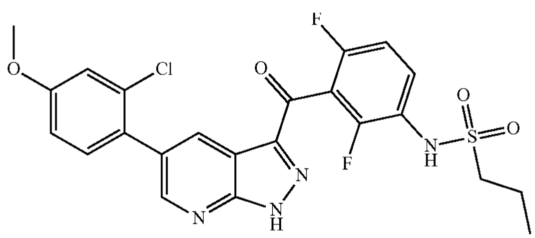 [SMILES: CCCS(=O)(=O)Nc1ccc(F)c(C(=O)c2n[nH]c3ncc(-c4ccc(OC)cc4Cl)cc23)c1F] | 520.94 | N-(3-(5-(2-chloro-4-methoxyphenyl)-1H-pyrazolo[3,4-b]pyridine-3-carbonyl)-2,4-difluorophenyl)propane-1-sulfonamide | 1H NMR (200 MHz, DMSO) δ 14.93 (s, 1H), 9.83 (s, 1H), 8.74 (s, 1H), 8.58 (s, 1H), 7.75-7.47 (m, 2H), 7.37-7.03 (m, 3H), 3.86 (s, 3H), 3.18-3.02 (m, 2H), 1.88-1.61 (m, 2H), 0.97 (t, J = 7.2 Hz, 3H); [M − H]⁻ = 519.1 |
| 6 | 4-methoxyphenylboronic acid | 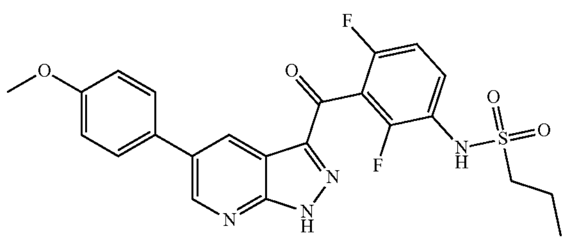 [SMILES: CCCS(=O)(=O)Nc1ccc(F)c(C(=O)c2n[nH]c3ncc(-c4ccc(OC)cc4)cc23)c1F] | 486.49 | N-(2,4-difluoro-3-(5-(4-methoxyphenyl)-1H-pyrazolo[3,4-b]pyridine-3-carbonyl)phenyl)propane-1-sulfonamide | 1H NMR (200 MHz, DMSO) δ 14.87 (s, 1H), 9.79 (s, 1H), 9.00 (d, J = 2.2 Hz, 1H), 8.69 (d, J = 2.2 Hz, 1H), 7.78 (d, J = 8.8 Hz, 1H), 7.63 (td, J = 9.0, 5.9 Hz, 1H), 7.31 (td, J = 9.0, 1.3 Hz, 1H), 7.11 (d, J = 8.7 Hz, 1H), 3.83 (s, 1H), 3.22-3.03 (m, 1H), 1.86-1.63 (m, 1H), 0.97 (t, J = 7.4 Hz, 1H); [M − H]⁻ = 485.1 |

TABLE 1-continued

| Boronic acid/Pina- col ester Ex. | Structure | MW | IUPAC | 1H-NMR/MS |
|---|---|---|---|---|
| 7 | 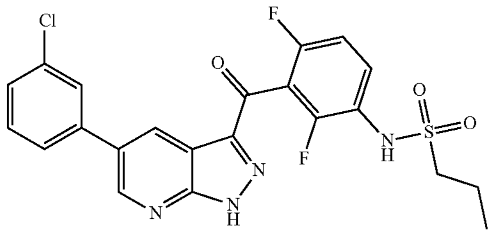 [SMILES: CCCS(=O)(=O)Nc1ccc(F)c(C(=O)c2n[nH]c3ncc(-c4cccc(Cl)c4)cc23)c1F] | 490.91 | N-(3-(5-(3-chlorophenyl)-1H-pyrazolo[3,4-b]pyridine-3-carbonyl)-2,4-difluorophenyl)-propane-1-sulfonamide | 1H NMR (200 MHz, DMSO) δ 9.05 (s, 1H), 8.80 (s, 1H), 8.06-7.19 (m, 6H), 3.18-3.03 (m, 2H), 1.91-1.61 (m, 2H), 0.97 (t, J = 7.2 Hz, 3H); [M − H]⁻ = 489.0 |
| 8 | 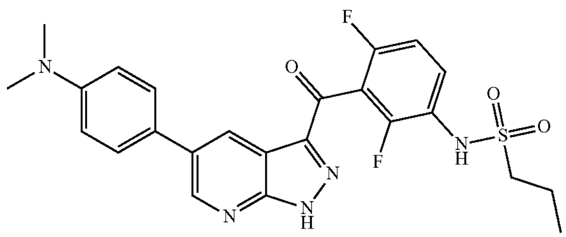 [SMILES: CCCS(=O)(=O)Nc1ccc(F)c(C(=O)c2n[nH]c3ncc(-c4ccc(N(C)C)cc4)cc23)c1F] | 499.54 | N-(3-(5-(4-(dimethylamino)-phenyl)-1H-pyrazolo[3,4-b]pyridine-3-carbonyl)-2,4-difluorophenyl)-propane-1-sulfonamide | 1H NMR (200 MHz, DMSO) δ 14.83 (s, 1H), 9.82 (s, 1H), 8.98 (d, J = 2.2 Hz, 1H), 8.63 (d, J = 2.2 Hz, 1H), 7.73-7.54 (m, 3H), 7.31 (td, J = 8.9, 1.5 Hz, 1H), 6.87 (d, J = 8.9 Hz, 2H), 3.19-3.05 (m, 2H), 2.97 (s, 6H), 2.97 (s, 6H), 1.86-1.64 (m, 2H), 0.97 (t, J = 7.4 Hz, 3H); [M − H]⁻ = 497.9 |
| 9 | 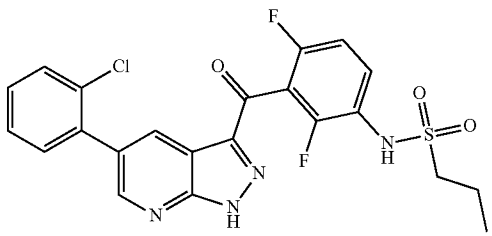 | 490.91 | N-(3-(5-(2-chlorophenyl)-1H-pyrazolo[3,4-b]pyridine-3-carbonyl)-2,4-difluorophenyl)-propane-1-sulfonamide | 1H NMR (200 MHz, DMSO) δ 8.79 (d, J = 2.1 Hz, 1H), 8.62 (d, J = 2.1 Hz, 1H), 7.75-7.43 (m, 5H), 7.31 (td, J = 9.0, 1.4 Hz, 1H), 3.11 (dd, J = 9.0, 6.3 Hz, 2H), 1.87-1.64 (m, 2H), 0.97 (t, J = 7.4 Hz, 3H); [M − H]⁻ = 488.9 |
| 10 | 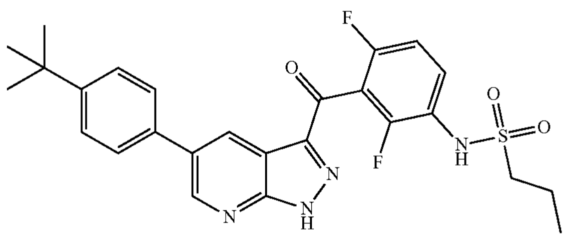 [SMILES: CCCS(=O)(=O)Nc1ccc(F)c(C(=O)c2n[nH]c3ncc(-c4ccc(C(C)(C)C)cc4)cc23)c1F] | 512.58 | N-(3-(5-(4-tert-butylphenyl)-1H-pyrazolo[3,4-b]pyridine-3-carbonyl)-2,4-difluoro-phenyl)propane-1-sulfonamide | 1H NMR (200 MHz, DMSO) δ 14.92 (s, 1H), 9.83 (s, 1H), 9.03 (d, J = 1.9 Hz, 1H), 8.73 (d, J = 1.7 Hz, 1H), 7.84-7.50 (m, 5H), 7.31 (t, J = 8.7 Hz, 1H), 3.22-3.01 (m, 2H), 1.85-1.63 (m, 2H), 1.34 (s, 9H), 0.97 (t, J = 7.4 Hz, 3H); [M − H]⁻ = 511.1 |

TABLE 1-continued

| Boronic acid/Pina-col ester Ex. | Structure | MW | IUPAC | 1H-NMR/MS |
|---|---|---|---|---|
| 11 | (4-isopropylphenyl)boronic acid | 498.55 | N-(2,4-difluoro-3-(5-(4-isopropylphenyl)-1H-pyrazolo[3,4-b]pyridine-3-carbonyl)phenyl)propane-1-sulfonamide | 1H NMR (400 MHz, DMSO) δ 14.92 (s, 1H), 9.83 (s, 1H), 9.02 (s, 1H), 8.73 (s, 1H), 7.75 (d, J = 7.9 Hz, 2H), 7.69-7.59 (m, 1H), 7.42 (d, J = 8.0 Hz, 2H), 7.31 (t, J = 8.8 Hz, 1H), 3.19-3.07 (m, 2H), 2.96 (dt, J = 13.6, 6.8 Hz, 1H), 1.82-1.67 (m, 2H), 1.25 (d, J = 6.9 Hz, 6H), 0.97 (t, J = 7.4 Hz, 3H); [M + Na]+ = 521.0 |
| 12 | (3,4-dimethylphenyl)boronic acid | 484.52 | N-(3-(5-(3,4-dimethylphenyl)-1H-pyrazolo[3,4-b]pyridine-3-carbonyl)-2,4-difluorophenyl)propane-1-sulfonamide | 1H NMR (200 MHz, DMSO) δ 14.44 (s, 1H), 9.37 (s, 1H), 8.54 (d, J = 2.1 Hz, 1H), 8.25 (d, J = 2.1 Hz, 1H), 7.25-7.04 (m, 3H), 6.93-6.76 (m, 2H), 2.73-2.56 (m, 2H), 1.87 (s, 3H), 1.83 (s, 3H), 1.41-1.17 (m, 2H), 0.51 (t, J = 7.4 Hz, 3H); [M − H]− = 483.1 |
| 13 | o-tolylboronic acid | 470.49 | N-(2,4-difluoro-3-(5-o-tolyl-1H-pyrazolo[3,4-b]pyridine-3-carbonyl)phenyl)propane-1-sulfonamide | 1H NMR (200 MHz, DMSO) δ 8.72 (d, J = 2.0 Hz, 1H), 8.49 (d, J = 2.1 Hz, 1H), 7.64 (td, J = 9.1, 5.8 Hz, 1H), 7.44-7.23 (m, 5H), 3.22-2.96 (m, 2H), 2.28 (s, 3H), 1.86-1.63 (m, 2H), 0.97 (t, J = 7.4 Hz, 3H); [M − H]− = 469.0 |
| 14 | (2-methoxyphenyl)boronic acid | 486.49 | N-(2,4-difluoro-3-(5-(2-methoxyphenyl)-1H-pyrazolo[3,4-b]pyridine-3-carbonyl)phenyl)propane-1-sulfonamide | 1H NMR (200 MHz, DMSO) δ 14.90 (s, 1H), 9.83 (s, 1H), 8.81 (d, J = 2.0 Hz, 1H), 8.61 (d, J = 2.0 Hz, 1H), 7.63 (td, J = 9.0, 5.9 Hz, 1H), 7.45 (dd, J = 12.8, 4.6 Hz, 2H), 7.38-7.05 (m, 3H), 3.82 (s, 3H), 3.17-3.04 (m, 2H), 1.87-1.61 (m, 2H), 0.97 (t, J = 7.5 Hz, 3H); [M − H]− = 485.1 |

TABLE 1-continued

| Ex. | Boronic acid/Pina- col ester | Structure | MW | IUPAC | 1H-NMR/MS |
|---|---|---|---|---|---|
| 15 | NH2-SO2-C6H4-B(OH)2 | (structure) | 535.54 | 4-(3-(2,6-difluoro-3-(propyl-sulfonamido)benzoyl)-1H-pyrazolo[3,4-b]pyridin-5-yl)benzene-sulfonamide | 1H NMR (200 MHz, DMSO) δ 14.53 (s, 1H), 9.37 (s, 1H), 8.64 (d, J = 2.2 Hz, 1H), 8.40 (d, J = 2.1 Hz, 1H), 7.62 (d, J = 8.5 Hz, 2H), 7.51 (d, J = 8.5 Hz, 2H), 7.28-7.06 (m, 2H), 7.02 (s, 2H), 6.86 (td, J = 8.8, 1.3 Hz, 1H), 2.76-2.53 (m, 2H), 1.40-1.18 (m, 2H), 0.51 (t, J = 7.4 Hz, 3H); [M − H]⁻ = 534.0 |
| 16 | 3-F-C6H4-B(OH)2 | (structure) | 474.46 | N-(2,4-difluoro-3-(5-(3-fluorophenyl)-1H-pyrazolo[3,4-b]pyridine-3-carbonyl)phenyl)propane-1-sulfonamide | 1H NMR (200 MHz, DMSO) δ 14.95 (s, 1H), 9.81 (s, 1H), 9.06 (d, J = 1.9 Hz, 1H), 8.81 (d, J = 1.7 Hz, 1H), 7.81-7.51 (m, 4H), 7.41-7.23 (m, 2H), 3.18-3.04 (m, 2H), 1.85-1.63 (m, 2H), 0.97 (t, J = 7.5 Hz, 3H); [M − H]⁻ = 472.9 |
| 17 | 3-MeO-C6H4-B(OH)2 | (structure) | 486.49 | N-(2,4-difluoro-3-(5-(3-methoxyphenyl)-1H-pyrazolo[3,4-b]pyridine-3-carbonyl)phenyl)propane-1-sulfonamide | 1H NMR (200 MHz, DMSO) δ 14.94 (s, 1H), 9.83 (s, 1H), 9.04 (d, J = 2.2 Hz, 1H), 8.76 (d, J = 2.2 Hz, 1H), 7.64 (td, J = 9.1, 6.0 Hz, 1H), 7.51-7.26 (m, 4H), 7.09-6.99 (m, 1H), 3.87 (s, 3H), 3.20-2.99 (m, 2H), 1.86-1.61 (m, 2H), 0.97 (t, J = 7.5 Hz, 3H); [M − H]⁻ = 485.0 |

TABLE 1-continued

| Ex. | Boronic acid/Pinacol ester | Structure | MW | IUPAC | 1H-NMR/MS |
|---|---|---|---|---|---|
| 18 | 4-aminophenyl boronic acid pinacol ester | (structure) | 471.48 | N-(3-(5-(4-aminophenyl)-1H-pyrazolo[3,4-b]pyridine-3-carbonyl)-2,4-difluorophenyl)propane-1-sulfonamide | 1H NMR (200 MHz, DMSO) δ 8.94 (s, 1H), 8.59 (s, 1H), 7.77-7.41 (m, 3H), 7.30 (d, J = 9.0 Hz, 1H), 6.72 (d, J = 7.9 Hz, 2H), 5.40 (s, 2H), 3.23-3.00 (m, 2H), 1.96-1.56 (m, 2H), 0.97 (t, J = 7.5 Hz, 3H); [M + Na]+ = 494.0 |
| 19 | 4-hydroxyphenyl boronic acid | (structure) | 472.47 | N-(2,4-difluoro-3-(5-(4-hydroxyphenyl)-1H-pyrazolo[3,4-b]pyridine-3-carbonyl)phenyl)propane-1-sulfonamide | 1H NMR (200 MHz, DMSO) δ 14.40 (s, 1H), 9.36 (s, 1H), 9.27 (s, 1H), 8.51 (d, J = 2.1 Hz, 1H), 8.19 (d, J = 2.0 Hz, 1H), 7.26-7.06 (m, 3H), 6.84 (t, J = 8.8 Hz, 1H), 6.47 (d, J = 8.5 Hz, 2H), 2.73-2.54 (m, 2H), 1.39-1.17 (m, 2H), 0.51 (t, J = 7.4 Hz, 3H); [M − H]− = 471.1 |
| 20 | 4-tolyl boronic acid | (structure) | 470.49 | N-(2,4-difluoro-3-(5-p-tolyl-1H-pyrazolo[3,4-b]pyridine-3-carbonyl)phenyl)propane-1-sulfonamide | 1H NMR (200 MHz, DMSO) δ 14.91 (s, 1H), 9.85 (s, 1H), 9.01 (d, J = 1.9 Hz, 2H), 8.72 (d, J = 2.0 Hz, 2H), 7.82-7.55 (m, 5H), 7.45-7.23 (m, 4H), 3.21-3.04 (m, 3H), 2.38 (s, 4H), 1.86-1.64 (m, 3H), 0.97 (t, J = 7.3 Hz, 4H); [M − H]− = 469.1 |
| 21 | 2-hydroxyphenyl boronic acid | (structure) | 472.47 | N-(2,4-difluoro-3-(5-(2-hydroxyphenyl)-1H-pyrazolo[3,4-b]pyridine-3-carbonyl)phenyl)propane-1-sulfonamide | 1H NMR (200 MHz, DMSO) δ 14.89 (s, 1H), 9.88 (s, 2H), 8.87 (d, J = 2.1 Hz, 1H), 8.71 (d, J = 2.1 Hz, 1H), 7.63 (td, J = 9.0, 6.0 Hz, 1H), 7.45 (dd, J = 7.3, 1.4 Hz, 1H), 7.38-7.21 (m, 2H), 7.10-6.89 (m, 2H), 3.20-3.02 (m, 2H), 1.86-1.64 (m, 2H), 0.97 (t, J = 7.4 Hz, 3H); [M − H]− = 470.9 |

TABLE 1-continued

| Ex. | Boronic acid/Pinacol ester | Structure | MW | IUPAC | 1H-NMR/MS |
|---|---|---|---|---|---|
| 22 | 3,5-dichlorophenylboronic acid | (structure) | 525.35 | N-(3-(5-(3,5-dichloro-phenyl)-1H-pyrazolo[3,4-b]pyridine-3-carbonyl)-2,4-difluoro-phenyl)propane-1-sulfon-amide | 1H NMR (200 MHz, DMSO) δ 9.06 (d, J = 2.2 Hz, 1H), 8.86 (d, J = 2.2 Hz, 1H), 7.96 (d, J = 1.8 Hz, 2H), 7.72-7.55 (m, 2H), 7.31 (td, J = 9.0, 1.5 Hz, 1H), 3.20-3.00 (m, 2H), 1.87-1.64 (m, 2H), 0.97 (t, J = 7.5 Hz, 3H); [M − H]⁻ = 523.0 |
| 23 | 4-nitrophenylboronic acid | (structure) | 501.46 | N-(2,4-difluoro-3-(5-(4-nitrophenyl)-1H-pyrazolo[3,4-b]pyridine-3-carbonyl)-phenyl)propane-1-sulfonamide | 1H NMR (200 MHz, DMSO) δ 24.19 (s, 1H), 18.97 (s, 1H), 18.29 (d, J = 2.0 Hz, 1H), 18.06 (d, J = 2.1 Hz, 1H), 17.53 (d, J = 8.7 Hz, 2H), 17.32 (d, J = 8.7 Hz, 2H), 16.79 (td, J = 9.0, 5.8 Hz, 1H), 16.47 (t, J = 8.7 Hz, 1H), 12.35-12.17 (m, 2H), 11.01-10.78 (m, 2H), 10.12 (t, J = 7.4 Hz, 3H); [M − H]⁻ = 500.0 |
| 24 | 4-(methylsulfonyl)phenylboronic acid | (structure) | 534.55 | N-(2,4-difluoro-3-(5-(4-(methylsulfonyl)phenyl)-1H-pyrazolo[3,4-b]pyridine-3-carbonyl)phenyl)propane-1-sulfonamide | 1H NMR (200 MHz, DMSO) δ 15.03 (s, 1H), 9.83 (s, 1H), 9.12 (d, J = 2.2 Hz, 1H), 8.88 (d, J = 2.2 Hz, 1H), 8.12 (q, J = 8.7 Hz, 4H), 7.72-7.55 (m, 1H), 7.32 (td, J = 9.0, 1.5 Hz, 1H), 3.30 (s, 3H), 3.21-3.03 (m, 2H), 1.85-1.64 (m, 2H), 0.97 (t, J = 7.4 Hz, 3H); [M − H]⁻ = 532.9 |
| 25 | 4-fluorophenylboronic acid | (structure) | 474.46 | N-(2,4-difluoro-3-(5-(4-fluorophenyl)-1H-pyrazolo[3,4-b]pyridine-3-carbonyl)phenyl)propane-1-sulfonamide | 1H NMR (200 MHz, DMSO) δ 14.91 (s, 1H), 9.89 (s, 1H), 9.02 (d, J = 2.1 Hz, 1H), 8.74 (d, J = 2.1 Hz, 1H), 7.89 (dd, J = 8.6, 5.4 Hz, 2H), 7.64 (td, J = 9.0, 5.9 Hz, 1H), 7.45-7.21 (m, 3H), 3.21-3.02 (m, 2H), 1.87-1.61 (m, 2H), 0.97 (t, J = 7.4 Hz, 3H); [M − H]⁻ = 473.0 |

TABLE 1-continued

| Boronic acid/Pinacol ester Ex. | Structure | MW | IUPAC | 1H-NMR/MS |
|---|---|---|---|---|
| 26 | (2-aminophenyl pinacol boronate; product structure with 2-aminophenyl on pyridine) | 471.48 | N-(3-(5-(2-aminophenyl)-1H-pyrazolo[3,4-b]pyridine-3-carbonyl)-2,4-difluorophenyl)-propane-1-sulfonamide | 1H NMR (200 MHz, DMSO) δ 14.39 (s, 1H), 9.41 (s, 1H), 8.24 (d, J = 2.1 Hz, 1H), 8.11 (d, J = 2.0 Hz, 1H), 7.17 (td, J = 9.1, 6.0 Hz, 1H), 6.85 (t, J = 8.7 Hz, 1H), 6.74-6.57 (m, 3H), 6.36 (d, J = 7.8 Hz, 1H), 6.23 (t, J = 7.5 Hz, 1H), 4.56 (s, 2H), 2.72-2.57 (m, 3H), 1.39-1.12 (m, 3H), 0.51 (t, J = 7.4 Hz, 4H); [M − H]⁻ = 470.0 |
| 27 | (3-aminophenyl pinacol boronate; product with 3-aminophenyl) | 471.48 | N-(3-(5-(3-aminophenyl)-1H-pyrazolo[3,4-b]pyridine-3-carbonyl)-2,4-difluorophenyl)-propane-1-sulfonamide | 1H NMR (400 MHz, DMSO) δ 14.91 (s, 1H), 9.80 (s, 1H), 8.94 (s, 1H), 8.66 (s, 1H), 7.64 (d, J = 5.7 Hz, 1H), 7.39-7.12 (m, 2H), 7.09-6.89 (m, 2H), 6.66 (d, J = 6.2 Hz, 1H), 5.30 (s, 2H), 3.12 (s, 2H), 1.75 (d, J = 5.9 Hz, 2H), 0.97 (s, 3H); [M + Na]⁺ = 494.0 |
| 28 | (3-(dimethylamino)phenyl boronic acid; product with 3-(dimethylamino)phenyl) | 499.54 | N-(3-(5-(3-(dimethylaminophenyl)-1H-pyrazolo[3,4-b]pyridine-3-carbonyl)-2,4-difluoro-phenyl)propane-1-sulfonamide | 1H NMR (200 MHz, DMSO) δ 9.11-8.84 (m, 1H), 8.70 (d, J = 2.1 Hz, 1H), 7.64 (td, J = 9.0, 6.0 Hz, 1H), 7.32 (q, J = 8.1 Hz, 2H), 7.11-6.99 (m, 2H), 6.81 (dd, J = 8.1, 1.8 Hz, 1H), 3.18-3.04 (m, 2H), 2.99 (s, 6H), 1.87-1.63 (m, 2H), 0.97 (t, J = 7.4 Hz, 3H); [M − H]⁻ = 498.0 |
| 29 | (3-methylphenyl boronic acid; product with m-tolyl) | 470.49 | N-(2,4-difluoro-3-(5-m-tolyl-1H-pyrazolo[3,4-b]pyridine-3-carbonyl)phenyl)propane-1-sulfonamide | 1H NMR (200 MHz, DMSO) δ 14.92 (s, 1H), 9.86 (s, 1H), 9.05 (d, J = 2.1 Hz, 1H), 8.77 (d, J = 2.1 Hz, 1H), 7.74-7.56 (m, 3H), 7.55-7.23 (m, 3H), 3.22-3.00 (m, 2H), 2.45 (s, 3H), 1.92-1.58 (m, 2H), 1.00 (t, J = 7.4 Hz, 3H); [M − H]⁻ = 468.9 |

TABLE 1-continued

| Ex. | Boronic acid/Pinacol ester | Structure | MW | IUPAC | 1H-NMR/MS |
|---|---|---|---|---|---|
| 30 | 3-(trifluoromethyl)phenylboronic acid | (structure) | 524.47 | N-(2,4-difluoro-3-(5-(3-(trifluoromethyl)phenyl)-1H-pyrazolo[3,4-b]pyridine-3-carbonyl)phenyl)propane-1-sulfonamide | 1H NMR (200 MHz, DMSO) δ 14.99 (s, 1H), 9.83 (s, 1H), 9.10 (d, J = 2.2 Hz, 1H), 8.86 (d, J = 2.2 Hz, 1H), 8.28-8.03 (m, 2H), 7.88-7.53 (m, 3H), 7.32 (td, J = 8.7, 1.4 Hz, 1H), 3.17-3.05 (m, 2H), 1.88-1.64 (m, 2H), 0.97 (t, J = 7.4 Hz, 3H); [M − H]⁻ = 522.9 |
| 31 | 2-fluorophenylboronic acid | (structure) | 474.46 | N-(2,4-difluoro-3-(5-(2-fluorophenyl)-1H-pyrazolo[3,4-b]pyridine-3-carbonyl)phenyl)propane-1-sulfonamide | 1H NMR (200 MHz, DMSO) δ 15.00 (s, 1H), 9.80 (s, 1H), 8.90 (t, J = 1.9 Hz, 1H), 8.73 (s, 1H), 7.82-7.22 (m, 6H), 3.22-3.01 (m, 2H), 1.91-1.62 (m, 2H), 0.97 (t, J = 7.4 Hz, 3H); [M − H]⁻ = 473.0 |
| 32 | 3-nitrophenylboronic acid | (structure) | 501.46 | N-(2,4-difluoro-3-(5-(3-nitrophenyl)-1H-pyrazolo[3,4-b]pyridine-3-carbonyl)phenyl)propane-1-sulfonamide | 1H NMR (200 MHz, DMSO) δ 14.99 (s, 1H), 9.84 (s, 1H), 9.13 (d, J = 2.2 Hz, 1H), 8.91 (d, J = 2.2 Hz, 1H), 8.64 (t, J = 1.9 Hz, 1H), 8.37-8.25 (m, 1H), 7.84 (t, J = 8.0 Hz, 1H), 7.64 (td, J = 9.0, 6.0 Hz, 1H), 7.32 (td, J = 9.0, 1.3 Hz, 1H), 3.21-3.04 (m, 1H), 1.88-1.61 (m, 1H), 0.97 (t, J = 7.4 Hz, 3H); [M − H]⁻ = 500.0 |
| 33 | 3,4-dichlorophenylboronic acid | (structure) | 525.35 | N-(3-(5-(3,4-dichloro-phenyl)-1H-pyrazolo[3,4-b]pyridine-3-carbonyl)-2,4-difluoro-phenyl)propane-1-sulfonamide | 1H NMR (200 MHz, DMSO) δ 9.05 (s, 1H), 8.83 (s, 1H), 8.17 (s, 1H), 8.00-7.52 (m, 3H), 7.31 (t, J = 8.8 Hz, 1H), 3.21-2.98 (m, 2H), 2.00-1.58 (m, 2H), 0.97 (t, J = 7.3 Hz, 3H); [M − H]⁻ = 522.9 |

TABLE 1-continued

| Ex. | Boronic acid/Pinacol ester | Structure | MW | IUPAC | 1H-NMR/MS |
|---|---|---|---|---|---|
| 34 | 4-(trifluoromethyl)phenylboronic acid | (structure) | 524.47 | N-(2,4-difluoro-3-(5-(4-(trifluoromethyl)phenyl)-1H-pyrazolo[3,4-b]pyridine-3-carbonyl)phenyl)propane-1-sulfonamide | 1H NMR (200 MHz, DMSO) δ 15.03 (s, 1H), 9.85 (s, 1H), 9.10 (d, J = 2.2 Hz, 1H), 8.86 (d, J = 2.2 Hz, 1H), 8.10 (d, J = 8.0 Hz, 2H), 7.90 (d, J = 8.4 Hz, 2H), 7.64 (td, J = 9.0, 5.9 Hz, 1H), 7.32 (td, J = 8.9, 1.4 Hz, 1H), 3.24-2.96 (m, 2H), 1.89-1.60 (m, 2H), 0.97 (t, J = 7.4 Hz, 3H); [M − H]⁻ = 522.9 |
| 35 | 2,4-dichlorophenylboronic acid | (structure) | 525.35 | N-(3-(5-(2,4-dichlorophenyl)-1H-pyrazolo[3,4-b]pyridine-3-carbonyl)-2,4-difluorophenyl)propane-1-sulfonamide | 1H NMR (200 MHz, DMSO) δ 15.03 (s, 1H), 9.83 (s, 1H), 8.78 (d, J = 2.1 Hz, 1H), 8.64 (d, J = 1.9 Hz, 1H), 7.84 (d, J = 1.7 Hz, 1H), 7.77-7.54 (m, 3H), 7.46-7.18 (m, 1H), 3.24-3.00 (m, 2H), 1.91-1.56 (m, 2H), 0.97 (t, J = 7.4 Hz, 3H); [M + Na]⁺ = 546.8 |
| 36 | 4-chloro-3-(trifluoromethyl)phenylboronic acid | (structure) | 558.91 | N-(3-(5-(4-chloro-3-(trifluoromethyl)phenyl)-1H-pyrazolo[3,4-b]pyridine-3-carbonyl)-2,4-difluorophenyl)propane-1-sulfonamide | 1H NMR (200 MHz, DMSO) δ 15.00 (s, 1H), 9.83 (s, 1H), 9.10 (d, J = 2.2 Hz, 1H), 8.89 (d, J = 2.0 Hz, 1H), 8.33-8.10 (m, 2H), 7.89 (d, J = 8.3 Hz, 1H), 7.64 (td, J = 9.0, 6.0 Hz, 1H), 7.31 (td, J = 8.8, 1.2 Hz, 1H), 3.21-3.02 (m, 2H), 1.87-1.62 (m, 2H), 0.97 (t, J = 7.4 Hz, 3H); [M − H]⁻ = 557.0 |
| 37 | 3-hydroxyphenylboronic acid | (structure) | 472.47 | N-(2,4-difluoro-3-(3-hydroxyphenyl)-1H-pyrazolo[3,4-b]pyridine-3-carbonyl)phenyl)propane-1-sulfonamide | 1H NMR (200 MHz, DMSO) δ 15.21 (s, 1H), 10.04 (s, 2H), 9.32 (d, J = 2.1 Hz, 1H), 9.03 (d, J = 2.1 Hz, 1H), 7.98 (td, J = 9.1, 6.0 Hz, 1H), 7.76-7.43 (m, 4H), 7.29-7.14 (m, 2H), 3.54-3.34 (m, 2H), 2.19-1.96 (m, 2H), 1.31 (t, J = 7.4 Hz, 3H); [M − H]⁻ = 471.0 |

TABLE 1-continued

| Ex. | Boronic acid/Pinacol ester | Structure | MW | IUPAC | ¹H-NMR/MS |
|---|---|---|---|---|---|
| 38 | 2-chloro-4-methoxyphenylboronic acid | (structure) | 474.89 | N-(3-(5-(2-chloro-4-methoxyphenyl)-1H-pyrazolo[3,4-b]pyridine-3-carbonyl)-2-fluorophenyl)-methanesulfonamide | 1H NMR (400 MHz, DMSO-d₆) δ = 14.76 (brs, 1H), 9.78 (brs, 1H), 8.69 (d, J = 2.4 Hz, 1H), 8.53 (d, J = 2.0 Hz, 1H), 7.65-7.55 (m, 2H), 7.50 (d, J = 8.8 Hz, 1H), 7.33 (t, J = 8.56 Hz, 1H), 7.21 (d, J = 2.4 Hz, 1H), 7.06 (dd, J = 2.4, 8.8 Hz, 1H), 3.82 (s, 3H), 3.05 (s, 3H). [M + H]⁺ = 475.04. |
| 39 | 4-fluoro-2-methylphenylboronic acid | (structure) | 442.44 | N-(2-fluoro-3-(5-(4-fluoro-2-methylphenyl)-1H-pyrazolo[3,4-b]pyridine-3-carbonyl)phenyl)methanesulfonamide | 1H NMR (400 MHz, DMSO-d₆) δ = 14.81 (brs, 1H), 9.82 (brs, 1H), 8.68 (d, J = 2.4 Hz, 1H), 8.47 (d, J = 2.4 Hz, 1H), 7.67-7.56 (m, 2H), 7.43-7.34 (m, 2H), 7.26 (dd, J = 2.4, 9.8 Hz, 1H), 7.17 (dt, J = 2.7, 8.4 Hz, 1H), 3.09 (s, 3H), 2.27 (s, 3H). [M + H]⁺ = 443.05. |
| 40 | 2,3-dihydrobenzo[b][1,4]dioxin-6-ylboronic acid | (structure) | 468.46 | N-(3-(5-(2,3-dihydro-benzo[b][1,4]dioxin-6-yl)-1H-pyrazolo[3,4-b]pyridine-3-carbonyl)-2-fluoro-phenyl)methanesulfonamide | 1H NMR (400 MHz, DMSO-d₆) δ = 14.73 (s, 1H), 9.84 (s, 1H), 8.94 (d, J = 2.4 Hz, 1H), 8.75-8.59 (m, 1H), 7.69-7.57 (m, 2H), 7.39-7.31 (m, 2H), 7.30-7.24 (m, 1H), 7.02 (d, J = 8.3 Hz, 1H), 4.31 (s, 4H), 3.09 (s, 3H). [M + H]⁺ = 468.90. |
| 41 | 2-chloro-4-methoxyphenylboronic acid | (structure) | 516.97 | N-(3-(5-(2-chloro-4-methoxyphenyl)-1H-pyrazolo[3,4-b]pyridine-3-carbonyl)-2-fluorophenyl)butane-1-sulfonamide | 1H NMR (400 MHz, DMSO-d₆) δ = 14.76 (brs, 1H), 9.80 (brs, 1H), 8.67 (d, J = 2.2 Hz, 1H), 8.52 (d, J = 2.0 Hz, 1H), 7.63-7.53 (m, 2H), 7.49 (d, J = 8.6 Hz, 1H), 7.31 (t, J = 7.9 Hz, 1H), 7.21 (d, J = 2.4 Hz, 1H), 7.06 (dd, J = 2.4, 8.6 Hz, 2H), 3.82 (s, 3H), 3.14-3.07 (m, 2H), 1.70-1.62 (m, 2H), 1.40-1.26 (m, 2H), 0.82 (t, J = 7.3 Hz, 3H). [M + H]⁺ = 517. |

TABLE 1-continued

| Boronic acid/Pina- col ester Ex. | Structure | MW | IUPAC | ¹H-NMR/MS |
|---|---|---|---|---|
| 42 | [structure] | 484.52 | N-(2-fluoro-3-(5-(4-fluoro-2-methylphenyl)-1H-pyrazolo[3,4-b]pyridine-3-carbonyl)phenyl)butane-1-sulfonamide | 1H NMR (400 MHz, DMSO-d₆) δ = 14.76 (brs, 1H), 9.84 (brs, 1H), 8.68 (d, J = 2.0 Hz, 1H), 8.47 (d, J = 2.0 Hz, 1H), 7.67-7.54 (m, 2H), 7.43-7.31 (m, 2H), 7.30-7.22 (m, 1H), 7.17 (dt, J = 2.5, 8.4 Hz, 1H), 3.23-3.05 (m, 2H), 2.28 (s, 3H), 1.77-1.64 (m, 2H), 1.33-145 (m, 2H), 0.86 (t, J = 7.4 Hz, 3H). [M + H]⁺ = 485.10. |
| 43 | [structure] | 510.54 | N-(3-(5-(2,3-dihydro-benzo-[b][1,4]dioxin-6-yl)-1H-pyrazolo[3,4-b]pyridine-3-carbonyl)-2-fluorophenyl)butane-1-sulfonamide | 1H NMR (400 MHz, DMSO-d₆) δ = 14.68 (brs, 1H), 9.82 (brs, 1H), 8.94 (d, J = 2.0 Hz, 1H), 8.65 (d, J = 2.0 Hz, 1H), 7.66-7.61 (m, 2H), 7.30-7.39 (m, 2H), 7.30-7.25 (m, 1H), 7.02 (d, J = 8.3 Hz, 1H), 4.31 (s, 4H), 3.23-3.10 (m, 2H), 1.79-1.65 (m, 2H), 1.49-1.32 (m, 2H), 0.86 (t, J = 7.3 Hz, 3H). [M + H]⁺ = 511.10. |

Example 44: Synthesis of N-(5-(4-chlorophenyl)-1H-pyrazolo[3,4-b]pyridin-3-yl)-2,6-difluoro-3-(propylsulfonamido)benzamide
Synthesis of 2,6-difluoro-3-(propylsulfonamido)benzoic acid (Int. E)
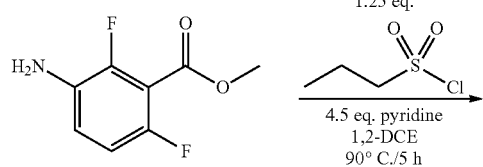
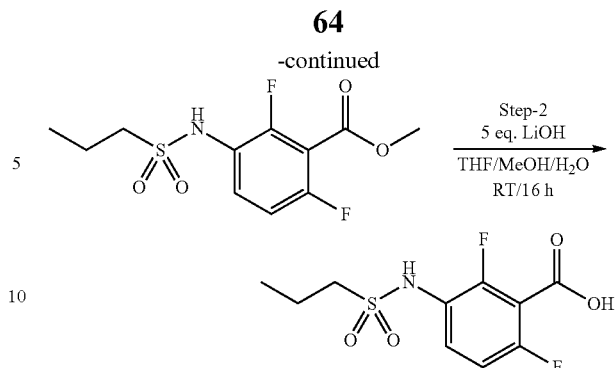
Synthesis of N-(5-(4-chlorophenyl)-1H-pyrazolo[3,4-b]pyridin-3-yl)-2,6-difluoro-3-(propylsulfonamido) benzamide
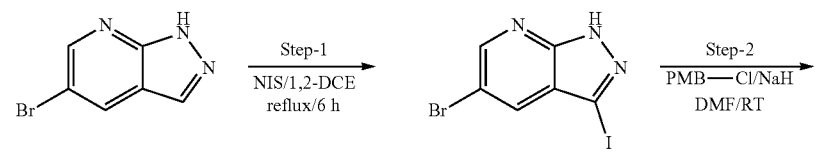
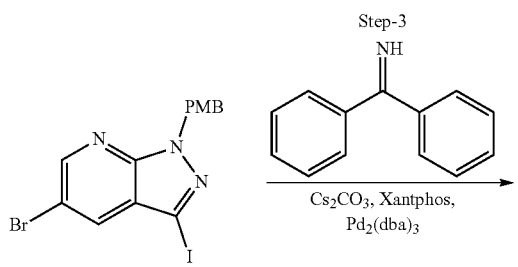
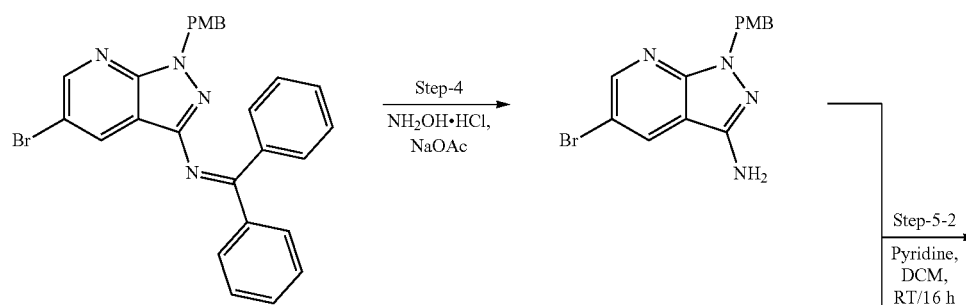
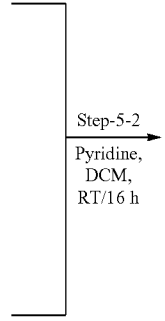
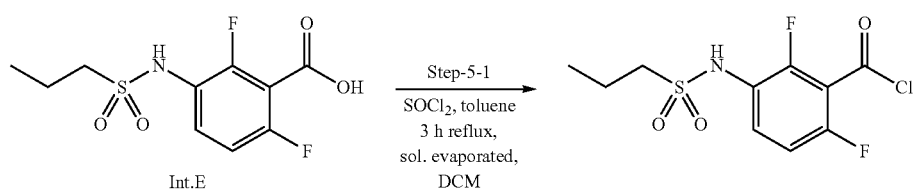

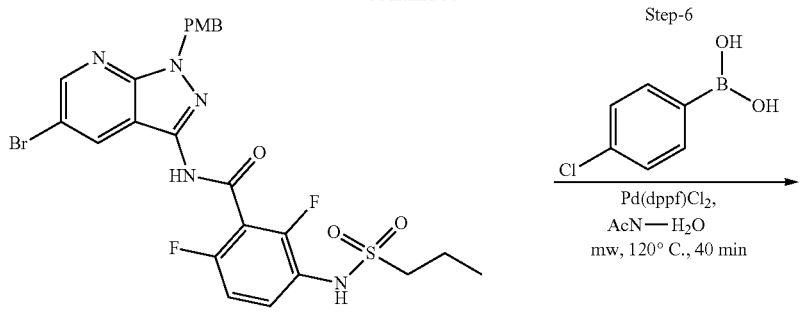
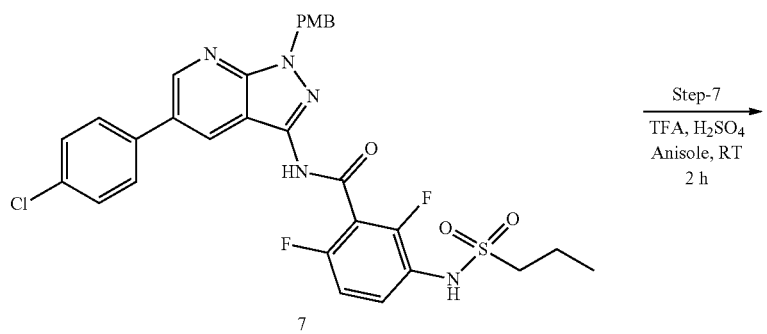
7
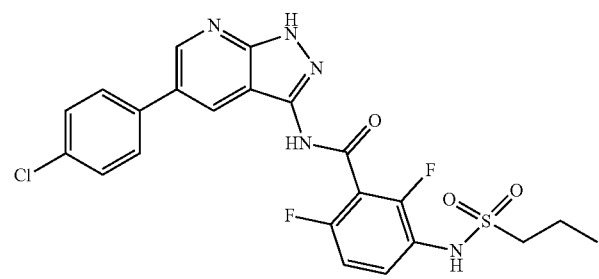
Example 45: Synthesis of 5-(4-chlorophenyl)-N-(2,6-difluoro-3-(propylsulfonamido)phenyl)-1H-pyrazolo[3,4-b]pyridine-3-carboxamide
Synthesis of N-(3-amino-2,4-difluorophenyl)propane-1-sulfonamide (Intermediate F)
Synthesis of 5-(4-chlorophenyl)-N-(2,6-difluoro-3-(propylsulfonamido)phenyl)-1H-pyrazolo[3,4-b]pyridine-3-carboxamide
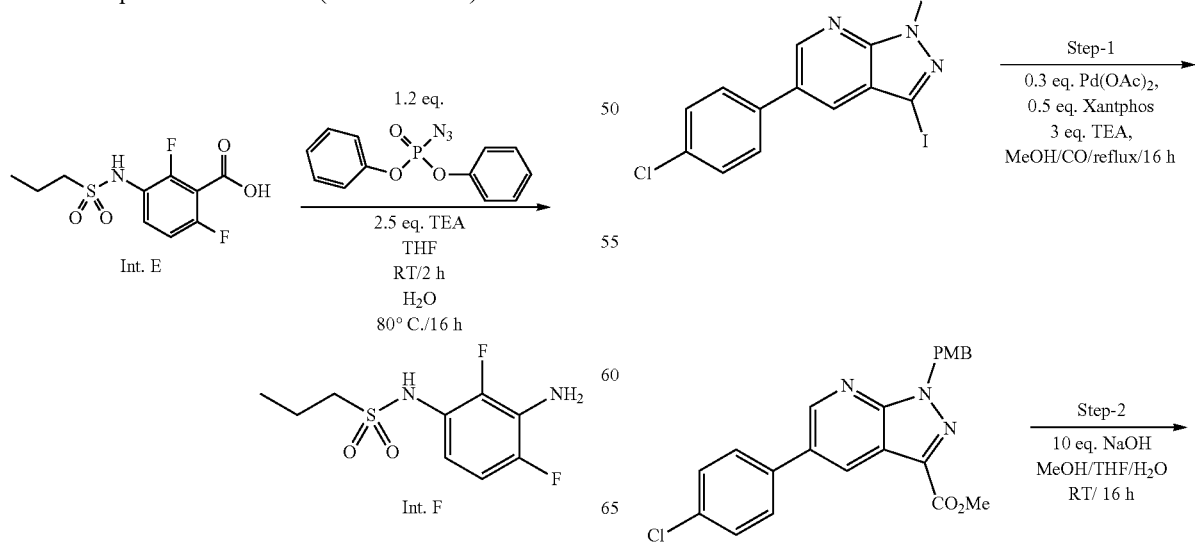

-continued
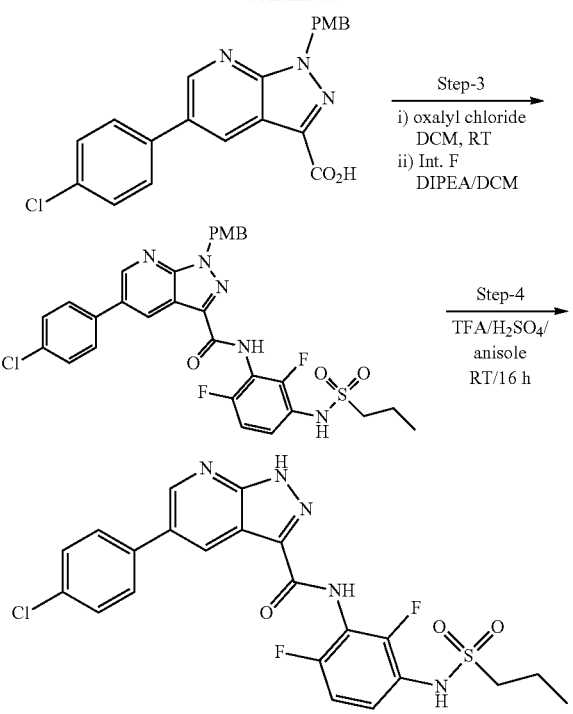
Example 46: Synthesis of N-(3-((5-(4-chlorophenyl)-1H-pyrazolo[3,4-b]pyridin-3-yl)thio)-2,4-difluorophenyl)propane-1-sulfonamide
Synthesis of N-(2,4-difluoro-3-mercaptophenyl)propane-1-sulfonamide (Intermediate C)
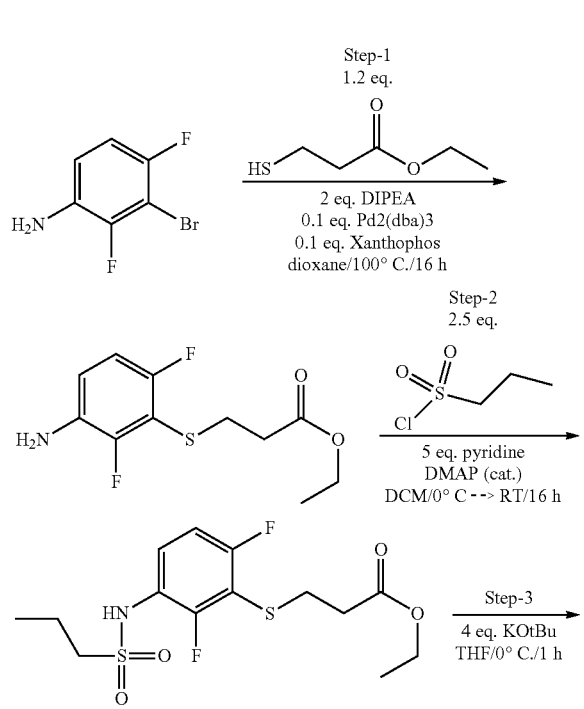
-continued
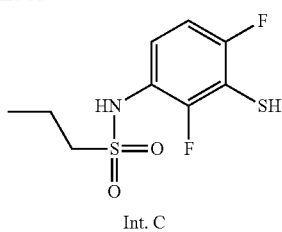
Synthesis of N-(3-((5-(4-chlorophenyl)-1H-pyrazolo[3,4-b]pyridin-3-yl)thio)-2,4-difluorophenyl)propane-1-sulfonamide
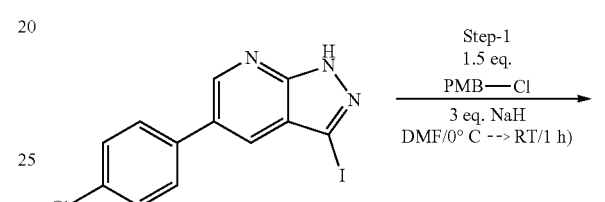
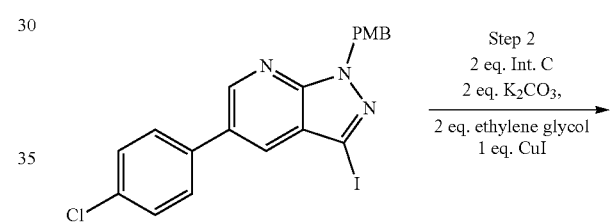
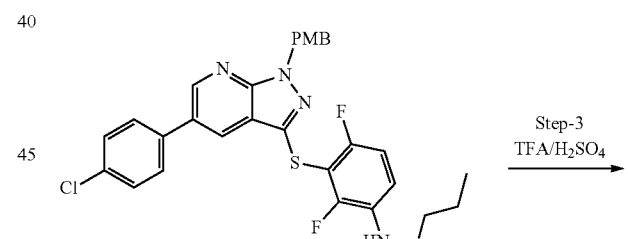
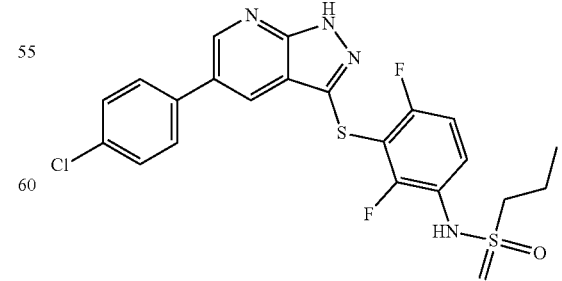

Example 47 and 48: Synthesis of N-(3-((5-(4-chlorophenyl)-1H-pyrazolo[3,4-b]pyridin-3-yl)sulfinyl)-2,4-difluorophenyl)propane-1-sulfonamide (Expl. 47) and N-(3-((5-(4-chlorophenyl)-1H-pyrazolo[3,4-b]pyridin-3-yl)sulfonyl)-2,4-difluorophenyl)propane-1-sulfonamide (Expl. 48)

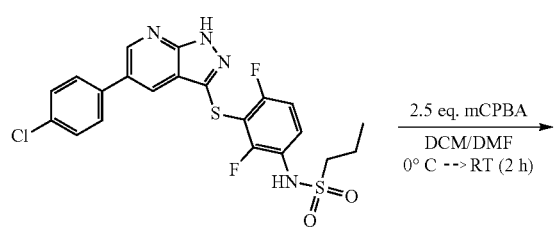

Expl. 46

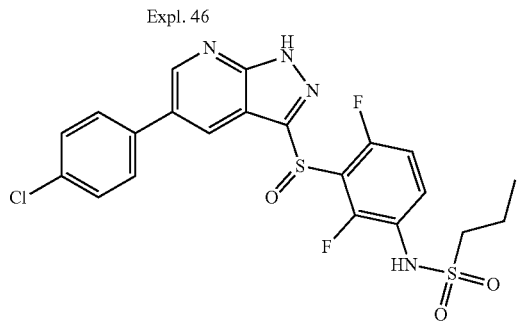

Expl. 47

+

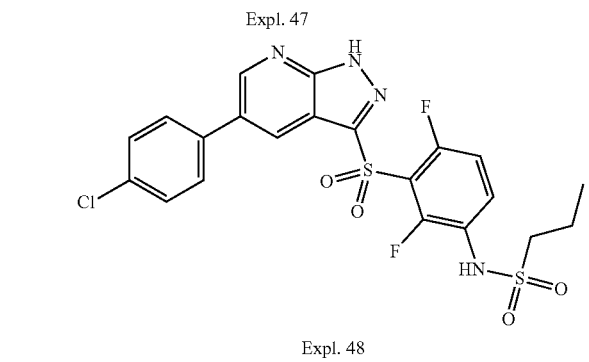

Expl. 48

Expl. 47 and Expl. 48 isolated by preparative chromatography

Example 49: Synthesis of N-(3-((5-(4-chlorophenyl)-1H-pyrazolo[3,4-b]pyridin-3-yl)(hydroxy)methyl)-2,4-difluorophenyl)propane-1-sulfonamide Synthesis of N-(2,4-difluoro-3-formylphenyl)propane-1-sulfonamide (Intermediate A)

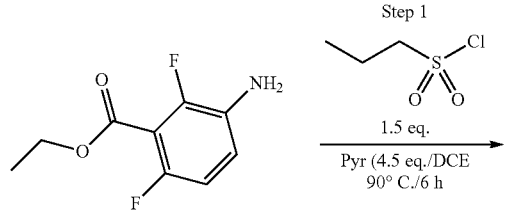

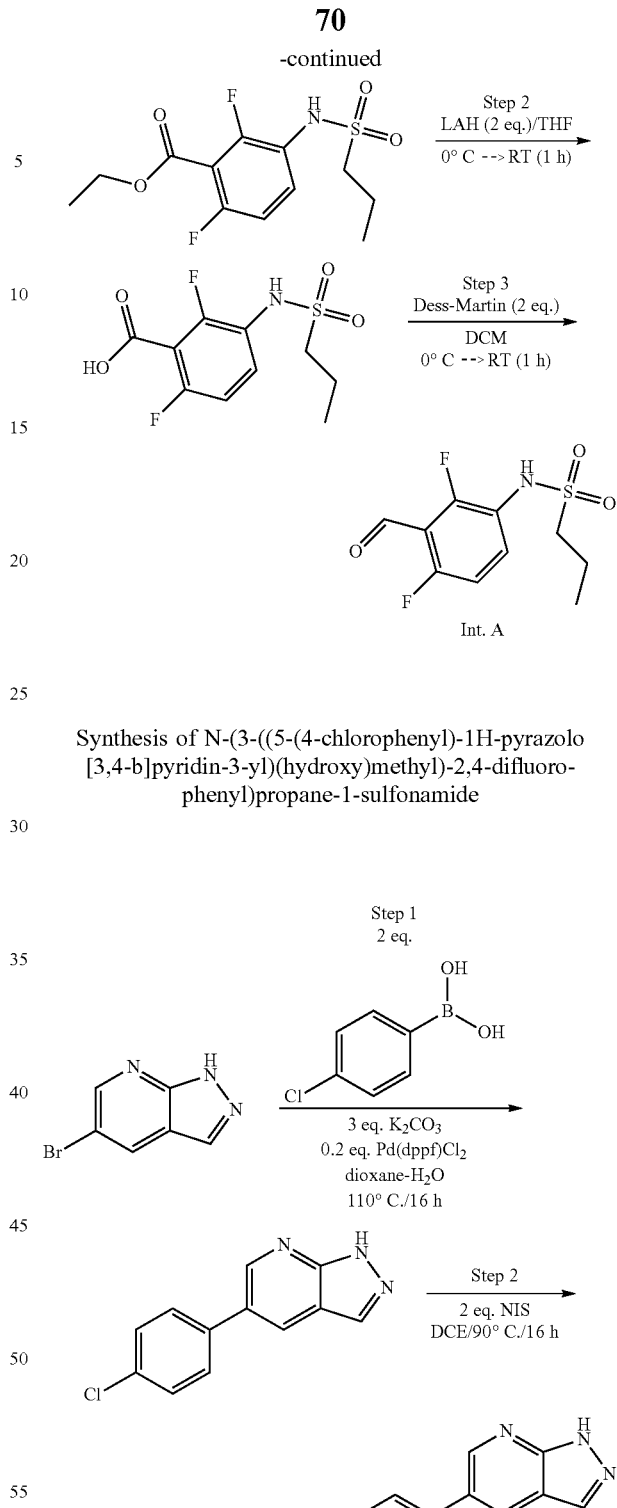

Int. A

Synthesis of N-(3-((5-(4-chlorophenyl)-1H-pyrazolo[3,4-b]pyridin-3-yl)(hydroxy)methyl)-2,4-difluorophenyl)propane-1-sulfonamide

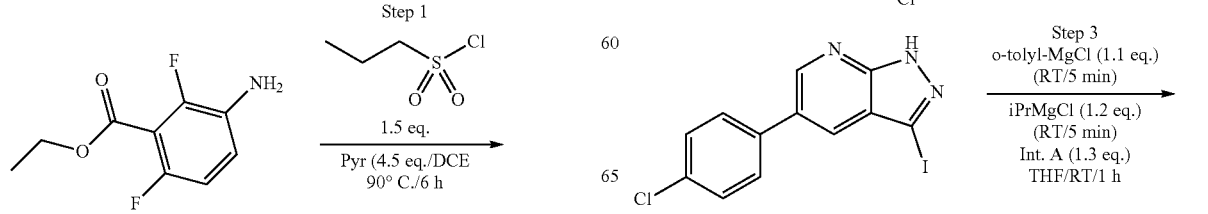

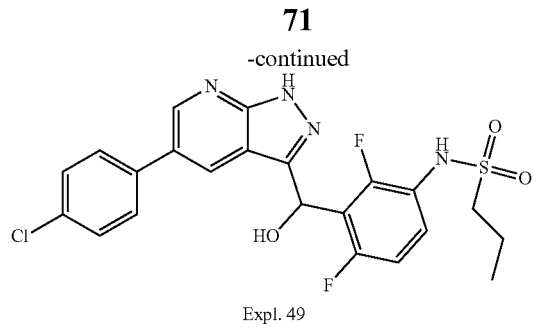

Expl. 49

Example 50: Synthesis of N-(3-((5-(4-chlorophenyl)-1H-pyrazolo[3,4-b]pyridin-3-yl)methyl)-2,4-difluorophenyl)propane-1-sulfonamide

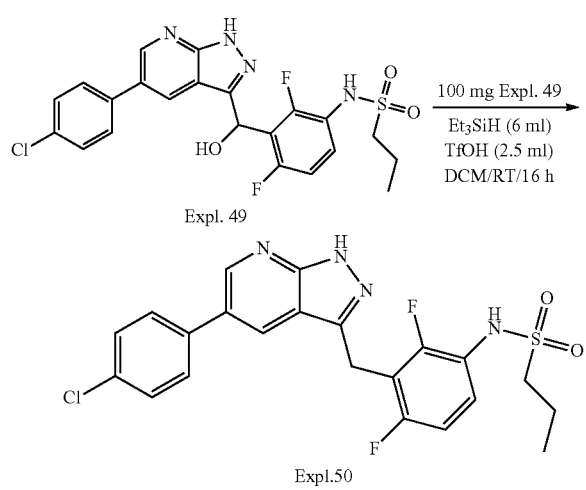

Example 51

The compounds of Example 51a-51m were prepared according to the procedure, illustrated in scheme 1.

Scheme 1

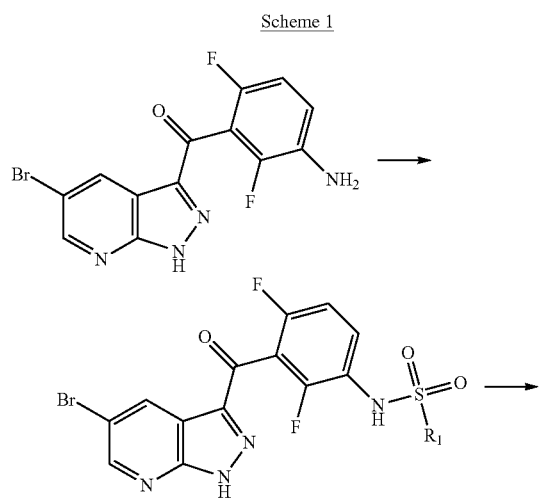

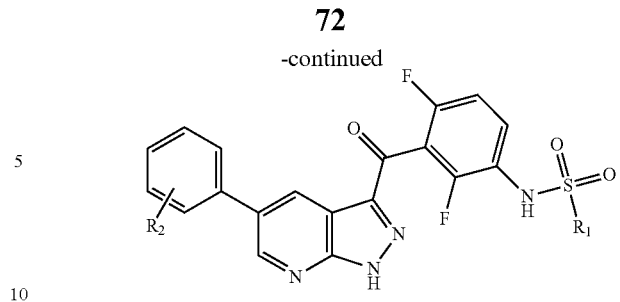

(3-Amino-2,6-difluorophenyl)(5-bromo-1H-pyrazolo[3,4-b]pyridin-3-yl)methanone (1) was prepared as described in Example 1 (Steps 1-4).

The subsequent conversion with a sulfonyl chloride, leading to intermediate 2 was performed in analogy to Example 1, Step 5.

The Suzuki coupling reactions to the final products 51a-51m were performed as follows (general procedure): A microwave vessel is charged with a magnetic stir bar, 5-bromo-1H-pyrazolopyridin derivatives, appropriate boronic acid or boronic acid pinacole ester (1.1 eq.) and XPhos Pd G3 or Pd G4 (0.05 eq.) and purged with argon. Degassed 1,4-dioxane (0.4 M) and degassed aqueous 1.5 M $K_2CO_3$ (3.5 eq., +1 eq. for every acidic functional group) are added and the mixture is heated to 120° C. (100° C. for amides) under microwave irradiation until complete conversion (30 to 60 minutes). After cooling, the mixture is diluted with EtOAc and neutralized with sat. $NH_4Cl$ solution (or acidified with 2N HCl for acidic functional groups). The solvents are removed and the product isolated by flash chromatography (using mixtures of DCM, EtOAc and/or MeOH), triturated if necessary and dried at 100° C. in a vacuum oven.

Example 51a: 4-(3-(2,6-difluoro-3-((phenylmethyl)sulfonamido)benzoyl)-1H-pyrazolo[3,4-b]pyridin-5-yl)benzenesulfonamide

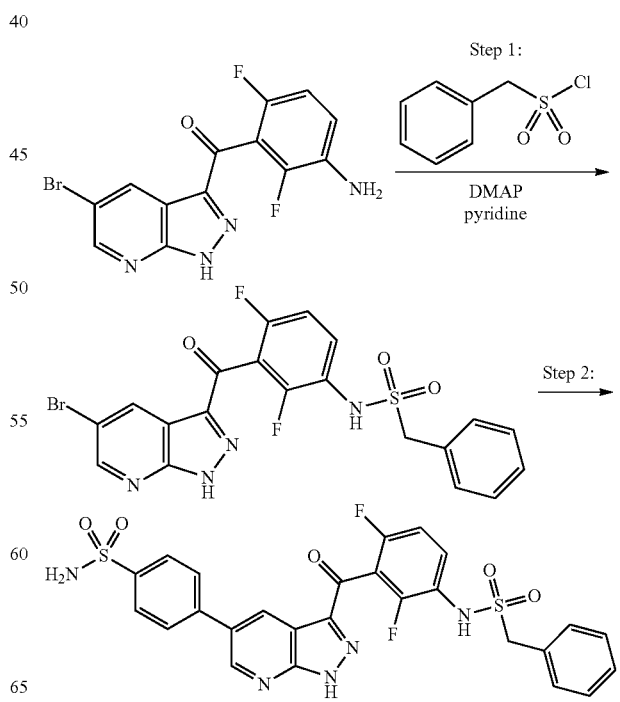

Step 1: N-[3-(5-bromo-1H-pyrazolo[3,4-b]pyridine-3-carbonyl)-2,4-difluorophenyl]-1-phenylmethane-sulfonamide (3-amino-2,6-difluorophenyl)-(5-bromo-1H-pyrazolo[3,4-b]pyridin-3-yl)methanone (350 mg, 0.991 mmol) and N,N-dimethylpyridin-4-amine (6.05 mg, 0.0496 mmol) were dissolved in pyridine (1.98 mL) and heated to 65° C. Phenylmethanesulfonyl chloride (283 mg, 1.49 mmol) was added and the mixture stirred for 2 h. The mixture was poured into aqueous 2N HCl and extracted with EtOAc. The organic phase was washed with 2N HCl and brine, dried over Na$_2$SO$_4$, filtered and the solvent removed under removed pressure. The residue was purified by flash chromatography (n-hexane+EtOAc) 0% to 50% and triturated with n-hexane. N-[3-(5-bromo-1H-pyrazolo[3,4-b]pyridine-3-carbonyl)-2,4-difluorophenyl]-1-phenylmethanesulfonamide (315 mg, 0.6210 mmol, 63% yield).

$^1$H NMR (200 MHz, CDCl$_3$) δ 14.22 (s, 1H), 8.96 (s, 1H), 8.79 (d, J=2.2 Hz, 1H), 8.59 (d, J=2.1 Hz, 1H), 7.52-7.25 (m, 6H), 6.87 (td, J=9.1, 1.6 Hz, 1H), 4.32 (s, 2H);

$^{13}$C NMR (101 MHz, CDCl$_3$) δ 182.7, 156.6 (dd, J=251, 6.8 Hz), 153.03 (d, J=7.7 Hz), 151.2, 150.6, 150.5, 141.6, 132.9, 130.8, 127.75 (dd, J=151.3, 7.9 Hz), 126.9, 121.87 (dd, J=13.1, 3.9 Hz), 117.12 (dd, J=22.8, 20.7 Hz), 115.7, 115.5, 111.61 (dd, J=22.5, 3.8 Hz), 58.8.

MS: [M−1]$^-$=504.7

Step 2: Suzuki Coupling According to General Procedure (See Example 2 Above)

Analytical Data:

$^1$H NMR (200 MHz, DMSO) δ 15.01 (s, 1H), 9.89 (s, 1H), 9.11 (d, J=1.7 Hz, 1H), 8.87 (d, J=1.7 Hz, 1H), 8.17-7.81 (m, 4H), 7.70-7.14 (m, 9H), 4.54 (s, 2H);

$^{13}$C NMR (101 MHz, DMSO) δ 182.6, 155.95 (dd, J=248.0, 6.2 Hz), 152.4, 152.14 (dd, J=251.0, 7.4 Hz), 149.8, 143.5, 142.0, 140.4, 132.0, 131.9, 131.5, 131.5, 131.4, 130.9, 129.2, 128.7, 128.6, 128.3, 128.3, 127.9, 127.5, 126.4, 126.3, 122.10 (dd, J=13.1, 3.5 Hz), 117.2, 117.0, 113.4, 111.90 (dd, J=22.0, 3.9 Hz) 58.5;

MS: [M−1]$^-$=581.8.

Example 51b: 4-(3-(2,6-difluoro-3-(methylsulfonamido)benzoyl)-1H-pyrazolo[3,4-b]pyridin-5-yl)benzenesulfonamide

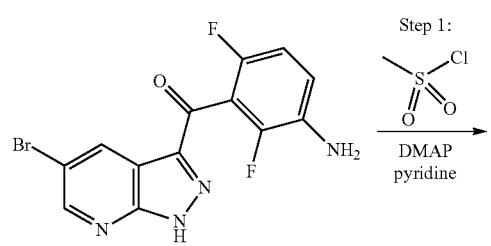

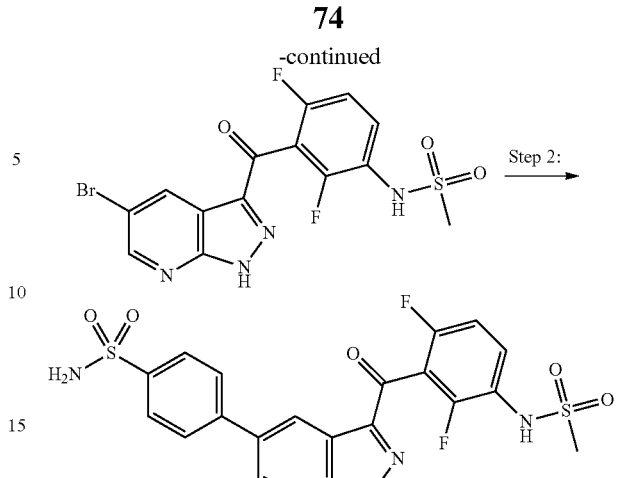

Step 1: N-[3-(5-bromo-1H-pyrazolo[3,4-b]pyridine-3-carbonyl)-2,4-difluorophenyl] methane-sulfonamide (3-amino-2,6-difluorophenyl)-(5-bromo-1H-pyrazolo[3,4-b]pyridin-3-yl)methanone (350 mg, 0.991 mmol) and N,N-dimethylpyridin-4-amine (6.05 mg, 0.0496 mmol) were dissolved in pyridine (1.98 mL) and heated to 65° C. Methanesulfonyl chloride (0.357 mL, 1.49 mmol) was added and the mixture stirred for 2 h. The mixture was poured into aqueous 2N HCl and extracted with EtOAc. The organic phase was washed with 2N HCl and brine, dried over Na$_2$SO$_4$, filtered and the solvent removed under removed pressure. The residue was purified by flash chromatography (DCM+EtOAc) 0% to 30% and triturated with n-hexane. N-[3-(5-bromo-1H-pyrazolo[3,4-b]pyridine-3-carbonyl)-2,4-difluorophenyl]methanesulfonamide (164 mg, 0.3800 mmol, 38% yield)

Analytical Data:

$^1$H NMR (200 MHz, DMSO) δ 15.07 (s, 1H), 9.82 (s, 1H), 8.80 (dd, J=4.8, 2.1 Hz, 2H), 7.65 (td, J=9.0, 5.9 Hz, 1H), 7.32 (td, J=8.9, 1.5 Hz, 1H), 3.07 (s, 3H);

$^{13}$C NMR (101 MHz, DMSO) δ 182.3, 156.4 (dd, J=248.8, 6.6 Hz), 152.92 (dd, J=251.8, 8.1 Hz), 151.0, 150.9, 141.0, 132.2, 130.1, 130.0, 121.80 (dd, J=13.2, 3.7 Hz), 116.84 (dd, J=23.0, 20.9 Hz), 115.7, 114.7, 112.16 (dd, J=22.4, 3.7 Hz), 40.4;

MS: [M−1]$^-$=428.7.

Step 2: Suzuki Coupling According to General Procedure

Analytical Data:

$^1$H NMR (200 MHz, DMSO) δ 14.99 (s, 1H), 9.85 (s, 1H), 9.10 (d, J=2.1 Hz, 1H), 8.86 (d, J=2.1 Hz, 1H), 8.03 (dd, J=20.8, 8.4 Hz, 4H), 7.65 (td, J=9.1, 6.1 Hz, 1H), 7.48 (s, 2H), 7.33 (t, J=8.8 Hz, 1H), 3.08 (s, 3H);

$^{13}$C NMR (101 MHz, DMSO) δ 182.5, 156.40 (dd, J=248.5, 6.7 Hz), 153.0 (dd, J=251.5, 8.0 Hz), 152.4, 149.8, 143.5, 142.0, 140.3, 131.5, 130.0, 129.9, 128.2, 127.9, 126.4, 121.8 (dd, J=13.3, 3.5 Hz), 117.13 (dd, J=23.0, 21.5 Hz), 113.4, 112.15 (dd, J=22.1, 3.1 Hz), 40.4;

MS: [M−1]$^-$=505.9.

Example 51c: 4-(3-(3-(butylsulfonamido)-2,6-difluorobenzoyl)-1H-pyrazolo[3,4-b]pyridin-5-yl) benzenesulfonamide

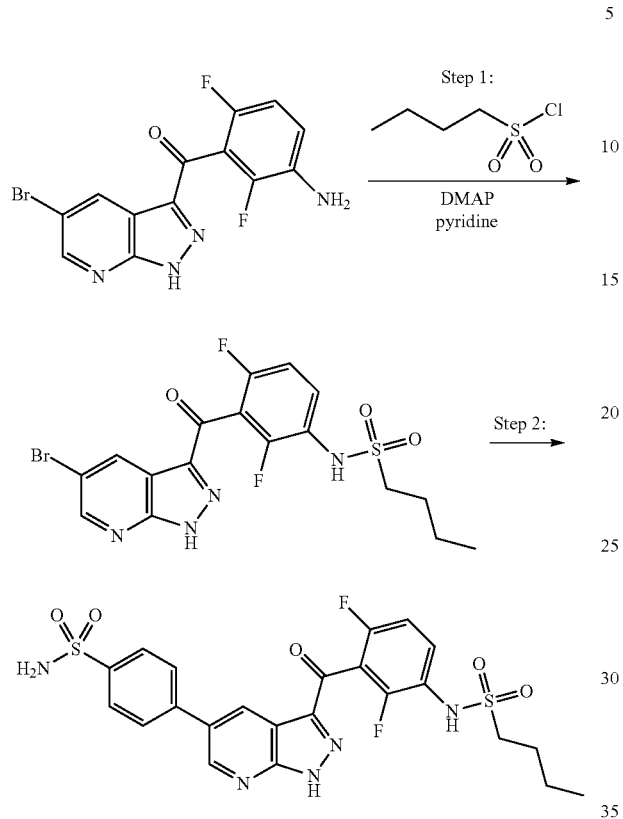

Step 1: N-[3-(5-bromo-1H-pyrazolo[3,4-b]pyridine-3-carbonyl)-2,4-difluorophenyl]butane-1-sulfonamide (3-amino-2,6-difluorophenyl)-(5-bromo-1H-pyrazolo[3,4-b]pyridin-3-yl)methanone (350 mg, 0.991 mmol) and N,N-dimethylpyridin-4-amine (6.05 mg, 0.0496 mmol) were dissolved in pyridine (1.98 mL) and heated to 65° C. Butane-1-sulfonyl chloride (0.357 mL, 1.49 mmol) was added and the mixture stirred for overnight. 0.25 eq. butane-1-sulfonyl chloride were added and stirring continued for 2 h at 65° C. The mixture was poured into aqueous 2N HCl and extracted with EtOAc. The organic phase was washed with 2N HCl and brine, dried over $Na_2SO_4$, filtered and the solvent removed under removed pressure. The residue was purified by flash chromatography (hexane+EtOAc) 10% to 50% and triturated with n-hexane. N-[3-(5-bromo-1H-pyrazolo[3,4-b]pyridine-3-carbonyl)-2,4-difluorophenyl]butane-1-sulfonamide (180 mg, 0.3800 mmol, 38% yield)

Analytical Data:

$^1$H NMR (200 MHz, DMSO) δ 15.03 (s, 1H), 9.83 (s, 1H), 9.02-8.62 (m, 2H), 3.21-3.03 (m, 2H), 1.70 (dt, J=15.0, 7.5 Hz, 2H), 1.37 (dq, J=14.5, 7.3 Hz, 2H), 0.84 (t, J=7.2 Hz, 3H);

$^{13}$C NMR (50 MHz, DMSO) δ 182.4, 151.1, 151.0, 141.1, 132.3, 115.8, 114.8, 51.8, 25.1, 20.7, 13.4;

MS: [M−1]$^-$=470.8.

Step 2: Suzuki Coupling According to General Procedure

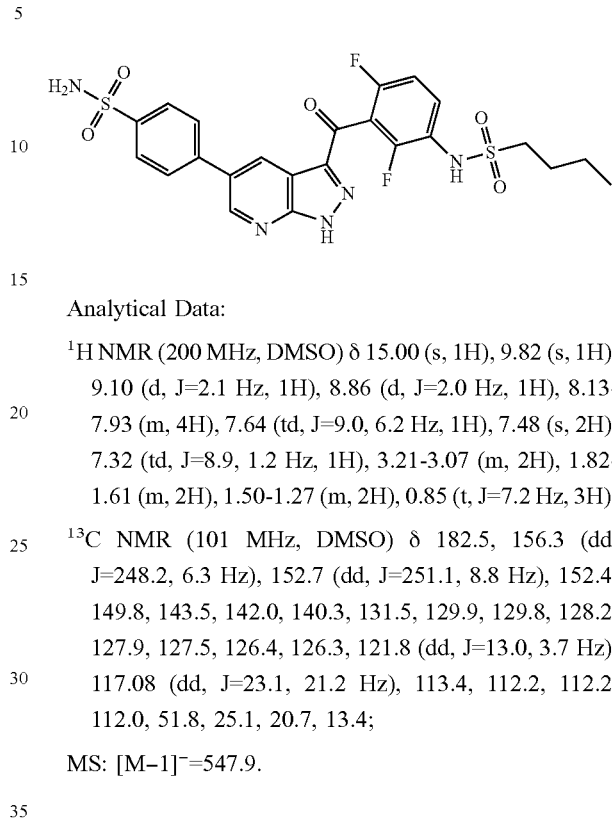

Analytical Data:

$^1$H NMR (200 MHz, DMSO) δ 15.00 (s, 1H), 9.82 (s, 1H), 9.10 (d, J=2.1 Hz, 1H), 8.86 (d, J=2.0 Hz, 1H), 8.13-7.93 (m, 4H), 7.64 (td, J=9.0, 6.2 Hz, 1H), 7.48 (s, 2H), 7.32 (td, J=8.9, 1.2 Hz, 1H), 3.21-3.07 (m, 2H), 1.82-1.61 (m, 2H), 1.50-1.27 (m, 2H), 0.85 (t, J=7.2 Hz, 3H);

$^{13}$C NMR (101 MHz, DMSO) δ 182.5, 156.3 (dd, J=248.2, 6.3 Hz), 152.7 (dd, J=251.1, 8.8 Hz), 152.4, 149.8, 143.5, 142.0, 140.3, 131.5, 129.9, 129.8, 128.2, 127.9, 127.5, 126.4, 126.3, 121.8 (dd, J=13.0, 3.7 Hz), 117.08 (dd, J=23.1, 21.2 Hz), 113.4, 112.2, 112.2, 112.0, 51.8, 25.1, 20.7, 13.4;

MS: [M−1]$^-$=547.9.

Example 51d: 4-(3-(2,6-difluoro-3-(propysulfonamido)benzoyl)-1H-pyrazolo[3,4-b]pyridin-5-yl)benzoic acid Suzuki Coupling According to General Procedure

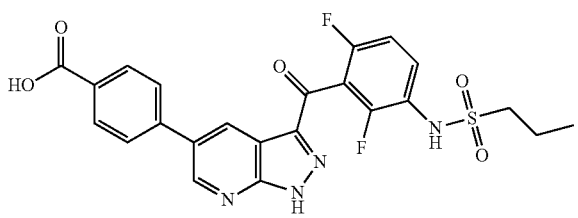 [SMILES: CCCS(=O)(=O)Nc1ccc(F)c(C(=O)c2n[nH]c3ncc(-c4ccc(C(=O)O)cc4)cc23)c1F]

Analytical Data:

$^1$H NMR (200 MHz, DMSO) δ 14.99 (s, 1H), 13.14 (bs, 1H), 9.83 (s, 1H), 9.10 (d, J=2.1 Hz, 1H), 8.84 (d, J=2.2 Hz, 1H), 8.04 (dd, J=22.3, 8.5 Hz, 4H), 7.64 (td, J=9.0, 5.9 Hz, 1H), 7.31 (td, J=8.9, 1.5 Hz, 1H), 3.21-3.03 (m, 2H), 1.86-1.61 (m, 2H), 0.97 (t, J=7.4 Hz, 3H);

$^{13}$C NMR (101 MHz, DMSO) δ 182.5, 167.0, 152.4, 149.8, 142.0, 141.3, 131.8, 130.2, 130.1, 128.1, 127.6, 113.5, 53.8, 16.8, 12.5;

MS: [M−1]$^-$=499.6.

Example 51e: N-[2,4-difluoro-3-[5-[4-(1H-tetrazol-5-yl)phenyl]-1H-pyrazolo[3,4-b]pyridine-3-carbonyl] phenyl]propane-1-sulfonamide Suzuki Coupling According to General Procedure

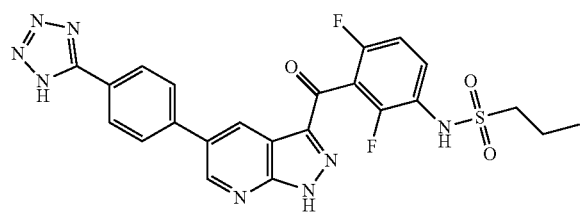 [SMILES: CCCS(=O)(=O)Nc1ccc(F)c(C(=O)c2n[nH]c3ncc(-c4ccc(-c5nnn[nH]5)cc4)cc23)c1F]

Analytical Data:
$^1$H NMR (200 MHz, DMSO) δ 14.99 (s, 1H), 9.83 (s, 1H), 9.14 (d, J=2.1 Hz, 1H), 8.88 (d, J=2.2 Hz, 1H), 8.17 (dd, J=19.9, 8.4 Hz, 4H), 7.65 (td, J=9.0, 6.1 Hz, 1H), 7.32 (td, J=9.0, 1.4 Hz, 1H), 3.20-3.05 (m, 2H), 1.90-1.59 (m, 2H), 0.97 (t, J=7.4 Hz, 3H);
$^{13}$C NMR (101 MHz, DMSO) δ 182.5, 156.29 (dd, J=248.3, 6.4 Hz), 152.8 (dd, J=251.2, 8.2 Hz), 152.4, 149.8, 142.0, 139.7, 131.7, 129.9, 129.8, 128.3, 127.9, 127.7, 127.6, 123.8, 121.79 (dd, J=13.4, 3.4 Hz), 117.1, 113.5, 112.12 (dd, J=22.6, 4.3 Hz), 53.8, 16.8, 12.5;
MS: [M−1]$^−$=522.9.

Example 51f: 4-(3-(2,6-difluoro-3-(propysulfonamido)benzoyl)-1H-pyrazolo[3,4-b]pyridin-5-yl) benzamide Suzuki Coupling According to General Procedure

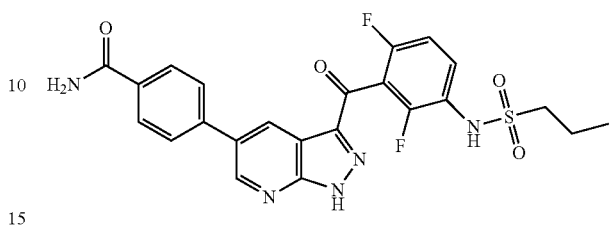

Analytical Data:
$^1$H NMR (400 MHz, DMSO) δ 14.97 (s, 1H), 9.83 (s, 1H), 9.10 (d, J=1.3 Hz, 1H), 8.83 (d, J=1.3 Hz, 1H), 8.13-7.92 (m, 5H), 7.64 (td, J=8.9, 6.2 Hz, 1H), 7.46 (s, 1H), 7.32 (t, J=8.7 Hz, 1H), 3.18-3.06 (m, 2H), 1.83-1.68 (m, 2H), 0.97 (t, J=7.5 Hz, 3H);
$^{13}$C NMR (101 MHz, DMSO) δ 182.6, 167.4, 152.4, 149.8, 142.0, 139.8, 133.7, 132.0, 128.4, 127.9, 127.2, 113.5, 53.8, 16.8, 12.6;
MS: [M−1]$^−$=498.0.

Example 51g: N-(2,4-difluoro-3-(5-(4-(methylsulfonamido)phenyl)-1H-pyrazolo[3,4-b]pyridine-3-carbonyl)phenyl)propane-1-sulfonamide

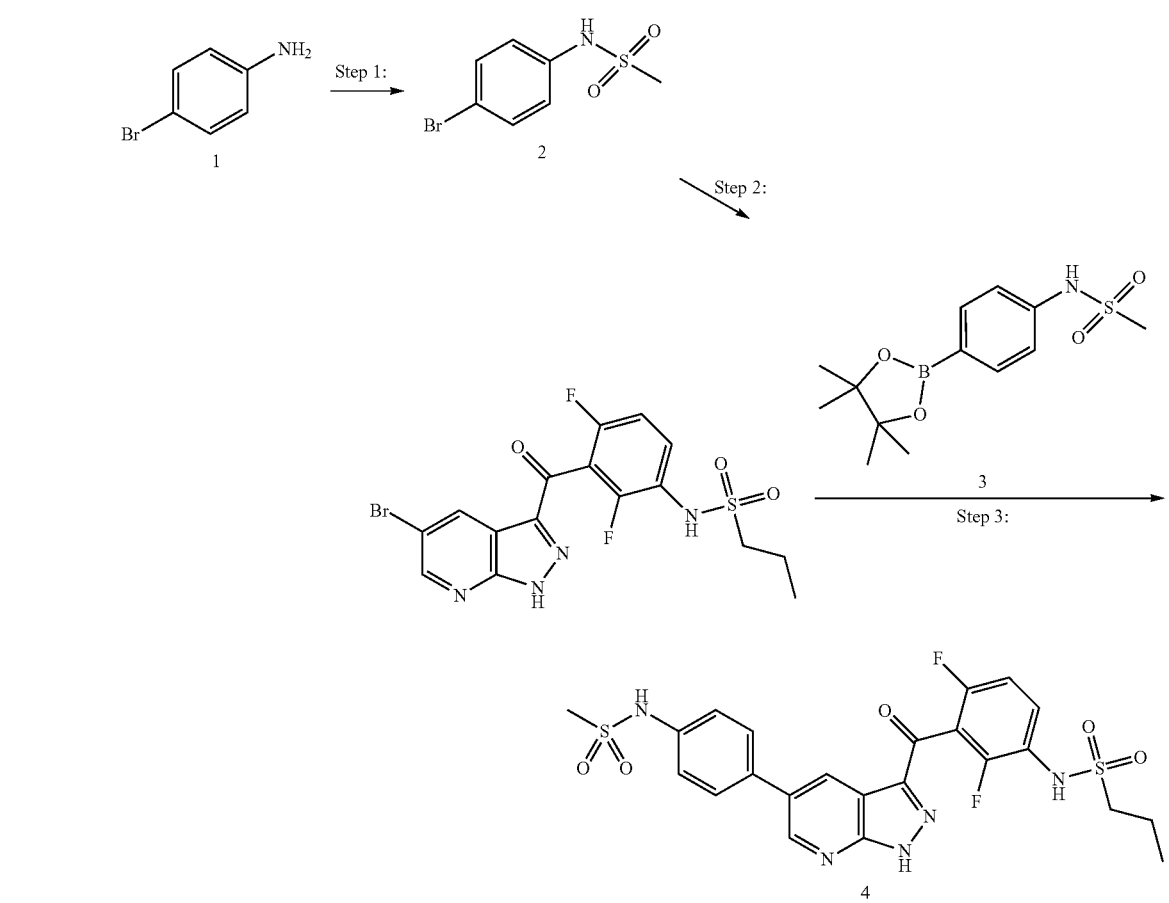

Step 1: N-(4-bromophenyl)methanesulfonamide (2)

4-bromoaniline (1, 2.08 g, 12.1 mmol) and 4-Dimethylaminopyridine (0.0739 g, 0.605 mmol) were dissolved in pyridine (12.1 mL) and methanesulfonyl chloride (1.03 mL, 13.3 mmol) was added at RT leading to an exothermic reaction. After RT was reached again (30 min) the mixture was poured into 2N HCl. The product was extracted with EtOAc, the extract washed with 2N HCl and brine, dried over $Na_2SO_4$, filtered and the solvent removed under reduced pressure and the residue triturated with n-hexane to yield N-(4-bromophenyl)methanesulfonamide (2.40 g, 9.6 mmol, 79% yield).
Analytical Data:
$^1$H NMR (200 MHz, DMSO) δ 9.91 (s, 1H), 7.60-7.42 (m, 2H), 7.22-7.09 (m, 2H), 3.00 (s, 3H);
$^{13}$C NMR (50 MHz, DMSO) δ 137.9, 132.2, 121.5, 115.9, 39.3; [M−1]$^-$=247.7.

Step 2: N-[4-(4,4,5,5-tetramethyl-1,3,2-dioxaborolan-2-yl)phenyl]methanesulfonamide (3)

A vessel was charged with N-(4-bromophenyl)methanesulfonamide (2, 252 mg, 1.01 mmol), Bis(pinacolato)diboron (281 mg, 1.11 mmol), Potassium acetate (297 mg, 3.02 mmol) and degassed dry 1,4-dioxane (5.04 mL). The vessel was evacuated and backfilled with argon (3×), XPhos Pd G4 (8.67 mg, 0.0101 mmol) was added and the mixture stirred at 85° C. for 4 h. After cooling to RT, the mixture was diluted with EtOAc and Acetic Acid (0.173 mL, 3.02 mmol), stirred for 30 minutes and filtered over Celite. The solvent was removed under reduced pressure. The residue was dissolved in a minimum amount of EtOAc, precipitated with n-heptane and the solids collected by suction filtration to yield N-[4-(4,4,5,5-tetramethyl-1,3,2-dioxaborolan-2-yl)phenyl]methanesulfonamide (281 mg, 0.9460 mmol, 94% yield) which was used without further purification.
Analytical Data:
$^1$H NMR (200 MHz, DMSO) δ 7.60 (d, J=8.5 Hz, 2H), 7.17 (d, J=8.5 Hz, 2H), 2.99 (s, 3H), 1.27 (s, 12H);
$^{13}$C NMR (50 MHz, DMSO) δ 142.4, 135.8, 117.9, 83.5, 24.7.

Step 3: Suzuki Coupling According to General Procedure

Analytical Data:
$^1$H NMR (200 MHz, DMSO) δ 14.93 (s, 1H), 9.98 (s, 1H), 9.83 (s, 1H), 9.02 (d, J=2.2 Hz, 1H), 8.73 (d, J=2.1 Hz, 1H), 7.84 (d, J=8.6 Hz, 2H), 7.64 (td, J=9.0, 6.1 Hz, 1H), 7.43-7.26 (m, 3H), 3.19-3.03 (m, 5H), 1.86-1.63 (m, 2H), 0.97 (t, J=7.4 Hz, 3H);
$^{13}$C NMR (101 MHz, DMSO) δ 182.5, 152.1, 149.6, 141.8, 138.5, 132.4, 128.3, 127.0, 120.0, 113.5, 53.8, 16.8, 12.5; [M−1]$^-$=547.8.

Example 51h: 4-(3-(2,6-difluoro-3-(propysulfonamido)benzoyl)-1H-pyrazolo[3,4-b]pyridin-5-yl)-N-methylbenzenesulfonamide Step 1: 4-bromo-N-methylbenzenesulfonamide (2)

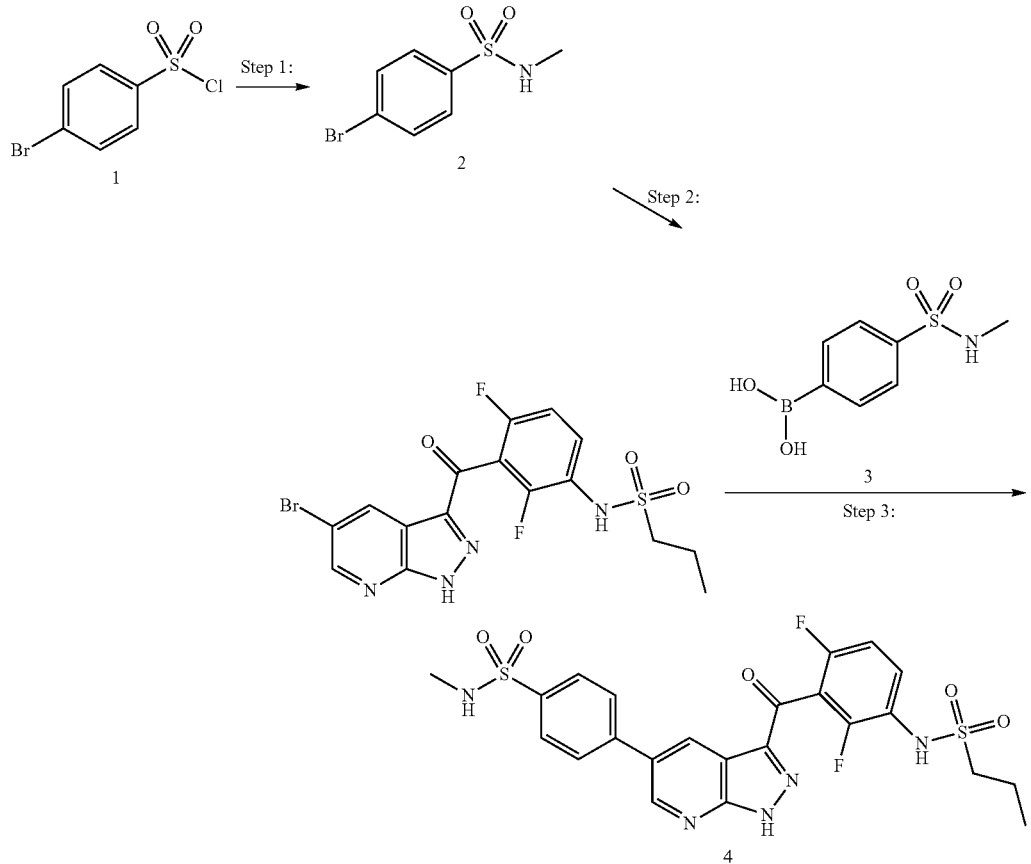

To a solution of 4-bromobenzenesulfonyl chloride (1, 2.52 g, 9.86 mmol) in tetrahydrofuran (49.3 mL) was added methylamine (14.8 mL, 29.6 mmol) 2M in THF. The reaction mixture was stirred at RT for 15 min, poured into NH$_4$Cl solution and extracted with EtOAc. The organic layer was dried over Na$_2$SO$_4$, concentrated and triturated with n-hexane to furnish 4-bromo-N-methylbenzenesulfonamide (2.15 g, 8.6 mmol, 87% yield)

Analytical Data:
$^1$H NMR (200 MHz, CDCl$_3$) δ 7.77-7.59 (m, 1H), 5.03 (dd, J=10.0, 4.9 Hz, 1H), 2.62 (d, J=5.2 Hz, 1H);
$^{13}$C NMR (50 MHz, CDCl$_3$) δ 137.8, 132.5, 128.9, 127.8, 29.3; [M−1]$^-$=247.8.

Step 2: [4-(methylsulfamoyl)phenyl]boronic acid (3)

To a solution of 4-bromo-N-methylbenzenesulfonamide (2, 1.05 g, 4.20 mmol) and triisopropyl borate (1.45 mL, 6.30 mmol) in tetrahydrofuran (8.40 mL) was added n-Butyl Lithium (4.20 mL, 10.5 mmol) at −70° C. The mixture was slowly warmed to 0° C., then 10% HCl solution was added until pH 3-4. The resulting mixture was extracted with EtOAc. The organic layer was extracted with NaOH (2M) and the aqueous phase washed with diethyl ether. The aqueous phase was acidified to pH 3, extracted with EtOAc (impurities and unconsumed reactant were still present) was dried over Na$_2$SO$_4$, and evaporated under reduced pressure. The residue was triturated with diethyl ether to give [4-(methylsulfamoyl)phenyl]boronic acid (187 mg, 0.8700 mmol, 21% yield).

Analytical Data:
$^1$H NMR (200 MHz, DMSO) δ 7.96 (d, J=8.1 Hz, 2H), 7.72 (d, J=8.0 Hz, 2H), 7.42 (q, J=4.9 Hz, 1H), 2.39 (d, J=5.0 Hz, 3H);
$^{13}$C NMR (50 MHz, DMSO) δ 140.6, 134.8, 125.7, 28.8.

Step 3: Suzuki Coupling According to General Procedure

Analytical Data:
$^1$H NMR (400 MHz, DMSO) δ 15.01 (s, 1H), 9.83 (s, 1H), 9.11 (d, J=2.1 Hz, 1H), 8.87 (d, J=2.0 Hz, 1H), 8.11 (d, J=8.3 Hz, 2H), 7.93 (d, J=8.3 Hz, 2H), 7.64 (td, J=9.0, 5.9 Hz, 1H), 7.58 (q, J=5.0 Hz, 1H), 7.32 (t, J=8.7 Hz, 1H), 3.19-3.02 (m, 2H), 1.80-1.70 (m, 2H), 0.97 (t, J=7.5 Hz, 3H);
$^{13}$C NMR (101 MHz, DMSO) δ 182.6, 152.5, 149.9, 142.0, 141.0, 138.8, 131.4, 128.4, 128.2, 127.5, 113.4, 53.8, 28.6, 16.8, 12.5;
MS: [M−1]$^-$=547.9.

Example 51i: 4-(3-(2,6-difluoro-3-(propylsulfonamido)benzoyl)-1H-pyrazolo[3,4-b]pyridin-5-yl)-N-ethylbenzenesulfonamide

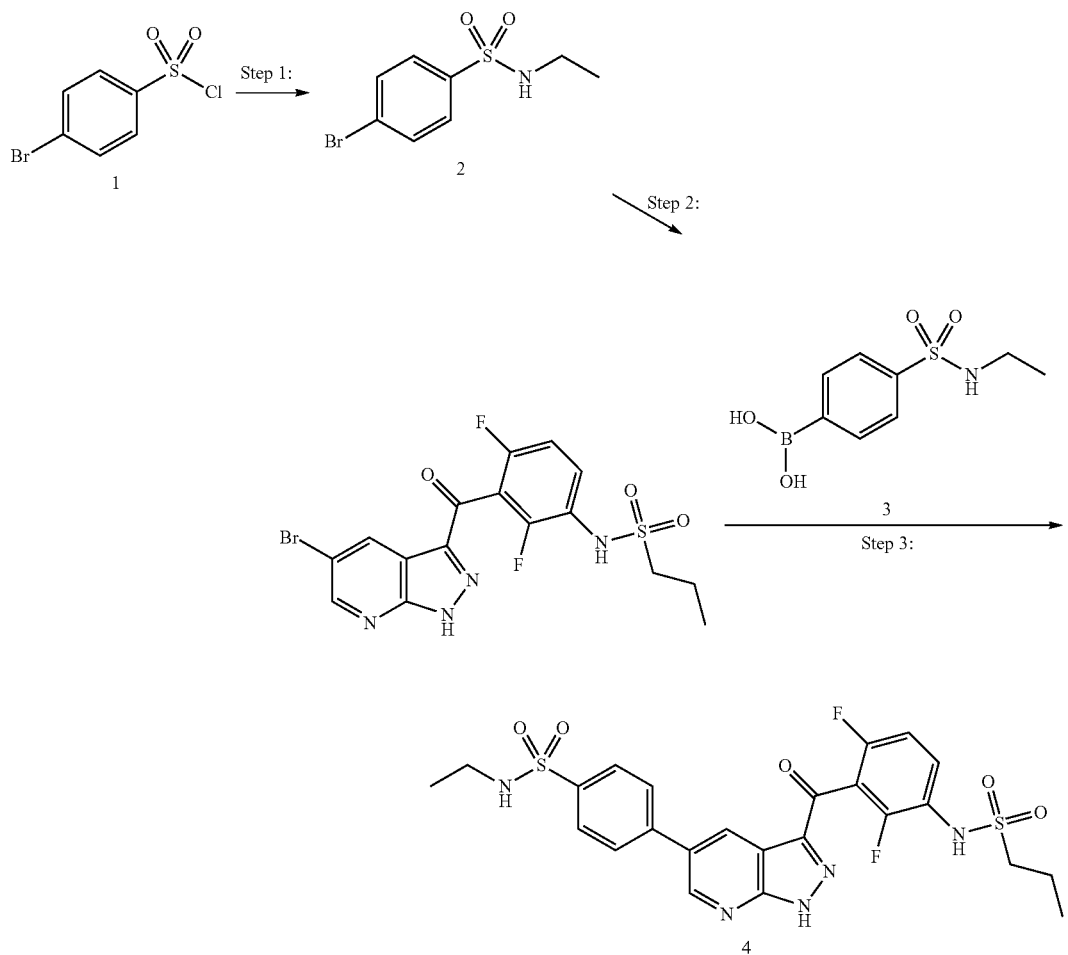

Step 1: 4-bromo-N-ethylbenzenesulfonamide (2)

4-bromobenzenesulfonyl chloride (1, 2.57 g, 10.1 mmol) was dissolved in DCM (25.1 mL). Triethylamine (3.50 mL, 25.1 mmol) and ethylamine hydrochloride (1.07 g, 13.1 mmol) were added and the mixture stirred at RT for 1 h. The mixture was diluted with half sat. NH$_4$Cl solution and extracted with EtOAc. The organic phase was washed with brine, dried over Na$_2$SO$_4$, filtered and the solvent removed under reduced pressure. The residue was triturated with n-hexane to yield 4-bromo-N-ethylbenzenesulfonamide (2.40 g, 9.09 mmol, 90% yield).

Analytical Data:
$^1$H NMR (200 MHz, CDCl$_3$) δ 7.92-7.47 (m, 4H), 5.17 (s, 1H), 3.08-2.81 (m, 2H), 1.08 (t, J=7.2 Hz, 3H);
$^{13}$C NMR (50 MHz, CDCl$_3$) δ 139.1, 132.4, 128.7, 127.6, 38.3, 15.1; [M−1]$^−$=261.7.

Step 2: [4-(ethylsulfamoyl)phenyl]boronic acid (3)

To a solution of 4-bromo-N-ethylbenzenesulfonamide (2, 1.06 g, 4.01 mmol) and triisopropyl borate (1.39 mL, 6.02 mmol) in tetrahydrofuran (20.1 mL) was added n-Butyl Lithium (4.01 mL, 10.0 mmol) at −70° C. The mixture was slowly warmed to 0° C., then 10% HCl solution was added until pH 3-4. The resulting mixture was extracted with EtOAc and the extract washed with brine, dried over Na$_2$SO$_4$, filtered and the solvent removed under reduced pressure. The residue was triturated with diethyl ether to yield [4-(ethylsulfamoyl)phenyl]boronic acid (368 mg, 1.61 mmol, 40% yield).

Analytical Data:
$^1$H NMR (200 MHz, DMSO) δ 8.41 (s, 2H), 7.94 (d, J=8.1 Hz, 2H), 7.74 (d, J=8.1 Hz, 2H), 7.52 (t, J=5.7 Hz, 1H), 2.87-2.67 (m, 2H), 0.93 (t, J=7.2 Hz, 3H);
$^{13}$C NMR (50 MHz, DMSO) δ 142.1, 135.0, 125.7, 37.9, 15.0.

Step 3: Suzuki Coupling According to General Procedure

Analytical Data:
$^1$H NMR (400 MHz, DMSO) δ 14.97 (s, 1H), 9.82 (s, 1H), 9.10 (d, J=2.1 Hz, 1H), 8.86 (d, J=2.1 Hz, 1H), 8.09 (d, J=8.3 Hz, 2H), 7.94 (d, J=8.5 Hz, 2H), 7.73-7.58 (m, 2H), 7.31 (t, J=8.7 Hz, 1H), 3.16-3.06 (m, 2H), 2.89-2.80 (m, 2H), 1.81-1.69 (m, 2H), 1.05-0.94 (m, 6H);
$^{13}$C NMR (101 MHz, DMSO) δ 182.5, 152.5, 149.8, 142.0, 140.8, 140.0, 131.4, 128.3, 128.2, 127.3, 113.4, 53.8, 37.6, 16.8, 14.8, 12.5;
MS: [M−1]$^−$=561.9.

Example 51j: 4-(3-(2,6-difluoro-3-(propysulfonamido)benzoyl)-1H-pyrazolo[3,4-b]pyridin-5-yl)-N-(2,3-dihydroxypropyl)benzenesulfonamide

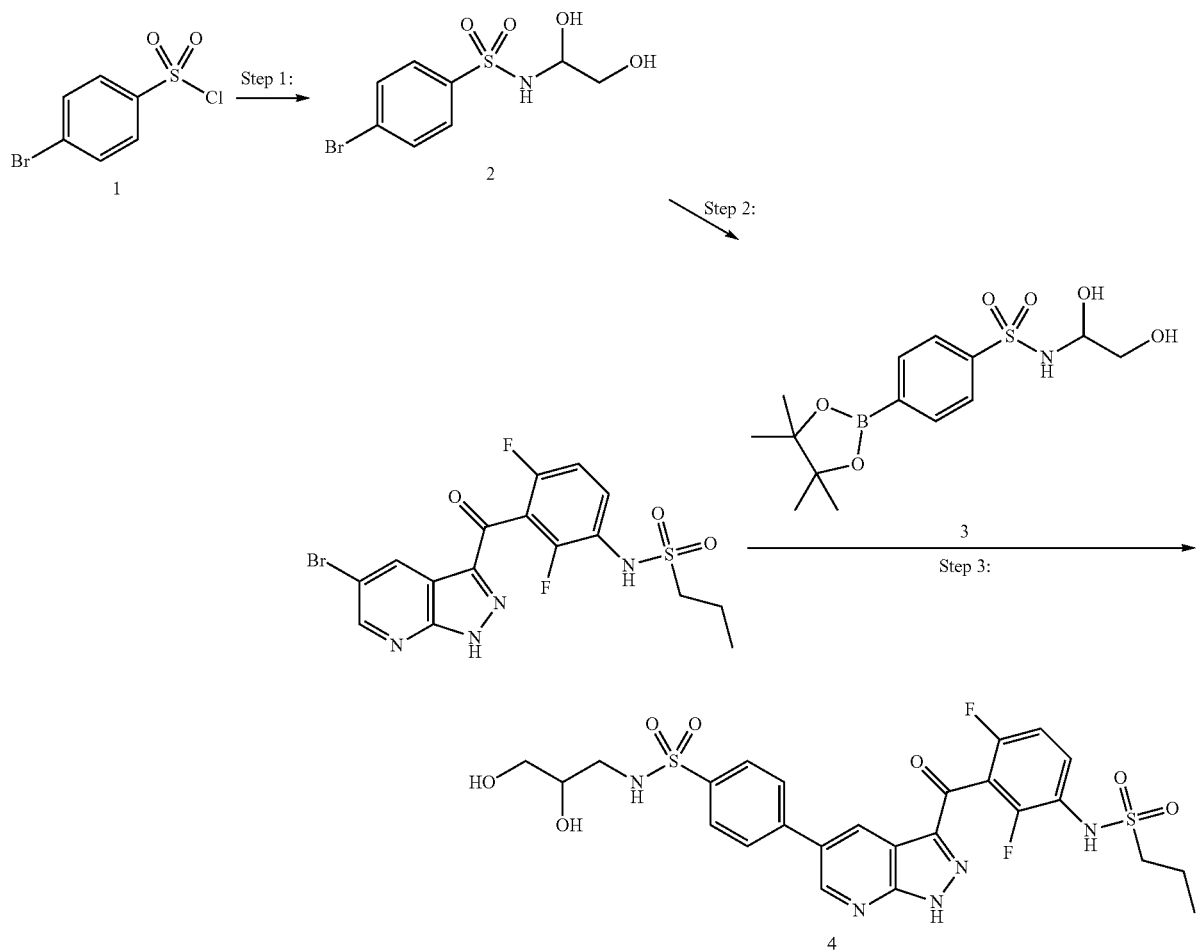

Step 1: 4-bromo-N-(2,3-dihydroxypropyl)benzenesulfonamide (2)

4-bromobenzenesulfonyl chloride (1, 2.10 g, 8.22 mmol) and triethylamine (2.29 mL, 16.4 mmol) were combined in DCM (41.1 mL). 3-aminopropane-1,2-diol (0.952 mL, 12.3 mmol) was added and the mixture stirred for 1 h at RT. After evaporation of the solvent, the residue was dissolved in EtOAc, washed with 1N HCl, water and brine. The extract was dried over $Na_2SO_4$, filtered and the solvent removed under reduced pressure. The product was washed with water and diethyl ether and dried to yield 4-bromo-N-(2,3-dihydroxypropyl)benzenesulfonamide (0.980 g, 3.16 mmol, 38% yield)

Analytical Data:
$^1$H NMR (200 MHz, DMSO) δ 7.77 (dd, J=17.1, 8.5 Hz, 5H), 4.79 (s, 1H), 4.56 (s, 1H), 3.46 (s, 1H) under water peak, 3.27 (s, 2H), 2.89 (dd, J=12.6, 4.2 Hz, 1H), 2.61 (dd, J=12.5, 7.1 Hz, 1H);
$^{13}$C NMR (50 MHz, DMSO) δ 139.9, 132.3, 128.7, 126.1, 70.3, 63.5, 46.1; [M−1]$^−$=307.8.

Step 2: N-(2,3-dihydroxypropyl)-4-(4,4,5,5-tetramethyl-1,3,2-dioxaborolan-2-yl)benzenesulfonamide (3)

A vessel was charged with 4-bromo-N-(2,3-dihydroxypropyl)benzenesulfonamide (2, 205 mg, 0.661 mmol), Potassium acetate (195 mg, 1.98 mmol), Bis(pinacolato) diboron (185 mg, 0.727 mmol) and degassed dry 1,4-dioxane (6.61 mL). The vessel was evacuated and backfilled with argon (3×), XPhos Pd G4 (5.69 mg, 0.00661 mmol) was added and the mixture stirred at 85° C. overnight. After cooling to RT, the mixture was diluted with EtOAc and stirred for 30 minutes, filtered over Celite and the solvent was removed under reduced pressure. The residue was dissolved in a minimum amount of EtOAc, precipitated with n-heptane and the solids collected by suction filtration to yield N-(2,3-dihydroxypropyl)-4-(4,4,5,5-tetramethyl-1,3,2-dioxaborolan-2-yl)benzenesulfonamide (202 mg, 0.5650 mmol, 86% yield) which was used without further purification.

Analytical Data:
$^1$H NMR (200 MHz, DMSO) δ 7.80 (q, J=8.0 Hz, 3H), 7.44 (s, 2H), 3.52-2.56 (m, 5H), 1.35-1.22 (m, 7H), 1.15 (s, 5H), 1.07 (s, 2H).

Step 3: Suzuki Coupling According to General Procedure

Analytical Data:
$^1$H NMR (400 MHz, DMSO) δ 15.00 (s, 1H), 9.82 (s, 1H), 9.11 (d, J=2.1 Hz, 1H), 8.87 (d, J=2.1 Hz, 1H), 8.09 (d, J=8.5 Hz, 2H), 7.95 (d, J=8.5 Hz, 2H), 7.68-7.60 (m, 2H), 7.32 (t, J=8.3 Hz, 1H), 4.82 (d, J=5.2 Hz, 1H), 4.58 (t, J=5.7 Hz, 1H), 3.50 (dq, J=10.6, 5.3 Hz, 1H), 3.32-3.22 (m, 2H), 3.14-3.08 (m, 2H), 2.94 (ddd, J=11.7, 6.6, 4.9 Hz, 1H), 2.66 (ddd, J=12.8, 7.0, 5.8 Hz, 1H), 1.83-1.69 (m, 2H), 0.97 (t, J=7.5 Hz, 3H);
$^{13}$C NMR (101 MHz, DMSO) δ 182.5, 152.5, 149.8, 142.0, 140.8, 140.0, 131.4, 128.3, 128.1, 127.3, 113.4, 70.3, 63.5, 53.8, 46.1, 16.8, 12.5;
MS: [M−1]$^−$=607.8.

Example 51k: N-((4-(3-(2,6-difluoro-3-(propylsulfonamido)benzoyl)-1H-pyrazolo[3,4-b]pyridin-5-yl)phenyl)sulfonyl)acetamide

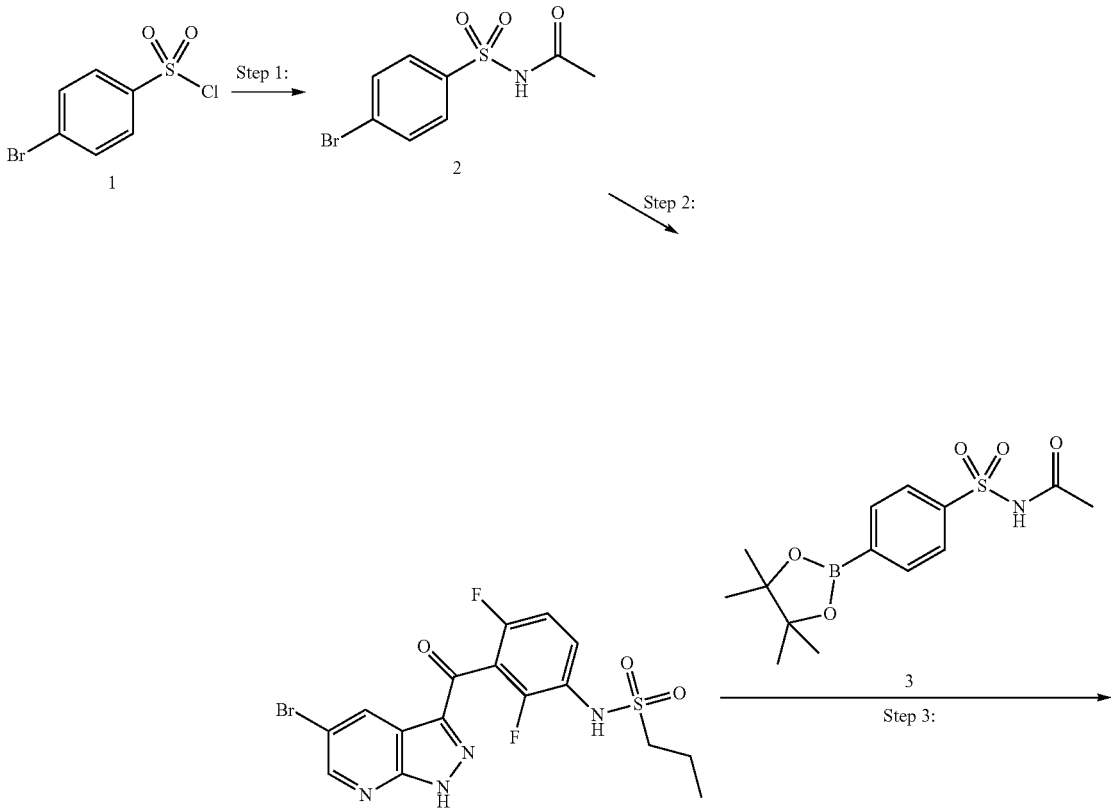

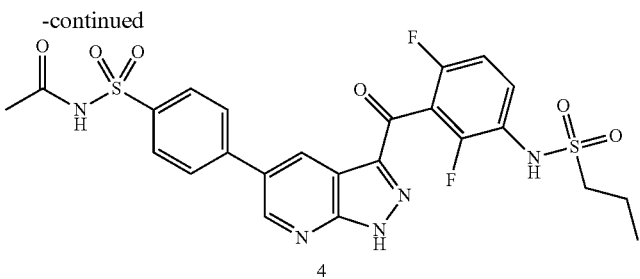

Step 1: N-(4-bromophenyl)sulfonylacetamide (2)

4-bromobenzenesulfonyl chloride (1, 2.32 g, 9.08 mmol) and acetamide (1.34 g, 22.7 mmol) (washed with diethyl ether prior to use) were dissolved in tetrahydrofuran (30.3 mL). Sodium Hydride (0.908 g, 22.7 mmol) (60%) was added portion wise at 0° C. and the mixture stirred for 2 h. The mixture was acidified with conc. HCl and water was added until phase separation occurred. The phases were separated and the aqueous extracted with EtOAc. The organic phase was washed with water and brine, dried over $Na_2SO_4$, filtered and the solvent removed under reduced pressure. The residue was triturated with water and dried in vacuo to yield N-(4-bromophenyl)sulfonylacetamide (1.33 g, 4.78 mmol, 53% yield).

Analytical Data:

$^1$H NMR (200 MHz, DMSO) δ 12.22 (s, 1H), 7.84 (s, 4H), 1.93 (s, 3H);

$^{13}$C NMR (50 MHz, DMSO) δ 169.0, 138.6, 132.3, 129.6, 127.7, 23.3; [M−1]⁻=275.8.

Step 2: N-[4-(4,4,5,5-tetramethyl-1,3,2-dioxaborolan-2-yl)phenyl]sulfonylacetamide (3)

A vessel was charged with N-(4-bromophenyl)sulfonylacetamide (2, 206 mg, 0.741 mmol), Potassium acetate (218 mg, 2.22 mmol), Bis(pinacolato)diboron (207 mg, 0.815 mmol) and degassed dry 1,4-dioxane (7.41 mL). The vessel was evacuated and backfilled with argon (3×), XPhos Pd G4 (6.37 mg, 0.00741 mmol) was added and the mixture stirred at 85° C. overnight. Additional XPhos Pd G4 and Bis(pinacolato)diboron were added and the mixture stirred for another 2 h. After cooling to RT, the mixture was diluted with EtOAc and stirred for 30 minutes and filtered over Celite. The filtrate was discarded and the filter washed with 2N HCl and EtOAc. The solvent was removed under reduced pressure and the residue triturated with n-heptane to yield N-[4-(4,4,5,5-tetramethyl-1,3,2-dioxaborolan-2-yl)phenyl]sulfonylacetamide (163 mg, 0.5010 mmol, 68% yield) which was used without further purification.

Analytical Data:

$^1$H NMR (200 MHz, DMSO) δ 12.14 (s, 1H), 8.02-7.81 (m, 4H), 1.92 (s, 3H), 1.30 (s, 12H);

$^{13}$C NMR (50 MHz, DMSO) δ 168.8, 141.8, 134.9, 126.8, 84.3, 24.6, 23.2.

Step 3: Suzuki Coupling According to General Procedure

Analytical Data:

$^1$H NMR (400 MHz, DMSO) δ 15.01 (s, 1H), 12.21 (s, 1H), 9.83 (s, 1H), 9.11 (d, J=2.1 Hz, 1H), 8.87 (d, J=2.1 Hz, 1H), 8.12 (d, J=8.5 Hz, 2H), 8.05 (d, J=8.5 Hz, 2H), 7.64 (td, J=9.0, 5.9 Hz, 1H), 7.32 (t, J=8.5 Hz, 1H), 3.11 (dd, J=5.7, 3.8 Hz, 2H), 1.96 (s, 3H), 1.83-1.69 (m, 2H), 0.97 (t, J=7.5 Hz, 3H);

$^{13}$C NMR (101 MHz, DMSO) δ 182.5, 168.9, 152.5, 149.9, 142.1, 138.8, 131.2, 128.6, 128.3, 128.1, 113.4, 53.8, 23.2, 16.8, 12.5;

MS: [M−1]⁻=575.7.

Example 511: 4-(3-(2,6-difluoro-3-(propylsulfonamido)benzoyl)-1H-pyrazolo[3,4-b]pyridin-5-yl)-N-(2,3-dihydroxypropyl)benzamide

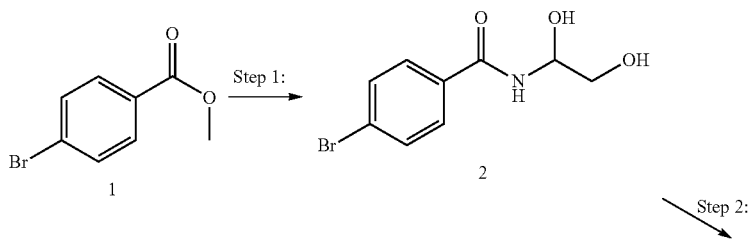

-continued

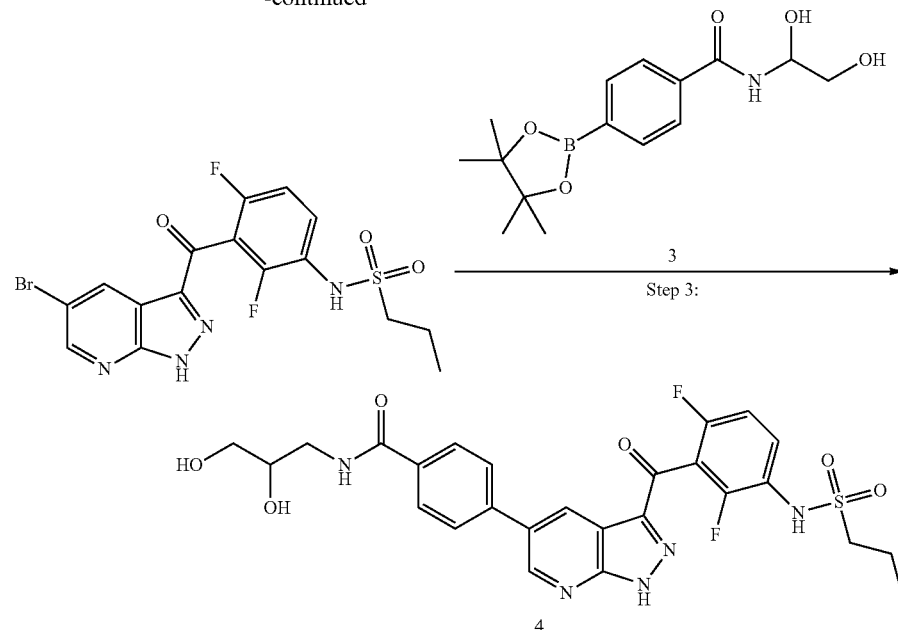

Step 1:
4-bromo-N-(2,3-dihydroxypropyl)benzamide (2)

Methyl 4-bromobenzoate (2.41 g, 11.2 mmol) and 3-aminopropane-1,2-diol (1.12 g, 12.3 mmol) were heated to 125° C. for 4 h. The mixture was diluted with MeOH, evaporated over Celite and purified over a short column. (DCM+MeOH+formic acid (99+0+1 to 90+9+1). After evaporation of the solvents, the oily residue was dried at 0.05 mbar until crystallization occurred. It was then triturated with diethyl ether to yield 4-bromo-N-(2,3-dihydroxypropyl)benzamide (1.90 g, 6.93 mmol, 62% yield) as white solid. $^1$H NMR (200 MHz, DMSO) δ 8.49 (s, 1H), 7.73 (d, J=22.1 Hz, 4H), 4.72 (d, J=48.1 Hz, 2H), 3.83-2.99 (m, 5H); $^{13}$C NMR (50 MHz, DMSO) δ 165.8, 133.7, 131.3, 129.5, 124.9, 70.4, 64.0, 43.2; [M−1]$^-$=271.7.

Step 2: N-(2,3-dihydroxypropyl)-4-(4,4,5,5-tetramethyl-1,3,2-dioxaborolan-2-yl)benzamide (3)

A vessel was charged with 4-bromo-N-(2,3-dihydroxypropyl)benzamide (656 mg, 2.39 mmol), Bis(pinacolato)diboron (669 mg, 2.63 mmol), Potassium acetate (705 mg, 7.18 mmol) and degassed dry 1,4-dioxane (12.0 mL). The vessel was evacuated and backfilled with argon (3×), XPhos Pd G3 (10.3 mg, 0.0120 mmol) was added and the mixture stirred at 85° C. 2 h. After cooling to RT, the mixture was diluted with EtOAc, stirred for 30 minutes and filtered over Celite. The solvent was removed under reduced pressure.

The residue was dissolved in a minimum amount of EtOAc, added dropwise to n-heptane with stirring and the solids collected by suction filtration to yield N-(2,3-dihydroxypropyl)-4-(4,4,5,5-tetramethyl-1,3,2-dioxaborolan-2-yl)benzamide (410 mg, 1.28 mmol, 53% yield) which was used without further purification.

Analytical Data:
$^1$H NMR (200 MHz, DMSO) δ 7.91-7.65 (m, 4H), 1.30 (s, 12H), 1.15 (s, 4H), 1.07 (s, 2H);
$^{13}$C NMR (101 MHz, DMSO) δ 134.2, 126.5, 83.8, 81.3, 73.5, 70.3, 64.0, 39.5, 24.9, 24.6, 24.4.

Step 3: Suzuki Coupling According to General Procedure

Analytical Data:
$^1$H NMR (200 MHz, DMSO) δ 9.10 (d, J=2.1 Hz, 1H), 8.83 (d, J=2.2 Hz, 1H), 8.54 (t, J=5.7 Hz, 1H), 8.00 (q, J=8.5 Hz, 4H), 7.64 (td, J=9.0, 5.8 Hz, 1H), 7.32 (td, J=9.1, 1.3 Hz, 1H), 4.87 (d, J=5.1 Hz, 1H), 4.62 (t, J=5.7 Hz, 1H), 3.80-3.58 (m, 1H), 3.26-3.02 (m, 3H), 1.75 (dq, J=14.9, 7.4 Hz, 2H), 0.97 (t, J=7.4 Hz, 3H);
$^{13}$C NMR (50 MHz, CDCl$_3$) δ 182.6, 166.1, 152.5, 142.0, 139.7, 133.9, 132.0, 128.2, 127.3, 113.6, 70.4, 64.0, 53.8, 43.1, 16.9, 12.6;
MS: [M−1]$^-$=571.7.

Example 51m: 4-(3-(2,6-difluoro-3-(propylsulfonamido)benzoyl)-1H-pyrazolo[3,4-b]pyridin-5-yl)-3-fluorobenzenesulfonamide

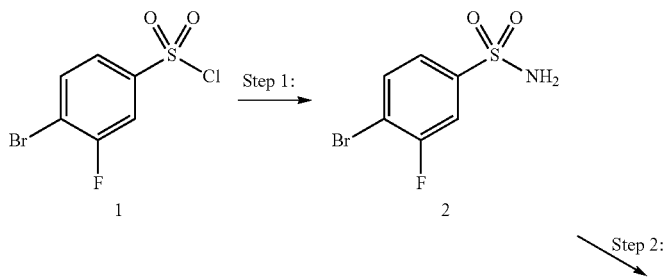

Step 1:

Step 2:

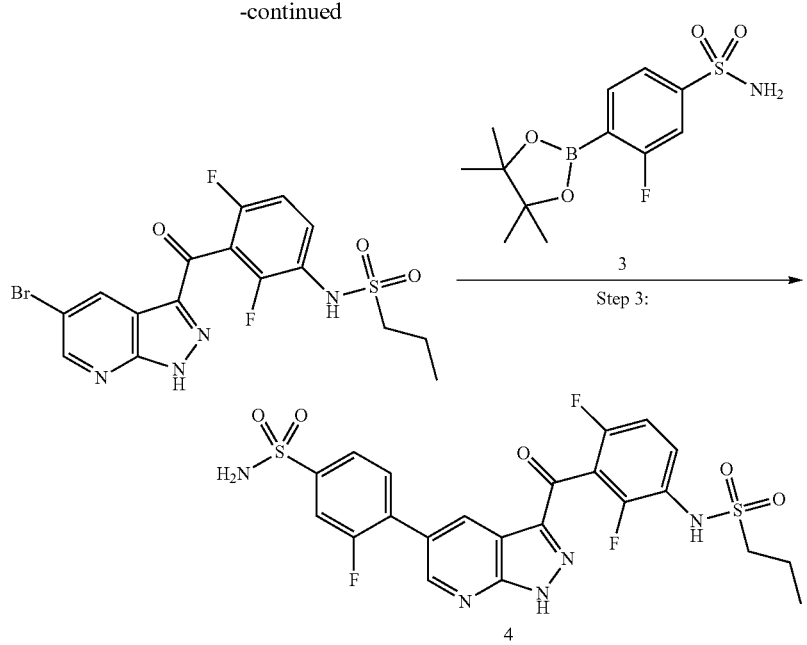

Step 1: 4-bromo-3-fluorobenzenesulfonamide (2)

To an ice cooled solution of 4-bromo-3-fluorobenzenesulfonyl chloride (1, 1.03 g, 3.77 mmol) in acetonitrile (1.88 mL) was added 25% ammonia solution (1.46 mL, 9.41 mmol) dropwise. The mixture was stirred for 10 min at RT, diluted with water and extracted with diethyl ether. The extract was washed with brine, dried over Na$_2$SO$_4$, filtered and the solvent removed under reduced pressure to yield 4-bromo-3-fluorobenzenesulfonamide (0.780 g, 3.07 mmol, 82% yield).

Analytical Data:
$^1$H NMR (200 MHz, DMSO) δ 7.95 (dd, J=8.2, 6.9 Hz, 1H), 7.75 (dd, J=8.4, 2.1 Hz, 1H), 7.64-7.57 (m, 3H);
$^{13}$C NMR (50 MHz, DMSO) δ 157.9 (d, J=249.0 Hz), 145.5 (d, J=6.1 Hz), 134.6, 123.2 (d, J=3.8 Hz), 114.1 (d, J=25.3 Hz), 112.3 (d, J=20.8 Hz).

Step 2: 3-fluoro-4-(4,4,5,5-tetramethyl-1,3,2-dioxaborolan-2-yl)benzenesulfonamide (3)

A vessel was charged with 4-bromo-3-fluorobenzenesulfonamide (2, 255 mg, 1.00 mmol), Bis(pinacolato)diboron (280 mg, 1.10 mmol), Potassium acetate (295 mg, 3.01 mmol) and degassed dry 1,4-dioxane (5.02 mL). The vessel was evacuated and backfilled with argon (3×), XPhos Pd G4 (4.32 mg, 0.00502 mmol) was added and the mixture stirred at 85° C. for overnight. After cooling to RT, the mixture was diluted with EtOAc and Acetic Acid (0.172 mL, 3.01 mmol), stirred for 30 minutes and filtered over Celite. The solvent was removed under reduced pressure. The residue was dissolved in a minimum amount of EtOAc, precipitated with n-heptane and the solids collected by suction filtration to yield 3-fluoro-4-(4,4,5,5-tetramethyl-1,3,2-dioxaborolan-2-yl)benzenesulfonamide (220 mg, 0.7310 mmol, 73% yield) which was used without further purification.

Analytical Data:
$^1$H NMR (200 MHz, DMSO) δ 7.91-7.09 (m, 5H), 1.42-0.95 (m, 12H);
$^{13}$C NMR (50 MHz, DMSO) δ 148.6 (d, J=8.2 Hz), 137.5 (d, J=8.3 Hz), 121.05 (d, J=2.1 Hz), 112.48 (d, J=27.6 Hz), 83.9, 73.6, 25.0, 24.7.

Step 3: Suzuki Coupling According to General Procedure

Analytical Data:
$^1$H NMR (200 MHz, DMSO) δ 15.06 (s, 1H), 9.83 (s, 1H), 8.95 (s, 1H), 8.81 (s, 1H), 7.99 (t, J=8.0 Hz, 1H), 7.88-7.74 (m, 2H), 7.73-7.55 (m, 3H), 7.40-7.23 (m, 1H), 3.22-2.98 (m, 2H), 1.88-1.59 (m, 2H), 0.97 (t, J=7.4 Hz, 3H).
MS: [M−1]$^-$=551.7.

Example 52

The compounds of Examples 52a-52c were prepared according to the procedure, illustrated in scheme 2.

Scheme 2

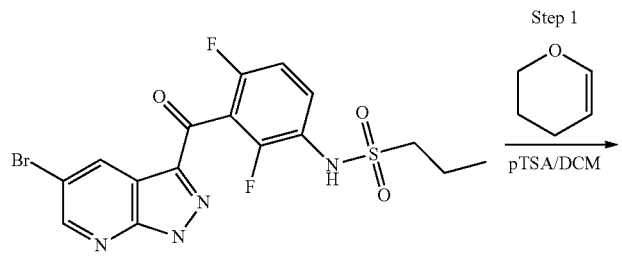

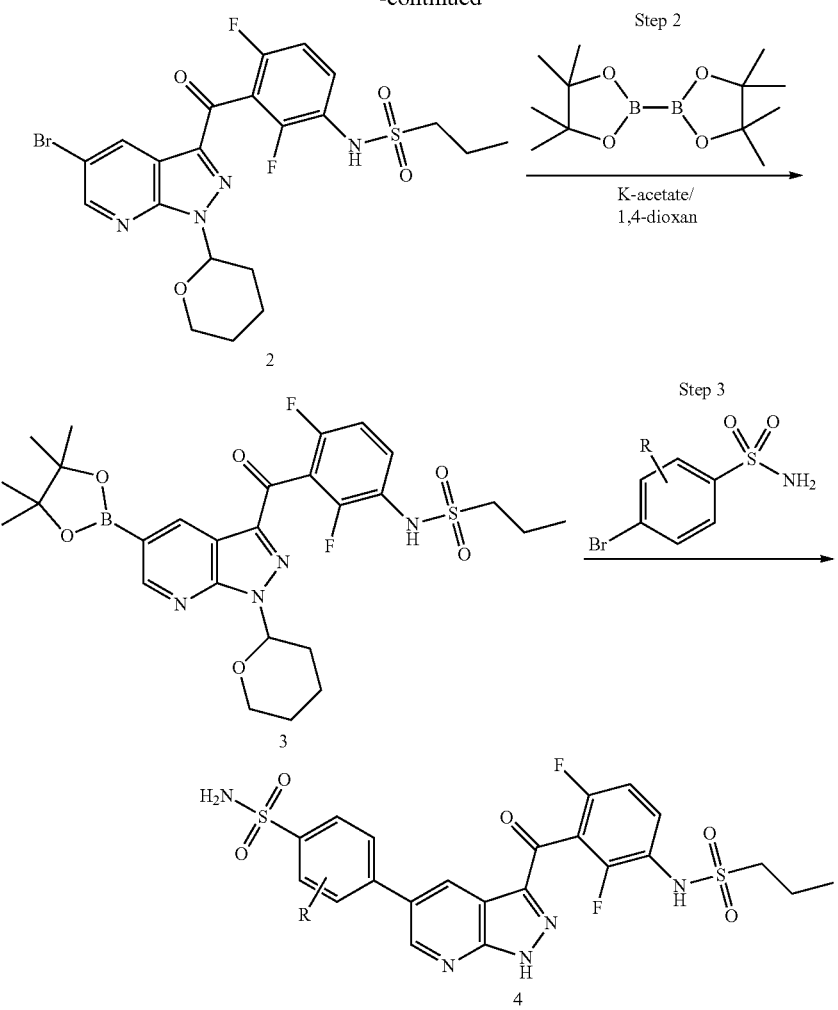

Step 1: N-[3-[5-bromo-1-(oxan-2-yl)pyrazolo[3,4-b]pyridine-3-carbonyl]-2,4-difluorophenyl]propane-1-sulfonamide (2)

To a suspensions of N-[3-(5-bromo-1H-pyrazolo[3,4-b]pyridine-3-carbonyl)-2,4-difluorophenyl] propane-1-sulfonamide (1, 0.333 g, 0.725 mmol) in DCM (2.90 mL) was added dihydropyran (0.132 mL, 1.45 mmol) and p-toluenesulfonic acid monohydrate (0.0276 g, 0.145 mmol) and the mixture was heated to reflux temperature for 45 minutes. After cooling, the mixture was washed with sat. $NaHCO_3$-solution, dried over $Na_2SO_4$, filtered and the solvent was removed under reduced pressure. The residue was dissolved in minimum amount of DCM and added dropwise to n-hexane with stirring. After 5 minutes the solids were collected by suction filtration and dried to yield N-[3-[5-bromo-1-(oxan-2-yl)pyrazolo[3,4-b]pyridine-3-carbonyl]-2,4-difluorophenyl] propane-1-sulfonamide (0.297 g, 0.5470 mmol, 75% yield), which was used without further purification.

Analytical Data:

$^1$H NMR (200 MHz, $CDCl_3$) δ 8.83 (s, 1H), 8.65 (s, 1H), 7.70 (dd, J=13.6, 8.1 Hz, 1H), 7.02 (d, J=9.6 Hz, 2H), 6.14 (d, J=9.2 Hz, 1H), 4.14-3.64 (m, 2H), 3.22-2.90 (m, 2H), 2.61-2.31 (m, 1H), 2.15-1.16 (m, 10H);

$^{13}$C NMR (50 MHz, $CDCl_3$) δ 182.4, 151.0, 149.7, 140.7, 133.7, 127.33 (d, J=8.6 Hz), 121.36 (dd, J=13.1, 3.8 Hz), 116.8, 116.6, 112.44 (dd, J=22.6, 3.7 Hz), 83.3, 77.2, 68.2, 54.1, 28.9, 24.8, 22.4, 17.3, 12.9;

MS: [M−1]$^-$=540.7.

Step 2: N-[2,4-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (3)

A vessel was charged with N-[3-[5-bromo-1-(oxan-2-yl)pyrazolo[3,4-b]pyridine-3-carbonyl]-2,4-difluorophenyl]propane-1-sulfonamide (2, 271 mg, 0.499 mmol), Bis(pinacolato)diboron (139 mg, 0.549 mmol) and anhydrous Potassium acetate (147 mg, 1.50 mmol). Degassed, dry 1,4-dioxane (4.99 mL) was added and the vessel evacuated and refilled with argon (3×). 1,1'-Bis(diphenylphosphino)ferrocene-dichloropalladium (1:1) (9.12 mg, 0.0125 mmol) was added and the mixture stirred at 85° C. for overnight. After cooling to RT the mixture was diluted with EtOAc, filtered over Celite and the solvent was removed. The residue was dissolved in DCM, petrol ether (60/90) was added and DCM removed under reduced pressure. After cooling for 1 h at 4° C. the solids were collected by suction filtration and dried to yield N-[2,4-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (267 mg, 0.4520 mmol, 91% yield) which was used without further purification.

Analytical Data:

$^1$H NMR (200 MHz, CDCl$_3$) δ 9.11 (s, 1H), 8.94 (s, 1H), 7.68 (d, J=5.9 Hz, 1H), 7.12-6.83 (m, 2H), 6.22 (d, J=9.0 Hz, 1H), 4.19-3.60 (m, 2H), 3.07 (s, 2H), 2.57-1.11 (m, 23H);

$^{13}$C NMR (50 MHz, CDCl$_3$) δ 182.5, 155.5, 152.4, 141.9, 139.3, 127.3 (d, J=9.0 Hz), 121.23 (dd, J=13.1, 4.0 Hz), 114.9, 112.33 (dd, J=23.2, 2.9 Hz), 84.4, 82.8, 77.2, 68.1, 54.1, 29.0, 24.9, 22.5, 17.2, 12.9;

MS: [M−1]$^-$=588.9.

Example 52a: 3-chloro-4-[3-[2,6-difluoro-3-(propylsulfonylamino)benzoyl]-1H-pyrazolo[3,4-b]pyridin-5-yl]benzenesulfonamide extract was washed with brine, dried over Na$_2$SO$_4$, filtered and the solvent removed under reduced pressure to yield 4-bromo-3-chlorobenzenesulfonamide (0.370 g, 1.37 mmol, 88% yield).

Analytical Data:

$^1$H NMR (200 MHz, DMSO) δ 8.01 (d, J=8.1 Hz, 2H), 7.89-7.47 (m, 3H);

$^{13}$C NMR (50 MHz, DMSO) δ 144.9, 134.8, 133.8, 127.3, 125.8, 125.5;

MS: [M−1]$^-$=267.7.

Step 2: 3-chloro-4-[3-[2,6-difluoro-3-(propylsulfonylamino)benzoyl]-1H-pyrazolo[3,4-b]pyridin-5-yl]benzenesulfonamide (3)

A vessel was charged with N-[2,4-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (71.0 mg, 0.120 mmol), Tetrakis Pd (6.95 mg, 0.00601 mmol) and 4-bromo-3-chlorobenzenesulfonamide (2, 39.0

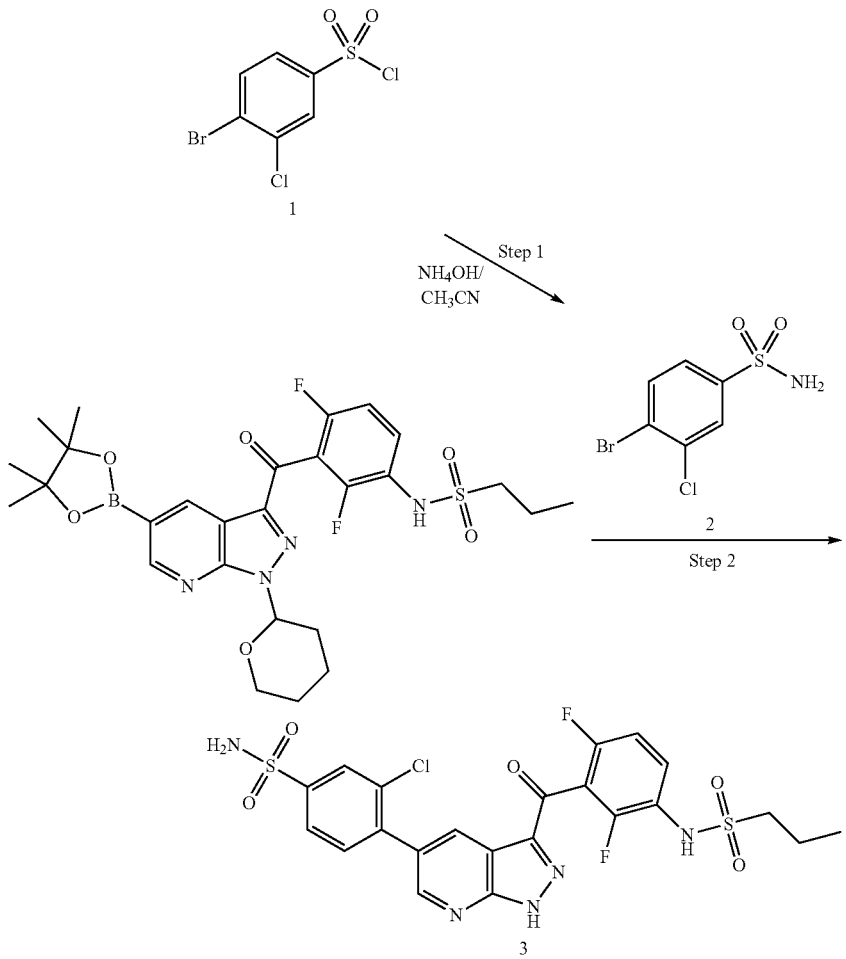

Step 1: 4-bromo-3-chlorobenzenesulfonamide (2)

To an ice cooled solution of 4-bromo-3-chlorobenzenesulfonyl chloride (1, 0.450 g, 1.55 mmol) in acetonitrile (7.76 mL) was added 25% ammonia solution (0.602 mL, 3.88 mmol) dropwise. The mixture was stirred for 10 min at RT, diluted with water and extracted with EtOAc. The mg, 0.144 mmol) and purged with argon. Degassed 1,4-dioxane (0.401 mL) and degassed aqueous 1.5M potassium carbonate (0.240 mL, 0.361 mmol) were added and the vessel was evacuated and backfilled with argon (3×). The mixture was heated to 55° C. for 1 h. The mixture was cooled to RT, diluted with iPrOH, conc. HCl was added until the mixture was strongly acidic and stirring was continued at 70° C. overnight. After cooling to RT, solid NaHCO₃ was added to neutralize the mixture, the solvents were removed and the residue purified by flash chromatography (DCM+EtOAc 20% to 60%) to yield 3-chloro-4-[3-[2,6-difluoro-3-(propylsulfonylamino)benzoyl]-1H-pyrazolo[3,4-b]pyridin-5-yl]benzenesulfonamide (23.0 mg, 0.0378 mmol, 31% yield).

Analytical Data:
$^1$H NMR (200 MHz, DMSO) δ 8.82 (d, J=2.0 Hz, 1H), 8.69 (d, J=1.8 Hz, 1H), 7.96-7.81 (m, 2H), 7.74-7.55 (m, 3H), 7.31 (t, J=8.7 Hz, 1H), 3.19-3.05 (m, 3H), 1.87-1.62 (m, 2H), 0.97 (t, J=7.5 Hz, 3H);
$^{13}$C NMR (101 MHz, DMSO) δ 183.1, 152.7, 151.3, 145.9, 142.5, 140.2, 133.4, 132.9, 131.2, 130.6, 127.3, 125.2, 122.4, 113.3, 54.4, 17.3, 13.1;
MS: [M-1]⁻=567.9.

Example 52b: 4-[3-[2,6-difluoro-3-(propylsulfonylamino)benzoyl]-1H-pyrazolo[3,4-b]pyridin-5-yl]-2-fluorobenzenesulfonamide removed under reduced pressure to yield 4-bromo-2-fluorobenzenesulfonamide (0.520 g, 2.05 mmol, 97% yield).

Analytical Data:
$^1$H NMR (200 MHz, DMSO) δ 7.87-7.67 (m, 4H), 7.60 (dd, J=8.6, 1.5 Hz, 1H);
$^{13}$C NMR (50 MHz, DMSO) δ 158 (d, J=258 Hz), 131.1 (d, J=15 Hz), 129.9, 127.9 (d, J=4 Hz), 126.4 (d, J=9 Hz), 120.5 (d, J=25 Hz);
MS: [M-1]⁻=251.8.

Step 2: 4-[3-[2,6-difluoro-3-(propylsulfonylamino)benzoyl]-1H-pyrazolo[3,4-b]pyridin-5-yl]-2-fluorobenzenesulfonamide (3)

A vessel was charged with N-[2,4-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (74.0 mg, 0.125 mmol), 4-bromo-2-fluorobenzenesulfonamide (35.0 mg, 0.138 mmol) and XPhos Pd G3 (1.06 mg, 0.00125 mmol) and purged with argon. Degassed 1,4-dioxane (0.418 mL) and degassed aqueous 1.5M Potassium

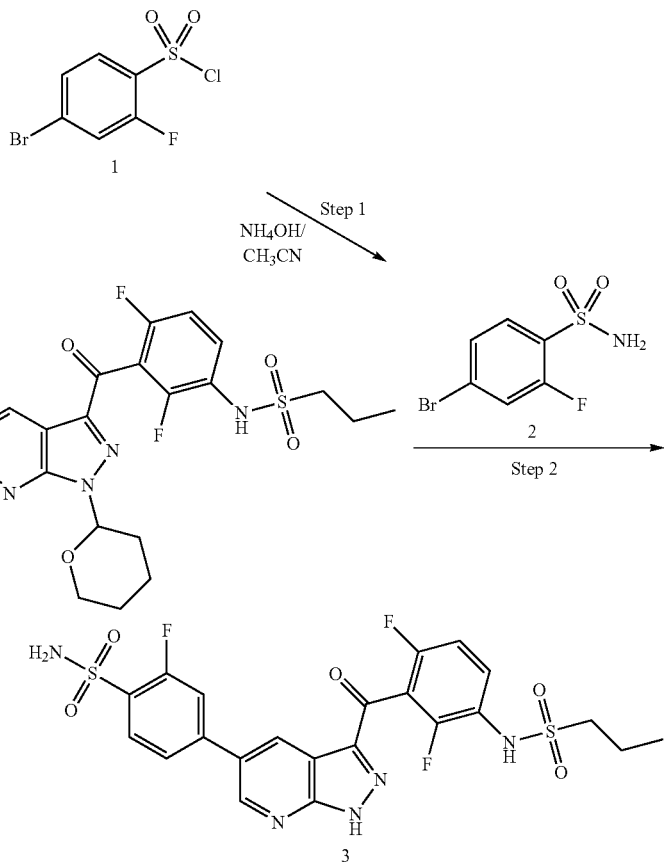

Step 1: 4-bromo-2-fluorobenzenesulfonamide (2)

To an ice cooled solution of 4-bromo-2-fluorobenzenesulfonyl chloride (1, 0.450 g, 1.55 mmol) in acetonitrile (10.6 mL) was added 25% ammonia solution (0.823 mL, 5.30 mmol) dropwise.

The mixture was stirred for 10 min at RT, diluted with water and extracted with EtOAc. The extract was washed with brine, dried over Na₂SO₄, filtered and the solvent Carbonate (0.251 mL, 0.376 mmol) were added and the vessel evacuated and backfilled with argon (3×). The mixture was heated to 55° C. for 2 h. The mixture was cooled to RT, diluted with iPrOH (3 mL), conc. HCl was added until the mixture was strongly acidic and stirring was continued at 70° C. overnight. After cooling to RT, solid NaHCO₃ was added to neutralize the mixture, the solvents were removed and the residue purified by flash chromatography (DCM+EtOAc 20% to 60%) to yield 4-[3-[2,6-difluoro-3-(propylsulfonylamino)benzoyl]-1H-pyrazolo[3,4-b]pyridin-5-yl]-2-fluorobenzene-sulfonamide (26.0 mg, 0.0460 mmol, 37% yield).

Analytical Data:
$^1$H NMR (200 MHz, DMSO) δ 15.01 (s, 1H), 9.81 (s, 1H), 9.13 (s, 1H), 8.91 (s, 1H), 8.14-7.53 (m, 6H), 7.43-7.21 (m, 1H), 3.21-3.06 (m, 2H), 1.90-1.63 (m, 2H), 0.97 (t, J=7.5 Hz, 3H);
$^{13}$C NMR (101 MHz, DMSO) δ 182.5, 159.6, 157.1, 155.0, 155.0, 154.0, 153.9, 152.5, 149.8, 143.2, 143.2, 142.0, 130.8, 130.7, 130.3, 130.2, 129.9, 129.8, 129.0, 128.6, 123.3, 123.3, 121.8, 121.8, 121.7, 121.7, 116.0, 115.7, 113.3, 112.2, 112.2, 112.0, 53.8, 16.7, 12.5, all peaks reported;
MS: [M−1]$^-$=551.9.

Example 52c: 4-[3-[2,6-difluoro-3-(propylsulfonylamino)benzoyl]-1H-pyrazolo[3,4-b]pyridin-5-yl]-3-methylbenzenesulfonamide Analytical Data:
$^1$H NMR (200 MHz, DMSO) δ 7.86-7.72 (m, 2H), 7.56 (ddd, J=8.4, 2.3, 0.5 Hz, 1H), 7.43 (s, 2H), 2.41 (s, 3H);
$^{13}$C NMR (50 MHz, DMSO) δ 143.5, 138.5, 132.8, 127.9, 125.0, 22.6;
MS: [M−1]$^-$=247.7.

Step 2: 4-[3-[2,6-difluoro-3-(propylsulfonylamino)benzoyl]-1H-pyrazolo[3,4-b]pyridin-5-yl]-3-methyl-benzenesulfonamide (3)

A vessel was charged with N-[2,4-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (75.0 mg, 0.127 mmol), 4-bromo-3-methylbenzenesulfonamide (34.9 mg, 0.140 mmol) and XPhos Pd G3 (2.69 mg, 0.00318 mmol) and purged with argon. Degassed 1,4-dioxane (0.423 mL) and degassed aqueous 1.5M Potassium Carbonate (0.254 mL, 0.381 mmol) were added and the vessel evacuated and backfilled with argon (3×). The mix-

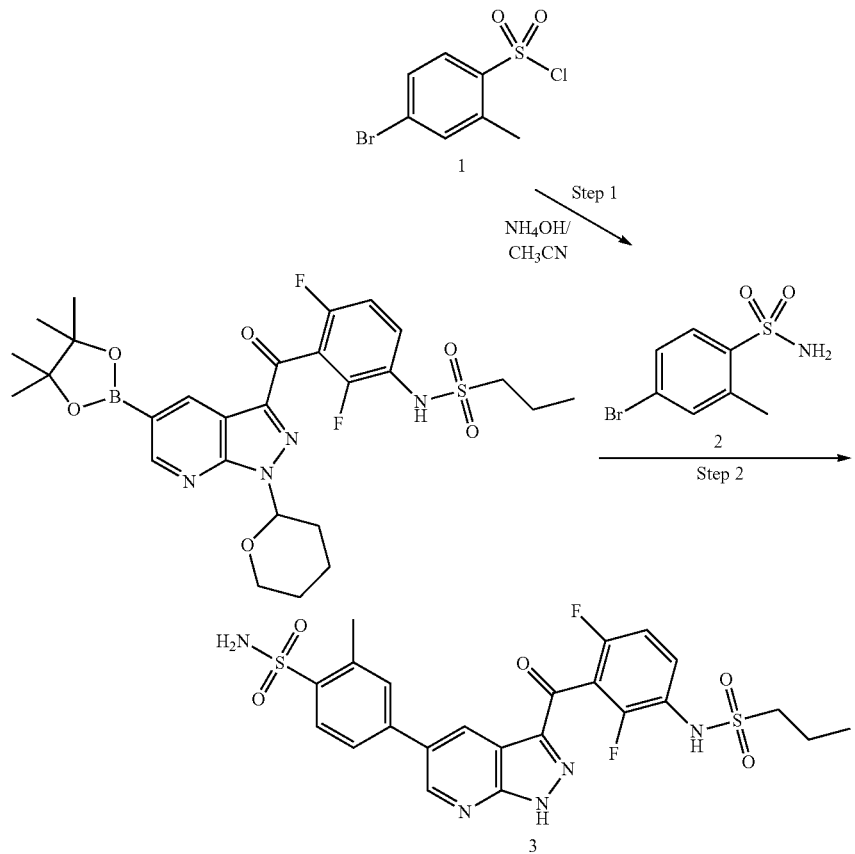

Step 1: 4-bromo-3-methylbenzenesulfonamide (2)

To an ice cooled solution of 4-bromo-3-methylbenzenesulfonyl chloride (1, 0.690 g, 2.76 mmol) in acetonitrile (1.48 mL) was added 25% ammonia solution (1.15 mL, 7.42 mmol) dropwise. The mixture was stirred for 10 min at RT, diluted with water and extracted with diethyl ether. The extract was washed with brine, dried over Na$_2$SO$_4$, filtered and the solvent removed under reduced pressure to yield 4-bromo-3-methylbenzenesulfonamide (0.690 g, 2.76 mmol, 93% yield).

ture was heated to 55° C. for 1.5 h. The solvent was removed under reduced pressure, the residue taken up THF 2 mL and 1.25M HCl in iPrOH and stirred at 70° C. overnight. The solvent was removed, the residue neutralized with NaHCO$_3$ and extracted with EtOAc. The solvent was removed and the residue purified by flash chromatography (DCM+EtOAc 10% to 50% %) and triturated with DCM to yield 4-[3-[2,6-difluoro-3-(propylsulfonylamino)benzoyl]-1H-pyrazolo[3,4-b]pyridin-5-yl]-3-methylbenzenesulfonamide (41.0 mg, 0.0739 mmol, 58% yield).

Analytical Data:

$^1$H NMR (400 MHz, DMSO) δ 15.00 (s, 1H), 9.82 (s, 1H), 8.76 (d, J=2.0 Hz, 1H), 8.55 (d, J=1.9 Hz, 1H), 7.84 (s, 1H), 7.78 (dd, J=8.0, 1.3 Hz, 1H), 7.67-7.56 (m, 2H), 7.44 (s, 2H), 7.31 (t, J=8.7 Hz, 1H), 3.16-3.07 (m, 2H), 1.80-1.69 (m, 2H), 0.97 (t, J=7.4 Hz, 3H);

$^{13}$C NMR (101 MHz, DMSO) δ 182.5, 152.0, 150.7, 143.7, 141.8, 141.0, 136.6, 132.4, 130.9, 129.9, 127.3, 123.3, 113.0, 53.8, 20.1, 16.8, 12.5;

MS: [M−1]$^-$=547.9.

Example 53

The compounds of Example 53a-53c were prepared according to the procedure, illustrated in scheme 3.

Scheme 3

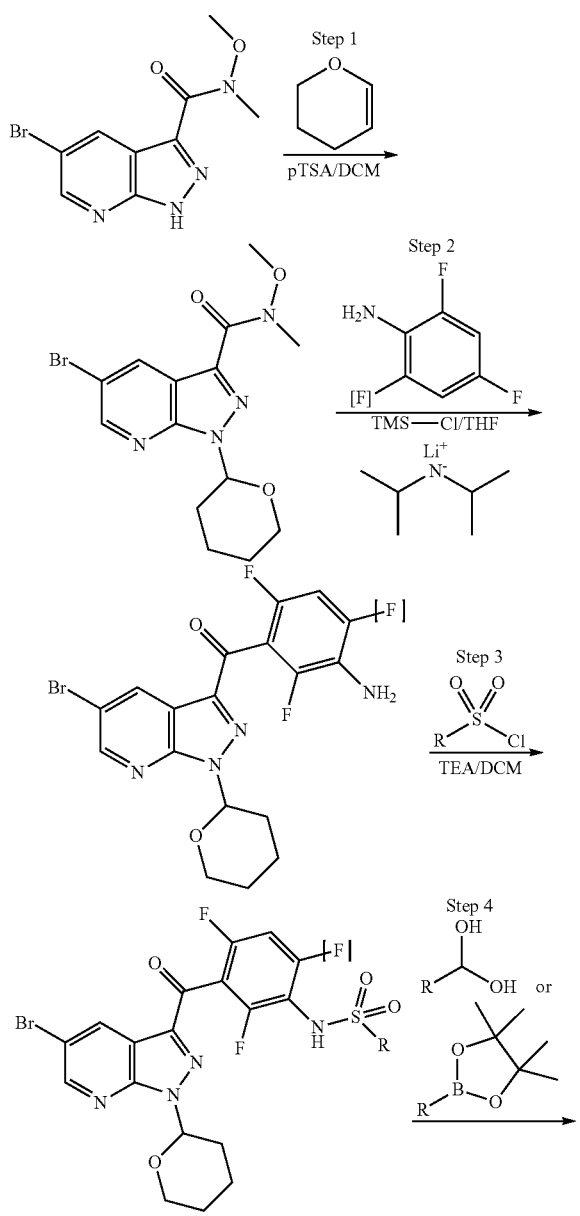

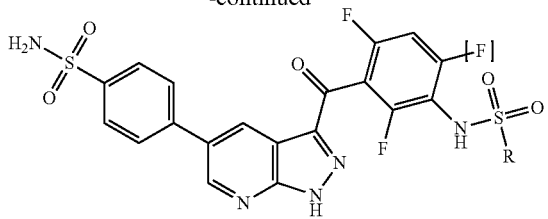

Step 1: 5-bromo-N-methoxy-N-methyl-1-(oxan-2-yl)pyrazolo[3,4-b]pyridine-3-carboxamide To a suspensions of 5-bromo-N-methoxy-N-methyl-1H-pyrazolo[3,4-b]pyridine-3-carboxamide (4.43 g, 15.5 mmol) in DCM (62.2 mL) was added dihydropyran (2.84 mL, 31.1 mmol) and p-Toluenesulfonic acid monohydrate (0.591 g, 3.11 mmol) and the mixture was heated to reflux temperature for 30 minutes. After cooling, the mixture was washed with sat. NaHCO$_3$-solution and brine, dried over Na$_2$SO$_4$, filtered and the solvent was removed under reduced pressure. The residue was purified by flash chromatography (hexane+ EtOAc 10% to 50%) to yield 5-bromo-N-methoxy-N-methyl-1-(oxan-2-yl)pyrazolo[3,4-b]pyridine-3-carboxamide (5.05 g, 13.7 mmol, 88% yield) as oil, which solidified after drying in high vacuum and standing.

Analytical Data:

$^1$H NMR (200 MHz, CDCl$_3$) δ 8.69 (d, J=2.0 Hz, 1H), 8.58 (d, J=2.2 Hz, 1H), 6.12 (dd, J=10.0, 2.4 Hz, 1H), 4.15-4.01 (m, 1H), 3.93-3.71 (m, 4H), 3.54 (s, 3H), 2.71-2.48 (m, 1H), 2.22-1.65 (m, 5H);

$^{13}$C NMR (50 MHz, CDCl$_3$) δ 150.5, 149.0, 136.5, 134.2, 118.3, 115.1, 83.0, 68.2, 61.9, 29.2, 25.0, 22.8;

MS: [M+H]$^+$=390.8.

Step 2a: (3-amino-2,6-difluorophenyl)-[5-bromo-1-(oxan-2-yl)pyrazolo[3,4-b]pyridin-3-yl]methanone

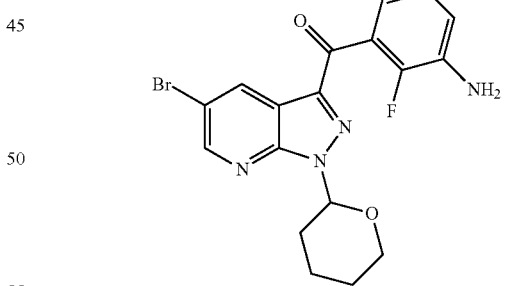

To a solution of 2,4-difluoroaniline (0.815 g, 6.32 mmol) and Chlorotrimethylsilane (1.60 mL, 12.6 mmol) in tetrahydrofuran (5.74 mL) cooled to −78° C. was added 2M Lithium diisopropylamide (6.32 mL, 12.6 mmol) in THF/heptane/ethylbenzene dropwise. The mixture was warmed to RT and stirred for 30 minutes. 5-bromo-N-methoxy-N-methyl-1-(oxan-2-yl)pyrazolo[3,4-b]pyridine-3-carboxamide (1.06 g, 2.87 mmol) was added and the mixture cooled to −30° C. Lithium diisopropylamide (3.16 mL, 6.32 mmol) in THF/heptane/ethylbenzene was added dropwise and the mixture stirred at −15° C. for 10 minutes. 2N HCl (20 mL)

was added and stirring continued at RT for 20 minutes. The mixture was adjusted to pH ~9 with 2N NaOH and extracted with EtOAc. The extract was washed with brine, dried over Na$_2$SO$_4$, filtered and the solvent was removed. The residue was purified by flash chromatography (hexane+EtOAc, 10% to 40%) to yield (3-amino-2,6-difluorophenyl)-[5-bromo-1-(oxan-2-yl)pyrazolo[3,4-b]pyridin-3-yl]methanone (0.732 g, 1.67 mmol, 58% yield) as yellow solid.

Analytical Data:
$^1$H NMR (200 MHz, DMSO) δ 8.86 (d, J=2.2 Hz, 1H), 8.79 (d, J=2.2 Hz, 1H), 7.31-6.69 (m, 2H), 6.14 (dd, J=9.8, 2.0 Hz, 1H), 5.28 (s, 2H), 4.02-3.85 (m, 1H), 3.81-3.62 (m, 1H), 2.42-2.14 (m, 1H), 2.04-1.46 (m, 5H);
$^{13}$C NMR (50 MHz, DMSO) δ 183.7, 151.0, 149.1, 140.3, 132.8, 116.3, 115.5, 82.9, 67.1, 28.4, 24.4, 21.6;
MS: [M+Na]$^+$=458.9.

Step 2b: (3-amino-2,4,6-trifluorophenyl)-[5-bromo-1-(oxan-2-yl)pyrazolo[3,4-b]pyridin-3-yl]methanone

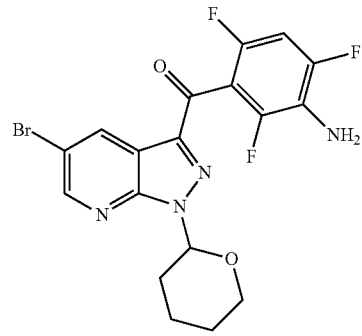 [SMILES: Nc1c(F)cc(F)c(C(=O)c2nn(C3CCCCO3)c3ncc(Br)cc23)c1F]

To a solution of 2,4,6-trifluoroaniline (0.789 g, 5.36 mmol) and Chlorotrimethylsilane (1.36 mL, 10.7 mmol) in tetrahydrofuran (4.88 mL) cooled to −78° C. was added 2M Lithium diisopropylamide (5.36 mL, 10.7 mmol) in THF/heptane/ethylbenzene dropwise. The mixture was warmed to RT and stirred for 30 minutes. 5-bromo-N-methoxy-N-methyl-1-(oxan-2-yl)pyrazolo[3,4-b]pyridine-3-carboxamide (0.900 g, 2.44 mmol) was added and the mixture cooled to −30° C. Lithium diisopropylamide (2.68 mL, 5.36 mmol) in THF/heptane/ethylbenzene was added dropwise and the mixture was stirred at −15° C. for 20 minutes. 2N HCl (20 mL) was added and stirring continued at RT for 10 minutes. The mixture pH was adjusted to pH 9 using 2N NaOH and extracted with EtOAc. The extracts were washed with brine, dried over Na$_2$SO$_4$ und the solvent was removed. TLC-MS revealed almost no deprotection of TMS-groups. The residue was dissolved in 10 mL THF, 1 mL conc. HCl was added. Deprotection was complete immediately. After dilution with EtOAc solid K$_2$CO$_3$ was added, the suspension filtered and the solvent removed. The residue was purified by flash chromatography (hexane+EtOAc 5% to 25%). Yield: 715 mg, 64%.

Analytical Data:
$^1$H NMR (200 MHz, DMSO) δ 8.85 (d, J=2.1 Hz, 1H), 8.79 (d, J=2.2 Hz, 1H), 7.34-7.16 (m, 1H), 6.14 (d, J=8.4 Hz, 1H), 5.36 (s, 2H), 4.03-3.82 (m, 1H), 3.84-3.58 (m, 1H), 2.44-2.17 (m, 1H), 2.05-1.51 (m, 5H);
$^{13}$C NMR (50 MHz, DMSO) δ 182.7, 151.0, 149.2, 140.2, 132.8, 116.3, 115.5, 82.9, 67.0, 28.4, 24.4, 21.6;
MS: [M+Na]$^+$=476.9.

Example 53a: 4-[3-[2,6-difluoro-3-(phenylsulfamoylamino)benzoyl]-1H-pyrazolo[3,4-b]pyridin-5-yl]benzenesulfonamide

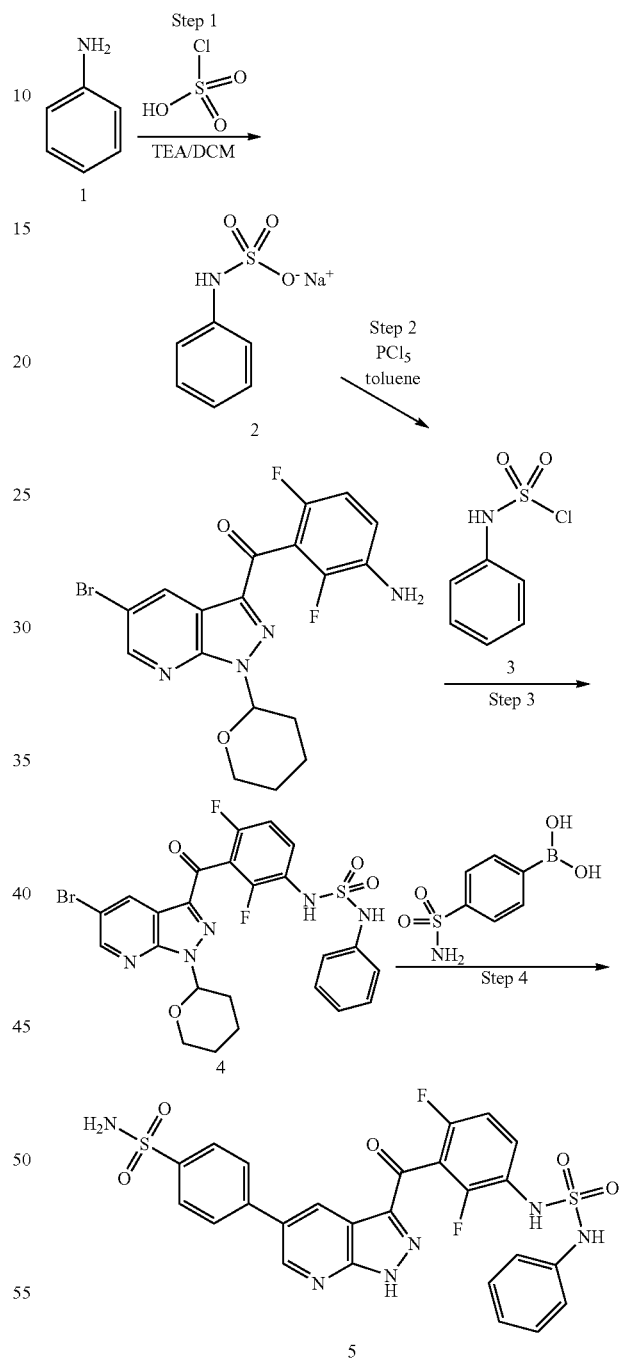

Step 1: Preparation of sodium N-phenylsulfamate (2)

Aniline (1, 3.95 g, 42.4 mmol) and Triethylamine (59.1 mL, 424 mmol) were dissolved in DCM (106 mL). Chlorosulfuric acid (2.82 mL, 42.4 mmol) was added drop wise at −5° C. and the mixture stirred for 10 minutes. The mixture was concentrated in vacuo and the solid dissolved in 1N Sodium hydroxide (84.8 mL, 84.8 mmol). The mixture was concentrated in vacuo to dryness. The product was suspended in about 500 mL boiling EtOH, filtered while hot and reduced to about 150 mL. After cooling to 7° C. overnight the product was collected by filtration and dried under vacuum to give sodium N-phenylsulfamate (3.94 g, 20.2 mmol, 48% yield) as a white solid.

Analytical Data:
$^1$H NMR (200 MHz, DMSO) δ 7.90 (s, 1H), 7.15-7.01 (m, 4H), 6.74-6.63 (m, 1H);
$^{13}$C NMR (50 MHz, DMSO) δ 143.7, 128.2, 118.5, 116.3.

Step 2: Preparation of phenylsulfamoyl chloride (3)

Sodium N-phenylsulfamate (2, 1.12 g, 5.74 mmol) and Phosphorus pentachloride (1.20 g, 5.74 mmol) were heated in toluene (19.1 mL) at 80° C. in an oil bath for 6 h. The reaction was filtered and concentrated in vacuo to yield N-phenylsulfamoyl chloride (0.990 g, 5.17 mmol, 90% yield) as oil which solidifies upon standing. Product was used without further purification and characterization.

Step 3: [5-bromo-1-(oxan-2-yl)pyrazolo[3,4-b]pyridin-3-yl]-[2,6-difluoro-3-(phenylsulfamoylamino)phenyl]methanone (4)

To a solution of (3-amino-2,6-difluorophenyl)-[5-bromo-1-(oxan-2-yl)pyrazolo[3,4-b]pyridin-3-yl]methanone (0.127 g, 0.290 mmol) and Triethylamine (0.0607 mL, 0.436 mmol) in DCM (1.45 mL) was added N-phenylsulfamoyl chloride (0.0724 g, 0.378 mmol) in DCM (1.45 mL) at 0° C. After stirring for 10 minutes at RT, the mixture was diluted with DCM, washed with water and NH$_4$Cl solution, dried over Na$_2$SO$_4$, filtered and the solvent was removed under reduced pressure to yield [5-bromo-1-(oxan-2-yl)pyrazolo[3,4-b]pyridin-3-yl]-[2,6-difluoro-3-(phenylsulfamoylamino)phenyl]methanone (0.170 g, 0.2870 mmol, 99% yield) which was used without further purification. To the sticky oil was added 2 mL Et$_2$O and the solvent was quickly removed in vacuo to obtain the product as foamed solid.

Analytical Data:
$^1$H NMR (200 MHz, CDCl$_3$) δ 8.89 (d, J=2.1 Hz, 1H), 8.71 (d, J=2.1 Hz, 1H), 7.73 (td, J=8.9, 5.4 Hz, 1H), 7.47-6.97 (m, 8H), 6.21 (dd, J=9.7, 2.1 Hz, 1H), 3.97 (dd, J=46.6, 10.1 Hz, 2H), 2.66-2.39 (m, 1H), 2.22-1.56 (m, 5H);
$^{13}$C NMR (50 MHz, CDCl$_3$) δ 182.4, 151.0, 149.6, 140.7, 136.0, 133.7, 129.5, 125.8, 121.6, 116.8, 116.6, 83.4, 68.2, 29.0, 24.8, 22.4;
MS: [M−1]$^-$=589.8.

Step 4: 4-[3-[2,6-difluoro-3-(phenylsulfamoylamino)benzoyl]-1H-pyrazolo[3,4-b]pyridin-5-yl]benzenesulfonamide (5)

A vessel was charged with [5-bromo-1-(oxan-2-yl)pyrazolo[3,4-b]pyridin-3-yl]-[2,6-difluoro-3-(phenylsulfamoylamino)phenyl]methanone (4, 0.0880 g, 0.149 mmol), (4-sulfamoylphenyl)boronic acid (32.8 mg, 0.163 mmol) and XPhos Pd G3 (3.77 mg, 0.00446 mmol) and purged with argon. Degassed 1,4-dioxane (0.495 mL) and degassed 1.5M aqueous Potassium Carbonate (0.297 mL, 0.446 mmol) was added and the mixture was stirred at 65° C. for 1.5 h. Sat. NH$_4$Cl solution and EtOAc were added and the phases were separated. The organic phase was dried over Na$_2$SO$_4$ and evaporated. The residue was taken up in THF (3 mL) and TFA (300 µL) were added at RT. After stirring overnight another 300 µL TFA were added and stirring continued for 2 h (10-12 h). (Still no conversion) The mixture was concentrated and taken up in DCM (3 mL) and sonicated. Another 300 µL TFA were added and stirring continued at RT. After 3 h 3 mL TFA were added at RT and the mixture was stirred overnight and quenched into NaHCO$_3$ solution. The aqueous was extracted with EtOAc, the extract was dried over Na$_2$SO$_4$ and the solvent was removed. The product was purified by flash chromatography (DCM+MeOH 3% to 13%) to furnish 4-[3-[2,6-difluoro-3-(phenylsulfamoylamino)benzoyl]-1H-pyrazolo[3,4-b]pyridin-5-yl]benzenesulfonamide (34.0 mg, 0.0547 mmol, 37% yield).

Analytical Data:
$^1$H NMR (200 MHz, DMSO) δ 14.96 (s, 1H), 10.20 (s, 1H), 10.09 (s, 1H), 9.09 (d, J=1.9 Hz, 1H), 8.84 (d, J=1.9 Hz, 1H), 8.14-7.89 (m, 4H), 7.60-7.41 (m, 3H), 7.37-7.15 (m, 5H), 7.02 (t, J=6.9 Hz, 1H);
MS: [M−1]$^-$=583.0.

Example 53b: 4-[3-[2,6-difluoro-3-(sulfamoylamino)benzoyl]-1H-pyrazolo[3,4-b]pyridin-5-yl]benzenesulfonamide

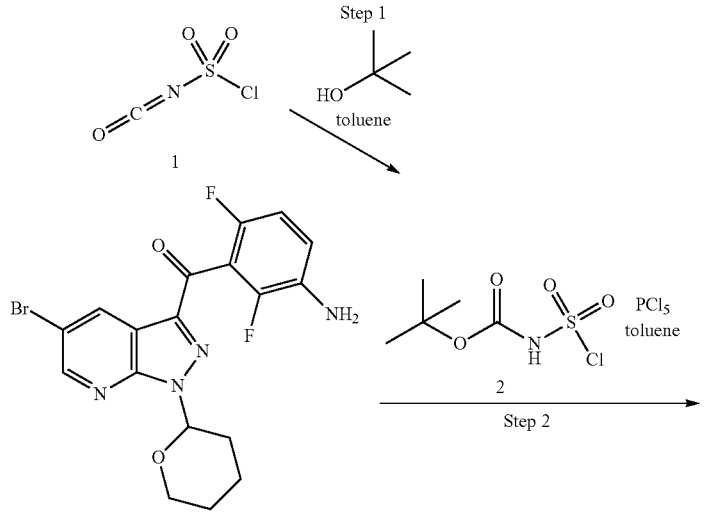

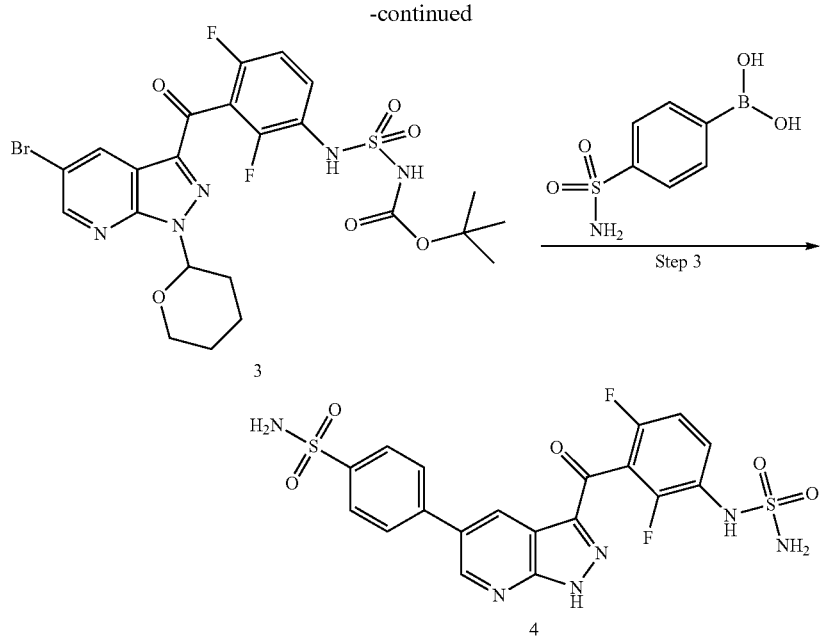

Step 1: Preparation of tert-butyl N-chlorosulfonylcarbamate (2)

To a solution of chlorosulfonylisocyanate (1, 1.78 mL, 20.4 mmol) in toluene (8.17 mL) was slowly added a solution of 2-methylpropan-2-ol (1.66 g, 22.5 mmol) in toluene (1.16 mL). The mixture was stirred at RT for 1 h. Hexane (23.1 mL) was added and the solution was stirred for 30 minutes. The precipitate formed was filtered and washed with hexane to give tert-butyl N-chlorosulfonylcarbamate (3.33 g, 15.4 mmol, 76% yield) as white solid which was stored under nitrogen at −20° C.
Analytical Data:
$^1$H NMR (200 MHz, CDCl$_3$) δ 8.86 (s, 1H), 1.56 (s, 9H); $^{13}$C NMR (50 MHz, CDCl$_3$) δ 148.0, 87.3, 27.9.

Step 2: tert-butyl N-[[3-[5-bromo-1-(oxan-2-yl)pyrazolo[3,4-b]pyridine-3-carbonyl]-2,4-difluorophenyl]sulfamoyl]carbamate (3)

To a solution of (3-amino-2,6-difluorophenyl)-[5-bromo-1-(oxan-2-yl)pyrazolo[3,4-b]pyridin-3-yl]methanone (3, 0.126 g, 0.288 mmol) and Triethylamine (0.0602 mL, 0.432 mmol) in DCM (1.15 mL) was added tert-butyl N-chlorosulfonylcarbamate (0.0808 g, 0.375 mmol) in DCM (1 mL) at 0° C. After stirring for 10 minutes at RT, the mixture was diluted with DCM, washed with water and NH$_4$Cl solution, dried over Na$_2$SO$_4$, filtered and the solvent was removed under reduced pressure to yield tert-butyl N-[[3-[5-bromo-1-(oxan-2-yl)pyrazolo[3,4-b]pyridine-3-carbonyl]-2,4-difluorophenyl]sulfamoyl]carbamate (0.176 g, 0.2860 mmol, 99% yield) as yellow foam which was used without further purification.
Analytical Data:
$^1$H NMR (200 MHz, CDCl$_3$) δ 8.89 (d, J=1.8 Hz, 1H), 8.70 (d, J=1.8 Hz, 1H), 7.74 (td, J=8.9, 5.8 Hz, 1H), 7.06 (t, J=8.4 Hz, 1H), 6.19 (d, J=7.6 Hz, 1H), 4.08 (d, J=11.1 Hz, 1H), 3.91-3.72 (m, 1H), 2.66-2.39 (m, 1H), 2.22-1.90 (m, 2H), 1.88-1.57 (m, 3H), 1.45 (s, 9H);

$^{13}$C NMR (50 MHz, CDCl$_3$) δ 182.4, 151.0, 150.4, 149.7, 140.7, 133.7, 116.8, 116.6, 84.2, 83.5, 77.2, 68.2, 46.0, 27.9, 24.8, 22.4.

MS: [M−1]$^−$=613.9.

Step 3: 4-[3-[2,6-difluoro-3-(sulfamoylamino)benzoyl]-1H-pyrazolo[3,4-b]pyridin-5-yl]benzenesulfonamide (4)

A vessel was charged with tert-butyl N-[[3-[5-bromo-1-(oxan-2-yl)pyrazolo[3,4-b]pyridine-3-carbonyl]-2,4-difluorophenyl]sulfamoyl]carbamate (3, 129 mg, 0.209 mmol), (4-sulfamoylphenyl)boronic acid (46.3 mg, 0.230 mmol) and XPhos Pd G3 (5.31 mg, 0.00628 mmol) and purged with argon. Degassed 1,4-dioxane (0.698 mL) and degassed 1.5M aqueous Potassium Carbonate (0.419 mL, 0.628 mmol) was added and the mixture was stirred at 65° C. for 1.5 h. Sat. NH$_4$Cl solution and EtOAc were added and the phases were separated. The organic phase was dried over Na$_2$SO$_4$ and evaporated. The residue was taken up in DCM (3 mL) and TFA (300 µL) was added at RT. After stirring overnight the mixture was quenched into NaHCO$_3$ solution and extracted with EtOAc. The extract was dried over Na$_2$SO$_4$ and the solvent was removed. The product was purified by flash chromatography (DCM+MeOH 1% to 11%) to furnish 4-[3-[2,6-difluoro-3-(sulfamoylamino)benzoyl]-1H-pyrazolo[3,4-b]pyridin-5-yl]benzenesulfonamide (37.0 mg, 0.0728 mmol, 35% yield).
Analytical Data:
$^1$H NMR (200 MHz, DMSO) δ 14.96 (s, 1H), 9.32 (s, 1H), 9.10 (d, J=2.0 Hz, 1H), 8.86 (d, J=2.0 Hz, 1H), 8.02 (dd, J=20.7, 8.4 Hz, 4H), 7.68 (td, J=8.9, 5.9 Hz, 1H), 7.47 (s, 2H), 7.36-7.13 (m, 3H);
MS: [M−1]$^−$=507.0.

Example 53c: 4-[3-[2,4,6-trifluoro-3-(propylsulfonylamino)benzoyl]-1H-pyrazolo[3,4-b]pyridin-5-yl]benzenesulfonamide

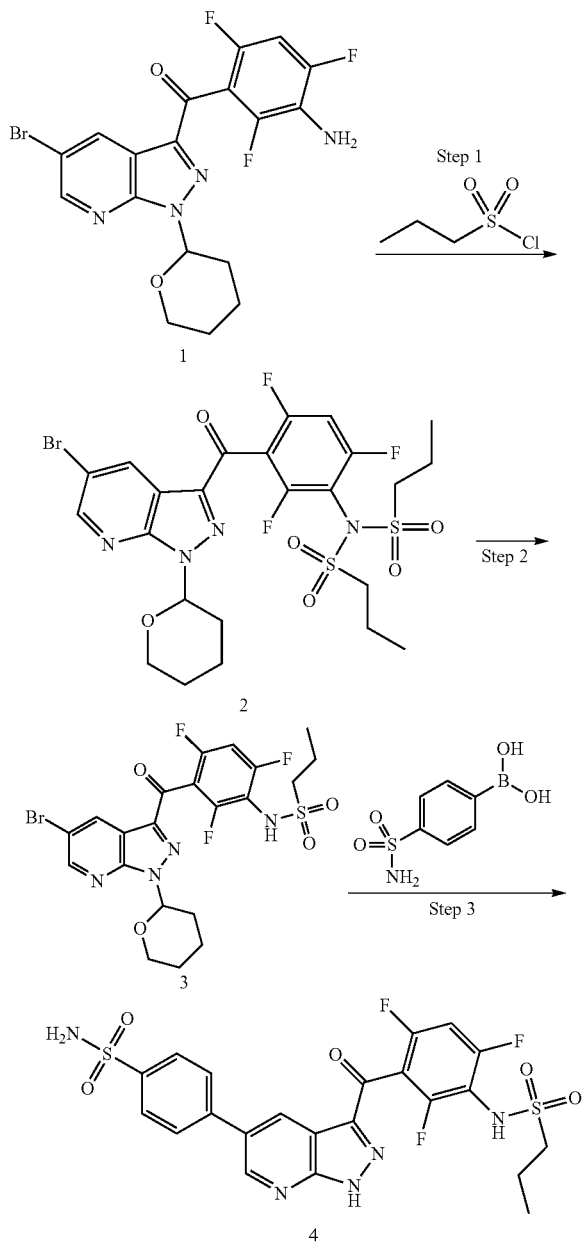

Step 1: N-[3-[5-bromo-1-(oxan-2-yl)pyrazolo[3,4-b]pyridine-3-carbonyl]-2,4,6-trifluorophenyl]-N-propylsulfonylpropane-1-sulfonamide (2)

To (3-amino-2,4,6-trifluorophenyl)-[5-bromo-1-(oxan-2-yl)pyrazolo[3,4-b]pyridin-3-yl]methanone (1, 0.289 g, 0.635 mmol) and Triethylamine (0.133 mL, 0.952 mmol) in DCM (2.54 mL) was added 1-Propanesulfonyl chloride (0.0715 mL, 0.635 mmol) slowly at 0° C. After stirring at RT for 15 minutes, the mixture was diluted with DCM, washed with NH₄Cl solution, dried over Na₂SO₄ and the solvents were removed. The residue was purified by flash chromatography (hexane+EtOAc, 0 to 25%) to yield N-[3-[5-bromo-1-(oxan-2-yl)pyrazolo[3,4-b]pyridine-3-carbonyl]-2,4,6-trifluorophenyl]-N-propylsulfonylpropane-1-sulfonamide (0.233 g, 0.3490 mmol, 55% yield). The resulting oil was dissolved in DCM, hexane was added, and the solvents were removed. Off white solid.

Analytical Data:
$^1$H NMR (200 MHz, CDCl₃) δ 8.81 (d, J=2.0 Hz, 1H), 8.65 (d, J=2.0 Hz, 1H), 6.97 (td, J=9.1, 1.8 Hz, 1H), 6.15 (dd, J=9.9, 2.2 Hz, 1H), 4.03 (d, J=11.1 Hz, 1H), 3.88-3.48 (m, 5H), 2.53 (dd, J=20.4, 11.9 Hz, 1H), 2.15-1.51 (m, 9H), 1.07 (td, J=7.4, 3.9 Hz, 6H);
$^{13}$C NMR (50 MHz, CDCl₃) δ 180.6, 151.1, 149.7, 140.4, 133.5, 116.8, 116.5, 83.2, 68.1, 58.3, 28.7, 24.8, 22.4, 16.7, 12.9;
MS: [M+Na]⁺=688.8.

Step 2: N-[3-[5-bromo-1-(oxan-2-yl)pyrazolo[3,4-b]pyridine-3-carbonyl]-2,4,6-trifluorophenyl]propane-1-sulfonamide (3)

To a solution of N-[3-[5-bromo-1-(oxan-2-yl)pyrazolo[3,4-b]pyridine-3-carbonyl]-2,4,6-trifluorophenyl]-N-propylsulfonylpropane-1-sulfonamide (2, 0.227 g, 0.340 mmol) in tetrahydrofuran (1.2 mL) and MeOH (0.40 mL) is added 1M aqueous NaOH (1.02 mL, 1.02 mmol). After stirring for 1 h, water (3 mL) was added and the organic solvents evaporated. 2N HCl was added to neutralize the mixture. The solids were collected by suction filtration and dried to yield N-[3-[5-bromo-1-(oxan-2-yl)pyrazolo[3,4-b]pyridine-3-carbonyl]-2,4,6-trifluorophenyl]propane-1-sulfonamide (0.159 g, 0.2830 mmol, 83% yield) as off white solid.

Analytical Data:
$^1$H NMR (200 MHz, DMSO) δ 9.70 (s, 1H), 8.84 (d, J=10.9 Hz, 2H), 7.62 (t, J=9.3 Hz, 1H), 6.15 (d, J=8.6 Hz, 1H), 4.08-3.59 (m, 2H), 3.25-3.06 (m, 2H), 2.40-2.16 (m, 1H), 2.08-0.76 (m, 10H);
$^{13}$C NMR (50 MHz, DMSO) δ 151.2, 149.2, 139.8, 132.7, 116.6, 115.5, 82.9, 67.1, 54.8, 28.4, 24.4, 21.7, 16.9, 12.6;
MS: [M−1]⁻=559.0.

Step 3: 4-[3-[2,4,6-trifluoro-3-(propylsulfonylamino)benzoyl]-1H-pyrazolo[3,4-b]pyridin-5-yl]benzenesulfonamide (4)

A vessel was charged with N-[3-[5-bromo-1-(oxan-2-yl)pyrazolo[3,4-b]pyridine-3-carbonyl]-2,4,6-trifluorophenyl]propane-1-sulfonamide (3, 0.113 g, 0.201 mmol), 4-(4,4,5,5-tetramethyl-1,3,2-dioxaborolan-2-yl)benzenesulfonamide (62.7 mg, 0.221 mmol), and XPhos Pd G3 (4.26 mg, 0.00503 mmol) and purged with argon. Degassed 1,4-dioxane (0.671 mL) and degassed 1.5M Potassium Carbonate (0.403 mL, 0.604 mmol) were added and the mixture was heated to 65° C. for 1 h. NH₄Cl solution was added and the mixture extracted with EtOAc. The extracts were washed with brine, dried over Na₂SO₄ and the solvent was removed. The residue was taken up in DCM (3 mL) and TFA (300 µL) was added and the mixture stirred at RT overnight. 3 mL TFA were added and stirring continued for 1 h. The reaction was quenched into NaHCO₃ solution, extracted with EtOAc, dried over Na₂SO₄ and the solvent was removed. The residue was purified by flash chromatography (DCM+MeOH 1% to 11%) to furnish 4-[3-[2,4,6-trifluoro-3-(propylsulfonylamino)benzoyl]-1H-pyrazolo[3,4-b]pyridin-5-yl]benzenesulfonamide (60.0 mg, 0.1070 mmol, 53% yield).

Analytical Data:

¹H NMR (400 MHz, DMSO) δ 15.02 (s, 1H), 9.66 (s, 1H), 9.10 (d, J=2.1 Hz, 1H), 8.85 (d, J=2.1 Hz, 1H), 8.02 (dd, J=37.6, 8.5 Hz, 4H), 7.59 (t, J=9.4 Hz, 1H), 7.47 (s, 2H), 3.14 (dd, J=8.7, 6.6 Hz, 2H), 1.88-1.73 (m, 2H), 0.99 (t, J=7.4 Hz, 3H);

¹³C NMR (101 MHz, DMSO) δ 181.5, 152.4, 149.9, 143.5, 141.8, 140.3, 131.5, 128.2, 127.9, 126.4, 113.4, 54.7, 16.8, 12.5;

MS: [M−1]⁻=552.0.

Example 53d: 4-[3-[3-(ethylsulfamoylamino)-2,6-difluorobenzoyl]-1H-pyrazolo[3,4-b]pyridin-5-yl]benzenesulfonamide (5)

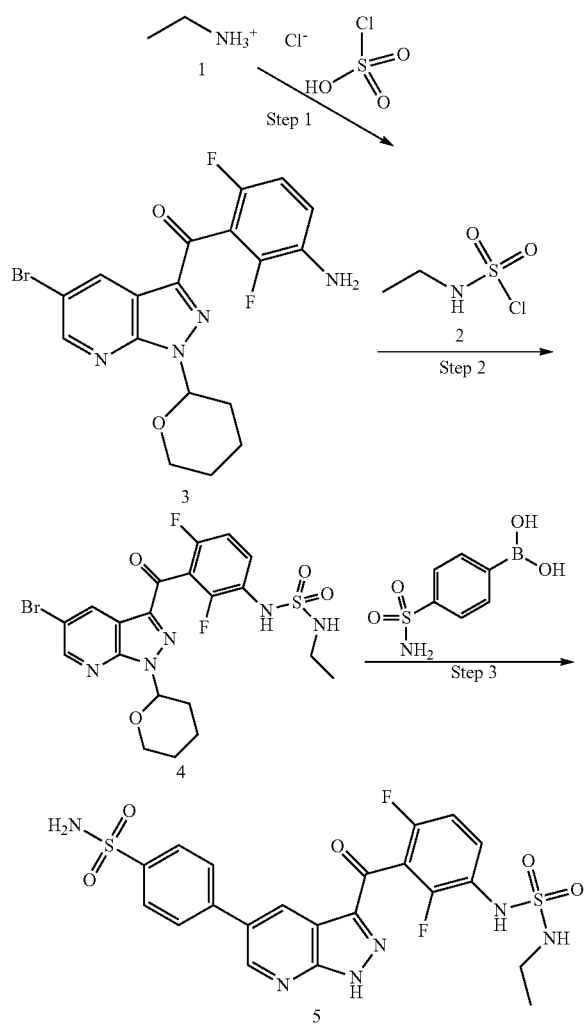

Step 1: N-ethylsulfamoyl chloride (2)

In analogy to literature procedure: A mixture of ethylamine hydrochloride (2.00 g, 24.5 mmol) and Sulfuryl chloride (7.93 mL, 98.1 mmol) in acetonitrile (4.91 mL) was heated to 75° C. overnight. The mixture was evaporated, treated with diethyl ether and filtered. The solvent was removed to yield N-ethylsulfamoyl chloride (3.28 g, 22.8 mmol, 93% yield), which was used without further characterization.

Step 2: [5-bromo-1-(oxan-2-yl)pyrazolo[3,4-b]pyridin-3-yl]-[3-(ethylsulfamoylamino)-2,6-difluorophenyl]methanone (4)

To a solution of (3-amino-2,6-difluorophenyl)-[5-bromo-1-(oxan-2-yl)pyrazolo[3,4-b]pyridin-3-yl]methanone (90.0 mg, 0.206 mmol) and Triethylamine (0.0373 mL, 0.268 mmol) in DCM (0.823 mL) was added N-ethylsulfamoyl chloride (35.5 mg, 0.247 mmol) in DCM (0.823 mL) at 0° C. After stirring for 10 minutes at RT, the mixture was diluted with DCM, washed with water and NH₄Cl solution, dried over Na₂SO₄, filtered and the solvent was removed under reduced pressure to yield [5-bromo-1-(oxan-2-yl)pyrazolo[3,4-b]pyridin-3-yl]-[3-(ethylsulfamoylamino)-2,6-difluorophenyl]methanone (4, 0.110 g, 0,202 mmol, 98% yield) as yellow foam, which was used without further purification.

Analytical Data:

1H NMR (200 MHz, CDCl₃) δ 8.85 (s, 1H), 8.67 (s, 1H), 7.69 (td, J=8.9, 5.6 Hz, 1H), 7.01 (t, J=8.9 Hz, 1H), 6.73 (s, 1H), 6.15 (d, J=7.5 Hz, 1H), 4.75 (t, J=5.9 Hz, 1H), 4.13-3.97 (m, 1H), 3.90-3.67 (m, 1H), 3.24-3.04 (m, 2H), 2.63-2.31 (m, 1H), 2.21-1.51 (m, 5H), 1.16 (t, J=7.2 Hz, 3H).

13C NMR (50 MHz, CDCl3) δ 182.6, 156.8 (dd, J=252.0, 6.7 Hz), 151.5 (dd, J=250.7, 7.5 Hz), 151.1, 149.7, 140.8, 133.8, 125.8 (dd, J=9.8, 2.0 Hz), 122.0 (dd, J=12.7, 3.5 Hz), 116.8, 116.6, 112.29 (dd, J=22.2, 3.8 Hz), 83.4, 68.3, 38.6, 29.0, 24.8, 22.5, 15.1.

Step 3: 4-[3-[3-(ethylsulfamoylamino)-2,6-difluorobenzoyl]-1H-pyrazolo[3,4-b]pyridin-5-yl]benzenesulfonamide (5)

A vessel was charged with [5-bromo-1-(oxan-2-yl)pyrazolo[3,4-b]pyridin-3-yl]-[3-(ethylsulfamoylamino)-2,6-difluorophenyl]methanone (4, 94.0 mg, 0.173 mmol), (4-sulfamoylphenyl)boronic acid (38.2 mg, 0.190 mmol) and XPhos Pd G3 (4.38 mg, 0.00518 mmol) and purged with argon. Degassed 1,4-dioxane (0.576 mL) and degassed 1.5 M aqueous Potassium Carbonate (0.345 mL, 0.518 mmol) was added and the mixture was stirred at 65° C. for 1.5 h. Sat. NH₄Cl solution and EtOAc were added and the phases were separated. The organic phase was dried over Na₂SO₄ and evaporated. The residue was taken up in DCM (3 mL) and TFA (300 μL) was added at RT. After 4 h the mixture was quenched into NaHCO₃ solution and extracted with EtOAc. The extract was dried over Na₂SO₄ and the solvent was removed. The product was purified by flash chromatography (DCM+MeOH 1% to 11%) to furnish 4-[3-[3-(ethylsulfamoylamino)-2,6-difluorobenzoyl]-1H-pyrazolo[3,4-b]pyridin-5-yl]benzenesulfonamide (5, 35.0 mg, 0.0652 mmol, 38% yield).

Analytical Data:

¹H NMR (400 MHz, DMSO) δ 14.97 (s, 1H), 9.54 (s, 1H), 9.10 (d, J=2.0 Hz, 1H), 8.86 (d, J=1.9 Hz, 1H), 8.02 (dd, J=38.5, 8.3 Hz, 4H), 7.64 (td, J=9.0, 5.9 Hz, 1H), 7.51-7.41 (m, 3H), 7.30 (t, J=8.7 Hz, 1H), 3.04-2.88 (m, 2H), 1.04 (t, J=7.2 Hz, 3H);

¹³C NMR (101 MHz, DMSO) δ 182.8, 162.8, 152.4, 149.8, 143.5, 142.0, 140.3, 131.4, 128.2, 127.9, 126.4, 113.4, 37.2, 14.6;

MS: [M−1]⁻=535.0.

Example 54: Synthesis of N-[3-(5-bromo-1H-pyrazolo[3,4-b]pyridine-3-carbonyl)-2,6-difluorophenyl]methanesulfonamide (6)

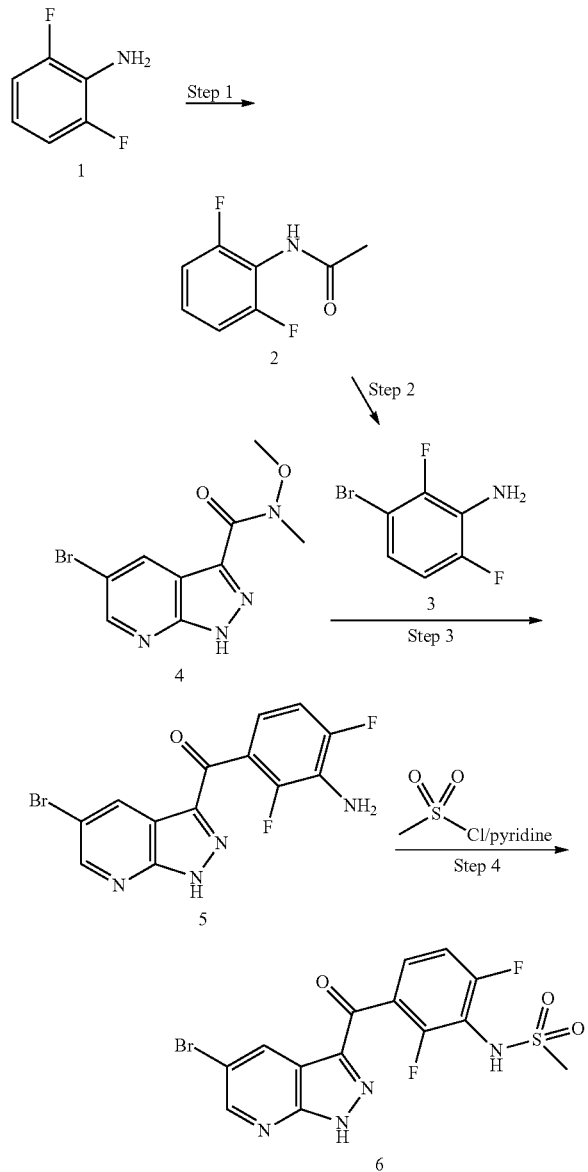

Step 1: N-(2,6-difluorophenyl)acetamide 2,6-difluoroaniline (1, 3.34 g, 25.9 mmol) and Acetic anhydride (2.56 mL, 27.2 mmol) were combined in DCM (34.5 mL) and stirred overnight at RT. The reaction mixture was diluted with DCM (50 mL), washed with water and saturated sodium bicarbonate, dried over $Na_2SO_4$ and evaporated to give N-(2,6-difluorophenyl)acetamide (2, 3.88 g, 22.7 mmol, 88% yield) as white solid.

Analytical Data:

$^1$H NMR (200 MHz, DMSO) δ 9.69 (s, 1H), 7.43-7.23 (m, 1H), 7.13 (t, J=7.9 Hz, 2H), 2.08 (s, 3H);

$^{13}$C NMR (50 MHz, DMSO) δ 168.5, 160.4, 160.3, 155.5, 155.4, 128.0, 127.8, 127.6, 115.1, 114.7, 114.4, 112.1, 112.0, 111.9, 111.8, 111.6, 111.6, 22.4, all peaks reported;

MS: [M+H]$^+$=171.9.

Step 2: 3-bromo-2,6-difluoroaniline (3)

N-(2,6-difluorophenyl)acetamide (2, 8.77 g, 51.2 mmol) was dissolved in Sulfuric acid (41.0 mL, 769 mmol) and N-Bromosuccinimide (9.12 g, 51.2 mmol) was added portion wise at rt. The reaction was stirred overnight at RT and quenched slowly into ice water (400 mL) with stirring. The solids were collected by suction filtration and washed with water, hexane, hexane+EtOAc (8+2) and hexane again. The solids were taken up in ethanol (30.0 mL) and conc. HCl (30 mL) and heated to reflux for 3 h. The mixture was poured into ice (400 g), neutralized with solid NaOH and the solids were collected by suction filtration, washed with water and dried in vacuo to yield 3-bromo-2,6-difluoroaniline (3, 7.83 g, 37.6 mmol, 73% yield).

Analytical Data:

$^1$H NMR (200 MHz, CDCl$_3$) δ 6.95-6.59 (m, 2H), 3.84 (s, 2H);

$^{13}$C NMR (50 MHz, CDCl$_3$) δ 152.2 (dd, J=133.8, 6.5 Hz), 147.5 (dd, J=132.7, 6.9 Hz), 125.4 (t, J=16.9 Hz), 122, 119.6 (d, J=8.4 Hz), 111.7 (dd, J=19.9, 3.1 Hz), 103.8 (dd, J=19.2, 3.8 Hz).

Step 3: (3-amino-2,4-difluorophenyl)-(5-bromo-1H-pyrazolo[3,4-b]pyridin-3-yl)methanone (5)

To 3-bromo-2,6-difluoroaniline (3, 12.9 g, 61.9 mmol) in tetrahydrofuran (76.9 mL) was added 2M Isopropylmagnesium chloride in THF (30.9 mL, 61.9 mmol) dropwise at 0° C. and stirred for 15 minutes at RT. After cooling to 0° C., chlorotrimethylsilane (7.85 mL, 61.9 mmol) was added, the mixture warmed to 25° C. and stirred for 20 minutes. The suspension was cooled to 0° C. and 2M Isopropylmagnesium chloride in THF (30.9 mL, 61.9 mmol) was added dropwise and stirred for 15 minutes at RT. After cooling to 0° C. chlorotrimethylsilane (7.85 mL, 61.9 mmol) was added stirring continued for 20 minutes at 25° C. The suspension was cooled to 0° C. again and 2M isopropylmagnesium chloride in THF (30.9 mL, 61.9 mmol) was added dropwise and the mixture was stirred for 10 minutes at 0° C. (Solution A). Meanwhile 2M isopropylmagnesium chloride in THF (13.5 mL, 26.9 mmol) was added dropwise to a suspension of 5-bromo-N-methoxy-N-methyl-1H-pyrazolo[3,4-b]pyridine-3-carboxamide (4, 7.67 g, 26.9 mmol) in tetrahydrofuran (76.9 mL) at 0° C. The resulting suspension was stirred for 5 minutes and transferred to solution A. The reaction was stirred overnight at RT, conc. HCl (26.9 mL, 323 mmol) was added and stirred for 10 minutes. Water was added until the phases became clear. The mixture was neutralized with 2N NaOH, saturated with NaCl and extracted with THF. The extracts were washed with brine, dried over $Na_2SO_4$ and filtered. After evaporation of the solvent, the solids were stirred in 100 mL DCM collected by suction filtration and dried to yield 6.35 g a first crop as light yellow solid. The filtrate was evaporated, triturated with diethyl ether and DCM to obtain a second crop (0.41 g). Total yield (3-amino-2,4-difluorophenyl)-(5-bromo-1H-pyrazolo[3,4-b]pyridin-3-yl)methanone (5, 6.76 g, 19.1 mmol, 71% yield).

Analytical Data:

$^1$H NMR (200 MHz, DMSO) δ 14.55 (s, 1H), 8.65 (dd, J=5.2, 2.1 Hz, 2H), 7.13-6.86 (m, 2H), 5.44 (s, 2H);

$^{13}$C NMR (50 MHz, DMSO) δ 186.1, 153.5 (dd, J=188, 9 Hz), 150.8, 150.3, 148.6 (dd, J=191, 9 Hz), 141.1, 132.5, 126.1 (t, J=17 Hz), 122.8 (dd, J=12, 3 Hz), 116.2 (dd, J=9, 3 Hz), 115.4, 115, 110.6 (dd, J=19, 3 Hz);

MS: [M−1]⁻=351.2.

Step 4: N-[3-(5-bromo-1H-pyrazolo[3,4-b]pyridine-3-carbonyl)-2,6-difluorophenyl]methane-sulfonamide (6)

To a suspension of (3-amino-2,4-difluorophenyl)-(5-bromo-1H-pyrazolo[3,4-b]pyridin-3-yl)methanone (5, 0.620 g, 1.76 mmol) in pyridine (2.83 mL, 35.1 mmol) was added methanesulfonyl chloride (0.544 mL, 7.02 mmol) at RT 50° C. for 2 h. The reaction was concentrated and taken up in 2 M Sodium hydroxide solution (13.2 mL, 26.3 mmol) and stirred for 15 minutes. The solution was poured into chilled 3N HCl 20 mL, extracted with EtOAc and the extracts were washed with 2N HCl, dried over Na$_2$SO$_4$ and evaporated. The product was purified by flash chromatography (DCM+EtOAc 0% to 40%) to yield N-[3-(5-bromo-1H-pyrazolo[3,4-b]pyridine-3-carbonyl)-2,6-difluorophenyl]methane-sulfonamide (0.390 g, 0.9040 mmol, 52% yield) as red solid.

Analytical Data:

$^1$H NMR (400 MHz, DMSO) δ 14.87 (s, 1H), 9.75 (s, 1H), 8.71 (d, J=13.9 Hz, 2H), 7.85 (d, J=6.6 Hz, 1H), 7.39 (t, J=8.5 Hz, 1H), 3.12 (s, 3H);

$^{13}$C NMR (101 MHz, DMSO) δ 184.7, 160.8 (dd, J=255, 3 Hz), 157.06 (dd, J=257.4, 4.2 Hz), 150.8, 150.5, 140.9, 132.4, 130.6 (dd, J=10, 3 Hz), 123.3 (dd, J=13, 3 Hz), 115.4, 115.1, 114.3 (t, J=17 Hz), 111.9 (dd, J=21, 3 Hz), 41.5;

MS: [M−1]⁻=429.1.

Example 54a: N-[2,6-difluoro-3-[5-[4-(1H-tetrazol-5-yl)phenyl]-1H-pyrazolo[3,4-b]pyridine-3-carbonyl]phenyl]methanesulfonamide

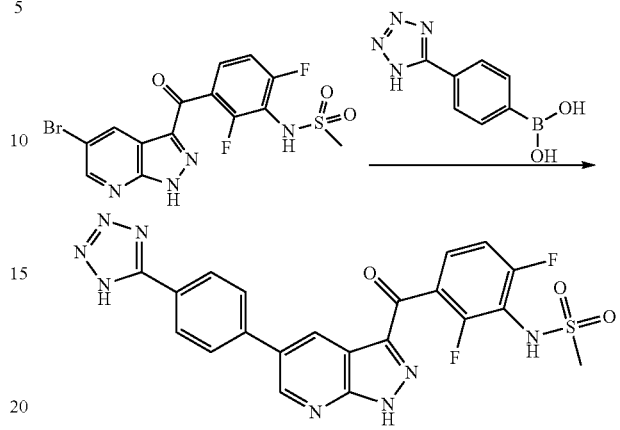

A microwave vessel was charged with N-[3-(5-bromo-1H-pyrazolo[3,4-b]pyridine-3-carbonyl)-2,6-difluorophenyl]methanesulfonamide (60.0 mg, 0.139 mmol), XPhos Pd G3 (3.53 mg, 0.00417 mmol) and [4-(1H-tetrazol-5-yl)phenyl]boronic acid (31.7 mg, 0.167 mmol) and purged with argon. Degassed 1,4-dioxane (0.464 mL) and degassed aqueous 1.5 M Potassium Carbonate (0.325 mL, 0.487 mmol) were added and the mixture was heated to 110° C. under microwave irradiation for 60 minutes. After cooling, the mixture was diluted with EtOAc and neutralized with sat. NH$_4$Cl solution. The organic phase was concentrated under reduced pressure and the product isolated by flash chromatography (DCM+MeOH (+1% formic acid) 5% to 15%), triturated with MeOH and dried at 100° C. in a vacuum oven to yield N-[2,6-difluoro-3-[5-[4-(1H-tetrazol-5-yl)phenyl]-1H-pyrazolo[3,4-b]pyridine-3-carbonyl]phenyl]methanesulfonamide (21.0 mg, 0.0423 mmol, 30% yield).

Analytical Data:

$^1$H NMR (200 MHz, DMSO) δ 14.85 (s, 1H), 9.75 (s, 1H), 9.10 (d, J=2.1 Hz, 1H), 8.86 (d, J=2.2 Hz, 1H), 8.25-8.00 (m, 4H), 7.97-7.81 (m, 1H), 7.41 (td, J=8.9, 1.3 Hz, 1H), 3.12 (s, 3H);

MS: [M−1]⁻=495.2.

Example 54b: 4-[3-[2,4-difluoro-3-(methanesulfonamido)benzoyl]-1H-pyrazolo[3,4-b]pyridin-5-yl]benzamide

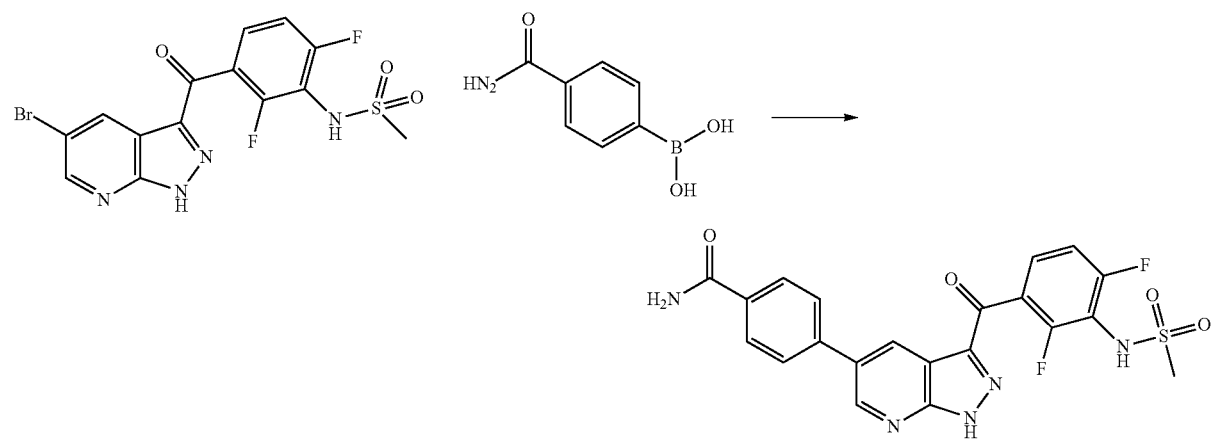

A microwave vessel was charged with N-[3-(5-bromo-1H-pyrazolo[3,4-b]pyridine-3-carbonyl)-2,6-difluorophenyl]methanesulfonamide (60.0 mg, 0.139 mmol), XPhos Pd G3 (5.89 mg, 0.00696 mmol) and (4-Carbamoylphenyl)boronic acid (27.5 mg, 0.167 mmol) and purged with argon. Degassed 1,4-dioxane (0.464 mL) and degassed aqueous 1.5 M Potassium Carbonate (0.325 mL, 0.487 mmol) were added and the mixture was heated to 110° C. under microwave irradiation for 60 minutes. After cooling, the mixture was diluted with EtOAc and neutralized with sat. $NH_4Cl$ solution. The solvents were removed under reduced pressure and the product isolated by flash chromatography (DCM+MeOH, 5% to 15%) and dried at 100° C. in a vacuum oven to yield 4-[3-[2,4-difluoro-3-(methanesulfonamido)benzoyl]-1H-pyrazolo[3,4-b]pyridin-5-yl]benzamide (40.0 mg, 0.0789 mmol, 57% yield).

Analytical Data:

$^1$H NMR (200 MHz, DMSO) δ 9.06 (d, J=1.9 Hz, 1H), 8.82 (d, J=2.0 Hz, 1H), 8.14-7.80 (m, 6H), 7.49-7.33 (m, 2H), 3.11 (s, 3H);

MS: [M−1]⁻=470.3

Example 54c: 4-[3-[2,4-difluoro-3-(methanesulfonamido)benzoyl]-1H-pyrazolo[3,4-b]pyridin-5-yl]benzenesulfonamide

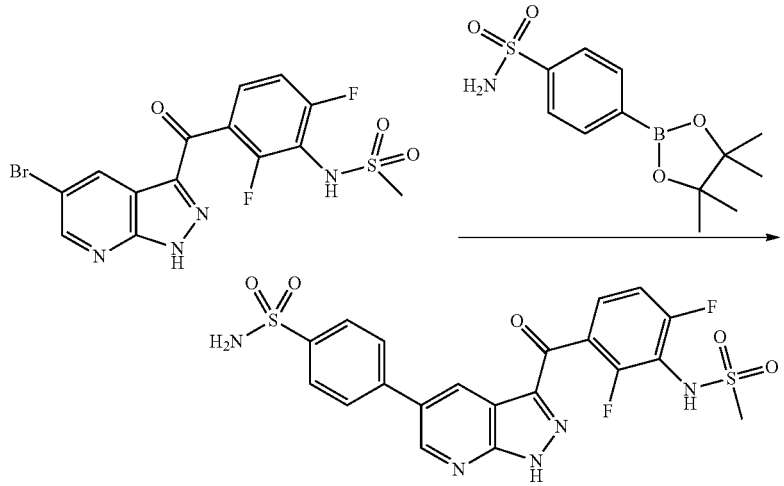

A microwave vessel was charged with N-[3-(5-bromo-1H-pyrazolo[3,4-b]pyridine-3-carbonyl)-2,6-difluorophenyl]methanesulfonamide (60.0 mg, 0.139 mmol), XPhos Pd G3 (5.89 mg, 0.00696 mmol) and 4-(4,4,5,5-tetramethyl-1,3,2-dioxaborolan-2-yl)benzenesulfonamide (47.3 mg, 0.167 mmol) and purged with argon. Degassed 1,4-dioxane (0.464 mL) and degassed aqueous 1.5 M potassium carbonate (0.325 mL, 0.487 mmol) were added and the mixture was heated to 110° C. under microwave irradiation for 60 minutes. After cooling, the mixture was diluted with EtOAc and neutralized with sat. $NH_4Cl$ solution. The solvents were removed under reduced pressure and the product isolated by flash chromatography (DCM+EtOAc, 50% to 100%) and dried at 100° C. in a vacuum oven to yield 4-[3-[2,4-difluoro-3-(methanesulfonamido)benzoyl]-1H-pyrazolo[3,4-b]pyridin-5-yl]benzenesulfonamide (31.0 mg, 0.0574 mmol, 41% yield). $^1$H NMR (200 MHz, DMSO) δ 9.07 (d, J=2.1 Hz, 1H), 8.84 (d, J=2.1 Hz, 1H), 8.12-7.78 (m, 4H), 7.50-7.32 (m, 2H), 3.11 (s, 3H); [M−1]⁻=506.2.

Example 55: Synthesis of 4-[3-[2,4-difluoro-3-(methanesulfonamido)benzoyl]-1H-pyrazolo[3,4-b]pyridin-5-yl]benzoic acid (4) and Ethyl 4-[3-[2,4-difluoro-3-(methanesulfonamido)benzoyl]-1H-pyrazolo[3,4-b]pyridin-5-yl]benzoate (5)

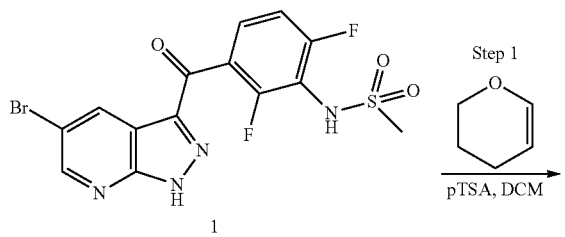

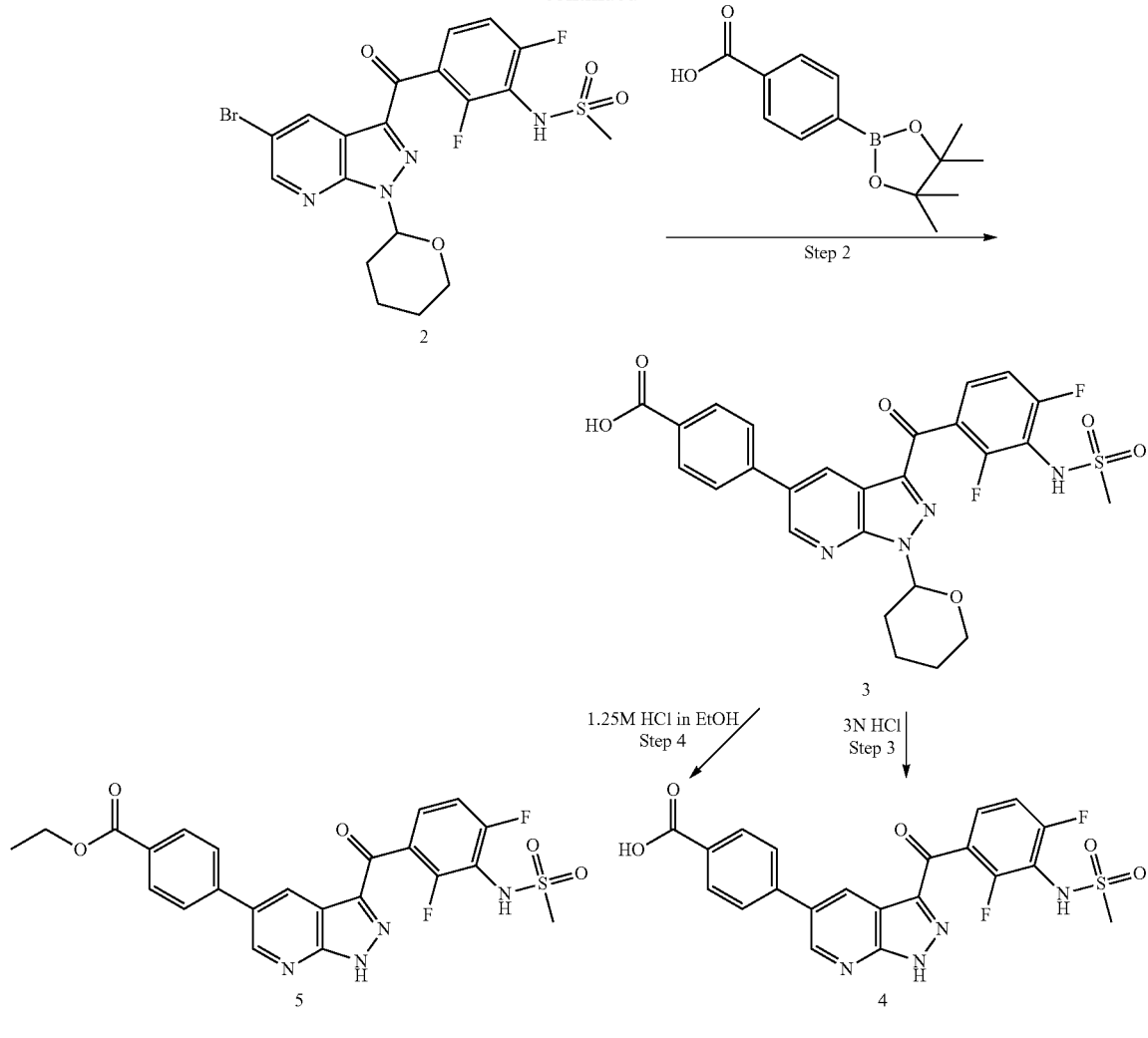

Step 1: N-[3-[5-bromo-1-(oxan-2-yl)pyrazolo[3,4-b]pyridine-3-carbonyl]-2,6-difluorophenyl]methane-sulfonamide (2)

To a suspension of N-[3-(5-bromo-1H-pyrazolo[3,4-b]pyridine-3-carbonyl)-2,6-difluorophenyl]methanesulfonamide (380 mg, 0.881 mmol) and p-toluenesulfonic acid monohydrate (33.5 mg, 0.176 mmol) in DCM (2.94 mL) was added dihydropyran (0.161 mL, 1.76 mmol) and the reaction was heated to reflux temperature for 1 h. The reaction was diluted with DCM, washed with sat. NaHCO$_3$ solution, dried over Na$_2$SO$_4$ and concentrated. The residue was triturated with n-hexane to yield N-[3-[5-bromo-1-(oxan-2-yl)pyrazolo[3,4-b]pyridine-3-carbonyl]-2,6-difluorophenyl]methane-sulfonamide (370 mg, 0.7180 mmol, 81% yield) as beige solid.

Analytical Data:
$^1$H NMR (200 MHz, DMSO) δ 9.78 (s, 1H), 8.80 (dd, J=13.4, 1.6 Hz, 2H), 7.88 (dd, J=14.6, 7.8 Hz, 1H), 7.43 (t, J=9.0 Hz, 1H), 6.14 (d, J=8.6 Hz, 1H), 3.94 (d, J=11.6 Hz, 1H), 3.72 (dd, J=14.6, 9.1 Hz, 1H), 3.13 (s, 3H), 2.46-2.19 (m, 1H), 2.00-1.18 (m, 5H);
$^{13}$C NMR (50 MHz, DMSO) δ 184.4, 150.8, 149.0, 139.9, 133.0, 116.1, 116.0, 82.7, 67.2, 41.5, 28.5, 24.5, 21.8; MS: [M−1]$^-$=513.2.

Step 2: 4-[3-[2,4-difluoro-3-(methanesulfonamido)benzoyl]-1-(oxan-2-yl)pyrazolo[3,4-b]pyridin-5-yl]benzoic acid (3)

N-[3-[5-bromo-1-(oxan-2-yl)pyrazolo[3,4-b]pyridine-3-carbonyl]-2,6-difluorophenyl]methanesulfonamide (355 mg, 0.689 mmol) and 4-(4,4,5,5-tetramethyl-1,3,2-dioxaborolan-2-yl)benzoic acid (188 mg, 0.758 mmol) d XPhos Pd G3 (17.5 mg, 0.0207 mmol) were combined in degassed 1,4-dioxane (2.30 mL) and 1.5 M potassium carbonate (2.07 mL, 3.10 mmol). The reaction was evacuated and flushed with argon (3×). XPhos Pd G3 (17.5 mg, 0.0207 mmol) was added and the reaction was stirred at 60° C. oil bath temperature for 3 h. After cooling the mixture was acidified with 2N HCl and extracted with EtOAc. The extract was washed with brine, dried over Na$_2$SO$_4$ and concentrated. The residue was purified by flash chromatography (DCM+MeOH 3% to 25%) and triturated with n-hexane to yield 4-[3-[2,4-difluoro-3-(methanesulfonamido)benzoyl]-1-(oxan-2-yl)pyrazolo[3,4-b]pyridin-5-yl]benzoic acid (276 mg, 0.4960 mmol, 72% yield).

Analytical Data:
$^1$H NMR (400 MHz, DMSO) δ 9.77 (s, 1H), 9.10 (d, J=2.1 Hz, 1H), 8.83 (d, J=2.1 Hz, 1H), 8.09 (d, J=8.3 Hz, 2H), 7.96 (d, J=8.3 Hz, 2H), 7.90 (dd, J=14.8, 7.6 Hz, 1H), 7.44 (t, J=8.8 Hz, 1H), 6.21 (dd, J=9.9, 2.0 Hz, 1H), 4.01-3.91 (m, 1H), 3.80-3.68 (m, 1H), 3.59 (t, J=6.6 Hz, 2H), 3.13 (s, 3H), 2.46-2.33 (m, 1H), 2.06-1.93 (m, 2H), 1.84-1.68 (m, 2H);

MS: [M−1]⁻=555.4.

Step 3: 4-[3-[2,4-difluoro-3-(methanesulfonamido)benzoyl]-1H-pyrazolo[3,4-b]pyridin-5-yl]benzoic acid (4)

4-[3-[2,4-difluoro-3-(methanesulfonamido)benzoyl]-1-(oxan-2-yl)pyrazolo[3,4-b]pyridin-5-yl]benzoic acid (203 mg, 0.365 mmol) was suspended in 3N HCl and heated to 70° C. with stirring overnight. The reaction was concentrated, the solids collected by suction filtration, washed with water and dried at 100° C. to yield 4-[3-[2,4-difluoro-3-(methanesulfonamido)benzoyl]-1H-pyrazolo[3,4-b]pyridin-5-yl]benzoic acid (133 mg, 0.2820 mmol, 77% yield).

Analytical Data:

¹H NMR (200 MHz, DMSO) δ 9.06 (d, J=2.1 Hz, 1H), 8.83 (d, J=2.1 Hz, 1H), 8.10 (d, J=8.3 Hz, 2H), 8.00-7.80 (m, 3H), 7.40 (td, J=9.0, 1.3 Hz, 1H), 3.12 (s, 3H);

MS: [M−1]⁻=471.2.

Step 4: Ethyl 4-[3-[2,4-difluoro-3-(methanesulfonamido)benzoyl]-1H-pyrazolo[3,4-b]pyridin-5-yl]benzoate (5)

4-[3-[2,4-difluoro-3-(methanesulfonamido)benzoyl]-1-(oxan-2-yl)pyrazolo[3,4-b]pyridin-5-yl]benzoic acid (50.0 mg, 0.0898 mmol) was stirred in 1.25 M HCl in ethanol (0.719 mL, 0.898 mmol) at 75° C. in a sealed vessel. After 3 h 200 μL H₂SO₄ were added and stirring continued at 75° C. overnight. The reaction was quenched into NaHCO₃ solution, the solids were collected by centrifugation and washed with water and diethyl ether and dried in vacuo to yield ethyl 4-[3-[2,4-difluoro-3-(methanesulfonamido)benzoyl]-1H-pyrazolo[3,4-b]pyridin-5-yl]benzoate (22.0 mg, 0.0440 mmol, 49% yield).

Analytical Data:

¹H NMR (200 MHz, DMSO) δ 14.86 (s, 1H), 9.74 (s, 1H), 9.06 (d, J=2.1 Hz, 1H), 8.83 (d, J=2.1 Hz, 1H), 8.18-7.80 (m, 5H), 7.41 (t, J=8.9 Hz, 1H), 4.36 (q, J=7.0 Hz, 2H), 3.12 (s, 3H), 1.35 (t, J=7.0 Hz, 3H);

MS: [M−1]⁻=499.4.

Example 56: Synthesis of [(2S)-2-amino-3-methoxy-3-oxopropyl] 4-[3-[2,4-difluoro-3-(methanesulfonamido)benzoyl]-1H-pyrazolo[3,4-b]pyridin-5-yl]benzoate hydrochloride

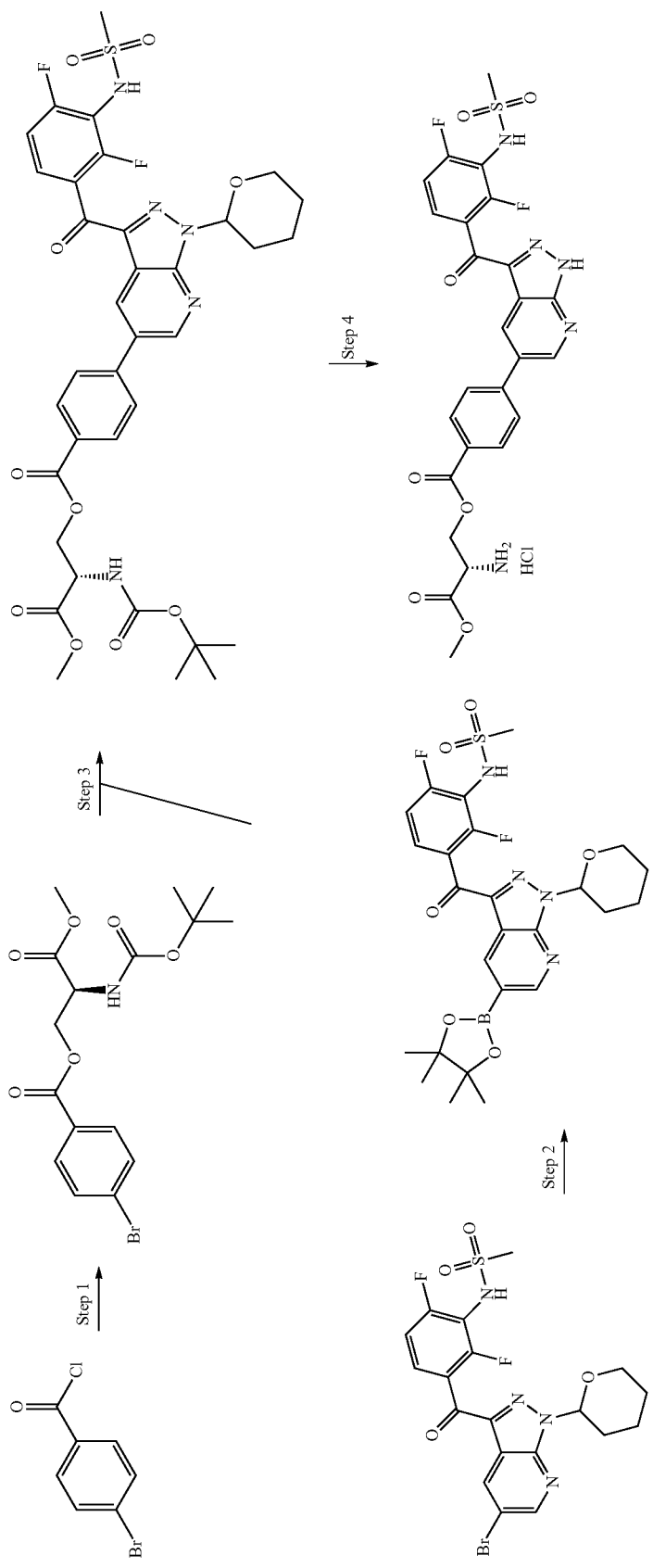

Step 1: [(2S)-3-methoxy-2-[(2-methylpropan-2-yl) oxycarbonylamino]-3-oxopropyl] 4-bromobenzoate 4-Bromobenzoyl chloride (1.13 g, 5.15 mmol) was dissolved in 25.7 ml THF and cooled to 0° C. Triethylamine (0.861 mL, 6.18 mmol) was added and to the resulting suspension was added methyl (2S)-3-hydroxy-2-[(2-methylpropan-2yl)oxycarbonylamino]-propanoate (1.35 g, 6.18 mmol) and 4-DMAP (31.5-mg, 0.257 mmol). The mixture was stirred at RT for 60 minutes, then diluted with EtOAc and washed with water, sat. NaHCO$_3$ and sat. NH$_4$Cl solution. After drying over Na$_2$SO$_4$, the solvent was removed in vacuo. The residue was dissolved in a small amount of MeOH and added to water with stirring. The solids were collected by suction filtration and dried to yield [(2S)-3-methoxy-2-[(2-methylpropan-2-yl)oxycarbonylamino]-3-oxopropyl] 4-bromobenzoate (1.70 g, 4.23 mmol, 82% yield).

Analytical Data:
$^1$H NMR (200 MHz, CDCl$_3$) δ 7.89-7.78 (m, 2H), 7.61-7.50 (m, 2H), 5.38 (d, J=8.0 Hz, 1H), 4.70 (dd, J=8.2, 4.0 Hz, 1H), 4.59 (d, J=4.0 Hz, 2H), 3.76 (d, J=4.3 Hz, 3H), 1.42 (d, J=4.2 Hz, 9H).
$^{13}$C NMR (50 MHz, CDCl$_3$) δ 170.4, 165.4, 155.2, 132.0, 131.3, 128.7, 128.5, 80.6, 65.3, 53.1, 52.9, 28.4.
MS (ESI+): m/z 424.04 [M+1]$^+$.

Step 2: N-(2,6-difluoro-3-(1-(tetrahydro-2H-pyran-2-yl)-5-(4,4,5,5-tetramethyl-1,3,2-dioxaborolan-2-yl)-1H-pyrazolo[3,4-b]pyridine-3-carbonyl)phenyl) methanesulfonamide A vessel was charged with N-[3-[5-bromo-1-(oxan-2-yl) pyrazolo[3,4-b]pyridine-3-carbonyl]-2,6-difluorophenyl] methanesulfonamide (0.630 g, 1.22 mmol), bis(pinacolato) diboron (341 mg, 1.34 mmol), anhydrous potassium acetate (360 mg, 3.67 mmol) and dry 1,4-dioxane (4.08 mL). The vessel was evacuated and filled with argon (3×). 1,1'-bis(diphenylphosphino) ferrocene-dichloropalladium (1:1) (17.9 mg, 0.0245 mmol) was added and the reaction was stirred at 80° C. overnight. After cooling, EtOAc was added, the suspension stirred for 30 minutes and filtered over celite. The solvent was concentrated, n-heptane was added and the solids were collected by suction filtration, washed with hexane and dried to furnish N-[2,6-difluoro-3-[1-(oxan-2-yl)-5-(4,4,5,5-tetramethyl-1,3,2-dioxaborolan-2-yl)pyrazolo[3,4-b]-pyridine-3-carbonyl]phenyl]methanesulfonamide (0.690 g, 1.23 mmol, quant.).

Analytical Data:
$^1$H NMR (200 MHz, DMSO) δ 8.94-8.71 (m, 2H), 7.19-6.88 (m, 2H), 6.18 (d, J=9.1 Hz, 1H), 4.05-3.61 (m, 2H), 2.64 (s, 3H), 2.44-1.10 (m, 18H).

Step 3: [(2S)-3-methoxy-2-[(2-methylpropan-2-yl) oxycarbonylamino]-3-oxopropyl] 4-[3-[2,4-difluoro-3-(methanesulfonamido)benzoyl]-1-(oxan-2-yl)pyrazolo[3,4-b]pyridin-5-yl]benzoate A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]methanesulfonamide (101 mg, 0.180 mmol), [(2S)-3-methoxy-2-[(2-methylpropan-2-yl)oxycarbonylamino]-3-oxopropyl] 4-bromobenzoate (79.5 mg, 0.198 mmol), potassium fluoride (31.3 mg, 0.539 mmol), Pd(dppf)Cl$_2$.DCM (7.33 mg, 0.00898 mmol) and degassed 1,4-dioxane/water (4+1) (0.6 mL) followed by evacuation and filling with argon (3×). The reaction mixture was heated to 65° C. overnight with stirring. The mixture was diluted with EtOAc, washed with brine and the solvents were removed. The product was isolated via flash chromatography (DCM/EtOAc gradient, from 0% to 20% EtOAc) to yield [(2S)-3-methoxy-2-[(2-methylpropan-2-yl)oxycarbonylamino]-3-oxopropyl] 4-[3-[2,4-difluoro-3-(methanesulfonamido)benzoyl]-1-(oxan-2-yl)pyrazolo[3,4-b]pyridin-5-yl]benzoate (68.0 mg, 0.0897 mmol, 50% yield) as white solid.

Analytical Data:
$^1$H NMR (400 MHz, acetone) δ 9.00 (d, J=2.0 Hz, 1H), 8.85 (d, J=2.1 Hz, 1H), 8.47 (s, 1H), 8.17 (d, J=8.3 Hz, 2H), 7.97-7.89 (m, 3H), 7.33 (t, J=8.5 Hz, 1H), 6.65 (d, J=7.6 Hz, 1H), 6.26 (dd, J=9.9, 2.3 Hz, 1H), 4.79-4.58 (m, 3H), 4.02 (d, J=11.4 Hz, 1H), 3.85-3.69 (m, 4H), 3.21 (s, 3H), 2.60-2.46 (m, 1H), 2.17-2.06 (m, 1H), 2.04-1.96 (m, 1H), 1.92-1.78 (m, 1H), 1.74-1.57 (m, 2H), 1.42 (s, 9H).
$^{13}$C NMR (101 MHz, acetone) δ 185.7, 171.1, 166.2, 162.2 (dd, J=256, 3 Hz), 158.7 (dd, J=258, 5 Hz), 156.4, 151.9, 150.3, 143.3, 142.2, 133.6, 131.6 (dd, J=11, 4 Hz), 131.3, 130.3, 130.2, 128.6, 124.7 (dd, J=14, 4 Hz), 116.2, 115.8 (t, J=17 Hz), 112.7 (dd, J=21, 4 Hz), 83.9, 79.8, 68.3, 65.4, 54.0, 52.8, 42.1, 29.8, 29.8, 28.6, 25.7, 23.1.
TLC-MS (ESI$^-$): m/z 756.5 [M−1]$^-$.

Step 4: [(2S)-2-amino-3-methoxy-3-oxopropyl] 4-[3-[2,4-difluoro-3-(methanesulfonamido)benzoyl]-1H-pyrazolo[3,4-b]pyridin-5-yl]benzoate hydrochloride

[(2S)-3-methoxy-2-[(2-methylpropan-2-yl)oxycarbonylamino]-3-oxopropyl] 4-[3-[2,4-difluoro-3-(methanesulfonamido)benzoyl]-1-(oxan-2-yl)pyrazolo[3,4-b]pyridin-5-yl]benzoate (63.0 mg, 0.0831 mmol) was stirred in trifluoroacetic acid (1 mL) at RT for 3 h. The mixture was heated to 50° C. for 40 min. After cooling on ice, 4N HCl (1.04 mL, 4.16 mmol) in 1,4-dioxane was added to the solution, stirring continued for 5 minutes and diethyl ether (3 mL) was added. The product was collected by suction filtration, washed with diethyl ether and dried in vacuo to yield [(2S)-2-amino-3-methoxy-3-oxopropyl] 4-[3-[2,4-difluoro-3-(methanesulfonamido)benzoyl]-1H-pyrazolo[3,4-b]pyridin-5-yl]benzoate hydrochloride (44.0 mg, 0.0721 mmol, 87% yield) as off white solid.

Analytical Data:
$^1$H NMR (400 MHz, DMSO) δ 14.92 (s, 1H), 9.76 (s, 1H), 9.10 (d, J=2.0 Hz, 1H), 8.97 (s, 2H), 8.86 (d, J=2.1 Hz, 1H), 8.20 (d, J=8.5 Hz, 2H), 8.03 (d, J=8.3 Hz, 2H), 7.88 (dd, J=14.7, 7.6 Hz, 1H), 7.41 (t, J=8.7 Hz, 1H), 4.73 (d, J=3.3 Hz, 2H), 4.67 (s, 1H), 3.81 (s, 3H), 3.12 (s, 3H).
$^{13}$C NMR (101 MHz, DMSO) δ 185.1, 167.4, 164.8, 152.2, 149.5, 142.3, 141.8, 131.1, 130.5, 128.5, 128.0, 127.5, 114.0, 62.2, 53.1, 51.3, 41.5, 40.1.
TLC-MS (ESI$^-$): m/z 572.4 [M−1].

Example 57: Synthesis of (2S)-2-amino-3-[4-[3-[2,4-difluoro-3-(methanesulfonamido)-benzoyl]-1H-pyrazolo[3,4-b]pyridin-5-yl]benzoyl]oxypropanoic acid hydrochloride Analytical Data:
$^1$H NMR (200 MHz, CDCl$_3$) δ 7.34 (s, 5H), 5.56 (s, 1H), 5.20 (s, 2H), 4.40 (s, 1H), 3.92 (qd, J=11.2, 3.7 Hz, 2H), 2.46 (s, 1H), 1.43 (s, 9H).

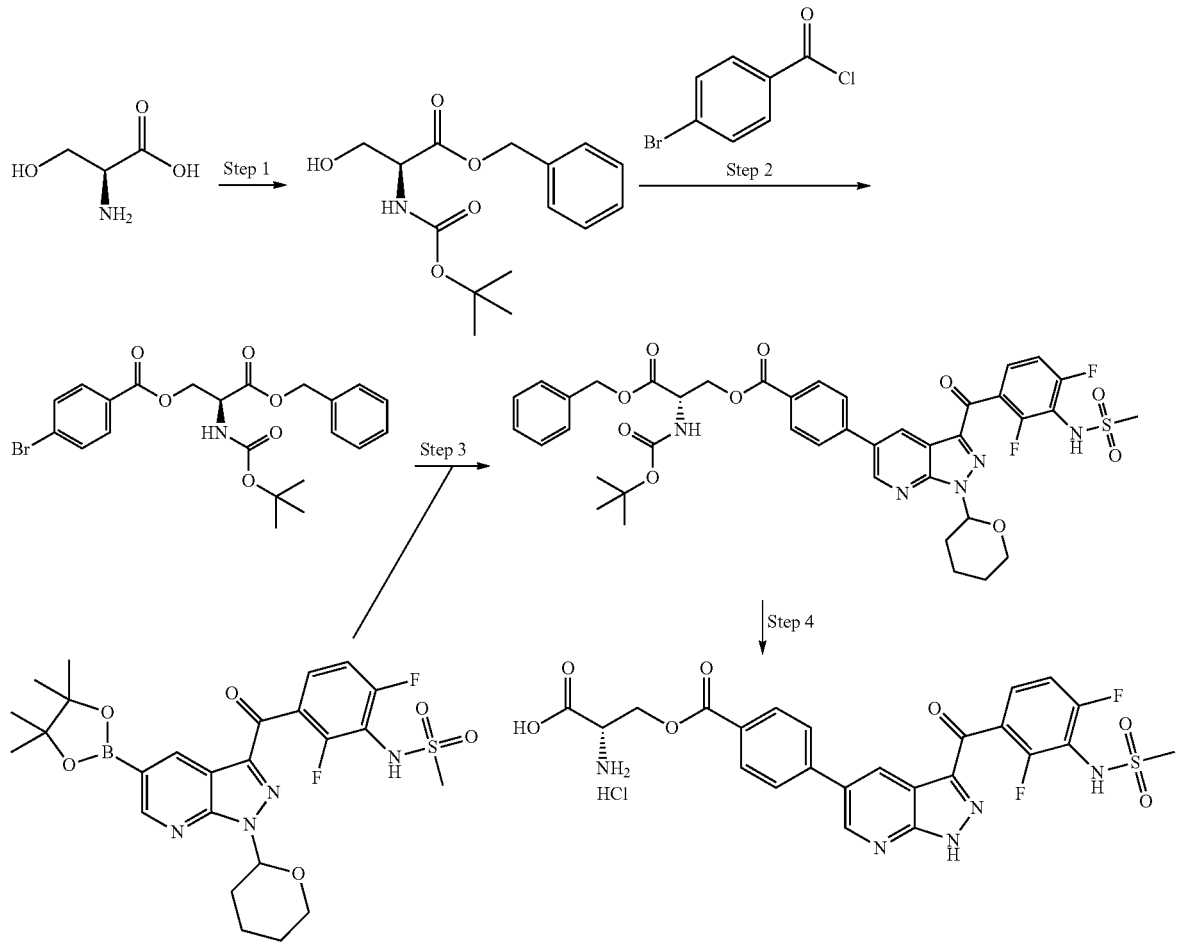

Step 1: benzyl (2S)-3-hydroxy-2-[(2-methylpropan-2-yl)oxycarbonylamino]propanoate A solution of di-tert-butyl dicarbonate (7.06 mL, 30.7 mmol) in 1,4-dioxane (14.5 mL) was added to a solution of (2S)-2-amino-3-hydroxypropanoic acid (2.69 g, 25.6 mmol) and potassium carbonate (3.54 g, 25.6 mmol) in water (14.5 mL). The solution was stirred for 16 h at RT. 1,4-Dioxane was evaporated and the aqueous solution was washed with 3× diethyl ether (10 mL). Water was evaporated in vacuo and remaining traces were azeotropically removed with EtOH. The resulting white powder was suspended in DMF (28.9 mL) and benzyl bromide (3.44 mL, 28.9 mmol) was added. The mixture was stirred at RT for 16 h. DMF was evaporated in vacuo and the residue was stirred with toluene (28.9 mL) and filtered. The phase was washed twice with water and brine and dried over Na$_2$SO$_4$. After filtration, the solvent was evaporated at 90° C. in vacuo. The oily benzyl (2S)-3-hydroxy-2-[(2-methylpropan-2-yl)oxycarbonylamino]propanoate (4.77 g, 16.2 mmol, 63% yield) was used in the next step without further purification.

Step 2: [(2S)-2-[(2-methylpropan-2-yl)oxycarbonylamino]-3-oxo-3-phenylmethoxypropyl] 4-bromobenzoate To a solution of 4-bromobenzoyl chloride (0.500 g, 2.28 mmol) in THF (11.4 mL) was added triethylamine (0.381 mL, 2.73 mmol) and 4-DMAP (0.0139 g, 0.114 mmol). To the resulting suspension was added benzyl (2S)-3-hydroxy-2-[(2-methylpropan-2-yl)oxycarbonylamino]propanoate (0.807 g, 2.73 mmol) in 2 mL THF and the reaction was stirred at RT for 60 minutes. The reaction was diluted with EtOAc, washed with water, sat. NaHCO$_3$ and sat. NH$_4$Cl solution. After drying over Na$_2$SO$_4$, the solvent was removed in vacuo. The product was purified by flash chromatography (n-hexane/EtOAc gradient, from 0% to 20% EtOAc) to yield [(2S)-2-[(2-methylpropan-2-yl)oxycarbonylamino]-3-oxo-3-phenylmethoxypropyl] 4-bromobenzoate (0.501 g, 1.05 mmol, 46% yield) as white solid.

Analytical Data:
$^1$H NMR (200 MHz, DMSO) δ 7.84 (d, J=8.5 Hz, 2H), 7.75-7.64 (m, 3H), 7.38-7.23 (m, 5H), 5.26-5.03 (m, 2H), 4.55 (dd, J=16.6, 7.0 Hz, 3H), 1.38 (s, J=14.3 Hz, 9H).

$^{13}$C NMR (50 MHz, DMSO) δ 169.6, 164.7, 155.4, 135.7, 131.7, 131.3, 128.5, 128.3, 128.0, 127.7, 127.5, 78.6, 66.3, 52.7, 28.1.

MS: [M+Na]$^+$=500.3.

Step 3: [(2S)-2-[(2-methylpropan-2-yl)oxycarbonylamino]-3-oxo-3-phenylmethoxypropyl] 4-[3-[2,4-difluoro-3-(methanesulfonamido)benzoyl]-1-(oxan-2-yl)pyrazolo[3,4-b]pyridin-5-yl]benzoate A vessel was charged with [(2S)-2-[(2-methylpropan-2-yl)oxycarbonylamino]-3-oxo-3-phenylmethoxypropyl] 4-bromobenzoate (124 mg, 0.260 mmol), N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]methanesulfonamide (146 mg, 0.260 mmol), Pd(dppf)Cl$_2$.DCM (10.6 mg, 0.0130 mmol), potassium fluoride (45.2 mg, 0.779 mmol) and degassed 1,4-dioxane/water (4+1) (0.8 mL) and the vessel was evacuated and filled with argon (3×). The reaction was heated to 50° C. with stirring for 6 h. The mixture was diluted with EtOAc, washed with brine and the solvents were removed. The product was isolated via flash chromatography (3 times column volume hexane/EtOAc (80/20 v/v, followed by DCM/EtOAc 80/20 v/v to elute the product) to yield [(2S)-2-[(2-methylpropan-2-yl)oxycarbonylamino]-3-oxo-3-phenylmethoxy-propyl] 4-[3-[2,4-difluoro-3-(methanesulfonamido)benzoyl]-1-(oxan-2-yl)pyrazolo[3,4-b]-pyridin-5-yl]benzoate (147 mg, 0.1760 mmol, 68% yield) as white solid.

Analytical Data:
$^1$H NMR (200 MHz, Acetone) δ 9.06 (s, 1H), 8.90 (s, 1H), 8.55 (s, 1H), 8.22-7.89 (m, 5H), 7.59-7.31 (m, 5H), 6.82 (d, J=7.6 Hz, 1H), 6.34 (d, J=9.2 Hz, 1H), 5.44-5.23 (m, 2H), 4.99-4.72 (m, 3H), 4.20-3.76 (m, 2H), 3.30 (s, 3H), 2.62 (dd, J=20.1, 9.7 Hz, 1H), 2.25-1.61 (m, 5H), 1.60-1.32 (m, 10H).

$^{13}$C NMR (50 MHz, Acetone) δ 185.7, 170.6, 166.1, 156.4, 151.7, 150.3, 143.1, 142.1, 136.8, 133.5, 131.3, 130.1, 129.3, 129.0, 128.9, 128.4, 116.1, 83.8, 79.8, 68.3, 67.6, 65.4, 54.2, 42.0, 29.7, 28.5, 25.7, 23.1.

TLC-MS (ESI$^-$): m/z 833.0 [M−1]$^-$.

Step 4: (2S)-2-amino-3-[4-[3-[2,4-difluoro-3-(methanesulfonamido)benzoyl]-1H-pyrazolo[3,4-b]pyridin-5-yl]benzoyl]oxypropanoic acid hydrochloride

[(2S)-2-[(2-methylpropan-2-yl)oxycarbonylamino]-3-oxo-3-phenylmethoxypropyl] 4-[3-[2,4-difluoro-3-(methanesulfonamido)benzoyl]-1-(oxan-2-yl)pyrazolo[3,4-b]pyridin-5-yl]benzoate (142 mg, 0.170 mmol) was dissolved in EtOAc (1.70 mL) and 14 mg palladium on activated carbon (10%) was added. The reaction was stirred under H$_2$ atmosphere (3 bar) overnight. The reaction was degassed, 5 mg palladium on activated carbon (10%) was added and the reaction stirred under 5 bar H$_2$ atmosphere (for 6 h). The reaction was filtered through celite and the solvent was removed. The residue was taken up in 2 ml TFA and stirred at RT for 2 h. 4N HCl in dioxane (2 mL) was added with ice cooling. After 5 minutes, 5 ml THF was added and the solids collected by suction filtration, washed with THF and dried in vacuo to yield (2S)-2-amino-3-[4-[3-[2,4-difluoro-3-(methanesulfon-amido)benzoyl]-1H-pyrazolo[3,4-b]pyridin-5-yl]benzoyl]oxypropanoic acid hydrochloride (50.0 mg, 0.0814 mmol, 48% yield) as off white solid.

Analytical Data:
$^1$H NMR (200 MHz, DMSO) δ 14.92 (s, 1H), 9.76 (s, 1H), 9.10 (d, J=2.1 Hz, 1H), 8.86 (d, J=2.1 Hz, 1H), 8.78 (s, 3H), 8.22 (d, J=8.5 Hz, 2H), 8.03 (d, J=8.5 Hz, 2H), 7.88 (dd, J=15.0, 7.6 Hz, 1H), 7.41 (td, J=8.9, 1.2 Hz, 1H), 4.71 (s, 2H), 4.53 (s, 1H), 3.12 (s, 3H).

$^{13}$C NMR (50 MHz, DMSO) δ 185.2, 168.4, 164.9, 152.3, 149.6, 142.4, 141.9, 131.1, 130.5, 128.6, 128.2, 127.6, 114.1, 66.3, 51.4, 41.5.

TLC-MS (ESI$^-$): m/z 558.2 [M−1]$^-$.

Example 58: Synthesis of 5-[3-[2,4-difluoro-3-(methanesulfonamido)benzoyl]-1H-pyrazolo[3,4-b]pyridin-5-yl]pyridine-2-carboxylic acid hydrochloride

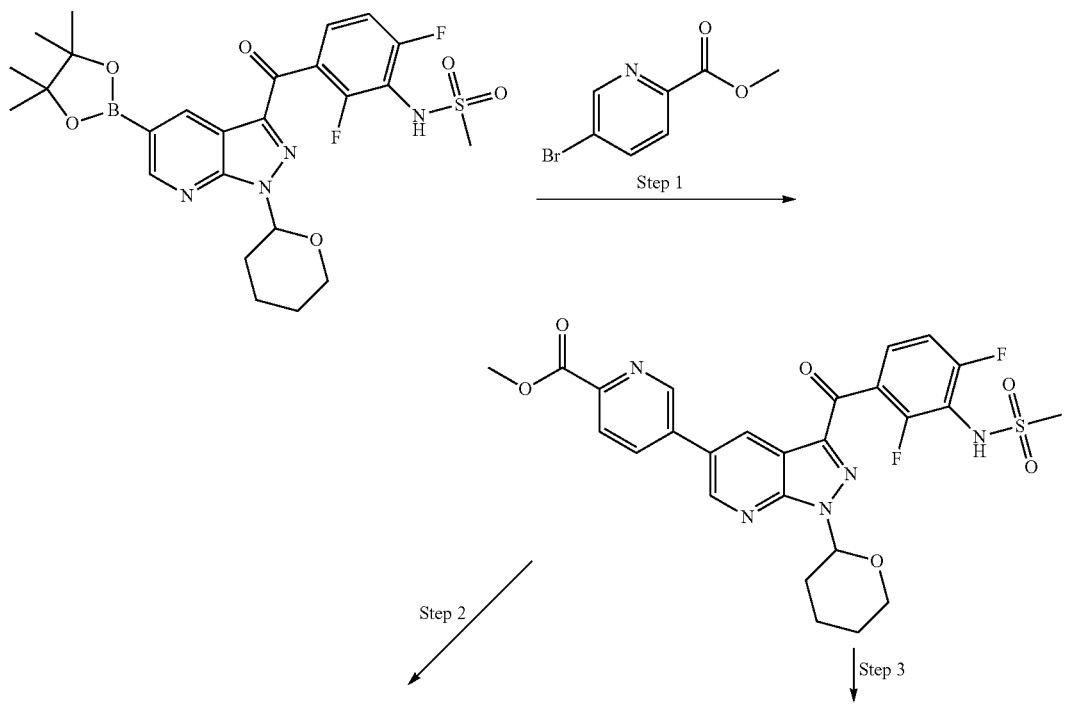

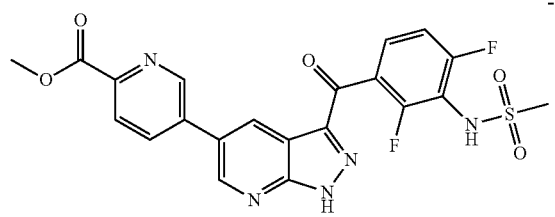

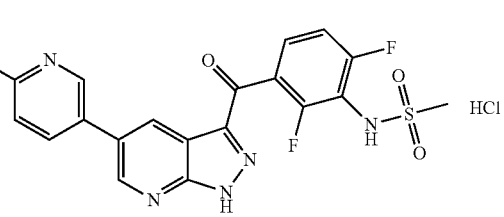

Step 1: Methyl 5-[3-[2,4-difluoro-3-(methanesulfonamido)benzoyl]-1-(oxan-2-yl)pyrazolo[3,4-b]pyridin-5-yl]pyridine-2-carboxylate A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]methanesulfonamide (132 mg, 0.235 mmol), methyl 5-bromopyridine-2-carboxylate (55.8 mg, 0.258 mmol), potassium fluoride (40.9 mg, 0.704 mmol), Pd(dppf)Cl$_2$.DCM (9.58 mg, 0.0117 mmol) and degassed 1,4-dioxane/water (4+1) (0.6 mL) and the vessel was evacuated and filled with argon (3×). The reaction was heated to 50° C. overnight with stirring. The mixture was diluted with EtOAc, washed with brine and the solvents were removed. The product was isolated via flash chromatography (DCM/EtOAc gradient, from 20% to 60% EtOAc) to yield methyl 5-[3-[2,4-difluoro-3-(methanesulfonamido)benzoyl]-1-(oxan-2-yl)pyrazolo[3,4-b]pyridin-5-yl]pyridine-2-carboxylate (97.0 mg, 0.1700 mmol, 72% yield) as white solid.

Analytical Data:
$^1$H NMR (400 MHz, acetone) δ 9.14 (d, J=1.9 Hz, 1H), 9.06 (d, J=2.1 Hz, 1H), 8.91 (d, J=2.1 Hz, 1H), 8.40 (dd, J=8.1, 2.3 Hz, 1H), 8.22 (d, J=8.1 Hz, 1H), 7.95 (dd, J=14.9, 7.5 Hz, 1H), 7.34 (dd, J=8.8, 8.0 Hz, 1H), 6.27 (dd, J=9.9, 2.4 Hz, 1H), 4.09-3.91 (m, 4H), 3.80 (td, J=11.2, 3.5 Hz, 1H), 3.21 (s, 3H), 2.54 (ddd, J=16.4, 13.3, 4.0 Hz, 1H), 2.19-2.06 (m, 1H), 2.05-1.97 (m, 1H), 1.94-1.77 (m, 1H), 1.76-1.56 (m, 2H).
$^{13}$C NMR (101 MHz, acetone) δ 185.7, 166.1, 162.3 (dd, J=256, 3 Hz), 158.7 (dd, J=258, 5 Hz), 152.0, 150.3, 149.3, 148.5, 142.3, 137.3, 136.7, 131.63 (dd, J=10.9, 3.2 Hz), 130.7, 125.9, 124.7 (dd, J=14, 4 Hz), 116.2, 115.8 (t, J=17 Hz), 112.8 (dd, J=21, 4 Hz), 83.9, 68.4, 52.8, 42.1, 29.8, 25.8, 23.1.
TLC-MS (ESI$^-$): m/z 570.4 [M–1]$^-$.

Step 2: methyl 5-[3-[2,4-difluoro-3-(methanesulfonamido)benzoyl]-1H-pyrazolo[3,4-b]pyridin-5-yl]pyridine-2-carboxylate To a solution of methyl 5-[3-[2,4-difluoro-3-(methanesulfonamido)benzoyl]-1-(oxan-2-yl)pyrazolo[3,4-b]pyridin-5-yl]pyridine-2-carboxylate (60.0 mg, 0.105 mmol) in MeOH (0.525 mL) was added methanesulfonic acid (0.0273 mL, 0.420 mmol) and the mixture was stirred at 65° C. for 1.5 h. The mixture was cooled to RT and added slowly into 15 ml diethyl ether, the solid was collected by suction filtration, washed with diethyl ether and dried in vacuo to yield methyl 5-[3-[2,4-difluoro-3-(methanesulfonamido)benzoyl]-1H-pyrazolo[3,4-b]pyridin-5-yl]pyridine-2-carboxylate (36.0 mg, 0.0739 mmol, 70% yield) as white solid.

Analytical Data:
$^1$H NMR (200 MHz, CDCl$_3$) δ 14.90 (s, 1H), 9.74 (s, 1H), 9.16 (dd, J=12.4, 1.9 Hz, 2H), 8.93 (d, J=2.0 Hz, 1H), 8.47 (dd, J=8.2, 2.3 Hz, 1H), 8.19 (d, J=8.3 Hz, 1H), 7.88 (dd, J=14.8, 7.7 Hz, 1H), 7.41 (t, J=8.7 Hz, 1H), 3.93 (s, 3H), 3.12 (s, 3H).
$^{13}$C NMR (50 MHz, CDCl$_3$) δ 185.1, 165.0, 152.4, 149.6, 148.3, 146.5, 141.9, 136.1, 136.0, 129.2, 128.4, 125.0, 114.0, 52.5, 41.5.
MS: [M+Na]$^+$=510.4.

Step 3: 5-[3-[2,4-difluoro-3-(methanesulfonamido)benzoyl]-1H-pyrazolo[3,4-b]pyridin-5-yl]pyridine-2-carboxylic acid hydrochloride Methyl 5-[3-[2,4-difluoro-3-(methanesulfonamido)benzoyl]-1-(oxan-2-yl)pyrazolo[3,4-b]pyridin-5-yl]pyridine-2-carboxylate (46.0 mg, 0.0805 mmol) was stirred in 3N HCl (2.68 mL, 8.05 mmol) at 70° C. overnight in an open vessel. The solvent was removed, residual water was azeotropically removed with toluene. The residue was dissolved in MeOH (1 mL) and added dropwise to diethyl ether. The solid was collected by suction filtration, washed with diethyl ether and dried in vacuo to yield 5-[3-[2,4-difluoro-3-(methanesulfonamido)benzoyl]-1H-pyrazolo[3,4-b]pyridin-5-yl]pyridine-2-carboxylic acid hydrochloride (33.0 mg, 0.0647 mmol, 80% yield).

Analytical Data:
$^1$H NMR (200 MHz, CDCl$_3$) δ 14.96 (s, 1H), 9.77 (s, 1H), 9.18 (s, 1H), 9.13 (d, J=1.9 Hz, 1H), 8.93 (d, J=1.9 Hz, 1H), 8.48 (d, J=8.1 Hz, 1H), 8.19 (d, J=7.8 Hz, 1H), 7.88 (dd, J=14.7, 7.8 Hz, 1H), 7.41 (t, J=8.6 Hz, 1H), 3.12 (s, 3H).
$^{13}$C NMR (101 MHz, DMSO) δ 185.0, 152.3, 149.5, 141.9, 136.1, 114.2, 114.0, 48.5, 41.5, 15.1.
TLC-MS (ESI$^-$): m/z 472.3 [M–1]$^-$.

Example 59: Synthesis of N-[2,6-difluoro-3-(5-pyridin-4-yl-1H-pyrazolo[3,4-b]pyridine-3-carbonyl)phenyl]methanesulfonamide hydrochloride

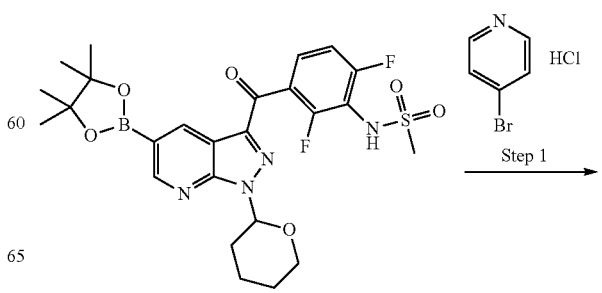

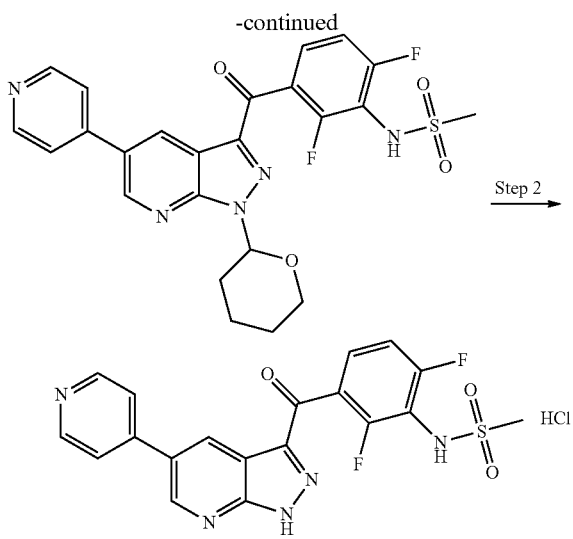

Step 1: N-[2,6-difluoro-3-[1-(oxan-2-yl)-5-pyridin-4-ylpyrazolo[3,4-b]pyridine-3-carbonyl]-phenyl]methanesulfonamide A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]methanesulfonamide (86.0 mg, 0.153 mmol), 4-bromopyridine hydrochloride (29.7 mg, 0.153 mmol), Pd(dppf)Cl$_2$.DCM (3.75 mg, 0.00459 mmol), degassed 1,4-dioxane (0.382 mL) and degassed 1.5 M aqueous potassium carbonate (0.408 mL, 0.612 mmol). The vessel was evacuated and filled with argon (3×) and heated to 60° C. for 2 h. After cooling, the reaction was diluted with EtOAc neutralized with NH$_4$Cl solution, the aqueous phase was discarded, and the organics were concentrated. The product was isolated by flash chromatography (DCM/MeOH gradient, from 2% to 12% MeOH). N-[2,6-difluoro-3-[1-(oxan-2-yl)-5-pyridin-4-ylpyrazolo[3,4-b]pyridine-3-carbonyl]phenyl]methanesulfonamide (63.0 mg, 0.1230 mmol, 80% yield).

Analytical Data:

$^1$H NMR (200 MHz, acetone) δ 9.03 (d, J=2.3 Hz, 1H), 8.89 (d, J=2.1 Hz, 1H), 8.72 (d, J=5.9 Hz, 3H), 7.94 (ddd, J=8.8, 7.5, 6.2 Hz, 1H), 7.80 (dd, J=4.5, 1.6 Hz, 2H), 7.34 (td, J=9.0, 1.7 Hz, 1H), 6.25 (dd, J=9.9, 2.3 Hz, 1H), 4.12-3.95 (m, 1H), 3.90-3.68 (m, 1H), 3.21 (s, 3H), 2.51 (dt, J=10.1, 7.1 Hz, 1H), 2.16-1.57 (m, 5H).

$^{13}$C NMR (50 MHz, acetone) δ 185.7, 152.1, 151.4, 150.1, 145.8, 142.2, 131.9, 131.6 (dd, J=10, 4 Hz), 130.3, 124.6 (dd, J=13, 4 Hz), 122.8, 116.1, 115.8, 112.8 (dd, J=21, 4 Hz), 83.8, 68.3, 42.0, 29.7, 25.7, 25.3, 23.1.

TLC-MS (ESI$^-$): m/z 512.6 [M−1]$^-$.

Step 2: N-[2,6-difluoro-3-(5-pyridin-4-yl-1H-pyrazolo[3,4-b]pyridine-3-carbonyl)phenyl]-methanesulfonamide hydrochloride N-[2,6-difluoro-3-[1-(oxan-2-yl)-5-pyridin-4-ylpyrazolo[3,4-b]pyridine-3-carbonyl]phenyl]methanesulfonamide (60.0 mg, 0.117 mmol) was heated to reflux in MeOH (2 mL) and 4N HCl in dioxane (0.5 mL) for 1 h. The solvent was removed and the residue triturated with THF to yield N-[2,6-difluoro-3-(5-pyridin-4-yl-1H-pyrazolo[3,4-b]pyridine-3-carbonyl)phenyl]methanesulfonamide hydrochloride (37.0 mg, 0.0794 mmol, 68% yield) as white solid.

Analytical Data:

$^1$H NMR (200 MHz, DMSO) δ 15.09 (s, 1H), 9.77 (s, 1H), 9.28 (d, J=2.3 Hz, 1H), 9.13 (d, J=2.3 Hz, 1H), 8.99 (d, J=6.7 Hz, 2H), 8.52 (d, J=6.7 Hz, 2H), 7.90 (dd, J=15.0, 7.6 Hz, 1H), 7.42 (td, J=8.9, 1.2 Hz, 1H), 3.12 (s, 3H).

$^{13}$C NMR (101 MHz, DMSO) δ 184.9, 160.7 (dd, J=255, 3 Hz), 157.1 (dd, J=257, 4 Hz), 153.0, 151.8, 149.7, 143.6, 142.3, 130.5, 127.3, 124.1, 123.4 (dd, J=13, 4 Hz), 114.3 (t, J=17 Hz), 112.0 (dd, J=21.3 Hz), 41.5.

TLC-MS (ESI$^-$): m/z 428.6 [M−1]$^-$.

Example 60: Synthesis of N-[2,6-difluoro-3-[5-[4-(methylsulfonimidoyl)phenyl]-1H-pyrazolo[3,4-b]pyridine-3-carbonyl]phenyl]methanesulfonamide

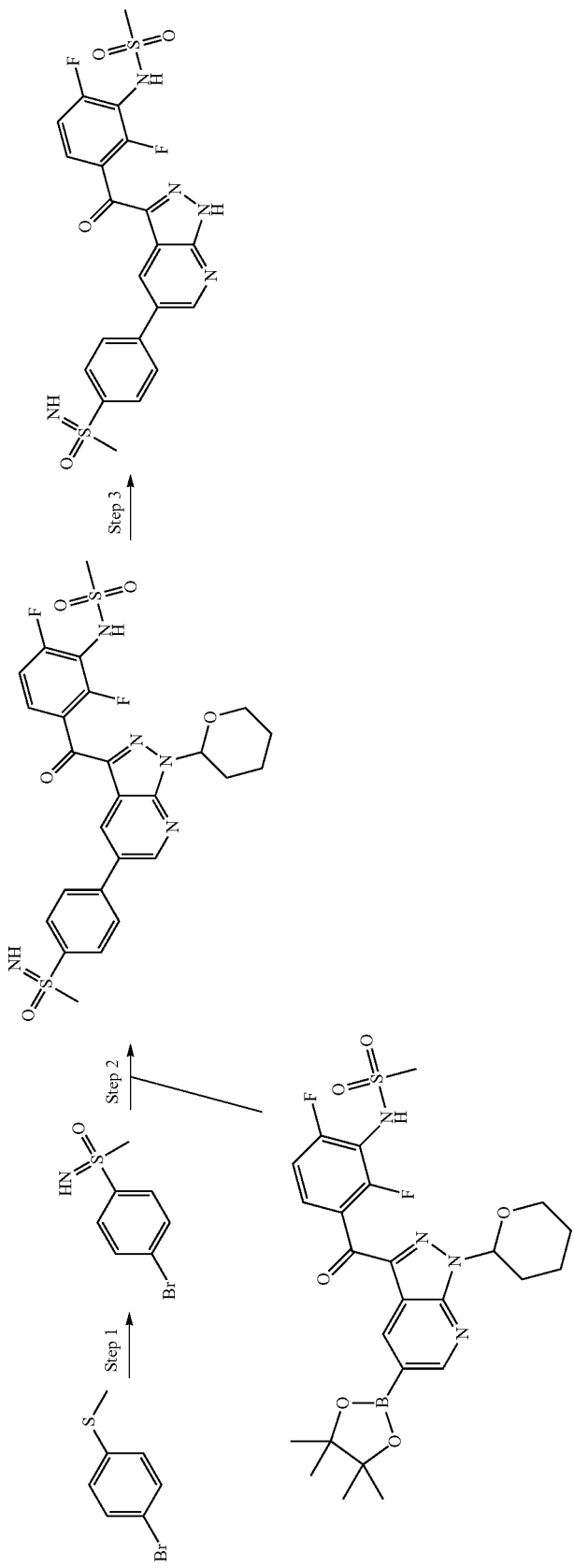

Step 1: (4-bromophenyl)-imino-methyl-oxo-λ^{6}-sulfane 1-bromo-4-methylsulfanylbenzene (0.970 g, 4.78 mmol), ammonium acetate (1.47 g, 19.1 mmol) and (diacetoxyiodo) benzene (3.85 g, 11.9 mmol) were combined in 9.55 mL MeOH at RT. The reaction was stirred for 1 h, diluted with water (20 mL) and extracted with EtOAc. The extracts were washed with water, dried over $Na_2SO_4$ and the solvents were removed in vacuo. The product was isolated by flash chromatography (DCM/MeOH, 97/3% v/v) (4-bromophenyl)-imino-methyl-oxo-λ^{6}-sulfane (0.570 g, 2.43 mmol, 51% yield).

Analytical Data:
$^1$H NMR (200 MHz, DMSO) δ 7.91-7.76 (m, 4H), 4.24 (s, 1H), 3.08 (s, 1H).
$^{13}$C NMR (50 MHz, DMSO) δ 143.5, 132.0, 129.4, 126.4, 45.6.
MS: [M+H]$^+$=234.1.

Step 2: N-[2,6-difluoro-3-[5-[4-(methylsulfonimidoyl)phenyl]-1-(oxan-2-yl)pyrazolo[3,4-b]pyridine-3-carbonyl]phenyl]methanesulfonamide A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]methanesulfonamide (93.0 mg, 0.165 mmol), (4-bromophenyl)-imino-methyl-oxo-λ^{6}-sulfane (38.7 mg, 0.165 mmol), Pd(dppf)Cl$_2$.DCM (4.05 mg, 0.00496 mmol), potassium fluoride (28.8 mg, 0.496 mmol) and degassed 1,4-dioxane/water (4:1, 0.5 mL). The vessel was evacuated and filled with argon (3×) and heated to 50° C. for 3 h. After cooling the reaction was diluted with EtOAc, washed with brine and the solvents were removed. The product was isolated by flash chromatography (DCM/MeOH gradient, from 1% to 8% MeOH). N-[2,6-difluoro-3-[5-[4-(methylsulfonimidoyl)phenyl]-1-(oxan-2-yl)pyrazolo[3,4-b]pyridine-3-carbonyl]phenyl]-methanesulfonamide (63.0 mg, 0.1070 mmol, 65% yield).

Analytical Data:
$^1$H NMR (200 MHz, acetone) δ 8.97 (d, J=1.9 Hz, 1H), 8.82 (d, J=2.0 Hz, 1H), 8.63 (s, 1H), 8.13 (d, J=8.3 Hz, 2H), 8.03-7.87 (m, 3H), 7.33 (td, J=8.9, 1.3 Hz, 1H), 6.24 (dd, J=9.7, 1.9 Hz, 1H), 4.11-3.93 (m, 1H), 3.87-3.70 (m, 1H), 3.18 (d, J=13.0 Hz, 7H), 2.66-2.37 (m, 1H), 2.18-1.52 (m, 5H).
$^{13}$C NMR (50 MHz, acetone) δ 151.8, 150.4, 142.7, 142.1, 130.3, 129.4, 129.0, 116.1, 83.8, 68.4, 46.6, 42.0, 35.2, 32.3, 29.8, 25.7, 23.1, 14.3.
TLC-MS (ESI$^-$): m/z 588.4 [M−1]$^-$.

Step 3: N-[2,6-difluoro-3-[5-[4-(methylsulfonimidoyl)phenyl]-1H-pyrazolo[3,4-b]pyridine-3-carbonyl]phenyl]methanesulfonamide To N-[2,6-difluoro-3-[5-[4-(methylsulfonimidoyl)phenyl]-1-(oxan-2-yl)pyrazolo[3,4-b]pyridine-3-carbonyl]phenyl]methanesulfonamide (63.0 mg, 0.107 mmol) in 2 mL MeOH was added 4N HCl in 1,4-dioxane (2 mL) and the reaction was stirred at reflux temperature for 1 h. After cooling, the mixture was concentrated, treated with dry THF/diethyl ether (1+1) and the solids were collected by suction filtration, washed with diethyl ether. The solids were taken up in water and neutralized with NaHCO$_3$ solution. The product was collected by suction filtration, washed with water and dried in vacuo to yield N-[2,6-difluoro-3-[5-[4-(methylsulfonimidoyl)phenyl]-1H-pyrazolo[3,4-b]pyridine-3-carbonyl]phenyl]methanesulfonamide (24.0 mg, 0.0451 mmol, 42% yield).

Analytical Data:
$^1$H NMR (200 MHz, DMSO) δ 9.08 (s, 1H), 8.85 (s, 1H), 8.07 (s, 4H), 7.87 (dd, J=14.8, 8.0 Hz, 1H), 7.41 (t, J=8.5 Hz, 1H), 4.31 (s, 1H), 3.13 (d, J=3.4 Hz, 6H).
$^{13}$C NMR (101 MHz, DMSO) δ 185.1, 152.3, 149.5, 143.5, 141.8, 141.1, 131.0, 128.6, 128.1, 127.9, 114.0, 45.8, 41.5.
MS: [M+H]$^+$=506.4.

Example 61: Synthesis of N-[3-[5-(4-chlorophenyl)-1H-pyrazolo[3,4-b]pyridine-3-carbonyl]-2,6-difluorophenyl]propane-1-sulfonamide

Step 1: N-[3-(5-bromo-1H-pyrazolo[3,4-b]pyridine-3-carbonyl)-2,6-difluorophenyl]propane-1-sulfonamide

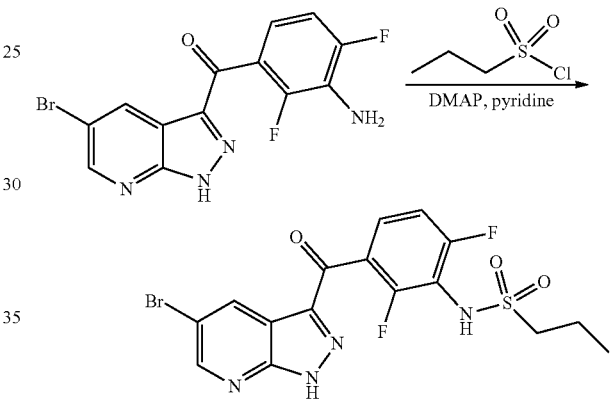

To a suspension of (3-amino-2,4-difluorophenyl)-(5-bromo-1H-pyrazolo[3,4-b]pyridin-3-yl)methanone (805 mg, 2.28 mmol) and triethylamine (3.50 mL, 25.1 mmol) in DCM (11.4 mL) was added 1-propanesulfonyl chloride (898 μL, 7.98 mmol) in DCM (11.4 mL) slowly at −10° C. and the reaction was stirred at −10° C. for 15 minutes. The reaction was diluted with DCM, washed with 2N HCl and brine, dried over Na$_2$SO$_4$ and evaporated. The residue was dissolved in THF (2 mL) and 2N KOH (2 mL) was added. After 10 minutes the reaction was diluted with water and THF was evaporated. The solution was added to 2N HCl (10 mL) with stirring, stirring was continued for 30 minutes and the solids were collected by suction filtration, washed with 2N HCl and water and dried at 100° C. to yield N-[3-(5-bromo-1H-pyrazolo[3,4-b]pyridine-3-carbonyl)-2,6-difluorophenyl]propane-1-sulfonamide (801 mg, 1.69 mmol, 74% yield).

Analytical Data:
$^1$H NMR (200 MHz, Acetone) δ 13.77 (s, 1H), 8.72 (d, J=12.1 Hz, 2H), 8.38 (s, 1H), 7.91 (dd, J=14.8, 7.6 Hz, 1H), 7.30 (t, J=8.7 Hz, 1H), 3.40-3.14 (m, 2H), 2.03-1.81 (m, 2H), 1.07 (t, J=7.4 Hz, 3H).
$^{13}$C NMR (50 MHz, Acetone) δ 185.7, 162.1 (dd, J=255, 4 Hz), 153.7 (dd, J=222, 4 Hz), 152.0, 151.6, 142.5, 133.7, 131.5 (dd, J=11, 4 Hz), 124.5 (dd, J=14, 4 Hz), 116.6, 116.2, 115.7 (t, J=17 Hz), 112.8, 112.7, 112.4, 112.3, 56.2, 18.1, 13.1.
MS: [M−1]$^-$=457.3.

Step 2: N-[3-[5-(4-chlorophenyl)-1H-pyrazolo[3,4-b]pyridine-3-carbonyl]-2,6-difluorophenyl]-propane-1-sulfonamide

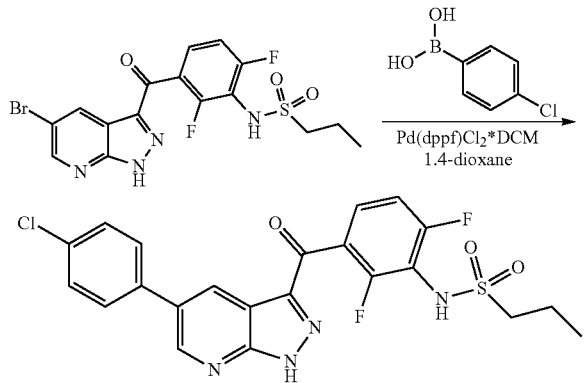

A microwave vessel was charged with N-[3-(5-bromo-1H-pyrazolo[3,4-b]pyridine-3-carbonyl)-2,6-difluorophenyl]propane-1-sulfonamide (60.0 mg, 0.131 mmol), (4-chlorophenyl)boronic acid (21.4 mg, 0.137 mmol) and Pd(dppf)Cl$_2$.DCM (5.33 mg, 0.00653 mmol) and purged with argon. Degassed 1,4-dioxane (0.435 mL) and degassed aqueous 1.5M K$_2$CO$_3$ (0.261 mL, 0.392 mmol) were added and the mixture stirred at 110° C. under microwave irradiation for 30 minutes. A spatula Pd(dppf)Cl$_2$ was added and heating continued for 30 minutes. After cooling, the mixture was neutralized with sat. NH$_4$Cl solution and diluted with EtOAc. The aqueous phase was discarded, and the solvent removed under reduced pressure. The residue was purified by flash chromatography (DCM/EtOAc gradient, from 0 to 35% EtOAc) and triturated with DCM to yield N-[3-[5-(4-chlorophenyl)-1H-pyrazolo[3,4-b]pyridine-3-carbonyl]-2,6-difluorophenyl]propane-1-sulfonamide (30.0 mg, 0.0605 mmol, 46% yield) as white solid.

Analytical Data:
$^1$H NMR (200 MHz, DMSO) δ 14.81 (s, 1H), 9.66 (s, 1H), 9.01 (d, J=2.1 Hz, 1H), 8.77 (d, J=2.1 Hz, 1H), 7.98-7.78 (m, 3H), 7.60 (d, J=8.4 Hz, 2H), 7.40 (t, J=8.7 Hz, 1H), 3.22-3.09 (m, 2H), 1.92-1.70 (m, 2H), 1.00 (t, J=7.5 Hz, 3H).
$^{13}$C NMR (101 MHz, DMSO) δ 185.2, 152.1, 149.4, 141.8, 136.2, 133.1, 131.3, 129.2, 128.1, 114.1, 55.0, 39.5, 16.9, 12.7.
MS: [M−1]$^-$=489.5.

Examples 62-67

In analogy to the procedure of Example 61, step 2 the following compounds were prepared:

| Expl. | Reactant | Product Chemical structure/name | Analytical data |
|---|---|---|---|
| 62 | 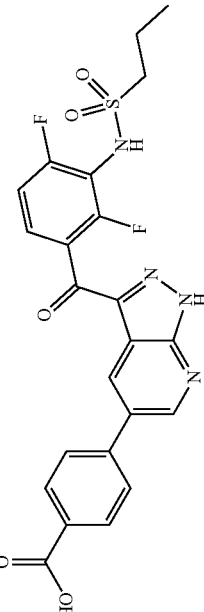 | 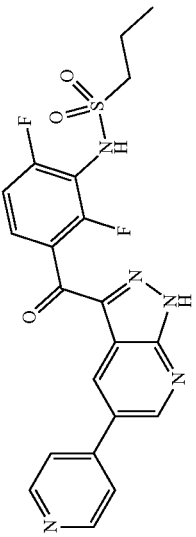

4-(3-(2,4-difluoro-3-(propylsulfon-amido)benzoyl)-1H-pyrazolo[3,4-b]pyridin-5-yl)benzoic acid | ¹H NMR (200 MHz, DMSO) δ 14.85 (s, 1H), 13.07 (s, 1H), 9.67 (s, 1H), 9.07 (d, J = 2.1 Hz, 1H), 8.84 (d, J = 2.0 Hz, 1H), 8.10 (d, J = 8.3 Hz, 2H), 8.01-7.79 (m, 3H), 7.40 (td, J = 9.0, 1.2 Hz, 1H), 3.24-3.01 (m, 2H), 1.94-1.68 (m, 2H), 1.00 (t, J = 7.4 Hz, 3H). ¹³C NMR (101 MHz, DMSO) δ 185.2, 167.1, 160.8 (dd, J = 255, 4 Hz), 157.1 (dd, J = 256, 4 Hz), 152.3, 149.5, 141.9, 141.5, 131.4, 130.5 (dd, J = 11, 4 Hz), 130.2, 128.5, 127.5, 123.6 (dd, J = 14, 4 Hz), 114.3 (d, J = 17 Hz), 114.1, 112.0 (dd, J = 22, 4 Hz), 54.9, 16.9, 12.6. TLC-MS (ESI-): m/z 499.7 [M − 1]⁻. |
| 63 | 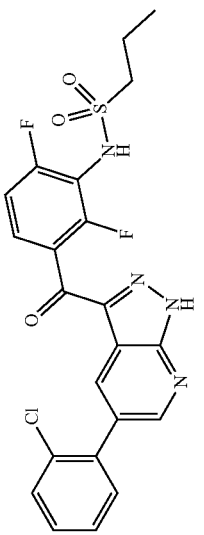 | N-(2,6-difluoro-3-(5-(pyridin-4-yl)-1H-pyrazolo[3,4-b]pyridine-3-carbonyl)phenyl)propane-1-sulfonamide | ¹H NMR (200 MHz, DMSO) δ 14.90 (s, 1H), 9.67 (s, 1H), 9.13 (s, 1H), 8.92 (s, 1H), 8.73 (s, 2H), 7.92 (d, J = 4.5 Hz, 3H), 7.40 (t, J = 8.7 Hz, 1H), 3.24-3.05 (m, 2H), 1.93-1.70 (m, 2H), 1.00 (t, J = 7.3 Hz, 3H). ¹³C NMR (101 MHz, DMSO) δ 185.1, 160.8 (dd, J = 255, 3 Hz), 157.1 (dd, J = 257, 4 Hz), 152.7, 150.2, 149.4, 144.7, 142.0, 130.5 (dd, J = 10, 4 Hz), 129.5, 128.9, 123.6 (dd, J = 13, 3 Hz), 121.9, 114.3 (t, J = 17 Hz), 114.0, 112.0 (dd, J = 22, 3 Hz), 54.9, 16.9, 12.6. TLC-MS (ESI-): m/z 456.3 [M − 1]⁻. |
| 64 | | N-(3-(5-(2-chlorophenyl)-1H-pyrazolo[3,4-b]pyridine-3-carbonyl)-2,6-difluorophenyl)propane-1-sulfonamide | TLC-MS (ESI-): m/z = 469.0, 489.0 [M − 1]⁻ |

-continued

| Expl. | Reactant | Product Chemical structure/name | Analytical data |
|---|---|---|---|
| 65 | 4-isopropylphenylboronic acid | N-(2,6-difluoro-3-(5-(4-isopropylphenyl)-1H-pyrazolo[3,4-b]pyridine-3-carbonyl)phenyl)propane-1-sulfonamide | TLC-MS (ESI⁻): m/z = 477.2, 497.2 [M − 1]⁻ |
| 66 | 4-fluoro-2-methylphenylboronic acid | N-(2,6-difluoro-3-(5-(4-fluoro-2-methylphenyl)-1H-pyrazolo[3,4-b]pyridine-3-carbonyl)phenyl)propane-1-sulfonamide | TLC-MS (ESI⁻): m/z = 467.2, 487.1 [M − 1]⁻ |
| 67 | 4-(4,4,5,5-tetramethyl-1,3,2-dioxaborolan-2-yl)benzenesulfonamide | 4-(3-(2,4-difluoro-3-(propylsulfonamido)benzoyl)-1H-pyrazolo[3,4-b]pyridin-5-yl)benzenesulfonamide | TLC-MS (ESI⁻): m/z = 514.1, 534.1 [M − 1]⁻ |

Example 68: Synthesis of N-[2,6-difluoro-3-(5-pyridin-4-yl-1H-pyrazolo[3,4-b]pyridine-3-carbonyl)phenyl]-1-phenylmethanesulfonamide

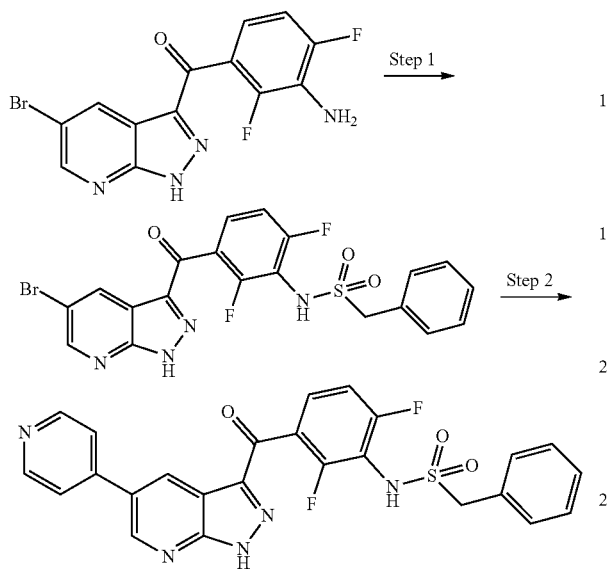

Step 1: N-[3-(5-bromo-1H-pyrazolo[3,4-b]pyridine-3-carbonyl)-2,6-difluorophenyl]-1-phenylmethanesulfonamide To a solution of (3-amino-2,4-difluorophenyl)-(5-bromo-1H-pyrazolo[3,4-b]pyridin-3-yl)methanone (830 mg, 2.35 mmol) and 4-DMAP (0.574 g, 4.70 mmol) in pyridine (4.74 mL, 58.8 mmol) was added phenylmethanesulfonyl chloride (583 mg, 3.06 mmol) at −10° C. and the mixture was stirred at −10° C. for 10 minutes until a homogeneous suspension was formed. Stirring was continued at RT for 10 minutes and the reaction was heated to 50° C. for 30 minutes. The reaction was concentrated under reduced pressure and taken up in 2N NaOH (3.53 mL, 7.05 mmol) and was stirred at RT for 10 minutes. The mixture was diluted with water and slowly added to 25 mL 2N HCl with stirring. After 10 minutes, the solids were collected by suction filtration, washed with water and dried at 100° C. to yield N-[3-(5-bromo-1H-pyrazolo[3,4-b]pyridine-3-carbonyl)-2,6-difluorophenyl]-1-phenylmethanesulfonamide (1.02 g, 2.01 mmol, 86% yield) as off-white solid.

Analytical Data:
$^1$H NMR (200 MHz, DMSO) δ 14.98 (s, 1H), 9.81 (s, 1H), 8.73 (dd, J=6.1, 2.2 Hz, 2H), 7.88 (dd, J=14.9, 7.6 Hz, 1H), 7.50-7.30 (m, 6H), 4.53 (s, 2H).
$^{13}$C NMR (50 MHz, DMSO) δ 184.8, 150.9, 150.6, 140.9, 132.5, 131.0, 129.4, 128.4, 128.3, 115.5, 115.2, 59.4.
MS: [M−1]$^−$=505.2.

Step 2: N-[2,6-difluoro-3-(5-pyridin-4-yl-1H-pyrazolo[3,4-b]pyridine-3-carbonyl)phenyl]-1-phenylmethanesulfonamide A microwave vessel was charged with N-[3-(5-bromo-1H-pyrazolo[3,4-b]pyridine-3-carbonyl)-2,6-difluorophenyl]-1-phenylmethanesulfonamide (75.0 mg, 0.148 mmol), 4-pyridinylboronic acid (21.8 mg, 0.177 mmol) and Pd(dppf)Cl$_2$.DCM (6.04 mg, 0.00739 mmol) and purged with argon. Degassed 1,4-dioxane (0.493 mL) and degassed aqueous 1.5M K$_2$CO$_3$ (0.345 mL, 0.517 mmol) were added and the mixture was heated to 110° C. under microwave irradiation for 60 minutes. After cooling, the reaction was diluted with EtOAc and neutralized with NH$_4$Cl solution. The aqueous phase was cut and the solvent evaporated. The residue was purified by flash chromatography (DCM+MeOH 2% to 10%) and triturated with DCM to yield N-[2,6-difluoro-3-(5-pyridin-4-yl-1H-pyrazolo[3,4-b]pyridine-3-carbonyl)phenyl]-1-phenylmethanesulfonamide (40.0 mg, 0.0783 mmol, 53% yield).

Analytical Data:
$^1$H NMR (400 MHz, DMSO) δ 14.91 (s, 1H), 9.77 (s, 1H), 9.13 (d, J=2.3 Hz, 1H), 8.92 (d, J=2.3 Hz, 1H), 8.72 (dd, J=4.7, 1.4 Hz, 2H), 8.07-7.68 (m, 3H), 7.53-7.26 (m, 6H), 4.53 (s, 2H). [M−1]$^−$=504.4.

Example 69: Synthesis of N-[2,6-difluoro-3-(5-pyridin-4-yl-1H-pyrazolo[3,4-b]pyridine-3-carbonyl)phenyl]ethanesulfonamide

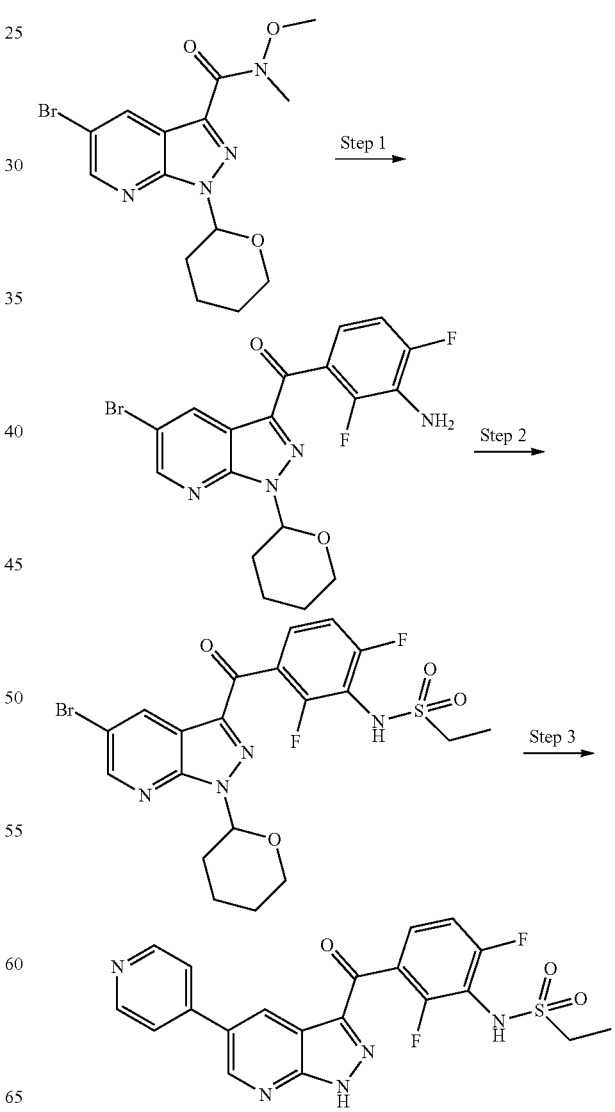

Step 1: (3-amino-2,4-difluorophenyl)-[5-bromo-1-(oxan-2-yl)pyrazolo[3,4-b]pyridin-3-yl]methanone To 3-bromo-2,6-difluoroaniline (4.69 g, 22.6 mmol) in tetrahydrofuran (19.6 mL) was added 2M isopropylmagnesium chloride in THF (11.3 mL, 22.6 mmol) dropwise at 0° C. and stirred for 15 minutes without further cooling. After cooling again to 0° C., chlorotrimethylsilane (2.86 mL, 22.6 mmol) was added, the mixture warmed to 25° C. and stirred for 20 minutes. The solution was cooled to 0° C. and chlorotrimethylsilane (2.86 mL, 22.6 mmol) was added stirring continued for 20 minutes at 25° C. The solution was cooled to 0° C. again and 2M isopropylmagnesium chloride in THF (11.3 mL, 22.6 mmol) was added dropwise and the mixture was stirred for 10 minutes at 0° C. 5-bromo-N-methoxy-N-methyl-1-(oxan-2-yl)pyrazolo[3,4-b]pyridine-3-carboxamide (3.62 g, 9.80 mmol) was dissolved in 10 mL THF and added to the mixture and stirring was continued for 1 h at RT. The reaction was quenched with sat. NH$_4$Cl solution, water was added until the aqueous phase became clear and the phases were separated. The aqueous was extracted with EtOAc, the extracts were washed with brine, dried over Na$_2$SO$_4$ and the solvent was removed. The oily residue was dissolved in 25 mL THF and 2 mL conc. HCl were added with stirring. After 5 minutes, the mixture was carefully neutralized with solid K$_2$CO$_3$, diluted with EtOAc and filtered. The solvents were removed and the residue purified by flash chromatography (n-hexane/EtOAc gradient, from 0% to 40% EtOAc) to yield (3-amino-2,4-difluorophenyl)-[5-bromo-1-(oxan-2-yl)pyrazolo[3,4-b]pyridin-3-yl]methanone (2.35 g, 5.37 mmol, 55% yield).

Analytical Data:
$^1$H NMR (200 MHz, DMSO) δ 8.76 (dd, J=13.9, 2.1 Hz, 2H), 7.15-6.89 (m, 2H), 6.12 (d, J=7.8 Hz, 1H), 5.51 (s, 2H), 4.08-3.56 (m, 2H), 2.46-2.20 (m, 1H), 2.06-1.46 (m, 5H).
$^{13}$C NMR (50 MHz, DMSO) δ 185.6, 153.6 (dd, J=190, 9 Hz), 150.6, 149.0, 146.8 (d, J=9 Hz), 140.2, 133.0, 126.3 (t, J=17 Hz), 122.3 (dd, J=11, 3 Hz), 116.4 (d, J=3 Hz), 116.2, 116.2, 115.7, 110.7 (dd, J=19, 3 Hz), 82.7, 67.0, 28.5, 24.4, 21.8.
MS: [M+Na+MeOH]$^+$=491.05.

Step 2: N-[3-[5-bromo-1-(oxan-2-yl)pyrazolo[3,4-b]pyridine-3-carbonyl]-2,6-difluorophenyl]-ethanesulfonamide To a solution of (3-amino-2,4-difluorophenyl)-[5-bromo-1-(oxan-2-yl)pyrazolo[3,4-b]pyridin-3-yl]methanone (286 mg, 0.654 mmol) and triethylamine (0.547 mL, 3.92 mmol) in DCM (3.27 mL) was added ethanesulfonyl chloride (143 μL, 1.50 mmol) at 0° C. The reaction was stirred at RT for 15 minutes and was washed with 2N HCl and brine. The solvent was removed and taken up in 2 mL THF and 2 mL 2N aqueous KOH and stirred for 10 minutes. The reaction was acidified with 2N HCl, diluted with water and extracted with EtOAc. The extract was washed with brine, dried over Na$_2$SO$_4$ and evaporated. The residue was purified by flash chromatography (n-hexane/EtOAc gradient, from 5% to 40% EtOAc) to yield N-[3-[5-bromo-1-(oxan-2-yl)pyrazolo[3,4-b]pyridine-3-carbonyl]-2,6-difluorophenyl]ethanesulfonamide (0.267 g, 0.5040 mmol, 77% yield).

Analytical Data:
$^1$H NMR (200 MHz, DMSO) δ 9.70 (s, 1H), 8.80 (dd, J=14.1, 2.1 Hz, 2H), 7.87 (dd, J=14.8, 7.7 Hz, 1H), 7.43 (td, J=8.9, 1.0 Hz, 1H), 6.14 (dd, J=9.6, 1.7 Hz, 1H), 4.07-3.87 (m, 1H), 3.83-3.62 (m, 1H), 3.20 (q, J=7.2 Hz, 2H), 2.34 (dd, J=22.5, 11.3 Hz, 1H), 2.07-1.46 (m, 5H), 1.33 (t, J=7.3 Hz, 3H).
$^{13}$C NMR (50 MHz, DMSO) δ 184.4, 161.8 (dd, J=191, 4 Hz), 156.7 (dd, J=193, 4 Hz), 150.8, 149.0, 139.9, 133.0, 130.8 (dd, J=11, 4 Hz), 122.9 (dd, J=13, 4 Hz), 116.1, 116.0, 114.4 (t, J=17 Hz), 112.2 (dd, J=21, 4 Hz), 82.7, 67.1, 47.7, 28.5, 24.5, 21.8, 8.0.
MS: [M–1]$^-$=527.1.

Step 3: N-[2,6-difluoro-3-(5-pyridin-4-yl-1H-pyrazolo[3,4-b]pyridine-3-carbonyl)phenyl]ethanesulfonamide A microwave vessel was charged with N-[3-[5-bromo-1-(oxan-2-yl)pyrazolo[3,4-b]pyridine-3-carbonyl]-2,6-difluorophenyl]ethanesulfonamide (76.0 mg, 0.144 mmol), 4-pyridinylboronic acid (19.4 mg, 0.158 mmol) and tri(tertbutyl)phosphine Pd G3 (6.08 mg, 0.00718 mmol) and was purged with argon. Degassed 1,4-dioxane (0.479 mL) and degassed 1.5M aqueous potassium carbonate (0.287 mL, 0.431 mmol) were added and the reaction was stirred at 70° C. for 45 minutes under microwave irradiation. The reaction was acidified with 2 mL 6N HCl diluted with 3 mL MeOH and heated to 70° C. under microwave irradiation for 60 minutes. The mixture was diluted with water, neutralized with 2N NaOH and extracted with THF. The extract was washed with brine, dried over Na$_2$SO$_4$ and the solvent was removed. The residue was purified by flash chromatography (DCM/MeOH gradient, from 2% to 10% MeOH) to yield N-[2,6-difluoro-3-(5-pyridin-4-yl-1H-pyrazolo[3,4-b]pyridine-3-carbonyl)phenyl]ethane-sulfonamide (42.0 mg, 0.0947 mmol, 66% yield).

Analytical Data:
$^1$H NMR (400 MHz, DMSO) δ 14.89 (s, 1H), 9.66 (s, 1H), 9.12 (d, J=2.1 Hz, 1H), 8.91 (d, J=2.3 Hz, 1H), 8.72 (d, J=5.9 Hz, 2H), 7.91-7.83 (m, 3H), 7.40 (t, J=8.8 Hz, 1H), 3.18 (q, J=7.3 Hz, 2H), 1.33 (t, J=7.3 Hz, 3H).
$^{13}$C NMR (101 MHz, DMSO) δ 185.0, 152.6, 150.3, 149.3, 144.4, 141.9, 129.5, 128.7, 121.8, 114.0, 47.7, 7.9.
MS: [M–1]$^-$=442.1.

Example 70: Synthesis of 4-(3-(2,4-difluoro-3-(propysulfonamido)benzoyl)-1H-pyrazolo[3,4-b]pyridin-5-yl)-3-methylbenzenesulfonamide Step 1: N-[3-[5-bromo-1-(oxan-2-yl)pyrazolo[3,4-b]pyridine-3-carbonyl]-2,6-difluorophenyl]propane-1-sulfonamide

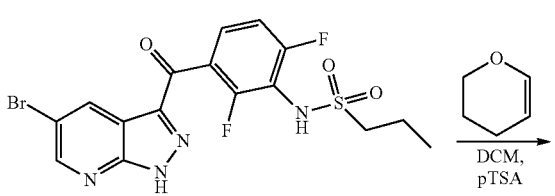

-continued

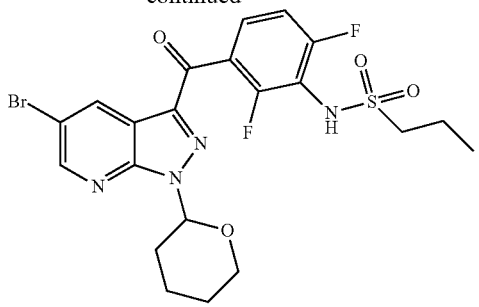

To a suspension of N-[3-(5-bromo-1H-pyrazolo[3,4-b]pyridine-3-carbonyl)-2,6-difluorophenyl]propane-1-sulfonamide (778 mg, 1.64 mmol) in DCM (8.47 mL) was added p-toluenesulfonic acid monohydrate (31.3 mg, 0.164 mmol) and dihydropyran (0.165 mL, 1.81 mmol) and the reaction was warmed to 40° C. for 1 h. The reaction was washed with NaHCO$_3$ solution and the solvent was removed. The residue was purified by flash chromatography (n-hexane+EtOAc, 5% to 45%) to yield N-[3-[5-bromo-1-(oxan-2-yl)pyrazolo[3,4-b]pyridine-3-carbonyl]-2,6-difluorophenyl]propane-1-sulfonamide (693 mg, 1.28 mmol, 78% yield).

Analytical Data:

$^1$H NMR (200 MHz, acetone) δ 8.73 (dt, J=8.0, 1.8 Hz, 2H), 8.39 (s, 1H), 7.92 (ddd, J=8.8, 7.4, 6.2 Hz, 1H), 7.32 (td, J=8.9, 1.7 Hz, 1H), 6.18 (dd, J=9.8, 2.4 Hz, 1H), 4.03-3.67 (m, 2H), 3.33-3.20 (m, 2H), 2.61-2.38 (m, 1H), 2.01-1.54 (m, 5H), 1.07 (t, J=7.5 Hz, 3H).

$^{13}$C NMR (50 MHz, acetone) δ 361.8, 339.4 (dd, J=178, 4 Hz), 334.3 (dd, J=181, 4 Hz), 327.9, 326.8, 317.5, 310.4, 308.0 (dd, J=11, 4 Hz), 300.7 (dd, J=13, 4 Hz), 293.8, 293.2, 292.2 (t, J=17 Hz), 289.0 (dd, J=22, 4 Hz), 260.2, 244.7, 232.6, 206.3, 206.0, 202.0, 199.4, 194.5, 189.5.

TLC-MS (ESI$^-$): m/z 541.0/543.0 [M−H]$^-$.

Step 2: N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide

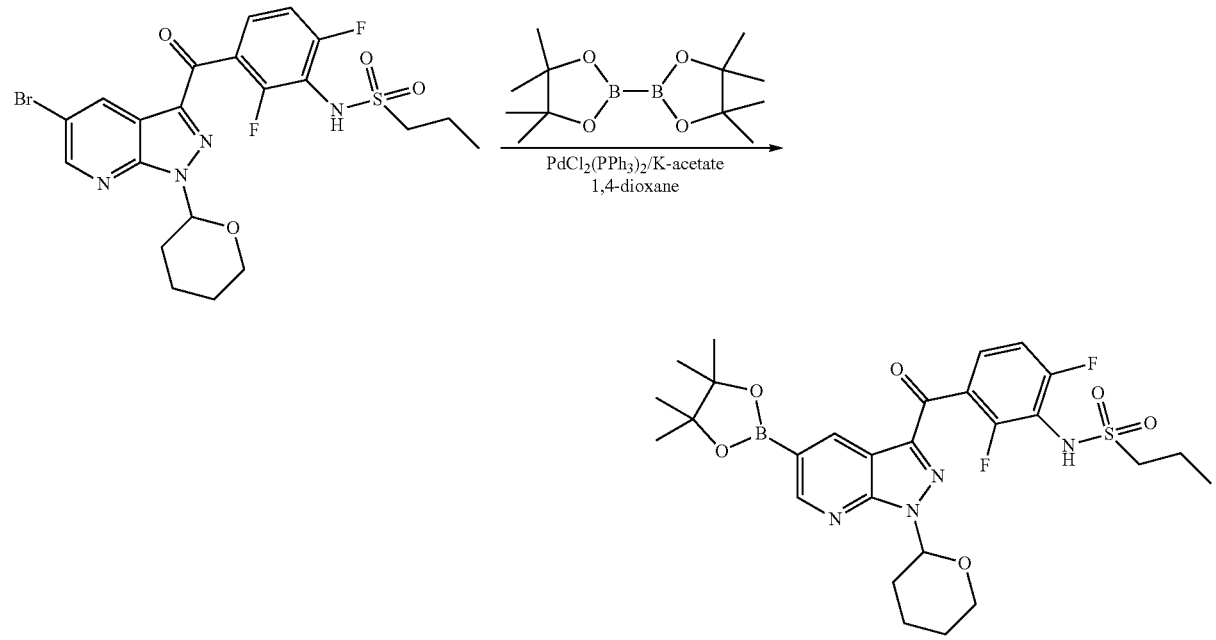

A vessel was charged with N-[3-[5-bromo-1-(oxan-2-yl)pyrazolo[3,4-b]pyridine-3-carbonyl]-2,6-difluorophenyl]propane-1-sulfonamide (875 mg, 1.61 mmol), bis(pinacolato)diboron (429 mg, 1.69 mmol), bis(triphenylphosphine)palladium(II) dichloride (22.6 mg, 0.0322 mmol), anhydrous potassium acetate (474 mg, 4.83 mmol) and dry 1,4-dioxane (8.05 mL). The vessel was evacuated and filled with argon (3×) and the reaction was heated to 80° C. for 3 h. After cooling, the reaction was diluted with EtOAc, filtered over celite and evaporated. The residue was taken up in EtOAc (ca. 20 mL) activated charcoal was added and the mixture was heated to reflux for 10 minutes. After cooling, the mixture was filtered over celite, the solvent was evaporated and the residue was sonicated with n-hexane. The solids were collected by suction filtration and in vacuo to yield N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (765 mg, 1.3 mmol, 80% yield) as colorless solid.

Step 3

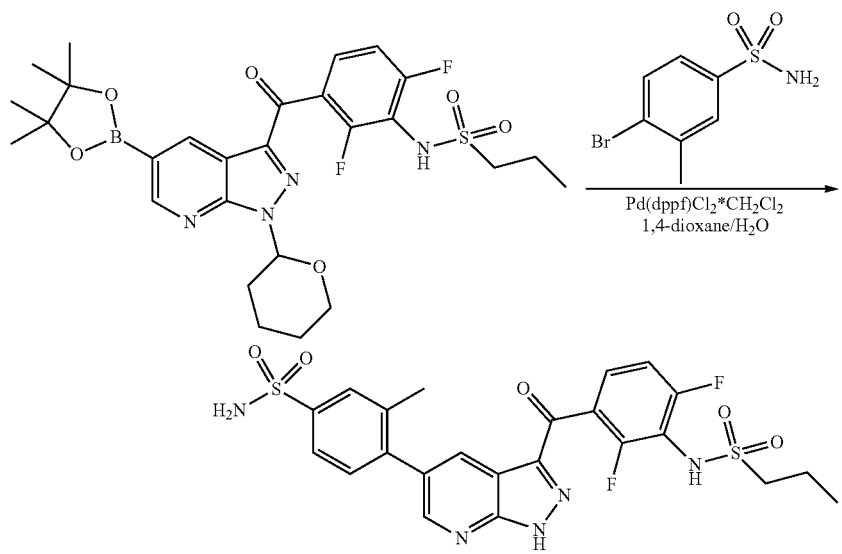

A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (100 mg, 0.169 mmol), potassium fluoride (29.5 mg, 0.508 mmol), 4-bromo-3-methylbenzenesulfonamide (46.6 mg, 0.186 mmol), Pd(dppf)Cl₂.DCM (6.92 mg, 0.00847 mmol) and 0.5 mL 1,4-dioxane/water (4+1). The vessel was evacuated and filled with argon (3×) and heated to 60° C. for 2 h. The reaction was acidified with conc. HCl (0.3 mL), diluted with MeOH (0.2 mL) and heated to 60° C. overnight. After cooling, the reaction was diluted with EtOAc and water. The organic phase was evaporated and the product was purified by flash chromatography (DCM/EtOAc gradient, from 10% to 50% EtOAc) 4-[3-[2,4-difluoro-3-(propylsulfonylamino)benzoyl]-1H-pyrazolo[3,4-b]pyridine-5-yl]-3-methylbenzenesulfonamide (42.0 mg, 0.0764 mmol, 45% yield)

Analytical Data:
TLC-MS (ESI⁻): m/z=528.2, 548.1 [M−H]⁻

Example 71: Synthesis of N-(2,6-difluoro-3-(5-(2-(trifluoromethyl)pyrimidin-5-yl)-1H-pyrazolo[3,4-b]pyridine-3-carbonyl)phenyl)propane-1-sulfonamide

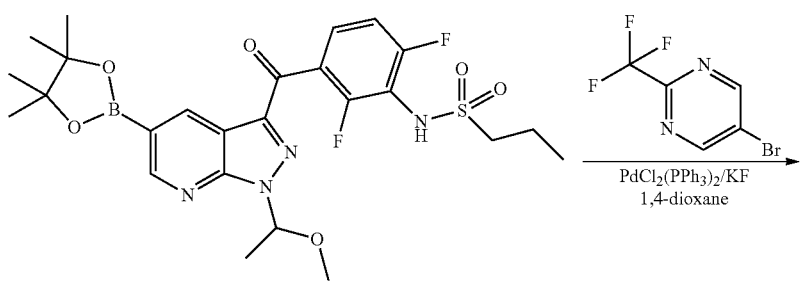

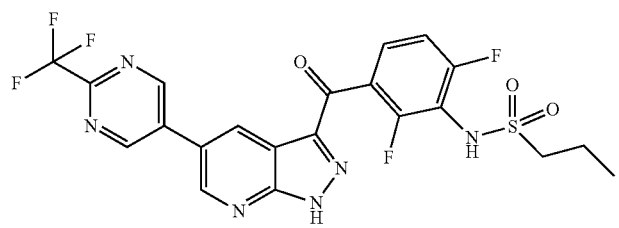

A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (88.0 mg, 0.149 mmol), 5-bromo-2-(trifluoromethyl)pyrimidine (37.2 mg, 0.164 mmol), potassium fluoride (26.0 mg, 0.447 mmol), bis(triphenylphosphine)palladium(II) dichloride (5.23 mg, 0.00745 mmol) and 0.5 mL 1,4-dioxane/water (4+1). The vessel was evacuated and filled with argon (3×) and heated to 60° C. for 2 h. The reaction was acidified with conc. HCl (0.3 mL), diluted with MeOH (0.2 mL) and heated to 60° C. overnight. After cooling, the reaction was diluted with EtOAc and water. The organic phase was evaporated and the product was purified by flash chromatography (DCM/EtOAc gradient, from 5% to 35% EtOAc) N-[2,6-difluoro-3-[5-[2-(trifluoromethyl)pyrimidin-5-yl]-1H-pyrazolo[3,4-b]pyridine-3-carbonyl]phenyl]propane-1-sulfonamide (42.0 mg, 0.0798 mmol, 54% yield).
Analytical Data:
TLC-MS (ESI⁻): m/z=505.1, 525.1 [M–H]⁻

Example 72: Synthesis of N-(3-(5-(4-chloro-2-methylphenyl)-1H-pyrazolo[3,4-b]pyridine-3-carbonyl)-2,6-difluorophenyl)propane-1-sulfonamide

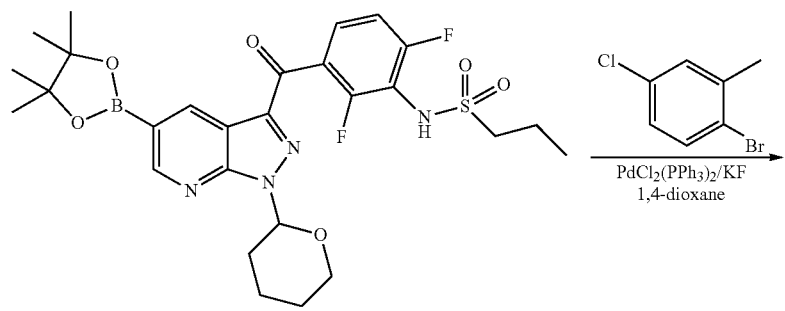

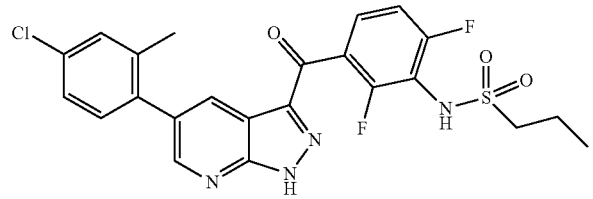

A vessel was charged with N-[2,6-difluoro-3-[1-(oxan-2-yl)-5-(4,4,5,5-tetramethyl-1,3,2-dioxaborolan-2-yl)pyrazolo[3,4-b]pyridine-3-carbonyl]phenyl]propane-1-sulfonamide (80.0 mg, 0.135 mmol), 1-bromo-4-chloro-2-methylbenzene (18.0 μL, 0.135 mmol), potassium fluoride (23.6 mg, 0.406 mmol), bis(triphenylphosphine)palladium(II) dichloride (4.76 mg, 0.00677 mmol) and 0.5 mL 1,4-dioxane/water (4+1). The vessel was evacuated and filled with argon (3×) and heated to 60° C. for 1 h. The reaction was acidified with conc. HCl (0.2 mL), diluted with MeOH (0.2 mL) and heated to 60° C. overnight. After cooling, the reaction was diluted with EtOAc and water. The organic phase was evaporated and the product was purified by flash chromatography (DCM/EtOAc gradient, 0%-40% EtOAc) to yield N-[3-[5-(4-chloro-2-methylphenyl)-1H-pyrazolo[3,4-b]pyridine-3-carbonyl]-2,6-difluorophenyl]propane-1-sulfonamide (32.0 mg, 0.0608 mmol, 45% yield).
Analytical Data:
TLC-MS (ESI⁻): m/z=483.3, 503.3 [M–H]⁻

Example 73: Synthesis of N-(3-(5-(4-(1H-tetrazol-5-yl)phenyl)-1H-pyrazolo[3,4-b]pyridine-3-carbonyl)-2,6-difluorophenyl)ethanesulfonamide Step 1: N-(3-(5-bromo-1H-pyrazolo[3,4-b]pyridine-3-carbonyl)-2,6-difluorophenyl) ethanesulfonamide

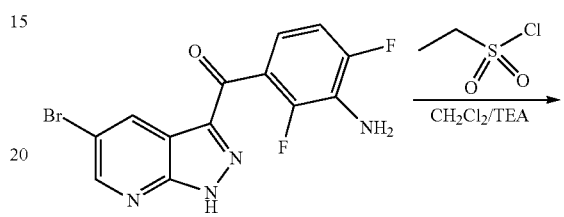

-continued

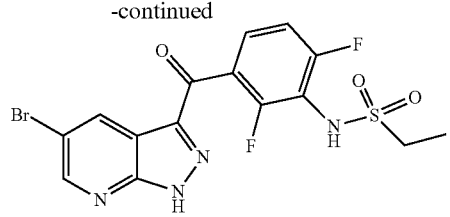

To a suspension of (3-amino-2,4-difluorophenyl)-(5-bromo-1H-pyrazolo[3,4-b]pyridine-3-yl)methanone (823 mg, 2.33 mmol) and triethylamine (3.57 mL, 25.6 mmol) in DCM (11.7 mL) was added ethanesulfonyl chloride (0.773 mL, 8.16 mmol) in DCM (11.7 mL) slowly at −10° C. and the reaction was stirred at −10° C. for 20 minutes. The reaction was washed with 2N HCl and brine and the solvent was removed. The residual gum was taken up in 10 mL THF and 2N NaOH (6.99 mL, 14.0 mmol) was added. After stirring for 30 minutes the solution acidified with 2N HCl.

Water was added, THF was removed in vacuo and the solids were collected by suction filtration, washed with water and dried at 100° C. to yield N-[3-(5-bromo-1H-pyrazolo[3,4-b]pyridine-3-carbonyl)-2,6-difluorophenyl]ethanesulfonamide (761 mg, 1.71 mmol, 73% yield).

Step 2: N-(3-(5-bromo-1-(tetrahydro-2H-pyran-2-yl)-1H-pyrazolo[3,4-b]pyridine-3-carbonyl)-2,6-difluorophenyl)ethanesulfonamide

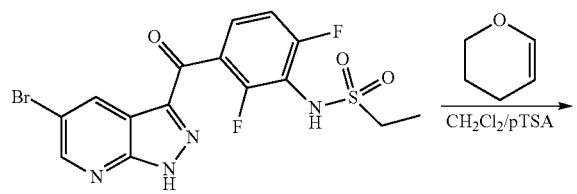

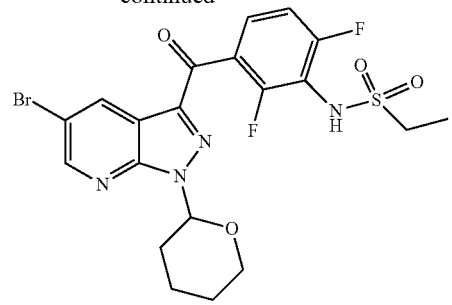

To a suspension of N-[3-(5-bromo-1H-pyrazolo[3,4-b]pyridine-3-carbonyl)-2,6-difluorophenyl]ethanesulfonamide (529 mg, 1.19 mmol) and p-toluenesulfonic acid monohydrate (22.6 mg, 0.119 mmol) in DCM (5.94 mL) was added dihydropyran (0.130 mL, 1.43 mmol) and the reaction was warmed to 30° C. for 1 h. The reaction was diluted with EtOAc, washed with sat. NaHCO₃ solution and brine, and the solvent was removed. The product was purified by flash chromatography (n-hexane/EtOAc gradient, 0%-40% EtOAc) to yield N-[3-[5-bromo-1-(oxan-2-yl)pyrazolo[3,4-b]pyridine-3-carbonyl]-2,6-difluorophenyl]ethanesulfonamide (534 mg, 1.01 mmol, 85% yield).

Step 3

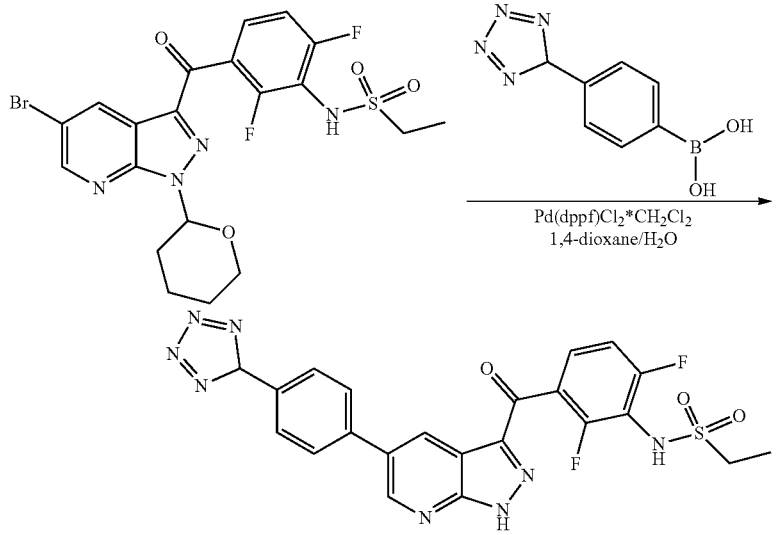

Analytical Data:
TLC-MS (ESI⁻): m/z=509.3 [M−H]⁻

Example 74: Synthesis of N-(3-(5-(4-(1H-tetrazol-5-yl)phenyl)-1H-pyrazolo[3,4-b]pyridine-3-carbonyl)-2,6-difluorophenyl)propane-1-sulfonamide

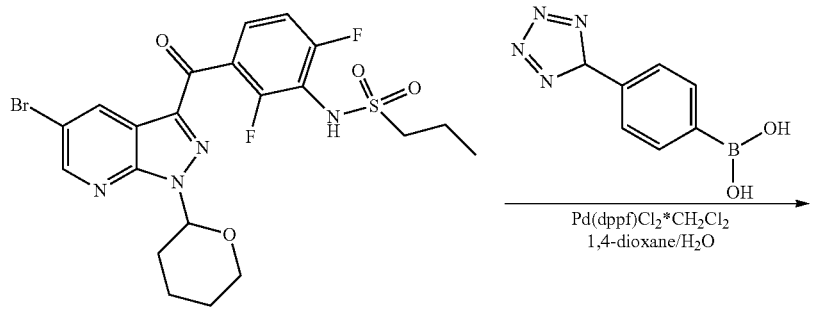

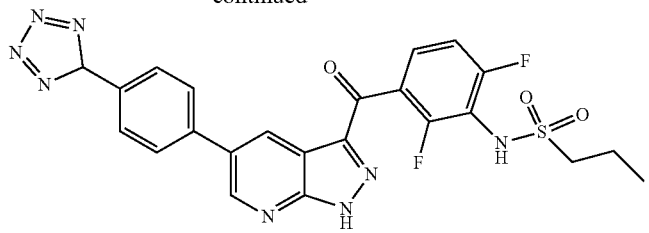

A vessel was charged with N-[3-[5-bromo-1-(oxan-2-yl)pyrazolo[3,4-b]pyridine-3-carbonyl]-2,6-difluorophenyl]propane-1-sulfonamide (80.0 mg, 0.147 mmol), [4-(1H-tetrazol-5-yl)phenyl]boronic acid (33.6 mg, 0.177 mmol) and Pd(dppf)Cl$_2$.DCM (6.01 mg, 0.00736 mmol) and purged with argon. Degassed 1,4-dioxane (0.491 mL) and degassed 1.5 M aqueous potassium carbonate (0.393 mL, 0.589 mmol) were added, the vessel was sealed and the reaction was heated to 80° C. for 2.5. The reaction was diluted with MeOH, acidified with conc. HCl and stirring was continued at 60° C. for 3 h. The reaction was poured into water and extracted with EtOAc. The extract was washed with brine, the solvent was removed and the product was purified by flash chromatography (DCM+MeOH (+1% formic acid), 5% to 10%), triturated with DCM and dried at 100° C. to yield N-[2,6-difluoro-3-[5-[4-(1H-tetrazol-5-yl)phenyl]-1H-pyrazolo[3,4-b]pyridine-3-carbonyl]phenyl]propane-1-sulfonamide (38.0 mg, 0.0724 mmol, 49% yield).

Analytical Data:
H NMR (200 MHz, DMSO) δ 14.99 (s, 1H), 9.83 (s, 1H), 9.14 (d, J=2.1 Hz, 1H), 8.88 (d, J=2.2 Hz, 1H), 8.17 (dd, J=19.9, 8.4 Hz, 4H), 7.65 (td, J=9.0, 6.1 Hz, 1H), 7.32 (td, J=9.0, 1.4 Hz, 1H), 3.20-3.05 (m, 2H), 1.90-1.59 (m, 2H), 0.97 (t, J=7.4 Hz, 3H).
$^{13}$C NMR (101 MHz, DMSO) δ 182.5, 156.29 (dd, J=248.3, 6.4 Hz), 152.8 (dd, J=251.2, 8.2 Hz), 152.4, 149.8, 142.0, 139.7, 131.7, 129.9, 129.8, 128.3, 127.9, 127.7, 127.6, 123.8, 121.79 (dd, J=13.4, 3.4 Hz), 117.1, 113.5, 112.12 (dd, J=22.6, 4.3 Hz), 53.8, 16.8, 12.5.
TLC-MS (ESI$^-$): m/z=522.9 [M−H]$^-$.

Example 75: Synthesis of N-(3-(5-(4-(1H-tetrazol-5-yl)phenyl)-1H-pyrazolo[3,4-b]pyridine-3-carbonyl)-2,6-difluorophenyl)-1-phenylmethanesulfonamide

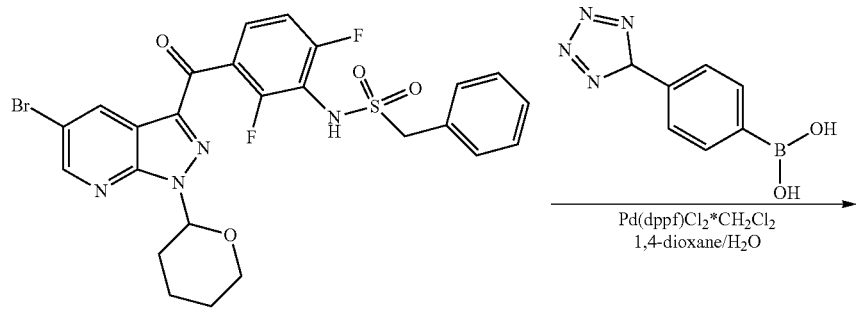

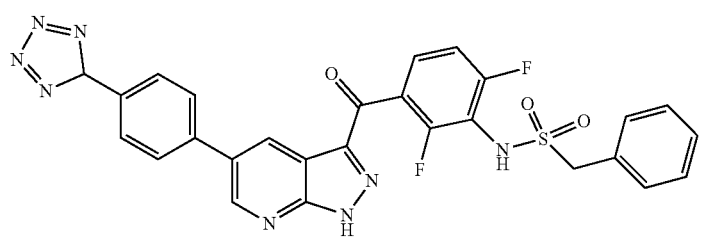

A vessel was charged with N-[3-[5-bromo-1-(oxan-2-yl)pyrazolo[3,4-b]pyridine-3-carbonyl]-2,6-difluorophenyl]-1-phenylmethanesulfonamide (76.0 mg, 0.129 mmol), [4-(1H-tetrazol-5-yl)phenyl]boronic acid (26.9 mg, 0.141 mmol) and Pd(dppf)Cl$_2$.DCM (5.25 mg, 0.00643 mmol) and purged with argon. Degassed 1,4-dioxane (0.428 mL) and degassed 1.5 M aqueous potassium carbonate (0.343 mL, 0.514 mmol) were added, the vessel was sealed and the reaction was heated to 80° C. for 2.5 h. The reaction was diluted with MeOH (1 mL), acidified with conc. HCl (1 mL) and stirring was continued at 60° C. for 3 h. The reaction was poured into water and extracted with EtOAc. The extract was washed with brine, the solvent was removed and the product was purified by flash chromatography (DCM/MeOH (+1% formic acid) gradient, from 5% to 15% MeOH (1% formic acid)), triturated with DCM and dried at 100° C. to yield N-[2,6-difluoro-3-[5-[4-(1H-tetrazol-5-yl)phenyl]-1H-pyrazolo[3,4-b]pyridine-3-carbonyl]phenyl]-1-phenylmethanesulfonamide (40.0 mg, 0.0699 mmol, 54% yield).

TLC-MS (ESI⁻): m/z 571.0 [M–H]⁻

Example 76: Synthesis of N-(2,6-difluoro-3-(5-(4-hydroxyphenyl)-1H-pyrazolo[3,4-b]pyridine-3-carbonyl)phenyl)propane-1-sulfonamide

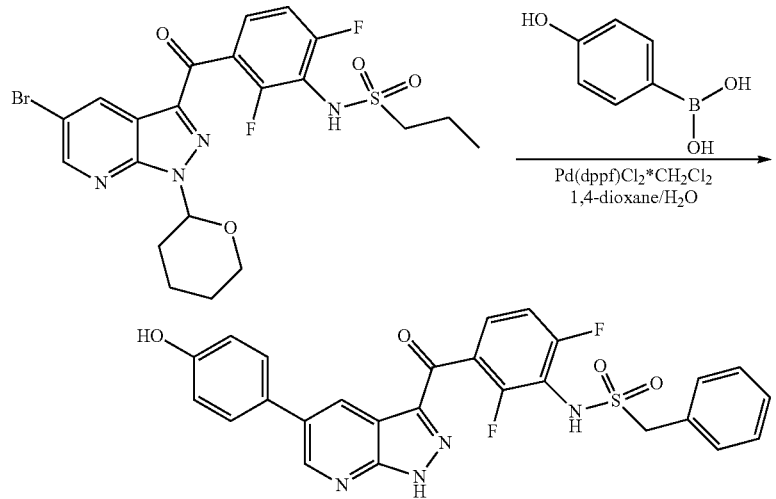

A vessel was charged with N-[3-[5-bromo-1-(oxan-2-yl)pyrazolo[3,4-b]pyridine-3-carbonyl]-2,6-difluorophenyl]propane-1-sulfonamide (72.0 mg, 0.133 mmol), (4-hydroxyphenyl)boronic acid (20.1 mg, 0.146 mmol), Potassium fluoride (23.1 mg, 0.398 mmol) and Pd(dppf)Cl$_2$ DCM (5.41 mg, 0.00663 mmol) and purged with argon. Degassed 1,4-dioxane/water (4+1) was added and the mixture stirred at 80° C. 20 minutes. After cooling, the mixture was diluted with 1 mL MeOH, acidified with 0.3 mL conc. HCl and stirred at 60° C. for 2 h. The reaction was taken up in water and EtOAc, the organic phase was washed with brine, dried over Na$_2$SO$_4$ and evaporated. The product was purified by flash chromatography (DCM 7 EtOAc gradient, from 20% to 60% EtOAc) and triturated with DCM to yield N-[2,6-difluoro-3-[5-(4-hydroxyphenyl)-1H-pyrazolo[3,4-b]pyridine-3-carbonyl]phenyl]propane-1-sulfonamide (39.0 mg, 0.0817 mmol, 62% yield).

Analytical Data:

$^1$H NMR (400 MHz, DMSO) δ 14.70 (s, 1H), 9.70 (s, 2H), 8.94 (d, J=1.9 Hz, 1H), 8.64 (d, J=2.0 Hz, 1H), 7.85 (dd, J=14.5, 7.8 Hz, 1H), 7.63 (d, J=8.5 Hz, 2H), 7.39 (t, J=8.8 Hz, 1H), 6.93 (d, J=8.5 Hz, 2H), 3.20-3.06 (m, 2H), 1.87-1.75 (m, 2H), 1.00 (t, J=7.4 Hz, 3H).

$^{13}$C NMR (101 MHz, DMSO) δ 185.2, 160.7 (dd, J=254, 4 Hz), 157.6, 157.0 (dd, J=256, 4 Hz), 151.7, 149.2, 141.5, 132.7, 130.3 (dd, J=10, 5 Hz), 128.5, 127.9, 126.6, 123.7 (dd, J=14, 4 Hz), 116.1, 114.2, 111.9 (dd, J=22, 3 Hz), 54.9, 16.9, 12.6.

TLC-MS (ESI⁻): m/z 450.9, 471.0 [M–H]⁻.

Example 77: Biological Activity

Example 77-1: Binding Assays

The kinase activities of the compounds of the invention were measured using KINOMEscan™ Profiling Service at DiscoveRx Corporation, 42501 Albrae St. Fremont, CA 94538, USA which is based on a competition binding assay that quantitatively measures the ability of a compound to compete with an immobilized, active-site directed ligand. The assay was performed by combining three components: DNA-tagged kinase; immobilized ligand; and a test compound. The ability of the test compound to compete with the immobilized ligand was measured via quantitative PCR of the DNA tag. The technology is described in detail in Fabian, M. A. et al. A small molecule-kinase interaction map for clinical kinase inhibitors. Nat. Biotechnol., 23, 329-336 (2005) and in Karaman, M. W. et al. A quantitative analysis of kinase inhibitor selectivity, Nat. Biotechnol., 26, 127-132 (2008).

For investigation of the affinity to MKK4, MKK7 and JNK1, the kinases were produced in HEK-293 cells and subsequently tagged with DNA for qPCR detection. Streptavidin-coated magnetic beads were treated with biotinylated small molecule ligands for 30 minutes at RT to generate affinity resins for kinase assays. The liganded beads were blocked with excess biotin and washed with blocking buffer (SEABLOCK™ (Pierce), 1% BSA, 0.05% TWEEN®20, 1 mM DTT) to remove unbound ligand and to reduce non-specific binding. Binding reactions were assembled by combining kinases, liganded affinity beads, and test compounds in 1× binding buffer (20% SEABLOCK™, 0.17×PBS, 0.05% TWEEN®20, 6 mM DTT). All reactions were performed in polystyrene 96-well plates in a final volume of 0.135 mL. The assay plates were incubated at RT with shaking for 1 hour and the affinity beads were washed with wash buffer (1×PBS, 0.05% TWEEN®20). The beads were then re-suspended in elution buffer (1×PBS, 0.05% TWEEN®20, 0.5 11M non-biotinylated affinity ligand) and incubated at RT with shaking for 30 minutes. The kinase concentration in the eluates was measured by qPCR.

Average Z' values and standard deviations were calculated for each kinase based on fourteen control wells per experiment in over 135 independent experiments spanning a period of sixteen months. Average Z'=0.71.

Potency of Test Compounds:

The compounds were screened at the indicated concentrations and results for binding interactions are reported as [% of control], where lower numbers indicate stronger binding, i.e. higher potency.

Details regarding the kinases tested are given in table 2 below.

The test compounds were provided as 10 mM stock solutions. The test solutions at indicated final concentrations were prepared at DiscoverX. The results are given in tables 3 to 6 below.

TABLE 2

|  | MKK4 | MKK7 | JNK1 |
| --- | --- | --- | --- |
| Group | STE | STE | CMCG |
| Kinase Construct | Partial Length | Full Length | Full length |
| Accession Number | NP_003001.1 | NP_660186.1 | NP_002741.1 |
| Species | Human | Human | Human |
| Kinase Form | Wild Type | Wild Type | Wild Type |
| Expression System | Mammalian | Mammalian | Mammalian |
| Amino Acid Start/Stop | S84/D399 | M1/R419 | M1/Q384 |
| Average Z' Panel | 0.67 | 0.78 | 0.79 |

MKK4 Potency:

Potency of Examples 2-43 against the protein kinase MKK4, expressed as residual percent of control binding (PoC), was determined at a concentration of 100 nM. The results are given in table 3 below (N/D means not determined).

TABLE 3

| Example | MKK4 |
| --- | --- |
| 2 | ++ |
| 3 | + |
| 4 | + |
| 5 | ++ |
| 6 | ++ |
| 7 | O |
| 8 | ++ |
| 9 | ++ |
| 10 | O |
| 11 | + |
| 12 | + |
| 13 | ++ |
| 14 | ++ |
| 15 | +++ |
| 16 | ++ |
| 17 | ++ |
| 18 | +++ |
| 19 | +++ |
| 20 | ++ |
| 21 | ++ |
| 22 | O |

TABLE 3-continued

| Example | MKK4 |
| --- | --- |
| 23 | ++ |
| 24 | ++ |
| 25 | ++ |
| 26 | + |
| 27 | ++ |
| 28 | + |
| 29 | + |
| 30 | O |
| 31 | ++ |
| 32 | + |
| 33 | O |
| 34 | + |
| 35 | + |
| 36 | + |
| 37 | ++ |
| 38 | + |
| 39 | + |
| 40 | ++ |
| 41 | + |
| 42 | + |
| 43 | + |
| 44 | O |
| 45 | O |
| 46 | O |
| 47 | O |
| 48 | O |
| 49 | O |
| 50 | O |
| 51a | +++ |
| 51b | +++ |
| 51c | +++ |
| 51d | +++ |
| 51e | +++ |
| 51f | +++ |
| 51g | +++ |
| 51h | ++ |
| 51i | ++ |
| 51j | ++ |
| 51k | +++ |
| 51l | +++ |
| 51m | ++ |
| 52a | ++ |
| 52b | ++ |
| 52c | ++ |
| 53a | ++ |
| 53b | O |
| 53c | +++ |
| 53d | + |
| 54a | N/D |
| 54b | N/D |
| 54c | N/D |
| 55 | N/D |
| 56 | N/D |
| 57 | N/D |
| 58 | +++ |
| 59 | N/D |
| 60 | N/D |
| 61 | +++ |
| 62 | +++ |
| 63 | +++ |
| 64 | N/D |
| 65 | N/D |
| 66 | N/D |
| 67 | N/D |
| 68 | +++ |
| 69 | +++ |
| 70 | N/D |
| 71 | N/D |
| 72 | N/D |
| 73 | N/D |
| 74 | N/D |
| 75 | N/D |
| 76 | N/D |

PoC < 1 = "+++";
1 ≤ PoC < 10 = "++";
10 ≤ PoC < 30 = "+";
PoC ≥ 30 = "O".

Selectivity Against JNK1:

Selectivity of Examples 2-67 against the off-target JNK1, determined by calculation of the ratio of residual percent of control binding (PoC) to JNK1 and MKK4, was determined at a concentration of 100 nM. The results are given in table 4 below.

TABLE 4

| Example | Selectivity vs. JNK1 |
|---|---|
| 2 | ++ |
| 3 | + |
| 4 | + |
| 5 | ++ |
| 6 | ++ |
| 7 | O |
| 8 | +++ |
| 9 | ++ |
| 10 | O |
| 11 | + |
| 12 | + |
| 13 | ++ |
| 14 | ++ |
| 15 | +++ |
| 16 | ++ |
| 17 | ++ |
| 18 | +++ |
| 19 | +++ |
| 20 | ++ |
| 21 | + |
| 22 | O |
| 23 | ++ |
| 24 | +++ |
| 25 | +++ |
| 26 | + |
| 27 | +++ |
| 28 | + |
| 29 | + |
| 30 | O |
| 31 | +++ |
| 32 | + |
| 33 | O |
| 34 | O |
| 35 | + |
| 36 | + |
| 37 | ++ |
| 38 | + |
| 39 | + |
| 40 | +++ |
| 41 | + |
| 42 | + |
| 43 | + |
| 44 | O |
| 45 | O |
| 46 | O |
| 47 | O |
| 48 | O |
| 49 | O |
| 50 | O |
| 51a | +++ |
| 51b | +++ |
| 51c | +++ |
| 51d | +++ |
| 51e | +++ |
| 51f | +++ |
| 51g | +++ |
| 51h | +++ |
| 51i | ++ |
| 51j | +++ |
| 51k | +++ |
| 51l | +++ |
| 51m | +++ |
| 52a | ++ |
| 52b | ++ |
| 52c | +++ |
| 53a | +++ |
| 53b | O |
| 53c | +++ |
| 53d | O |
| 54a | N/D |
| 54b | N/D |
| 54c | N/D |
| 55 | N/D |
| 56 | N/D |
| 57 | N/D |
| 58 | +++ |
| 59 | +++ |
| 60 | N/D |
| 61 | +++ |
| 62 | +++ |
| 63 | +++ |
| 64 | N/D |
| 65 | N/D |
| 66 | N/D |
| 67 | N/D |
| 68 | +++ |
| 69 | +++ |
| 70 | N/D |
| 71 | N/D |
| 72 | N/D |
| 73 | N/D |
| 74 | N/D |
| 75 | N/D |
| 76 | N/D |

PoC(JNK1)/PoC(MKK4) ≥ 30 = "+++";
30 > PoC(JNK1)/PoC(MKK4) ≥ 10 = "++";
10 > PoC(JNK1)/PoC(MKK4) ≥ 3 = "+";
PoC(JNK1)/PoC(MKK4) < 3 = "O".

MKK4 Potency and Selectivity Against MKK7:

Selectivity of Examples 2-43 against the off-target MKK7, determined by calculation of the ratio of residual percent of control binding (P) to MKK7 and MKK4, was determined at a concentration of 100 nM. The results are given in table 5 below.

TABLE 5

| Example | Selectivity vs. MKK7 |
|---|---|
| 2 | +++ |
| 3 | + |
| 4 | + |
| 5 | ++ |
| 6 | ++ |
| 7 | O |
| 8 | +++ |
| 9 | ++ |
| 10 | O |
| 11 | + |
| 12 | + |
| 13 | ++ |
| 14 | +++ |
| 15 | +++ |
| 16 | ++ |
| 17 | ++ |
| 18 | +++ |
| 19 | +++ |
| 20 | ++ |
| 21 | ++ |
| 22 | O |
| 23 | ++ |
| 24 | +++ |
| 25 | +++ |
| 26 | + |
| 27 | +++ |
| 28 | + |
| 29 | + |
| 30 | O |
| 31 | +++ |
| 32 | + |
| 33 | O |
| 34 | + |
| 35 | + |

TABLE 5-continued

| Example | Selectivity vs. MKK7 |
| --- | --- |
| 36 | + |
| 37 | +++ |
| 38 | + |
| 39 | + |
| 40 | +++ |
| 41 | + |
| 42 | + |
| 43 | + |
| 44 | O |
| 45 | O |
| 46 | O |
| 47 | O |
| 48 | O |
| 49 | O |
| 50 | O |
| 51a | +++ |
| 51b | +++ |
| 51c | +++ |
| 51d | +++ |
| 51e | +++ |
| 51f | +++ |
| 51g | +++ |
| 51h | +++ |
| 51i | +++ |
| 51j | +++ |
| 51k | +++ |
| 51l | +++ |
| 51m | +++ |
| 52a | ++ |
| 52b | ++ |
| 52c | +++ |
| 53a | +++ |
| 53b | O |
| 53c | +++ |
| 53d | + |
| 54a | N/D |
| 54b | N/D |
| 54c | N/D |
| 55 | N/D |
| 56 | N/D |
| 57 | N/D |
| 58 | +++ |
| 59 | +++ |
| 60 | N/D |
| 61 | +++ |
| 62 | +++ |
| 63 | +++ |
| 64 | N/D |
| 65 | N/D |
| 66 | N/D |
| 67 | N/D |
| 68 | +++ |
| 69 | ++ |
| 70 | N/D |
| 71 | N/D |
| 72 | N/D |
| 73 | N/D |
| 74 | N/D |
| 75 | N/D |
| 76 | N/D |

PoC(MKK7)/PoC(MKK4) ≥ 30 = "+++";
30 > PoC(MKK7)/PoC(MKK4) ≥ 10 = "++";
10 > PoC(MKK7)/PoC(MKK4) ≥ 3 = "+";
PoC(MKK7)/PoC(MKK4) < 3 = "O".

MKK4 Potency and Selectivity Against BRaf:

Selectivity of Examples 2-43 against the off-target BRaf, determined by calculation of the ratio of residual percent of control binding (PoC) to BRaf and MKK4, was determined at a concentration of 100 nM. The results are given in table 6 below.

TABLE 6

| Example | Selectivity vs. BRaf |
| --- | --- |
| 2 | ++ |
| 3 | O |
| 4 | + |
| 5 | ++ |
| 6 | O |
| 7 | O |
| 8 | O |
| 9 | + |
| 10 | O |
| 11 | + |
| 12 | O |
| 13 | + |
| 14 | +++ |
| 15 | + |
| 16 | O |
| 17 | + |
| 18 | ++ |
| 19 | ++ |
| 20 | O |
| 21 | + |
| 22 | O |
| 23 | + |
| 24 | O |
| 25 | ++ |
| 26 | + |
| 27 | O |
| 28 | O |
| 29 | O |
| 30 | O |
| 31 | ++ |
| 32 | O |
| 33 | O |
| 34 | O |
| 35 | + |
| 36 | O |
| 37 | + |
| 38 | + |
| 39 | + |
| 40 | +++ |
| 41 | + |
| 42 | + |
| 43 | + |
| 44 | O |
| 45 | O |
| 46 | O |
| 47 | O |
| 48 | O |
| 49 | O |
| 50 | O |
| 51a | +++ |
| 51b | ++ |
| 51c | + |
| 51d | ++ |
| 51e | + |
| 51f | + |
| 51g | + |
| 51h | O |
| 51i | O |
| 51j | O |
| 51k | O |
| 51l | O |
| 51m | O |
| 52a | + |
| 52b | O |
| 52c | + |
| 53a | +++ |
| 53b | O |
| 53c | +++ |
| 53d | O |
| 54a | N/D |
| 54b | N/D |
| 54c | N/D |
| 55 | N/D |
| 56 | N/D |
| 57 | N/D |
| 58 | +++ |
| 59 | +++ |
| 60 | N/D |

TABLE 6-continued

| Example | Selectivity vs. BRaf |
|---------|----------------------|
| 61 | +++ |
| 62 | +++ |
| 63 | +++ |
| 64 | N/D |
| 65 | N/D |
| 66 | N/D |
| 67 | N/D |
| 68 | +++ |
| 69 | +++ |
| 70 | N/D |
| 71 | N/D |
| 72 | N/D |
| 73 | N/D |
| 74 | N/D |
| 75 | N/D |
| 76 | N/D |

PoC(BRaf)/PoC(MKK4) ≥ 30 = "+++";
30 > PoC(BRaf)/PoC(MKK4) ≥ 10 = "++";
10 > PoC(BRaf)/PoC(MKK4) ≥ 3 = "+";
PoC(BRaf)/PoC(MKK4) < 3 = "O".

Example 77-2: Functional Enzyme Assays (a) Material
Recombinant kinase proteins (commercially available)
MEKK2, recombinant, active: ProQinase product #0583-0000-1
MKK4, recombinant, activated: ProQinase product #0948-0000-1
MKK4, recombinant, non activated: ProQinase product #0948-0000-2
Substrate Proteins
Casein (Sigma C-4765)
JNK1 K55R/K56R, recombinant, inactive: ProQinase product #0524-0000-1
(b) Methods
(b-1) MEKK2 Dependent MKK4 Activation
MKK4 (non activated) is incubated with MEKK2 (active) in a ratio of 10:1 (w/w), corresponding to a molar ratio of 20:1, in the presence of compound or vehicle and 20 µM ATP for 30 min at 30° C. The activation step is done in 50 mM HEPES pH 7.5, 50 mM NaCl, 3.8 mM MgCl2, 2.5 mM DTT, 10% (v/v) glycerol. Final DMSO concentration is 1%. The activation mixture is pipetted in the following order:
  2.5 µl compound in 4% DMSO
  2.5 µl ATP/MgCl2 mix
  5 µl premixed kinase solution MKK4:MEKK2 10:1 (w/w)
Protein concentrations in the activation mix are 1 µM MKK4 and 50 nM MEKK2.
(b-2) Protein Kinase Assay
A radiometric protein kinase assay was used for measuring the kinase activity of the respective protein kinases. All kinase assays were performed in 96-well polypropylene plates. After the reactions were stopped, the assay mixtures were transferred to 96-well MSFC filter-plates (Millipore). The reaction mix was passed through the filter membrane by aspiration, the membrane was washed 3 times with 150 mM $H_3PO_4$, once with ethanol, dried and liquid scintillation cocktail was added. Radioactivity was determined by counting of the samples in a Microbeta multiwell scintillation counter (Wallac). The reactions were pipetted in the following order:
a) MEKK2-MKK4 activation mix
  20 µl standard assay buffer
  10 µl MEKK2-MKK4 activation mix
  5 µl radioactive $^{33}$P-γ-ATP solution (typically 106 cpm/well)
  10 µl of substrate solution
b) Single Kinases
  20 µl standard assay buffer
  5 µl compound in 10% DMSO
  20 µl enzyme-substrate mix
  10 µl of substrate solution
The assay contained 70 mM HEPES-NaOH, pH 7.5, 3 mM MgCl$_2$, 3 mM MnCl$_2$, 3 □M Na-orthovanadate, 1.2 mM DTT, ATP (variable amounts, corresponding to the apparent ATP-K$_m$ of the respective kinase, see Table 1), [$^{33}$P-γ-ATP (approx. 8×10$^5$ cpm per well), protein kinase (variable amounts; see Table 1), and substrate (variable amounts; see Table 7 below).
The results are given in table 8 below.

TABLE 7

Enzymes, substrates, and assay conditions (amounts/well)

| # | Kinase Name | Kinase Conc. ng/50 µl | Kinase Conc. nM | ATP Conc. µM | Substrate Name | Substrate µg/50 µl | Substrate nM |
|---|---|---|---|---|---|---|---|
| 1 | MKK4-MEKK2 mix | 25 | 10 | 0.2 | JNK1 KRKR | 1 | 430 |
| 2 | MKK4 active | 25 | 10 | 0.2 | JNK1 KRKR | 1 | 430 |
| 3 | MEKK2 | 150 | 30 | 0.2 | Casein | 1 | 870 |

TABLE 8

Potency of Test Compounds

| Expl | Cascade | MKK4 | MEKK2 |
|------|---------|------|-------|
| 2 | + | +++ | O |
| 3 | + | +++ | O |
| 4 | + | + | O |
| 5 | + | +++ | O |
| 8 | O | + | O |
| 9 | + | ++ | + |
| 13 | + | +++ | + |
| 14 | + | ++ | O |
| 15 | + | +++ | + |
| 17 | + | + | O |
| 18 | ++ | +++ | + |
| 19 | + | +++ | + |
| 21 | + | ++ | + |
| 23 | O | O | O |
| 24 | O | ++ | O |
| 25 | + | ++ | O |
| 27 | ++ | +++ | + |
| 31 | + | +++ | + |
| 32 | + | ++ | O |
| 37 | ++ | +++ | + |
| 39 | O | + | O |
| 40 | O | + | O |
| 41 | + | + | O |
| 42 | + | + | O |
| 51a | ++ | ++ | + |
| 51b | + | ++ | + |
| 51c | ++ | +++ | + |
| 51d | +++ | +++ | + |
| 51e | +++ | +++ | + |
| 51f | + | +++ | + |
| 51g | + | ++ | + |
| 51j | + | +++ | O |
| 76 | N/D | +++ | N/D |
| 51k | +++ | +++ | O |
| 51l | + | ++ | + |
| 51m | + | +++ | + |
| 52a | N/D | +++ | N/D |

TABLE 8-continued

Potency of Test Compounds

| Expl | Cascade | MKK4 | MEKK2 |
|---|---|---|---|
| 52b | N/D | ++ | N/D |
| 52c | N/D | ++ | N/D |
| 53a | N/D | ++ | N/D |
| 53b | N/D | ++ | N/D |
| 53c | N/D | +++ | N/D |
| 53d | N/D | ++ | N/D |
| 54a | N/D | +++ | N/D |
| 54b | N/D | +++ | N/D |
| 54c | N/D | +++ | N/D |
| 55 | N/D | +++ | N/D |
| 57 | N/D | +++ | N/D |
| 58 | N/D | +++ | N/D |
| 59 | N/D | +++ | N/D |
| 61 | N/D | +++ | N/D |
| 62 | N/D | +++ | N/D |
| 63 | N/D | +++ | N/D |
| 64 | N/D | +++ | N/D |
| 65 | + | ++ | + |
| 66 | + | +++ | + |
| 67 | +++ | +++ | +++ |
| 68 | N/D | +++ | N/D |
| 69 | N/D | +++ | N/D |
| 70 | ++ | +++ | ++ |
| 71 | ++ | +++ | ○ |
| 72 | + | ++ | + |
| 73 | N/D | +++ | N/D |
| 74 | +++ | +++ | + |
| 75 | ++ | +++ | + |

*: potency derived from IC$_{50}$-values (PoC) according to the following classification rule:

| IC$_{50}$ ≥ 10 µM | 10 > IC$_{50}$ ≥ 1 µM | 1 > IC$_{50}$ ≥ 0.5 µM | IC$_{50}$ < 0.5 µM |
|---|---|---|---|
| ○ | + | ++ | +++ |

The invention claimed is:

1. A compound having formula (Ic) or a pharmaceutically acceptable salt, solvate, or optical isomer thereof,

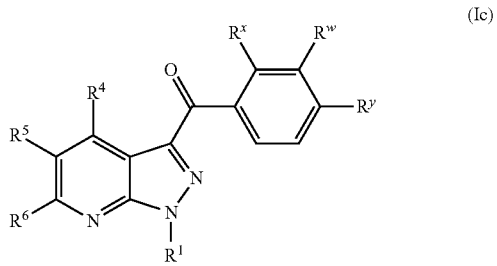

wherein the variables in formula (Ic) have the meanings as follows:
$R^1$ is H, alkyl or heterocycloalkyl having 4 to 5 ring carbon atoms and 1 or 2 heteroatoms independently selected from O, NH or N-alkyl;
$R^w$ is —NR$^{10}$SO$_2$R$^{12}$ or —N=S(=O)R$^{10}$NR$^{10}$R$^{10}$;
$R^x$ is F;
$R^y$ is F;
$R^4$ is
H,
halogen, or
alkyl;
$R^5$ is a heteroaromatic 5- or 6-membered monocyclic or heteroaromatic 9- or 10-membered bicyclic group having 1, 2 or 3 heteroatoms independently selected from O, N and S which group is optionally substituted with 1 or 2 groups independently selected from alkyl, haloalkyl, alkoxy,
—NR$^{10}$R$^{10}$,
halogen,
—NR$^{10}$-cycloalkyl,
tetrazolyl,
—O-alkylene-NR$^{10}$R$^{10}$,
—NR$^{10}$-alkylene-Oalkyl,
—CN,
—CONR$^{10}$R$^{10}$,
—COOR$^{10}$)
alkylSO(=NR$^{10}$)—,
—CONR$^{10}$—O-alkylene-OH,
—CONR$^{10}$—O-alkylene-O-alkyl,
morpholinyl,
piperazinyl,
oxadiazolyl and
phenylcarbonyl;
$R^6$ is H, or alkyl;
$R^{10}$ at each occurrence independently is H, alkyl, phenyl which is optionally substituted with hydroxyl or alkoxy or is phenylalkyl wherein the phenyl group is optionally substituted with halogen; and
$R^{12}$ is H, alkyl, phenylalkyl, or —NR$^{10}$R$^{10}$.

2. The compound of claim 1, or a pharmaceutically acceptable salt, solvate, or optical isomer thereof, wherein $R^5$ is a heteroaromatic 5- or 6-membered monocyclic group having 1, 2 or 3 heteroatoms independently selected from O, N and S which group is optionally substituted with 1 or 2 groups independently selected from alkyl, haloalkyl, alkoxy, —NR$^{10}$R$^{10}$, halogen, —NR$^{10}$-cycloalkyl, tetrazolyl, —O-alkylene-NR$^{10}$R$^{10}$, —N$^{10}$-alkylene-Oalkyl, —CN, —CONR$^{10}$R$^{10}$, —COOR$^{10}$, alkylSO(=NR$^{10}$)—, —CONR$^{10}$—O-alkylene-OH, and —CONR$^{10}$—O-alkylene-O-alkyl.

3. The compound of claim 2, or a pharmaceutically acceptable salt, solvate, or optical isomer thereof, wherein the heteroaromatic group is unsubstituted or substituted with 1 or 2 groups independently selected from alkyl, haloalkyl, or —COOR$^{10}$.

4. The compound of claim 1, or a pharmaceutically acceptable salt, solvate, or optical isomer thereof, wherein
$R^w$ is —NR$^{10}$SO$_2$R$^{12}$;
$R^x$ is F; and
$R^y$ is F;
$R^5$ is a heteroaromatic 5- or 6-membered monocyclic group having 1, 2 or 3 heteroatoms independently selected from O, N and S which group is unsubstituted or substituted with 1 or 2 groups independently selected from alkyl, haloalkyl, alkoxy, —NR$^{10}$R$^{10}$, halogen, —NR$^{10}$-cycloalkyl, tetrazolyl, —O-alkylene-NR$^{10}$R$^{10}$, —NR$^{10}$-alkylene-Oalkyl, —CN, —CONR$^{10}$R$^{10}$, —COOR$^{10}$, alkylSO(=NR$^{10}$)—, —CONR$^{10}$—O-alkylene-OH and —CONR$^{10}$—O-alkylene-O-alkyl.

5. The compound of claim 1, or a pharmaceutically acceptable salt, solvate, or optical isomer thereof, selected from the group consisting of
N-[2,6-difluoro-3-(5-pyridin-4-yl-1H-pyrazolo[3,4-b]pyridine-3-carbonyl)phenyl]-methanesulfonamide;
N-[2,6-difluoro-3-(5-pyridin-4-yl-1H-pyrazolo[3,4-b]pyridine-3-carbonyl)phenyl]-1-phenylmethanesulfonamide;
N-[2,6-difluoro-3-(5-pyridin-4-yl-1H-pyrazolo[3,4-b]pyridine-3-carbonyl)phenyl]-ethanesulfonamide; and
N-(2,6-difluoro-3-(5-(2-(trifluoromethyl)pyrimidin-5-yl)-1H-pyrazolo[3,4-b]pyridine-3-carbonyl)phenyl)propane-1-sulfonamide;

or a pharmaceutically acceptable salt, solvate or optical isomer thereof.

6. A pharmaceutical composition comprising a compound of claim 1, or a pharmaceutically acceptable salt, solvate, or optical isomer thereof.

7. The compound of claim 1 or a pharmaceutically acceptable salt, solvate or optical isomer thereof, wherein $R^5$ is pyridyl, pyridyl substituted with —$COOR^{10}$, pyrimidinyl or pyrimidinyl substituted with $CF_3$.

8. The compound of claim 1 or a pharmaceutically acceptable salt, solvate or optical isomer thereof, wherein $R^5$ is pyridyl or pyridyl substituted with —$COOR^{10}$.

9. The compound of claim 1 or a pharmaceutically acceptable salt, solvate or optical isomer thereof, wherein $R^1$ and $R^4$, independently of each other, are H or alkyl.

10. The compound of claim 1 or a pharmaceutically acceptable salt, solvate or optical isomer thereof, wherein $R^{10}$ is H or alkyl.

11. The compound of claim 1 or a pharmaceutically acceptable salt, solvate or optical isomer thereof, wherein $R^{12}$ is alkyl or phenylalkyl.

12. The compound of claim 1 or a pharmaceutically acceptable salt, solvate or optical isomer thereof, wherein $R^{12}$ is $C_1$-$C_3$-alkyl or benzyl.

13. The compound of claim 1 or a pharmaceutically acceptable salt, solvate or optical isomer thereof, wherein $R^1$, $R^4$ and $R^6$ are H.

14. The compound of claim 1 or a pharmaceutically acceptable salt, solvate or optical isomer thereof, wherein $R^w$ is —$NR^{10}SO_2R^{12}$.

15. The compound of claim 1 which is N-(2,6-difluoro-3-(5-(pyridin-4-yl)-1H-pyrazolo[3,4-b]pyridine-3-carbonyl)phenyl)propane-1-sulfonamide or a pharmaceutically acceptable salt or solvate thereof.

16. The compound of claim 1, which is N-(2,6-difluoro-3-(5-(pyridin-4-yl)-1H-pyrazolo[3,4-b]pyridine-3-carbonyl)phenyl)propane-1-sulfonamide or a pharmaceutically acceptable salt thereof.

17. The compound of claim 1, which is N-(2,6-difluoro-3-(5-(pyridin-4-yl)-1H-pyrazolo[3,4-b]pyridine-3-carbonyl)phenyl)propane-1-sulfonamide.

18. A method of selectively inhibiting protein kinase MKK4 over protein kinases JNK1 and MKK7, which comprises administering an effective amount of a compound as defined in claim 1, or a pharmaceutically acceptable salt, solvate, or optical isomer thereof to a subject in need thereof.

19. A method of promoting liver regeneration or reducing or preventing hepatocyte death, which comprises administering an effective amount of a compound as defined in claim 1, or a pharmaceutically acceptable salt, solvate, or optical isomer thereof to a subject in need thereof.

* * * * *